(12) United States Patent
Ginsburg et al.

(10) Patent No.: US 11,837,334 B2
(45) Date of Patent: *Dec. 5, 2023

(54) WHOLE-LIFE, MEDICATION MANAGEMENT, AND ORDERING DISPLAY SYSTEM

(71) Applicant: DHRpro, LLC, Merion Station, PA (US)

(72) Inventors: Leonard H. Ginsburg, Merion, PA (US); Nancy Wilson Crawford, Glen Mills, PA (US); Ryan Twomey-Allaire, Orlando, WV (US)

(73) Assignee: SHRPRO, LLC, Merion Station, PA (US)

( * ) Notice: Subject to any disclaimer, the term of this patent is extended or adjusted under 35 U.S.C. 154(b) by 41 days.

This patent is subject to a terminal disclaimer.

(21) Appl. No.: 17/008,586

(22) Filed: Aug. 31, 2020

(65) Prior Publication Data

US 2021/0174916 A1 Jun. 10, 2021

Related U.S. Application Data

(60) Provisional application No. 63/026,547, filed on May 18, 2020, provisional application No. 62/987,165, (Continued)

(51) Int. Cl.
*G16H 10/60* (2018.01)

(52) U.S. Cl.
CPC .................................. *G16H 10/60* (2018.01)

(58) Field of Classification Search
CPC ........ G16H 40/63; G16H 40/67; G16H 10/60; G06Q 10/06
(Continued)

(56) References Cited

U.S. PATENT DOCUMENTS

| 7,171,277 | B2 | 1/2007 | Engleson et al. |
| 7,987,428 | B2 * | 7/2011 | Handy ............... G06F 16/26 715/764 |

(Continued)

FOREIGN PATENT DOCUMENTS

| CA | 2887622 A1 * | 4/2014 | ............. G06Q 10/06 |
| CA | 2942566 C | 10/2022 | |

(Continued)

OTHER PUBLICATIONS

Google patents search, Jun. 16, 2022 (Year: 2022).*

(Continued)

*Primary Examiner* — Dilek B Cobanoglu
(74) *Attorney, Agent, or Firm* — SCHWEGMAN LUNDBERG & WOESSNER, P.A.

(57) ABSTRACT

Some embodiments include a system and computer-implemented method for aggregating and tracking medical delivery to a patient including a non-transitory computer-readable medium in data communication with at least one processor, where the non-transitory computer-readable medium includes software instructions for a medical services tracking system and method. Upon execution of the software instructions, information from a patient database or server can be received and displayed a medical record dashboard. A user can view and edit access to the information, and a user selectable link can display medical record information. The system and method enable auto-population of medical data entry fields based at least one part on at least one claim made or billing signed off by a physician for at least one medical service or procedure previously provided to or performed on at least one patient.

70 Claims, 61 Drawing Sheets

Related U.S. Application Data filed on Mar. 9, 2020, provisional application No. 62/983,350, filed on Feb. 28, 2020, provisional application No. 62/907,410, filed on Sep. 27, 2019, provisional application No. 62/893,688, filed on Aug. 29, 2019.

(58) Field of Classification Search
  USPC ............................................................ 705/3, 500
  See application file for complete search history.

(56) References Cited

U.S. PATENT DOCUMENTS

| | | | |
|---|---|---|---|
| 8,321,383 B2 | 11/2012 | Schumacher et al. | |
| 9,104,789 B2 | 8/2015 | Gross et al. | |
| 9,483,614 B2 * | 11/2016 | Ash | G16H 10/60 |
| 9,626,479 B2 * | 4/2017 | Zaleski | G16H 40/63 |
| 10,685,743 B2 | 6/2020 | Ginsburg et al. | |
| 11,205,505 B2 | 12/2021 | Ginsburg | |
| 11,587,654 B2 | 2/2023 | Ginsburg et al. | |
| 2001/0032100 A1 | 10/2001 | Mahmud et al. | |
| 2002/0002473 A1 | 1/2002 | Schrier et al. | |
| 2006/0064020 A1 | 3/2006 | Burnes et al. | |
| 2006/0080620 A1 | 4/2006 | Dvorak et al. | |
| 2006/0085223 A1 | 4/2006 | Anderson et al. | |
| 2006/0294092 A1 | 12/2006 | Giang et al. | |
| 2008/0033754 A1 | 2/2008 | Smith et al. | |
| 2008/0086332 A1 | 4/2008 | Hertel et al. | |
| 2008/0086333 A1 | 4/2008 | Hertel et al. | |
| 2008/0243548 A1 | 10/2008 | Cafer | |
| 2009/0192823 A1 | 7/2009 | Hawkins et al. | |
| 2009/0204421 A1 | 8/2009 | Guimaraes | |
| 2009/0222286 A1 | 9/2009 | Elsholz | |
| 2009/0265188 A1 | 10/2009 | Lamy et al. | |
| 2010/0057646 A1 | 3/2010 | Martin et al. | |
| 2010/0094649 A1 | 4/2010 | White | |
| 2010/0131293 A1 | 5/2010 | Linthicum et al. | |
| 2010/0131482 A1 | 5/2010 | Linthicum et al. | |
| 2010/0131883 A1 | 5/2010 | Linthicum et al. | |
| 2010/0274584 A1 | 10/2010 | Kim | |
| 2011/0004494 A1 | 1/2011 | Denny, Jr. et al. | |
| 2011/0071464 A1 | 3/2011 | Palerm | |
| 2011/0202370 A1 | 8/2011 | Green, III et al. | |
| 2011/0276348 A1 | 11/2011 | Ahn et al. | |
| 2012/0029303 A1 | 2/2012 | Shaya | |
| 2012/0078664 A1 | 3/2012 | Hasan et al. | |
| 2012/0130197 A1 | 5/2012 | Kugler et al. | |
| 2012/0130741 A1 * | 5/2012 | Sparandara | G16H 10/60 |
| | | | 705/500 |
| 2012/0131498 A1 | 5/2012 | Gross et al. | |
| 2012/0131507 A1 | 5/2012 | Sparandara et al. | |
| 2012/0215560 A1 | 8/2012 | Ofek et al. | |
| 2012/0232918 A1 | 9/2012 | Mack et al. | |
| 2012/0253841 A1 | 10/2012 | Erlandsen et al. | |
| 2012/0286955 A1 | 11/2012 | Welch et al. | |
| 2013/0024206 A1 | 1/2013 | Hughes et al. | |
| 2013/0027411 A1 | 1/2013 | Hebler et al. | |
| 2013/0041677 A1 | 2/2013 | Nusimow et al. | |
| 2013/0080192 A1 | 3/2013 | Bucur et al. | |
| 2013/0083185 A1 | 4/2013 | Coleman, III | |
| 2013/0159022 A1 | 6/2013 | Verbeek et al. | |
| 2013/0191161 A1 | 7/2013 | Churchwell et al. | |
| 2013/0290005 A1 | 10/2013 | Vesto et al. | |
| 2014/0012597 A1 | 1/2014 | Nolte et al. | |
| 2014/0074509 A1 | 3/2014 | Amarasingham et al. | |
| 2014/0207486 A1 * | 7/2014 | Carty | G16H 40/67 |
| | | | 705/2 |
| 2014/0236627 A1 | 8/2014 | Odessky et al. | |
| 2014/0236631 A1 | 8/2014 | Perrin et al. | |
| 2014/0236635 A1 | 8/2014 | Liberty et al. | |
| 2014/0249833 A1 | 9/2014 | Conti et al. | |
| 2014/0304005 A1 | 10/2014 | Hughes et al. | |
| 2015/0052032 A1 | 2/2015 | Aharoni | |
| 2015/0185972 A1 * | 7/2015 | Ash | G16H 40/63 |
| | | | 715/810 |
| 2015/0254403 A1 | 9/2015 | Laperna | |
| 2015/0269323 A1 | 9/2015 | Ginsburg | |
| 2016/0063212 A1 | 3/2016 | Monier et al. | |
| 2016/0125149 A1 | 5/2016 | Abramowitz | |
| 2016/0147978 A1 | 5/2016 | Adams et al. | |
| 2016/0162638 A1 | 6/2016 | Albro et al. | |
| 2016/0198996 A1 | 7/2016 | Dullen | |
| 2016/0321399 A1 * | 11/2016 | Ramachandran | G16Z 99/00 |
| 2016/0321404 A1 | 11/2016 | Ginsburg | |
| 2016/0328526 A1 | 11/2016 | Park et al. | |
| 2016/0357914 A1 | 12/2016 | Morris et al. | |
| 2017/0068780 A1 | 3/2017 | Dobrean | |
| 2017/0116373 A1 | 4/2017 | Ginsburg et al. | |
| 2018/0261306 A1 | 9/2018 | Naito et al. | |
| 2018/0330457 A1 | 11/2018 | Hawkins et al. | |
| 2018/0336457 A1 | 11/2018 | Pal et al. | |
| 2019/0259479 A1 | 8/2019 | Ginsburg | |
| 2020/0005916 A1 | 1/2020 | Brooks et al. | |
| 2020/0265932 A1 | 8/2020 | Ginsburg et al. | |
| 2020/0294640 A1 | 9/2020 | Ginsburg | |
| 2021/0110897 A1 | 4/2021 | Ginsburg et al. | |
| 2022/0084641 A1 | 3/2022 | Ginsburg | |
| 2022/0084645 A1 | 3/2022 | Ginsburg et al. | |
| 2022/0084664 A1 | 3/2022 | Ginsburg | |
| 2022/0215919 A9 | 7/2022 | Ginsburg et al. | |
| 2022/0367016 A1 | 11/2022 | Ginsburg | |
| 2023/0073347 A1 | 3/2023 | Ginsburg et al. | |
| 2023/0238090 A1 | 7/2023 | Ginsburg | |
| 2023/0253082 A1 | 8/2023 | Ginsburg et al. | |

FOREIGN PATENT DOCUMENTS

| | | |
|---|---|---|
| IN | 202217055674 A | 7/2023 |
| JP | 2011504379 A | 2/2011 |
| JP | 2017510015 | 4/2017 |
| KR | 20030095691 A | 12/2003 |
| KR | 20110021370 A | 3/2011 |
| KR | 101142568 B1 | 5/2012 |
| KR | 102434498 B1 | 8/2022 |
| WO | 2015143455 | 9/2015 |
| WO | 2018017927 | 1/2018 |
| WO | 2018057918 | 3/2018 |
| WO | 2021042077 | 3/2021 |
| WO | 2021174169 | 9/2021 |
| WO | 2021183347 | 9/2021 |

OTHER PUBLICATIONS

"International Application Serial No. PCT US2021 020159, Invitation to Pay Additional Fees dated Jun. 4, 2021", 7 pgs.

"International Application Serial No. PCT US2021 020751, International Search Report dated Jul. 2, 2021", 3 pgs.

"International Application Serial No. PCT US2021 020751, Written Opinion dated Jul. 2, 2021", 10 pgs.

"International Application Serial No. PCT US2021 020159, International Search Report dated Aug. 3, 2021", 6 pgs.

"International Application Serial No. PCT US2021 020159, Written Opinion dated Aug. 3, 2021", 12 pgs.

International Search Report and Written Opinion for Application No. PCT/US2020/048849, dated Feb. 2, 2021.

"U.S. Appl No. 15/275,223, Preliminary Amendment filed Mar. 16, 2017", 11 pgs.

"International Application Serial No. PCT US2015 022091, International Search Report dated Jun. 29, 2015", 3 pgs.

"International Application Serial No. PCT US2015 022091, Written Opinion dated Jun. 29, 2015", 5 pgs.

"International Application Serial No. PCT US2015 022091, International Preliminary Report on Patentability dated Sep. 29, 2016", 7 pgs.

"International Application Serial No. PCT US2017 052993, International Search Report dated Dec. 1, 2017", 2 pgs.

"International Application Serial No. PCT US2017 052993, Written Opinion dated Dec. 1, 2017", 9 pgs.

"Application Serial No. 14 666,278, Non Final Office Action dated Dec. 21, 2017", 20 pgs.

(56) References Cited

OTHER PUBLICATIONS

"U.S. Appl. No. 14/666,278, Non Final Office Action dated Jan. 9, 2018", 22 pgs.
"U.S. Appl. No. 15/204,900, Non Final Office Action dated Jan. 9, 2018", 32 pgs.
"U.S. Appl. No. 14/666,278, Response filed Jun. 11, 2018 to Non Final Office Action dated Jan. 9, 2018", 33 pgs.
"Placement of Inventor work by MD Office in EyeNet Extra", distributed as a Supplement to an EyeNetmagazine available in Oct. 2014 at the American Academy of Ophthalmology AAO 2014 Conference, (Oct. 18-21, 2014), 2 pages.
"International Application Serial No. PCT US2017 052993, International Preliminary Report on Patentability dated Apr. 4, 2019", 11 pgs.
"U.S. Appl. No. 15/275,223, Supplementary Preliminary Amendment Filed May 1, 2019", 14 pgs.
"Australian Application Serial No. 2015230980, First Examination Report dated Dec. 24, 2019", 3 pgs.
"Medication Ordering Screenshots 1A, 1B, 1C", MDoffice EHR, 3 pgs.
"Scheduling Screenshots 2A, 2B, 2C", MDoffice EHR, 3 pgs.
"Test Ordering Screenshots 3A, 3B, 3C, 3D, 3E", MDoffice EHR, 5 pgs.
"U.S. Appl. No. 15/275,223, Notice of Allowance dated Feb. 3, 2020", 21 pgs.
"U.S. Appl. No. 15/275,223, Corrected Notice of Allowability dated Mar. 24, 2020", 2 pgs.
"Australian Application Serial No. 2015230980, Subsequent Examiners Report dated Jul. 23, 2020", 3 pgs.
"International Application Serial No. PCT US2020 052964, International Search Report dated Dec. 22, 2020", 2 pgs.
"International Application Serial No. PCT US2020 052964, Written Opinion dated Dec. 22, 2020", 7 pgs.
"Israel Application Serial No. 265575, Notification of Defects in Patent Application dated Dec. 31, 2020", with English translation, 10 pages.
"U.S. Appl. No. 16/399,974, Preliminary Amendment filed Mar. 3, 2020", 15 pgs.
"U.S. Appl. No. 16/399,974, Preliminary Amendment filed Mar. 25, 2021", 13 pgs.
"U.S. Appl. No. 17/008,631, Preliminary Amendment filed Dec. 30, 2020", 3 pgs.
"U.S. Appl. No. 16/399,974, Examiner Interview Summary dated Nov. 4, 2021", 3 pgs.
"U.S. Appl. No. 16/399,974, Notice of Allowance dated Nov. 15, 2021", 31 pgs.
"U.S. Appl. No. 16/399,974, 312 Amendment filed Nov. 15, 2021", 23 pgs.
"U.S. Appl. No. 16/865,859, Preliminary Amendment filed Dec. 23, 2021", 21 pgs.
"U.S. Appl. No. 17/456,286, Non Final Office Action dated Feb. 16, 2022", 35 pages.
"U.S. Appl. No. 16/802,547, Restriction Requirement U.S. Appl. Feb. 24, 2022", 6 pgs.
"International Application Serial No. PCT US2020 048849, International Preliminary Report on Patentability dated Mar. 10, 2022", 9 pgs.
"U.S. Appl. No. 16/802,547, Response filed Mar. 31, 2022 to Restriction Requirement dated Feb. 24, 2022", 10 pgs.
"U.S. Appl. No. 17/456,286, Examiner Interview Summary dated Apr. 22, 2022", 2 pgs.
"U.S. Appl. No. 16/802,547, Non Final Office Action dated May 2, 2022", 39 pgs.
"U.S. Appl. No. 17/456,286, Examiner Interview Summary dated May 11, 2022", 2 pgs.
"U.S. Appl. No. 17/456,286, Response filed Jun. 16, 2022 to Non Final Office Action dated Feb. 16, 2022", 17 pgs.
"U.S. Appl. No. 17/456,286, Examiner Interview Summary dated Jun. 29, 2022", 2 pgs.
"U.S. Appl. No. 17/456,286, Notice of Allowance dated Jul. 25, 2022", 9 pgs.
"U.S. Appl. No. 16/865,859, Supplemental Preliminary Amendment Filed Jul. 25, 2022".
"U.S. Appl. No. 17/008,631, Restriction Requirement dated Aug. 12, 2022", 6 pgs.
"U.S. Appl. No. 17/035,648, Non Final Office Action dated Sep. 1, 2022", 17 pgs.
"International Application Serial No. PCT US2021 020159, International Preliminary Report on Patentability dated Sep. 9, 2022", 14 pgs.
"International Application Serial No. PCT US2021 020751, International Preliminary Report on Patentability dated Sep. 22, 2022", 12 pgs.
"U.S. Appl. No. 16/802,547, Response filed Oct. 3, 2022 to Non Final Office Action dated May 2, 2022", 12 pgs.
"U.S. Appl. No. 16/802,547, Examiner Interview Summary dated Oct. 7, 2022", 2 pgs.
"U.S. Appl. No. 17/940,908, Preliminary Amendment filed Nov. 23, 2022", 7 pgs.
"U.S. Appl. No. 16/802,547, Final Office Action dated Jan. 31, 2023", 37 pgs.
"U.S. Appl. No. 17/035,648, Response filed Feb. 1, 2023 to Non Final Office Action dated Sep. 1, 2022", 15 pgs.
"U.S. Appl. No. 17/035,648, Final Office Action dated Mar. 23, 2023", 29 pgs.
"U.S. Appl. No. 16/802,547, Examiner Interview Summary dated Apr. 25, 2023", 2 pgs.
"U.S. Appl. No. 16/802,547, Preliminary Amendment filed Jan. 11, 2022", 11 pgs.
"U.S. Appl. No. 16/802,547, Non Final Office Action dated Aug. 17, 2023", 36 pgs.
"U.S. Appl. No. 16/802,547, Response filed May 31, 2023 to Final Office Action dated Jan. 31, 2023", 22 pgs.
"U.S. Appl. No. 16/865,859, Notice of Allowance dated Oct. 17, 2022", 11 pgs.
"U.S. Appl. No. 17/008,631, Final Office Action dated Aug. 16, 2023", 16 pgs.
"U.S. Appl. No. 17/008,631, Non Final Office Action dated Feb. 2, 2023", 16 pgs.
"U.S. Appl. No. 17/008,631, Response filed Jan. 12, 2023 to Restriction Requirement dated Aug. 12, 2022", 9 pgs.
"U.S. Appl. No. 17/008,631, Response filed Aug. 2, 2023 to Non Final Office Action dated Feb. 2, 2023", 11 pgs.
"U.S. Appl. No. 17/035,648, Advisory Action dated Jun. 13, 2023", 4 pgs.
"U.S. Appl. No. 17/035,648, Examiner Interview Summary dated May 30, 2023", 2 pgs.
"U.S. Appl. No. 17/035,648, Non Final Office Action dated Aug. 16, 2023", 17 pgs.
"U.S. Appl. No. 17/035,648, Response filed May 23, 2023 to Final Office Action dated Mar. 23, 2023", 17 pgs.
"U.S. Appl. No. 17/456,286, Notice of Allowance dated Jan. 26, 2023", 19 pgs.
"U.S. Appl. No. 17/456,286, Amendment Under 37 CFR 1.114 filed Oct. 24, 2022", 15 pgs.
"U.S. Appl. No. 18/101,873, Preliminary Amendment filed Jan. 26, 2023.", 14 pgs.
"Australian Application Serial No. 2015230980, Response filed Jun. 29, 2020 to First Examination Report dated Dec. 24, 2019", 23 pgs.
"Australian Application Serial No. 2015230980, Voluntary Amendment filed May 16, 2019", 14 pgs.
"Canadian Application Serial No. 2,942,566, Office Action dated May 18, 2021", 6 pgs.
"Canadian Application Serial No. 2,942,566, Office Action dated Jul. 4, 2022", With English translation, 1 pg.
"Canadian Application Serial No. 2,942,566, Response filed Sep. 18, 2021 to Office Action dated May 18, 2021", 43 pgs.
"Canadian Application Serial No. 3,076,349, Office Action dated May 26, 2021", 6 pgs.
"Canadian Application Serial No. 3,076,349, Office Action dated Jul. 4, 2022", With English translation, 1 pg.

(56) References Cited

OTHER PUBLICATIONS

"Canadian Application Serial No. 3,076,349, Response filed Nov. 25, 2022 to Office Action dated May 26, 2021", 67 pgs.
"Korean Application Serial No. 1020167029340, Notice of Preliminary Rejection dated Aug. 27, 2021", with English translation, 26 pages.
"Korean Application Serial No. 1020167029340, Response Filed Jan. 24, 2022 to Notice of Preliminary Rejection dated Aug. 27, 2021", with English claims, 22 pages.
"European Application Serial No. 21760037.8, Extended European Search Report dated Oct. 23, 2023", 12 pgs.

\* cited by examiner

Patient: Patient A        (34, Female)        Race: Caucasian        Outstanding Balance: $200
DOB: 05/12/1982        Phone: (610) 999-3433

| Topic | Data |
|---|---|
| Patient since | June 6, 2012 |
| Referred by | Dr. Mark Twain |
| Interesting facts | 3 kids, went to some college, friends with the Kleins |

Revenue Summary

| Year | Billed | Insurance | Patient | Write-Offs | Adjustments | |
|---|---|---|---|---|---|---|
| 2014 | $30,000 | $20,000 | $5,000 | $2,000 | $3,000 | > |
| 2013 | $42,000 | $40,000 | $2,000 | $0 | $0 | > |
| 2012 | $10,000 | $9,000 | $1,000 | $0 | $0 | > |
| Total | $82,000 | $69,000 | $8,000 | $2,000 | $3,000 | > |

| Start Date | Stop Date | Last ... | Medication | Dos... | | Fre... | Status | Discontinued |
|---|---|---|---|---|---|---|---|---|
| 3/16/2020 | | | Pred Forte 1% drops suspension | 1 drop | ... | four times a day | Active | |
| 9/12/2019 | 4/8/2019 | | Latanoprost 0.005% Eye Drops | | OD | QHS | Active | No Longer Needed |
| 7/25/2019 | 9/12/2019 | | Combigan prednisolone acetate 1% | 1 drop | OD | twice a day | Active | Poor Compliance |
| 5/29/2019 | 3/25/2020 | | Latanoprost 0.005% | | OU | four times a day | Active | |

```
┌─────────────────────────────────────────────────────┐
│ Patient data/information from the at least one      │
│ patient database is received.                       │
│                                                     │
│                       4102                          │
└─────────────────────────────────────────────────────┘
                          │
                          ▼
┌─────────────────────────────────────────────────────┐
│ The received patient information is compared with   │
│ configuration rules to determine which portions of  │
│ the received patient data/information are to be     │
│ displayed and which portions of the received        │
│ patient data/information is not to be displayed in  │
│ the medical records dashboard.                      │
│                       4104                          │
└─────────────────────────────────────────────────────┘
                          │
                          ▼
┌─────────────────────────────────────────────────────┐
│ Collapsible data entry fields of the medical records│
│ dashboard that are determined to not have any       │
│ patient data to display are identified as collapsed │
│ data entry fields.                                  │
│                       4106                          │
└─────────────────────────────────────────────────────┘
                          │
                          ▼
┌─────────────────────────────────────────────────────┐
│ Patient data/information is displayed in the data   │
│ entry fields of the medical records dashboard in    │
│ accordance with the configuration rules and data    │
│ entry fields of the medical records dashboard       │
│ identified as collapsed data entry fields are       │
│ collapsed and not displayed.          4108          │
└─────────────────────────────────────────────────────┘
                          │
                          ▼
                      ┌───────┐
                      │ EXIT  │                4100
                      └───────┘
```

FIG. 41

WHOLE-LIFE, MEDICATION MANAGEMENT, AND ORDERING DISPLAY SYSTEM

CROSS-REFERENCE TO RELATED APPLICATIONS

The present application claims benefit of and is also a non-provisional of U.S. Provisional patent Application No. 62/893,688, filed Aug. 29, 2019 and a Provisional Patent Application No. 62/907,410, filed Sep. 27, 2019 and a Provisional patent Application No. 62/983,350, filed Feb. 28, 2020 and a Provisional patent Application No. 62/987,165, filed Mar. 9, 2020 and a Provisional Patent Application No. 63/026,547, filed May 18, 2020. The contents of these patent applications are hereby incorporated by reference in their entireties.

BACKGROUND

Caregivers are often called upon to make rapid life and death decisions based on a patient's conditions in the context of a medical history as presented, for example, in an Electronic Medical Record ("EMR"). However, the visual display systems for conventional EMRs are often difficult to understand and require the user to move through multiple screens, interfaces, and menus to obtain the disparate information needed to make a care decision. This is problematic when caring for multiple patients in a busy practice and is particularly problematic in a critical care setting.

Conventional informational systems, such as EMR systems, provide computerized interfaces between medical professionals and their staff and patients and are designed to facilitate and streamline the business of medical care. Such systems enable a medical care provider to track the delivery of medical care, access a patient's medical records, track billing for services provided, and follow a patient's progress. However, such conventional informational systems, such as EMR systems, have mostly not met their promise because the systems include complex interfaces that require users to navigate through multiple layers, folders and/or windows to access even basic patient information. Recently, a Healthcare Information and Management Systems Society (HIMSS) survey showed that 40% of physicians would not recommend their EMR to a colleague, 63.9% said note writing took longer with electronic health records, and 32% were slower to read other clinician's notes. A recent study by Medical Economics indicated that 67% of physicians are displeased with their EMR systems.

Moreover, the complex interfaces associated with EMRs are particularly problematic at the point of care as they slow caregivers down and distract them from meaningful face-time, caring for patients. As a result, many caregivers defer their interaction with the EMR systems until after the patients have been treated. A recent study reported in the Annals of Internal Medicine reported that physicians are spending almost half of their time in the office on EMR and desk work and spend just 27% on face time with patients, which is what the vast majority of physicians went into medicine to do. Once the physician gets home, they average another one to two hours completing health records. Thus, the complex interfaces of current EMR systems have led to diminished quality of a caregiver's practice of medicine, diminished patient quality of care, and negatively impacted caregiver job satisfaction. More user-friendly interfaces enabling caregivers ready access to the information accessible through EMR systems at the point of care is needed to improve the caregiver-patient interactions and would be particularly useful in avoiding medical errors and missed diagnoses and increase compliance with insurance billing rules and regulations.

Communication of medical findings between caregivers seeing patients treated by multiple health care providers has also become more difficult. Now, rather than a phone call, simple fax or one page dictated medical summary, caregivers are now sending voluminous amounts of information as the EMR gets stuffed with insurance documentation requirements and cut and paste options from "previous visits." Some medical conditions, such as diabetes, require multiple medical personnel to treat the patient. A single patient may have an eye doctor, family physician, endocrinologist, podiatrist, cardiologist, nephrologist, dietician/exercise physiologist, and diabetes education program coordinator. Primary care physicians can be audited and, if the annual report from a consultant is not in the chart, they can be financially penalized.

What is needed is a simple, elegant solution that enables caregivers to synthesize information and populate and document a chart when seeing a patient using a single presentation instance and enables a caregiver to identify medical problems through data visualization, where data is presented and displayed in an intuitive, easy to read manner and which enables the rapid identification of billing and collections and which enables easy sharing of medical findings, information and conclusions among multiple caregivers.

SUMMARY

The above and other needs in the art are addressed by a data command center visual display system and associated methods for displaying data on a display screen from multiple data sources and allowing navigation amongst the data without leaving the display of the visual display system. Numerous technical issues rooted in computer technology must be solved for the data to be presented to the visual display system so that the data may be displayed in the command center using a single display interface. For example, the visual display system must provide access to the requisite health information systems and third-party support services whereby the data may be accessed, processed, and presented without unacceptable delay. Also, the display data must be collected and ordered to facilitate the various combinations of the data into respective display panels that may be navigated on the display screen. For example, it is desirable for the data to be configured in a task-based or specialty-specific display configuration for use by physicians, for example. To do this, various features in prior art systems needed to be acquired and combined in a new way to facilitate access to the features without having to navigate away from the display screen. For example, conventional EMR systems provide interfaces to third party prescription ordering systems but require the user the navigate to another system and away from the EMR interface. Accessing ordering screens without leaving the display screen becomes particularly difficult where the display screen space is limited as is the case for many physicians who use portable display devices and mobile computers. The structural embodiments described herein address these technical issues to generate the command center visual display system embodiments described herein.

In exemplary embodiments, such a data command center visual display system in accordance with the present principles includes a patient database that stores patient identification information, patient insurance information, patient medical history information, a computer readable storage medium having stored thereon instructions thereon, and a processor that executes the instructions to perform operations including creating a plurality of adjustable display panels configured to display predetermined combinations of the patient identification information, patient insurance information, patient medical history information, and creating a patient flowsheet that integrates the patient medical history information into a table that presents the patient's medical history by visit to at least one physician with respective procedures or actions performed during each visit represented as first icons identifying the procedure or action performed and second icons enabling selection of a new procedure or action, where the first and second icons provide links to associated patient medical information and ordering display panels that may be accessed without leaving the display screen. In response to selection of the second icon by a user of the visual display system, an ordering display panel is presented to the display screen in addition to the adjustable display panels and patient flowsheet. The desired procedures or actions may be ordered from the ordering display panels while relevant portions of the patient's medical history are still visible on the display screen. The scope of the claims also contemplates corresponding methods performed by the visual display system and users thereof.

In exemplary embodiments, the ordering display panel comprises an ePrescribing panel for ordering medication or a medical procedure ordering panel for ordering a medical procedure. By way of example, the medical procedure ordering panel for ordering a medical procedure may further provide a link to the quality reporting panel that displays quality reporting metrics and/or peer data related to the procedure that is being ordered. All of such ordering display panels are configured in the context of the screen display to save real estate (conserve display space) so that the ordering display screen may be displayed while still being able to view the medical history data, for example.

In other exemplary embodiments, the ordering display panel comprises an imaging order panel for ordering a medical image of the patient or a lab order panel for ordering a lab test of the patient. In still other embodiments, instructions are provided that when executed create an image icon in an adjustable display panel and/or the patient flowsheet that, when selected by the user of the visual data system, opens a display window for viewing of one or more images without leaving the display screen.

In other exemplary embodiments, the visual display system incorporates financial data with the patient medical history data into the display panels. Such a visual display system includes a patient database that stores patient identification information, patient insurance information, patient medical history information, and patient payment information, a computer readable storage medium having stores thereon instructions thereon, and a processor that executes the instructions to perform operations including creating a plurality of adjustable display panels configured to display predetermined combinations of the patient identification information, patient insurance information, patient medical history information, and patient payment information, and creating a patient flowsheet that integrates the patient medical history information and patient payment information into a table that presents the patient's medical history by visit to at least one physician with respective procedures or actions performed during each visit represented as first icons identifying the procedure or action performed and second icons indicating whether the procedure or action has been paid for in part or in full, the first and second icons providing links to associated patient medical history information and/or patient payment information. In response to selection by a user of the visual display system, the adjustable display panels and patient flowsheet are moved into a task-based or specialty-specific display configuration such that the patient identification information, patient insurance information, patient medical history information, and patient payment information may be accessed without leaving the display screen. The task-based or specialty-specific display configuration is then presented to the display screen. In exemplary embodiments, selection of the first icons or second icons open display windows to associated medical history data and/or financial data and overlay a portion of the display screen with the display windows whereby the associated medical history data and/or financial data may be viewed by the user of the visual display system while the adjustable display panels and the patient flowsheet are displayed in a background on the display screen. Throughout this description, it will be appreciated that all financial data in the system, including costs to patient, is compartmentalized such that no user may see financial details for users or organizations not authorized in accordance with applicable policies and law. Also, the scope of the claims also contemplates corresponding methods performed by the visual display system and users thereof.

The visual display system includes a number of features that enable accessing information on the display screen. For example, third icons are provided in the patient flowsheet or display panels that include links to compliance information about compliance with insurance guidelines and/or good clinical practice guidelines for a procedure or action associated with each third icon. In exemplary embodiments, the compliance information includes aggregated medical treatment guidelines and an overview outlining similarities and differences amongst different medical treatment guidelines making up the aggregated medical treatment guidelines. The aggregated medical treatment guidelines may include information related to recommended follow-up with the patient, information related to procedures permitted or prevented by the patient's insurance or contra-indications, and information relating to proper billing for the procedure or action associated with a third icon selected from the patient flowsheet or display panels. In exemplary embodiments, the visual display system provides access to a clinical decision support system that uses a rules engine and/or natural language processing to aggregate the medical treatment guidelines and to generate the overview outlining similarities and differences amongst different medical treatment guidelines making up the aggregated medical treatment guidelines. The clinical decision support system and/or natural language processing system may further compare medical data to notice patterns, errors and anomalies in different entries or notes, find discrepancies in payments, alert the user of the visual display system about inconsistent medical documentation or improper orders, speed up the process of complying with regulations, alert the user of the visual display system that a plan or order is inconsistent with a preferred practice plan for a patient, or warn the user of the visual display system that billing certain procedures might not be covered. The natural language processing system may also be accessed parse notes in the patient flowsheet or display panels for potential ICD10 codes or alternative diagnosis.

The visual display system also includes a display configuration that enables users of the visual display system to order medications, diagnostic tests, images, procedures, and the like directly from the patient flowsheet or display panel.

For example, an icon or link in the patient flowsheet or display panel may include an ePrescribing panel for ordering medication or a medical procedure ordering panel for ordering a medical procedure. The medical procedure ordering panel may further include a link to a quality reporting panel that displays quality reporting metrics and/or peer data related to the procedure that is being ordered. In other embodiments, an icon or link in the patient flowsheet or display panel may include an imaging order panel for ordering a medical image of the patient or a lab order panel for ordering a lab test of the patient. In still other embodiments, an image icon is provided in an adjustable display panel and/or the patient flowsheet that, when selected by the user of the visual data system, opens a display window for viewing of one or more images without leaving the display screen. In other embodiments, an alert icon is provided in an adjustable display panel and/or the patient flowsheet that, when selected by the user of the visual data system, opens an alert message without leaving the display screen. In still other embodiments, one of the display panels may be configured to accept today's visit notes from the user of the visual display system in connection with a patient visit for storage for access with other data of the one display panel.

Other novel features in exemplary embodiments include a moveable note icon for association with context information in a corresponding one of the adjustable display panels and/or the patient flowsheet. The note icon moves with the context information as the context information is moved on the display screen. When the note icon is selected, the user of the visual display system may enter a note relating to the context information.

In still other embodiments, data input by the user of the visual display system may trigger auto-population of information in the adjustable display panels and patient flowsheet and auto-population of the patient's medical record in an electronic medical record system. In the exemplary embodiments, the auto-population occurs without the user of the video display system leaving the display screen.

In other embodiments, new clinical information for the patient is provided to a diagnosis evaluation algorithm for comparison of the new clinical information with previous corresponding clinical information for the patient to determine whether the new clinical information is indicative of an improvement or worsening of the patient's medical condition. The visual display system further generates diagnosis indicators providing a visual representation of an improvement of a medical problem, disease, or symptom, or a worsening of a medical problem, disease, or symptom as a result of taking a particular medication or undergoing a particular medical procedure and displays the diagnosis indicators in the adjustable display panels and/or the patient flowsheet.

Other embodiments of the visual display system allow for increased speed of data presentation by a local database that stores a subset of patient identification information, patient insurance information, patient medical history information, and patient payment information, where the subset includes the patient identification information, patient insurance information, patient medical history information, and patient payment information for patients having an appointment within a predetermined time window.

The visual display system in exemplary embodiments includes interfaces to an external health information system and third party service systems. In exemplary embodiments, the external health information system includes at least one of an electronic medical records system, a practice management system, a health information exchange, a picture archive and communications system, a clearing house/billing system, and a laboratory system. On the other hand, the third party service systems may include one or more of an ePrescribing system, an insurance verification/referral/pre-authorization system, a system for establishing medical necessity by verifying that a procedure or medication is associated with a correct ICD10 code supporting its use, a clinical services pricing and location system, a claim status checking system, services in support of the National Correct Coding Initiative, services to proactively ensure claims are coded correctly to prevent issues in billing, claims compliance services that evaluate claims against National Coverage Determination (NCD) and Local Coverage Determination (LCD) guidelines as well as local insurance regulations to establish and document medical necessity, a natural language processing system, and artificial intelligence/cognitive systems that provide clinical decision support.

In exemplary embodiments, the patient identification information, patient insurance information, patient medical history information, and patient payment information is stored in the patient database in transactional tables that capture clinical and billing data and reporting tables where data is aggregated for a particular physician, practice, health system or other entity. Each table uses a surrogate primary key that is a unique value within the table used to identify a row that is not directly tied to data in that row. In the exemplary embodiments, XML code moves and stores different display panel and flowsheet views. The XML code further identifies a collection of panels and tabs, wherein within each panel is a panel ID that links the panel to a tab, the panel's position, and whether or not the panel is stacked with another panel. The XML code may also set up the display panels and patient flowsheet on the display screen by, for example, identifying a collection of columns and, for each column, a name of the column along with a data source. The display panels so configured are presented to the display screen for selection and display panel frames on the display screen are manipulated for receiving selected display panels.

In other exemplary embodiments, the patient flowsheet is organized around patient medical information corresponding to a particular disease state and/or procedures and/or insurance coverage and/or actions for treating the particular disease state.

The patient database may also be adapted to include patient medical history information from a plurality of medical care providers whereby the patient flowsheet may be adapted to include medical history information from more than one medical care provider in order to provide shared treatment of the patient in the patient flowsheet. In other embodiments, a summary table may be provided that illustrates everything the user of the visual display system has done for each patient in a particular time frame or for each patient having a particular disease state in a particular time frame. The summary table may also include information from other medical care providers who are providing shared treatment of the patient. If financial data, cost, charge, payment is on the summary table with the medical data, this data is compartmentalized such that no user may see financial details for users or organizations not authorized in accordance with applicable policies and law.

In yet other embodiments, a data command center visual display system is provided that presents dynamic data to a display screen. The command center visual display system includes a plurality of adjustable display panels configured to display predetermined combinations of patient identification information and patient medical information. A patient flowsheet is created that includes a table that presents the patient's medical information by medical service, medical procedure, diagnostic test, medication, and diagnosis that is prescribed, ordered, performed, or selected during respective encounters with at least one medical care provider. In response to selection by a user, at least two adjustable display panels containing medical information relating to one or more patients in the patient flowsheet are presented to the display in a single view. The user may edit or move the medical information or the patient identification information within the display panels while the display panels are simultaneously open.

In some embodiments, a method for rules-based data display in a data command center including a medical records dashboard including one or more windows including information received or derived from at least one patient database, the medical records dashboard comprising a display on a screen, using the one or more windows, of at least one of medical services, clinical data, examination findings, diagnostic tests, and the procedures performed on one or more patients, the one or more windows comprising a plurality of data entry fields, including at least one collapsible data entry field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, the method includes receiving patient-related data from the at least one patient database, comparing the received patient-related data with configuration rules to determine which portions of the received patient-related data are to be displayed in data entry fields of the medical records dashboard, identifying collapsible data entry fields of the at least one collapsible data entry field of the medical records dashboard that are determined to not have any patient-related data to display as collapsed data entry fields, displaying patient-related data in the data entry fields of the medical records dashboard in accordance with the configuration rules and collapsing data entry fields of the medical records dashboard identified as collapsed data entry fields.

In some embodiments, a data command center visual display system that displays data on a display screen includes a computing device comprising at least one processor, a non-transitory computer-readable medium, having stored thereon, software instructions that when executed by the at least one processor of the computing device, cause the computing device to perform operations comprising at least, linking to and receiving patient related medical records including patient data from at least one patient data source, and displaying a medical records dashboard including one or more windows, the medical record dashboard capable of displaying, using the one or more windows, patient data from at least one patient data source including at least one of medical services, clinical data, examination findings, diagnostic tests, and the procedures performed on one or more patients, the one or more windows comprising a plurality of data entry fields, including at least one collapsible data entry field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, wherein a display of patient data in the medical records dashboard is determined by: comparing the patient data with configuration rules to determine which portions of the patient data are to be displayed in the data entry fields of the medical records dashboard, identifying collapsible data entry fields of the at least one collapsible data entry field of the medical records dashboard that are determined to not have patient data to display as collapsed data entry fields, and displaying patient data in the data entry fields of the medical records dashboard in accordance with the configuration rules and collapsing data entry fields of the medical records dashboard identified as collapsed data entry fields.

In some embodiments, a method for unique patient identification of a subject patient in a data command center including patient-related data received or derived from at least one patient database includes collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning phase.

In some embodiments, a data command center visual display system for determining a unique patient identification includes a computing device comprising at least one processor, a non-transitory computer-readable medium, having stored thereon, software instructions that when executed by the at least one processor of the computing device, cause the computing device to perform operations comprising at least: linking to and receiving patient related medical records including patient data from at least one patient data source, collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning.

In some embodiments, a method for medication management and display in a data command center comprising one or more windows for display and including information received or derived from at least one patient database, the data command center displaying on a screen, using the one or more windows, at least one of medical services, clinical data, examination findings, diagnostic tests, and procedures performed on one or more patients, the one or more windows comprising a plurality of data entry fields for displaying the information received or derived from the at least one patient database, wherein the at least one of the medical services, the clinical data, the examination findings, the diagnostic tests, and the procedures are arranged in on the screen according to at least one of a time and a date that the medical services, the clinical data, the examination findings, the diagnostic tests and the procedures were performed on the one or more patients, includes determining, from at least one of the information received or derived from the at least one patient database and the at least one of the medical services, the clinical data, the examination findings, the diagnostic tests, and the procedures, medications administered to the one or more patients, generating a respective graphical representation for each of the determined medications administered to the one or more patients, and displaying at least one generated, respective graphical representation of at least one medication administered to a patient in the at least one or more windows in context with at least one of the information received or derived from the at least one patient database and the at least one of the medical services, the clinical data, the examination findings, the diagnostic tests, and the procedures, wherein the at least one generated, respective graphical representation of the at least one medication administered to the patient is arranged in on the screen according to at least one of the times and the dates that the at least one medication was being administered to the patient.

In some embodiments, a data command center visual display system that displays data on a display screen includes a computing device comprising at least one processor, a non-transitory computer-readable medium, having stored thereon, software instructions that when executed by the at least one processor of the computing device, cause the computing device to perform operations including at least, linking to and receiving patient related medical records including patient data from at least one patient data source, wherein the patient data includes at least one of medical services, clinical data, examination findings, diagnostic tests, and procedures performed on one or more patients, determining, from at least one of the patient data and the at least one of the medical services, the clinical data, the examination findings, the diagnostic tests, and the procedures, medications administered to the one or more patients, generating a respective graphical representation for each of the determined medications administered to the one or more patients, and displaying using the one or more windows, at least one of medical services, clinical data, examination findings, diagnostic tests, and procedures performed on one or more patients and at least one generated, respective graphical representation of at least one medication administered to a patient in context with at least one of the patient data and the at least one of the medical services, the clinical data, the examination findings, the diagnostic tests, and the procedures, wherein the at least one of the medical services, the clinical data, the examination findings, the diagnostic tests, and the procedures are arranged on the screen according to at least one of a time and a date that the medical services, the clinical data, the examination findings, the diagnostic tests and the procedures were performed on the one or more patients, and wherein the at least one generated, respective graphical representation of the at least one medication administered to the patient is arranged on the screen according to at least one of the times and the dates that the at least one medication was being administered to the patient.

In some embodiments, a method for a display of a graphical representation of complete medical history of a patient in a data command center comprising one or more windows for display and including patient-related data received or derived from at least one patient database, the method includes determining, from the patient-related data, a complete medical history of at least one patient including at least one of medical services, clinical data, examination findings, diagnostic tests, medications administered to and procedures performed on a patient, generating a graphical representation of the determined complete medical history of the patient including the at least one of medical services, clinical data, examination findings, diagnostic tests, medications administered to and procedures performed on the patient, and displaying the generated graphical representation in the at least one or more windows according to at least one of a time and a date that the at least one of the medical services, the clinical data, the examination findings, the diagnostic tests, and the procedures the medical services, the clinical data, the examination findings, the diagnostic tests and the procedures were performed on the one or more patients and at least one of the times and the dates that the medications were being administered to the patient, wherein a user is enabled to select a location in the displayed graphical representation and details regarding the at least one of medical services, clinical data, examination findings, diagnostic tests, medications administered to and procedures performed on the patient related to that selected location are presented to the user.

Other and further embodiments in accordance with the present principles are described below.

DESCRIPTION OF THE DRAWINGS

FIG. 4A depicts an example of a medical records dashboard of the Data Command Center in accordance with an embodiment of the present principles.

FIG. 4D depicts greater detail of at least some portions of the medical records dashboard of FIG. 4A in accordance with some embodiments of the present principles.

FIG. 5A depicts the medical records dashboard including a medical summary update process in accordance with some embodiments of the present principles.

FIG. 5B depicts a portion of the medical records dashboard including a notes update procedure in accordance with an embodiment of the present principles.

FIG. 6 depicts a user record access process of the medical records dashboard in accordance with an embodiment of the present principles.

FIG. 10 depicts a medical record update marker process of the medical records dashboard in accordance with an embodiment of the present principles.

FIG. 14 depicts a portion of a medical records dashboard configured for display as a function of disease of a patient and specifically configured to display data related to patients with diabetes in accordance with another embodiment of the present principles.

FIG. 15 depicts an embodiment of a medical records dashboard which can be displayed following a user's selection of at least one medical records dashboard from the medical records dashboard selection window in accordance with another embodiment of the present principles.

FIG. 20 depicts an embodiment of a Patient Information Panel of the Data Command Center menu, which can be activated when the Patient Information Bar is selected in accordance with an embodiment of the present principles.

FIG. 22B depicts an embodiment of a Surgeries tab of a medical records dashboard of a Data Command Center in accordance with an embodiment of the present principles.

FIG. 24 depicts an embodiment of a co-managed medical records dashboard in the Data Command Center of the present principles in accordance with one embodiment.

FIG. 31 depicts an embodiment of the control panel #1 of the Medication Management chart of FIG. 30 in accordance with an embodiment of the present principles.

FIG. 35 depicts a medical records dashboard including a third embodiment of a Medication Management chart in accordance with an embodiment of the present principles.

FIG. 41 depicts a flow diagram of a method for rules-based data display in a data command center comprising a medical records dashboard in accordance with an embodiment of the present principles.

Figure 1:
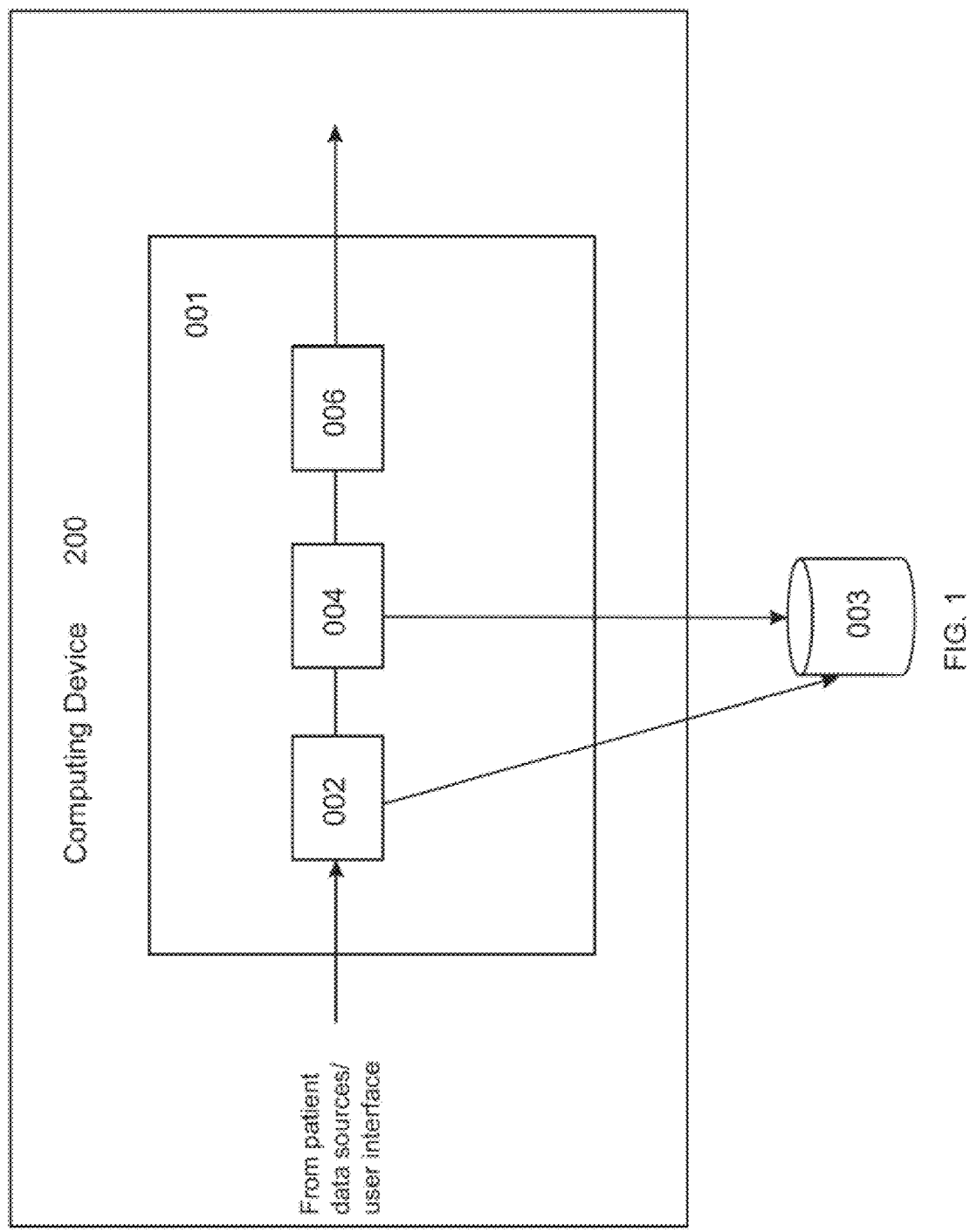
FIG. 1 depicts a high-level block diagram of a Data Command Center in accordance with an embodiment of the present principles.

The figures are not drawn to scale and may be simplified for clarity. It is contemplated that elements and features of one embodiment may be beneficially incorporated in other embodiments without further recitation.

DETAILED DESCRIPTION

Embodiments of the present principles generally relate to a Data Command Center for displaying data on a display screen from multiple data sources and enabling navigation amongst the data on a single display. While the concepts of the present principles are susceptible to various modifications and alternative forms, specific embodiments thereof are shown by way of example in the drawings and are described in detail below. It should be understood that there is no intent to limit the concepts of the present principles to the particular forms disclosed. On the contrary, the intent is to cover all modifications, equivalents, and alternatives consistent with the present principles and the appended claims. For example, although embodiments of the present principles will be described primarily with respect to inter-function with an EMR system, such teachings should not be considered limiting. Embodiments in accordance with the present principles can inter-function with other informational systems such as Health Information Exchanges (HIEs), Billing Clearinghouses, Insurance Companies, Picture Archiving and Communication Systems (PACS) as well as third party services and the like.

In addition, the tool embodiments of the present principles are not limited in application to the details of construction and the arrangement of components set forth in the following description or illustrated in the following drawings. Embodiments of the present principles are capable of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, the term "medical care provider" is intended to represent any healthcare provider/clinical professional such as a doctor, physician, podiatrist, chiropractor, dentist, veterinarian, ancillary staff, nurses, physician's assistant, medical care provider, physical therapist, all allied health professionals, and/or hospital staff member. All such healthcare providers/clinical professional can implement embodiments of the present principles of the tool as interchangeable users.

As used herein a row, column, or line of items (even a diagonal line) is intended to represent a sequencing or evaluation of information in any direction. In the embodiments depicted herein, information does not have to be depicted as having a visual or physical separation in the vertical or horizontal direction to be defined as being a row or column. In accordance with the present principles items next to each other horizontally, lined up in such a way that straight lines above and below can be drawn and items fall between those two horizontal lines, can be considered as being in a row. Items in rows can be related by similar time or other common or same denominator, such as a medical service, procedure, image or financial number, so that a user can quickly visualize trends or changes in those items. Similarly, items next to each other vertically, lined up in such a way that straight lines to the left and to the right can be drawn can be considered as being in a column. In some embodiments, items can be arranged diagonally and be considered to be in a row or a column.

As used herein, Practice Management Systems (PMs) are programs that perform the billing collection and reconciliation of payments as well as scheduling patients. PMs can also be referred to as Revenue Cycle Management (RCM) and have associated billing companies that use software to help practices and medical care providers get the bills out and collect money from insurance companies. In some embodiment, these entities can integrate with and work through clearing houses.

In the embodiments described herein, the terms window screen, scrolling screen, display view, snapshot and the like can be used interchangeably and are intended to represent a single instance of the presentation of medical information associated with a at least one patient. In the described embodiments, the single instance can be presented on one or more windows, in a single or multiple screens, a scrolling screen, in one or more views and using one or more snapshots. For example, in some embodiments in accordance with the present principles a user can access different panels from a scrolling screen and converge the panels into a single view or snapshot. That is, in accordance with the present principles, a user is able to compile data/information from various windows, screens, scrolling screens, displays, snapshots and the like and create a single instance presentation including the data/information of interest to the user for at least one patient. In accordance with the present principles, a single instance presentation can be presented on more than one monitor at a time. As used herein, the term single instance presentation is intended to describe a single display interface that is not limited to a single monitor. That is, in some embodiments, what defines a single instance presentation is the fact that there is a single interface, a single control that controls the presentation of the date/information, which can be then be viewed on one or more monitors or other means.

The term medical tests as described herein is intended to describe medical procedures performed for or on patients including but not limited to image or imaging, diagnostic tests, radiological tests or procedures, laboratories, chemistry and hematological tests, photography, genetic testing, nuclear scans, ultrasounds, x-rays, optical coherent tomography photographs and angiographies, assessments and plans, letters, examination findings and any medical testing or medical services that tests or screens patients for a medical condition, which in some instance can be identified by CPT codes. It should be further noted that in some instances, terms like diagnosis can be reflected by ICD 9 or 10 or similar identifying factors, and medications can be interchangeable.

As used herein, the terms icon, symbol, and indicator are all interchangeable and are intended to describe a visual element enabling the access of additional underlying information and having the ability to convey additional information simply by their presentation. That is, such visual elements can convey information by their display which can include such visual presentations including but not limited to words, numbers, blinking elements, flashing elements, color changing elements, elements in italics, underlined elements, and the like or any means that draws the attention of a user.

The reference to a medical records dashboard of the present principles described throughout the teachings herein is intended to refer to any embodiment of a medical records dashboard according to the present principles that is applicable to a currently described embodiment.

FIG. 1 depicts a high-level block diagram of a Data Command Center (DCC) 001 in accordance with an embodiment of the present principles. In the embodiment of FIG. 1, the Data Command Center 001 illustratively comprises an integration module 002 (i.e., to interface data between an EMR and the DCC), a Rules module 004 (i.e., to determine where and how the data is to be displayed), and a display module 006 (i.e., to display the data in the appropriate place). In the embodiment of FIG. 1, the integration module 002 and the rules module 004 can be in communication with a data storage 003. For example, the integration module 002 can store data from patient data sources in the data storage 003 and the rules module 004 can access the data storage 003 to retrieve data and/or information stored therein.

Figure 2:
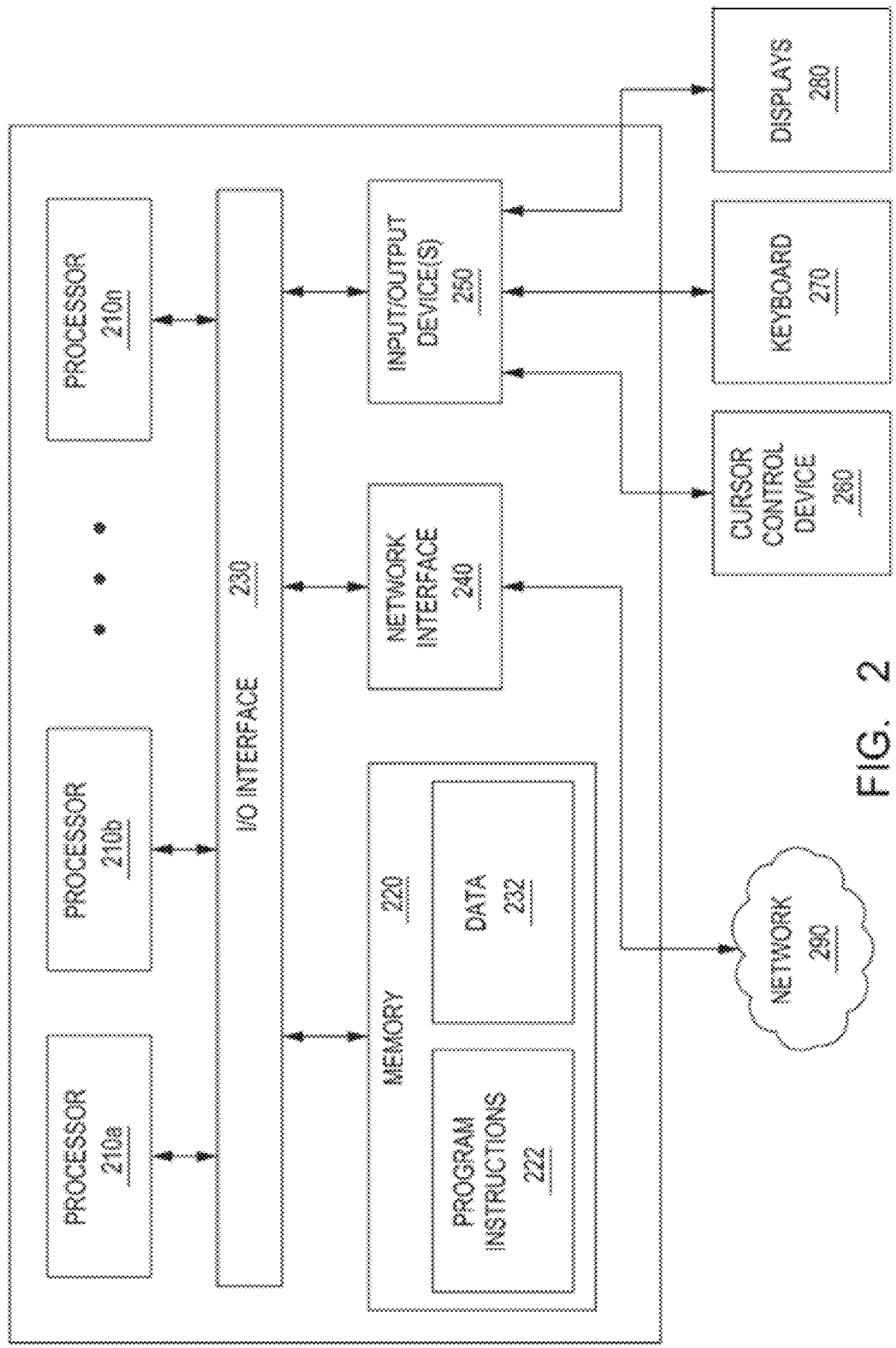
FIG. 2 depicts a high-level block diagram of a computing device 200 suitable for use with embodiments of a Data Command Center in accordance with the present principles.

As depicted in FIG. 1, embodiments of a Data Command Center in accordance with the present principles, such as the Data Command center 001 of FIG. 1, can be implemented in a computing device 200. FIG. 2 depicts a high-level block diagram of a computing device 200 suitable for use with embodiments of a Data Command Center in accordance with the present principles such as the user Data Command center 001 of FIG. 1. In some embodiments, the computing device 200 can be configured to implement methods of the present as processor-executable program instructions 222 (e.g., program instructions executable by processor(s) 210) in various embodiments.

In the embodiment of FIG. 2, the computing device 200 includes one or more processors 210a-210n coupled to a system memory 220 via an input/output (I/O) interface 230. The computing device 200 further includes a network interface 240 coupled to I/O interface 230, and one or more input/output devices 250, such as cursor control device 260, keyboard 270, and display(s) 280. In various embodiments, a user interface can be generated and displayed on display 280. In some cases, it is contemplated that embodiments can be implemented using a single instance of computing device 200, while in other embodiments multiple such systems, or multiple nodes making up the computing device 200, can be configured to host different portions or instances of various embodiments. For example, in one embodiment some elements can be implemented via one or more nodes of the computing device 200 that are distinct from those nodes implementing other elements. In another example, multiple nodes may implement the computing device 200 in a distributed manner.

In different embodiments, the computing device 200 can be any of various types of devices, including, but not limited to, a personal computer system, desktop computer, laptop, notebook, tablet or netbook computer, mainframe computer system, handheld computer, workstation, network computer, a camera, a set top box, a mobile device, a consumer device, video game console, handheld video game device, application server, storage device, a peripheral device such as a switch, modem, router, or in general any type of computing or electronic device.

In various embodiments, the computing device 200 can be a uniprocessor system including one processor 210, or a multiprocessor system including several processors 210 (e.g., two, four, eight, or another suitable number). Processors 210 can be any suitable processor capable of executing instructions. For example, in various embodiments processors 210 may be general-purpose or embedded processors implementing any of a variety of instruction set architectures (ISAs). In multiprocessor systems, each of processors 210 may commonly, but not necessarily, implement the same ISA.

System memory 220 can be configured to store program instructions 222 and/or data 232 accessible by processor 210. In various embodiments, system memory 220 can be implemented using any suitable memory technology, such as static random-access memory (SRAM), synchronous dynamic RAM (SDRAM), nonvolatile/Flash-type memory, or any other type of memory. In the illustrated embodiment, program instructions and data implementing any of the elements of the embodiments described above can be stored within system memory 220. In other embodiments, program instructions and/or data can be received, sent or stored upon different types of computer-accessible media or on similar media separate from system memory 220 or computing device 200.

In one embodiment, I/O interface 230 can be configured to coordinate I/O traffic between processor 210, system memory 220, and any peripheral devices in the device, including network interface 240 or other peripheral interfaces, such as input/output devices 250. In some embodiments, I/O interface 230 can perform any necessary protocol, timing or other data transformations to convert data signals from one component (e.g., system memory 220) into a format suitable for use by another component (e.g., processor 210). In some embodiments, I/O interface 230 can include support for devices attached through various types of peripheral buses, such as a variant of the Peripheral Component Interconnect (PCI) bus standard or the Universal Serial Bus (USB) standard, for example. In some embodiments, the function of I/O interface 230 can be split into two or more separate components, such as a north bridge and a south bridge, for example. Also, in some embodiments some or all of the functionality of I/O interface 230, such as an interface to system memory 220, can be incorporated directly into processor 210.

Network interface 240 can be configured to allow data to be exchanged between the computing device 200 and other devices attached to a network (e.g., network 290), such as one or more external systems or between nodes of the computing device 200. In various embodiments, network 290 can include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 240 can support communication via wired or wireless general data networks, such as any suitable type of Ethernet network, for example; via digital fiber communications networks; via storage area networks such as Fiber Channel SANs, or via any other suitable type of network and/or protocol.

Input/output devices 250 can, in some embodiments, include one or more display terminals, keyboards, keypads, touchpads, scanning devices, voice or optical recognition devices, or any other devices suitable for entering or accessing data by one or more computer systems. Multiple input/output devices 250 can be present in computer system or can be distributed on various nodes of the computing device 200. In some embodiments, similar input/output devices can be separate from the computing device 200 and can interact with one or more nodes of the computing device 200 through a wired or wireless connection, such as over network interface 240.

Those skilled in the art will appreciate that the computing device 200 is merely illustrative and is not intended to limit the scope of embodiments. In particular, the computer system and devices can include any combination of hardware or software that can perform the indicated functions of various embodiments, including computers, network devices, Internet appliances, PDAs, wireless phones, pagers, and the like. The computing device 200 can also be connected to other devices that are not illustrated, or instead can operate as a stand-alone system. In addition, the functionality provided by the illustrated components can in some embodiments be combined in fewer components or distributed in additional components. Similarly, in some embodiments, the functionality of some of the illustrated components may not be provided and/or other additional functionality can be available.

The computing device 200 can communicate with other computing devices based on various computer communication protocols such a Wi-Fi, Bluetooth® (and/or other standards for exchanging data over short distances includes protocols using short-wavelength radio transmissions), USB, Ethernet, cellular, an ultrasonic local area communication protocol, etc. The computing device 200 can further include a web browser.

Although the computing device 200 is depicted as a general purpose computer, the computing device 200 is programmed to perform various specialized control functions and is configured to act as a specialized, specific computer in accordance with the present principles, and embodiments can be implemented in hardware, for example, as an application specified integrated circuit (ASIC). As such, the process steps described herein are intended to be broadly interpreted as being equivalently performed by software, hardware, or a combination thereof.

Those skilled in the art will also appreciate that, while various items are illustrated as being stored in memory or on storage while being used, these items or portions of them can be transferred between memory and other storage devices for purposes of memory management and data integrity. Alternatively, in other embodiments some or all of the software components can execute in memory on another device and communicate with the illustrated computer system via inter-computer communication. Some or all of the system components or data structures can also be stored (e.g., as instructions or structured data) on a computer-accessible medium or a portable article to be read by an appropriate drive, various examples of which are described above. In some embodiments, instructions stored on a computer-accessible medium separate from the computing device 200 can be transmitted to the computing device 200 via transmission media or signals such as electrical, electromagnetic, or digital signals, conveyed via a communication medium such as a network and/or a wireless link. Various embodiments can further include receiving, sending or storing instructions and/or data implemented in accordance with the foregoing description upon a computer-accessible medium or via a communication medium. In general, a computer-accessible medium can include a storage medium or memory medium such as magnetic or optical media, e.g., disk or DVD/CD-ROM, volatile or non-volatile media such as RAM (e.g., SDRAM, DDR, RDRAM, SRAM, and the like), ROM, and the like.

Figure 3:
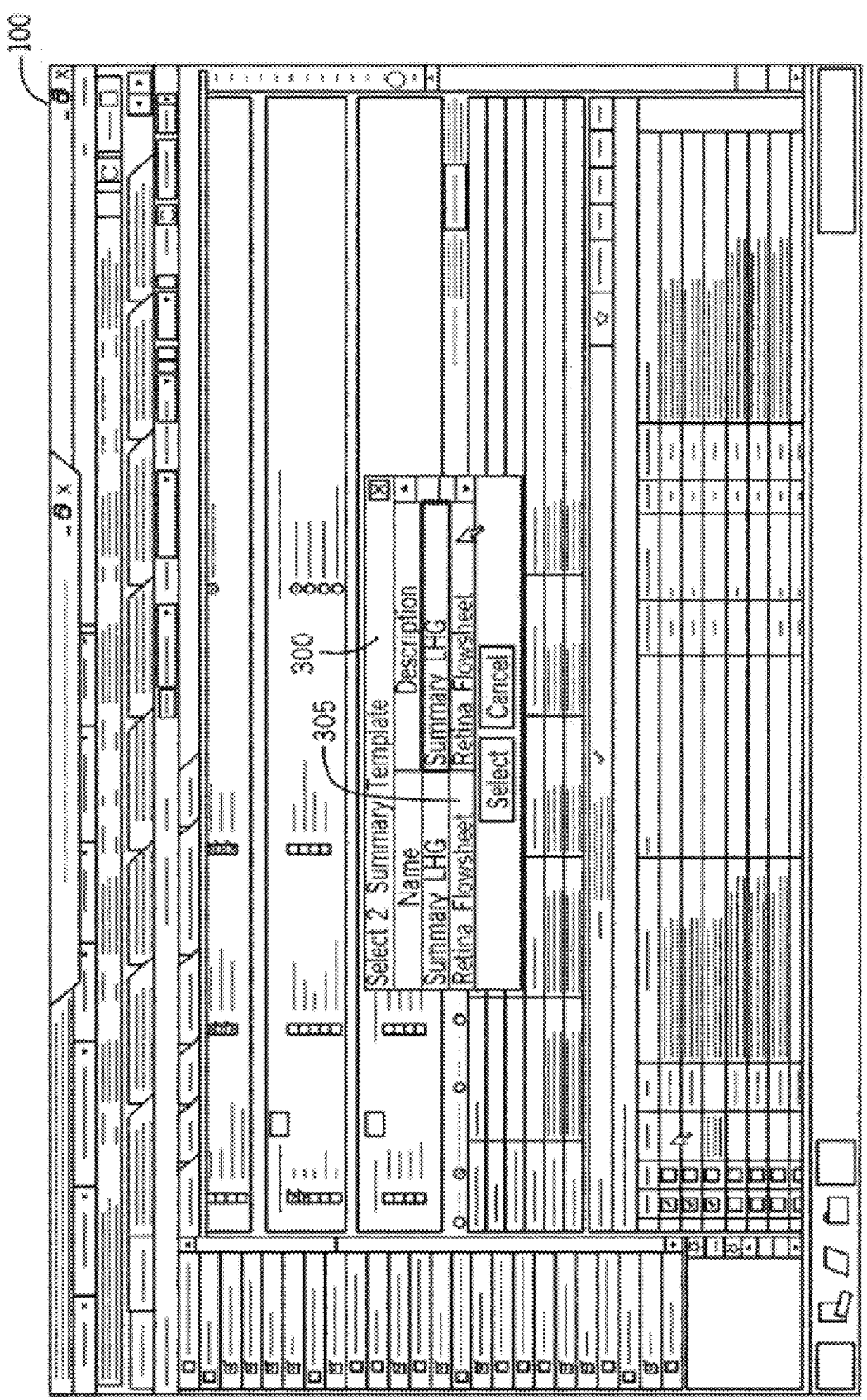
FIG. 3 depicts a high-level diagram of a medical records dashboard selection window of, for example, a medical record system useful for selecting and launching at least a portion of a Data Command Center (CC) in accordance with an embodiment of the present principles.

In some embodiments, a Data Command Center (CC) in accordance with the present principles is implemented as a data interface to a medical record system (e.g., EMR). In such embodiments a medical care provider can utilize a conventional medical record system to launch or enter a Data Command Center (CC) in accordance with the present principles including a medical-services tracking system that can display information dashboards, tables, charts, windows, as will be described herein. For example, FIG. 3 depicts a high-level diagram of a medical records dashboard selection window of, for example, a medical record system useful for selecting and launching at least a portion of a Data Command Center (CC) in accordance with an embodiment of the present principles. For example, as depicted in FIG. 3, a medical records dashboard selection window 300 can include one or more selectable medical records dashboards from which a user can select to access at least one medical records dashboard. For example, in one non-limiting example embodiment, the user can select a "Retina Flowsheet" 305 to access and/or launch a medical records dashboard including a retina flowsheet in a Data Command Center (CC) in accordance with the present principles. In some further embodiments, the at least one medical records dashboard can include any number of selectable medical records for any medical condition, and/or any medical diagnosis, and/or any medical treatment.

Figure 4A:
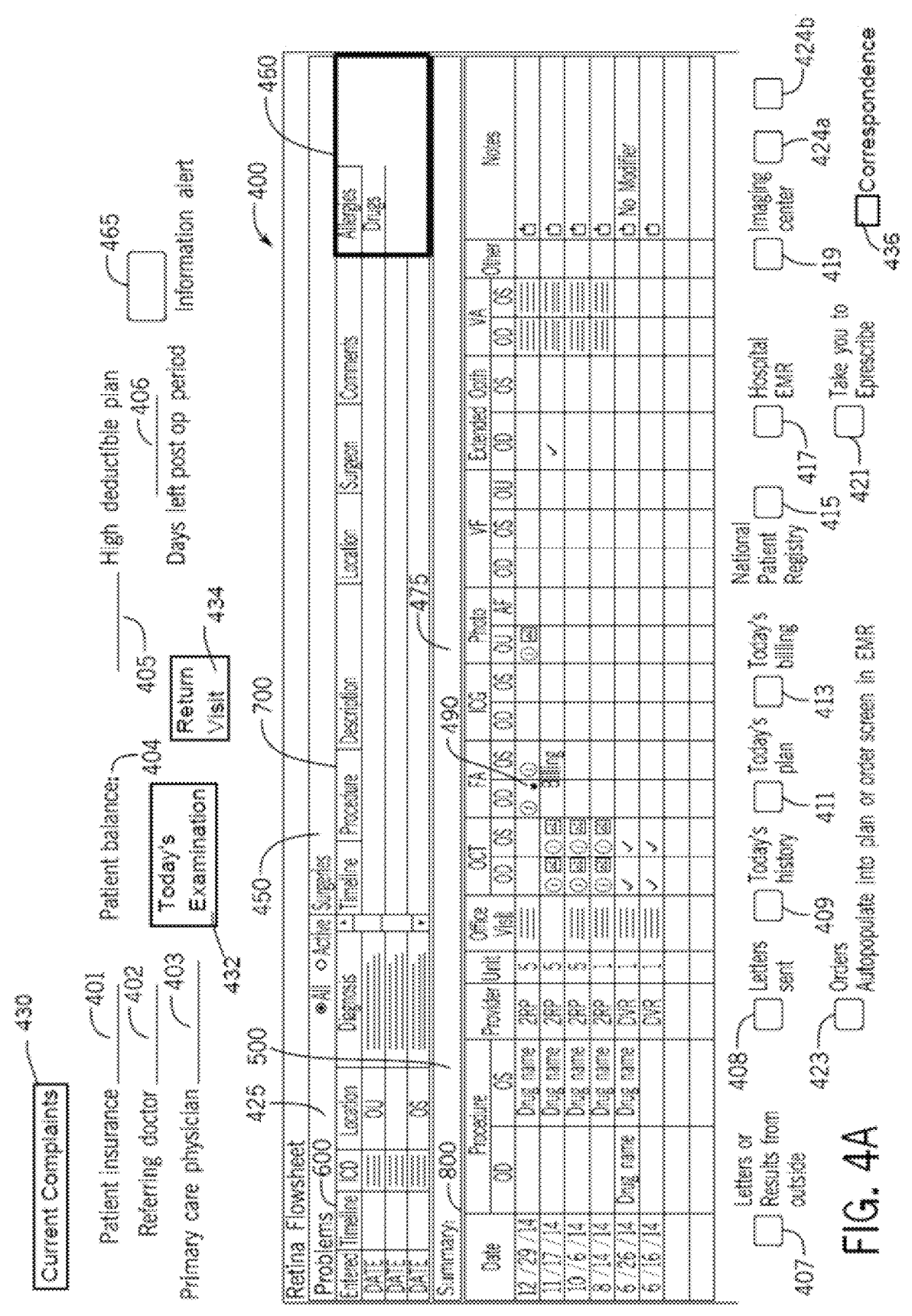

For example, FIG. 4A depicts a medical records dashboard 400 of the Data Command center 001 in accordance with an embodiment of the present principles. The medical records dashboard 400 is capable of displaying data from one or more medical records, and/or track medical procedures and services based on claims made or billing signed off by a physician for one or more delivered medical procedures or services. For example, in some embodiments the integration module 002 of the Data Command center 001 can dynamically link to various external databases comprising patient information that can be displayed in the medical records dashboard 400 by the display module 006 in accordance with rules for display in the rules module 004. For example, in some embodiments, the Data Command center 001 can function as a portal to patient information prepared by the user or patient information from other sources.

In some embodiments, the medical records dashboard 400 can be auto-populated by the display module 006 in accordance with rules in the rules module 004 as a function of claims made or billing signed off by a physician. In such embodiments, any data displayed within the medical records dashboard 400 is derived from one or more claim records that have been billed for one or more procedures or services have previously been provided to the patient. In some other embodiments, auto-population can be enabled in both directions interacting as a switchboard between the entire EMR and the medical records dashboard 400 along with what is added to any window, sub-window, column or entry in the medical records dashboard 400 being automatically added to the appropriate part of the chart for documentation before finalizing the encounter.

The medical records dashboard 400 can display information related to any medical procedures or services in relation to care of a patient. For example, in some embodiments, the medical records dashboard 400 can display information related to medical procedures or services in relation to retinal eye medical care of a patient. In some embodiments, the medical records dashboard 400 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, a summary section of the medical records dashboard 400 can be dynamic and can be changed at every visit rather than being written to an unchangeable document or file (e.g., such as a PDF). Further, any patient data that is input, received, analyzed, or created can be auto-populated into any portion of the dashboard 400, and/or can form a dataflow out of the medical records dashboard 400 to another electronic system or server, or another user, observer, or other third-party.

In some embodiments, the medical records dashboard 400 can display various windows and sub-windows based on a user preference and/or current or previous user interaction with the medical records dashboard 400. For example and with reference to FIG. 4A, in some embodiments, the medical records dashboard 400 can display a problems window 425 and/or a surgeries window 450 where information related to a patient's medical problems and surgeries can be displayed in information columns 600, 700 respectively. Further, in some embodiments, patient information related to allergies and drugs can be displayed within the allergies/drug section 460. This information can be auto-populated from a variety of sources, or inputted by a user.

In some embodiments, the medical records dashboard 400 can include a summary window 475 enabling a user to view and edit summary information related to the patient, any details of care provided to the patient, and/or and any medical diagnosis information prepared by a medical practitioner. Further, in some embodiments, the medical records dashboard 400 can also display detailed information related to any medical procedures or services provided to the patient, including procedures or services that are auto-populated by claims made, or billings or payments including billing signed off by a physician as detailed above. For example, in some embodiments, the medical records dashboard 400 can display visual display window 500 including information columns 800 that can be auto-populated by claims made or billings signed off by a physician. The auto-population can include billings, payments, or other information from anywhere in the EMR chart. For example in some embodiments, the information that is auto-populated can include treatment summaries, and/or diagnosis summaries, and/or patient feedback summaries, and/or other physician summaries, and so on. For example, in some embodiments, the Data Command center 001 can display and/or auto-populate at least one field, table, or window with at least one of a patient's prior medical procedures, diagnostic tests, surgeries, current medications, current illnesses, treated illnesses, and so on. The Data Command center 001 can auto-populate various data fields via an electronic dataflow established between the Data Command center 001 and one or more computer systems of servers that comprise patient information (e.g., such as electronic medical records). The dataflow can comprise a two-way flow from the source of patient data to the Data Command center 001 and from the Data Command center 001 to the source. In some embodiments, this information can be any medical diagnosis information, any medical procedures or services provided to the patient, procedures or services by claims made, or billings or payments including billing signed off by a physician as detailed earlier, any information from anywhere in the EMR chart including treatment summaries, and/or diagnosis summaries, the patient's prior medical procedures, diagnostic tests, surgeries, current medications, current illnesses, treated illnesses, and/or patient feedback summaries, and/or other physician summaries, patient outcome summaries, treatment summaries, and/or diagnosis summaries, and/or patient feedback summaries, and/or other physician summaries or treatments. Further, in some embodiments, the information that is auto-populated can include patient outcome summaries. For example, in some embodiments, the Data Command center 001 processes a plurality of patient outcomes and displays an analysis of patient outcomes based at least in part on patient information from treatment summaries, and/or diagnosis summaries, and/or patient feedback summaries, and/or other physician summaries or treatments. In some embodiments, the patient outcomes can include or comprise physician quality reporting system (PQRS) quality measures. In some embodiments, calculated or reported patient outcomes can include or comprise at least one PQRS measures code.

As depicted in FIG. 4A, the medical records dashboard 400 can include miscellaneous information identifying the patient, information related to the patient's insurance plan, physicians and referring physicians, and the patient's current balance. Other information can relate to the patient's prior visit, prior diagnosis or procedure and any important information relevant to the next visit. Additional information can relate to the current visit, including history of illness and chief or current medical complaint, billing information, and retrievable medical information including pharmacy information. For example and as depicted in FIG. 4A, in some embodiments, the medical records dashboard 400 can include a patient insurance entry 401, referring physician entry 402, and primary care physician entry 403. The medical records dashboard 400 can also include patient balance entry 404, and a high deductible plan entry 405. Important patient information related to a pending or current visit can include a "days left post-op period" entry 406 and/or an information alert 465. In some embodiments, the information alert 465 can be auto-populated based on other information or entries in the medical records dashboard 400. In other embodiments, the information alert 465 can be set by any user to alert the user or other user of information relevant to the patient. In some embodiments, the information alert 465 can comprise a daily technician update, including information to medical information such as blood pressure, or whether the patient is pregnant, or any other urgent information with which a member of a health care team can alert another member. Further, this information can become permanent or can be deleted from the medical records dashboard 400, and from any record or table accessible from the medical records dashboard 400, including any medical record. Further, this information can serve as or be configured as a "sticky note" that can be removed from any of the above-mentioned records. For example, the "sticky note" can be an electronic sticky note riding on the dashboard or any record accessible from the dashboard.

Furthermore, the medical records dashboard 400 can provide improvement as described where test interpretations and evaluation of patients, once documented and billed, usually become date stamped, and cannot be easily amended without applying a new date of amendment. In some embodiments, the Data Command center 001 can improve and follow care that will not necessarily be used as part of a particular day's medical record. Therefore, months or years apart, physicians can add notes into the table when new findings, discoveries, or realizations warrant it without feeling encumbered that they are "changing past medical record" and a disclosure of such can be at the bottom of the medical records dashboard 400. Allowing physicians and technicians to add and change notes within the medical records dashboard 400 (rather than changing a patient's EMR chart) can enable a user to summarize critically important health/history/treatment data, which can then be used as a faster point of reference while examining the patient. Notes that exist on the medical records dashboard 400 can flag or alert a user to an important medical change, and can be used as an additional form of communication to strengthen lines of communication between technicians/clinic staff and physicians to better ensure that a medical care provider is quickly directed to important medical information.

In some embodiments, a daily technician update can be accessed or otherwise made visible to the user in at least one portion of the dashboard 400. In some embodiments, the information alert 465 can be displayed in a specific color and/or with a specific graphic and/or animation. For example, in some embodiments, the information alert 465 can comprise a flashing red animation. To protect the medical care provider during an audit, a statement on the medical records dashboard 400 can be added that "notes on this table" are not necessarily added at the time listed as the date and not for documentation in a medical record, but as a rapid reminder medical decision making and cliff note reference tool. As another example, if this patient's records were ever sent to another medical care provider or insurance company or were audited, this is critical information that a medical care provider is often not privy to and an icon on the table will alert the physician of this fact. By selecting this or another icon, the history of this audit or records release request or other occurrence can be seen. So, if an insurance company is requesting a medical necessity report or other information that is needed by a billing office or anyone else, the medical care provider can be informed on the medical records dashboard 400 so that the medical care provider can instantly decide what is needed.

As depicted in FIG. 4A, the medical records dashboard 400 can include an icon 407 enabling access to one or more letters or results from external data sources or third parties. In some embodiments, the medical records dashboard 400 can further include an icon 408 enabling access to letters sent 408, which can be written, typed, and/or dictated from the user and/or another medical care provider. In some embodiments, the medical records dashboard 400 includes an entry or access to the current day's history, the current day's plan, and/or to the current day's billing. For example, as depicted in FIG. 4A, the medical records dashboard 400 includes a "Today's history" button or icon 409, a "Today's plan" button or icon 411, and a "Todays billing" button or icon 413. In some embodiments, the medical records dashboard 400 can include a correspondence button or icon 436, which can be used to view, access, enter, and/or auto-populate correspondence related to a patient's care. Such correspondence can include any medical record and/or any correspondence generated while the patient is under care by the user and/or any other physician or medical practitioner, medical services provider, and/or medical insurance company.

In some embodiments, the medical records dashboard 400 can display a summary of the patient's problem list in which a user can input patient information and constantly update and change. For example, the medical records dashboard 400 of FIG. 4A includes an icon/button 430 for enabling the entry of or access to current complaints of the patient. In some embodiments, if a user activates (e.g., by clicking using a cursor) the button 430, information related to the patient's current medical problems or complaints can be shown and/or displayed and/or updated by a user. In some embodiments, the information can be auto-populated into the medical records dashboard 400.

In some embodiments, the medical records dashboard 400 can include a today's examination access icon/button 432 enabling a user to access, view and/or input patient information, patient examination results, tests, notes, or any information relevant to the medical care of the patient. By activating (e.g., by clicking using a cursor) today's examination access icon/button 432, information related to the patient's examination including medical problems or complaints patient information, patient examination results, tests, notes, etc., can be presented and/or displayed and/or updated using one or more windows and the like. In some embodiments, the information associated with the today's examination access icon/button 432 can be auto-populated into the medical records dashboard 400 by, for example, the display module 006 following auto-population rules of the rules module 004.

In some embodiments, any stored or displayed patient's examination records/data can be cleared from the medical records dashboard 400 following some time period once a patient visit is complete. In some embodiments, the medical records dashboard 400 can remove the display of or access to a previous patient's examination details once the patient visit has ended. In some embodiments, the medical records dashboard 400 can remove display or access to a previous patient's examination details later in the day of the patient's visit, or before the following day, or at any time selected by the user. In some embodiments, the information can be auto-populated into any EMR system for recordation into one or more EMR's of the patient. In some embodiments, for any auto-populated information that includes technical information without any associated professional interpretation, the Data Command center 001 via the medical records dashboard 400 can provide a visual and/or audible alert to enable a user to provide an update for auto-population to an EMR system.

In some embodiments, the medical records dashboard 400 can include at least one link to information from external databases, providers, hospitals (e.g., such as a discharge summary), clinics and/or testing laboratories, etc., (e.g., where the information can include the overall diagnostic imaging center of the practice for certain pieces of equipment and into the machine to actually see all of the study). In the latter example, the medical records dashboard 400 can receive information from at least one coupled database and/or server and/or controller. For example, as depicted in the embodiment of FIG. 4A, the Data Command center 001 via the medical records dashboard 400 can have entry or access to third party data sources via icons/buttons, including but not limited to, the National Patient Registry icon/button 415, the hospital EMR icon/button 417, the imaging center icon/button 419 and the ePrescribe icon/button 421.

In some embodiments, orders can be auto-populated into the medical records dashboard 400 or order screen of an EMR using, for example, the Orders icon/button 423. For example, in some embodiments, during or after completion of a patient examination, any medical service, medical test or diagnostic, or other medical service can be auto-populated into an order section of the medical records dashboard 400. Any recommendation for a return visit can be viewed, accessed, and/or auto-populated using the return visit icon/button 434 of the medical records dashboard 400. For example, in some embodiments, the recommendations can be any advised next steps in the patient's care, any diagnosis, prescriptions, tests, etc. In some embodiments, the aforementioned "Today's plan" icon/button 411 can be used to view, access, and/or auto-populate details including for a day's activities for the patient examination.

In some embodiments, an "Imaging Center" icon/button 424a of the medical records dashboard 400 enables a user access to the piece or pieces of diagnostic equipment that were used that or another day for performing tests on a patient(s) so the user can now measure and/or access the test results. Such functionality can be internal to the user's practice so that any diagnostic equipment can be accessed. The ability to access the diagnostic equipment and data directly, in accordance with the present principles, enables a user access to not just one single piece of diagnostic equipment but all equipment available and all tests available can be evaluated and the evaluation of changes of such tests over time can be made.

In the embodiment of the medical records dashboard 400 of FIG. 4A, the icon/button 424b enables a user access to a company sponsoring a clinical research website (i.e., sometimes a pharmaceutical company and other times a company that invented a device). Such functionality enables a clinical researcher access to such a website and input any data that was obtained from a patient visit using the access provided using the access provided. In a research application in accordance with the present principles, a researcher is provided access to diagnostic equipment and/or to a research spreadsheet where the researcher can access and input data.

Figure 4B:
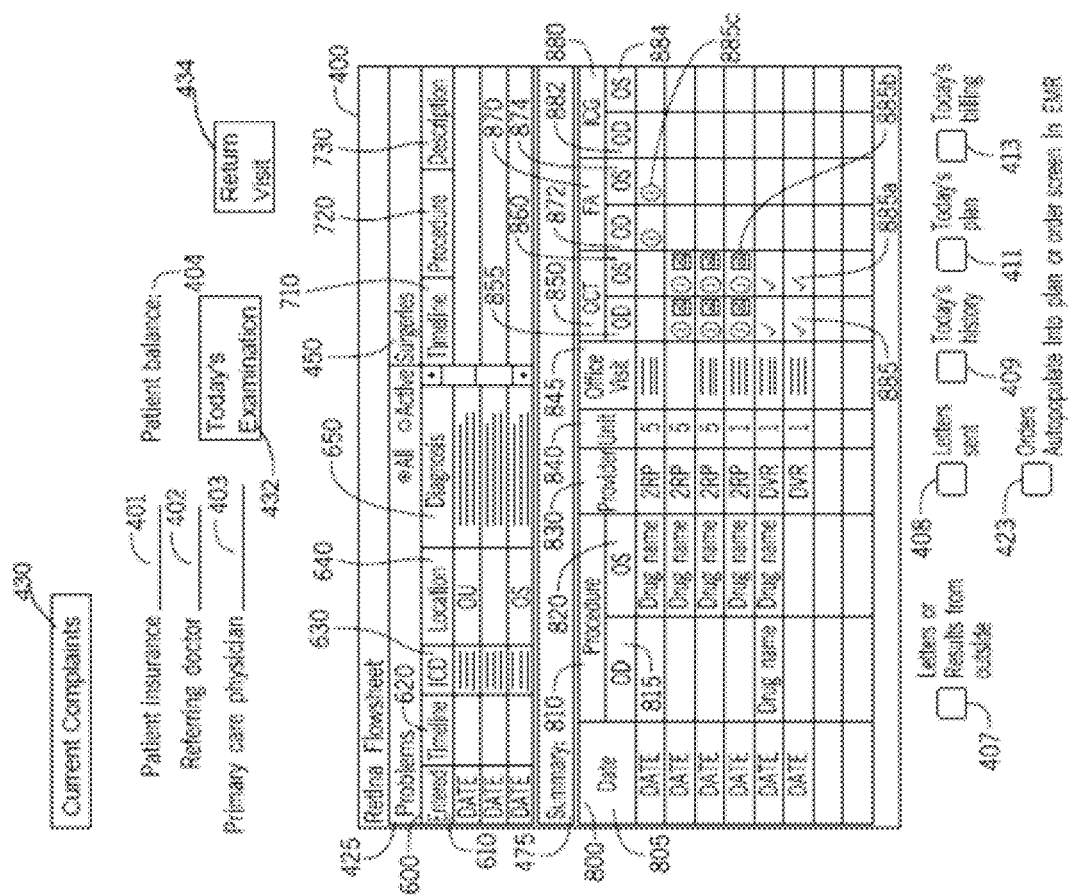
FIG. 4B depicts a portion of the medical records dashboard of FIG. 4A in accordance with some embodiments of the present principles.
Figure 4C:
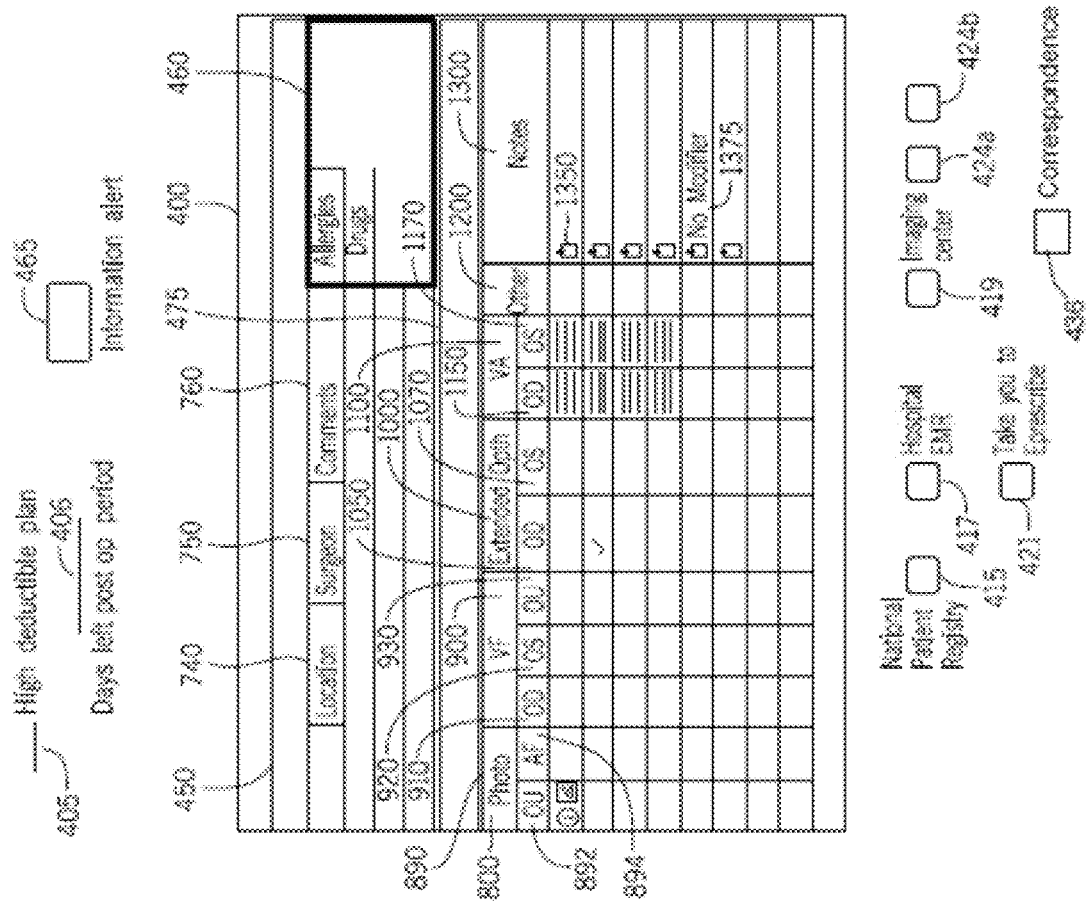
FIG. 4C depicts greater detail of at least some portions of the medical records dashboard of FIG. 4A in accordance with some embodiments of the present principles.
Figure 4D:
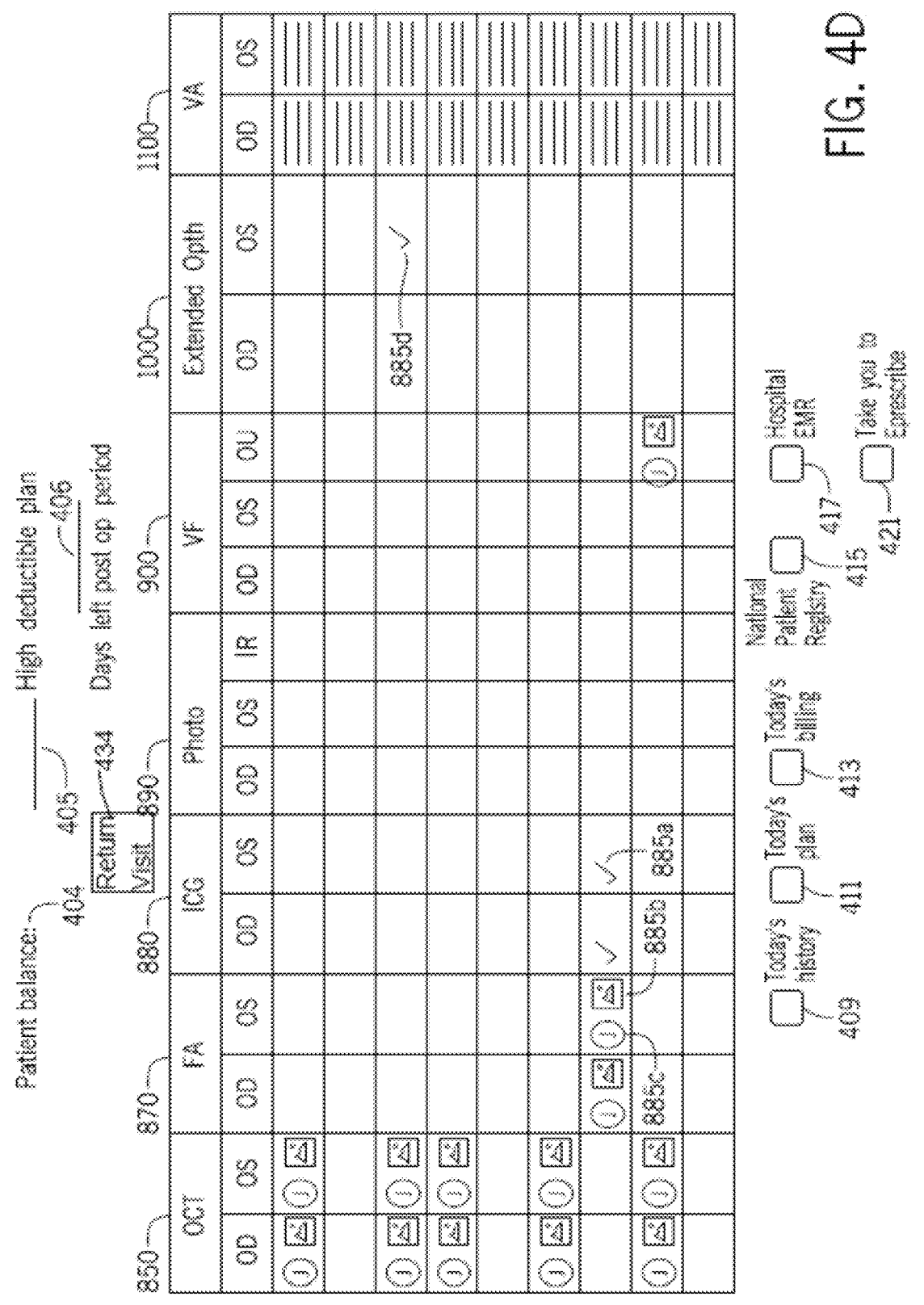

Further details of the problems window 425, surgeries window 450, and command center visual display window 500 are provided in FIGS. 4B-4D illustrating enlarged views of portions of the medical records dashboard 400. For example, FIG. 4B depicts a portion of the medical records dashboard 400 of FIG. 4A in accordance with some embodiments of the present principles. As illustrated in FIG. 4B, in some embodiments, the information columns 600 of the problems window 425 can include a date column 610, a timeline column 620, an "ICD" column 630 for international classification of disease codes including international classification of disease codes, such as version 9 or version 10, (hereinafter collectively referred to as "ICD code" information), location of the problem or disorder (shown as "OD", "OS", "OU" identifying right eye, left eye, both eyes), or from any part of the body, and a diagnosis column 650 for detailing information related to an initial diagnosis or final diagnosis of a patient's problem or disorder that can be auto-populated or input manually. Further, in some embodiments, the information columns 700 of the surgeries window 450 can include information related to services or procedures that were provided to the patient (procedure columns 720), a description of the services or procedures performed (description columns 730), and when the services or procedures were provided (timeline columns 710).

FIG. 4C depicts greater detail of at least some portions of the medical records dashboard 400 of FIG. 4A in accordance with some embodiments of the present principles. Referring to FIG. 4C, in some embodiments, the surgeries window 450 can include location information 740, surgeon or physician information 750, and a comments section 760. Referring to the display window 500 of FIG. 4C, the information columns 800 can include a date column 805, and a procedure column 810 illustrating or providing access to information detailing one or more procedures performed on the patient. Further, the procedure column 810 can include an "OD" column 815, and "OS" column 820 providing right and left eye procedure information, or could be a body part (i.e., orthopedic surgery limb versus spine). In some embodiments, information related to the medical care provider, the location where the procedure was performed, and office visit information can be provided to the user in column 830, and unit column 840, and office visit column 845.

FIG. 4D depicts greater detail of at least some portions of the medical records dashboard 400 of FIG. 4A in accordance with some embodiments of the present principles. Referring to FIG. 4D, in some embodiments the user can view information related to tests and procedures performed on the patient. For example, in some embodiments, such information can include information related to one or more medical imaging procedures such as an optical coherence tomography ("OCT"), or fluorescein angiography ("FA"), and/or indocyanine green chorioangiography ("ICG"), or any current procedural terminology code (hereinafter "CPT code"), including any CPT code found in the American Medical Association CPT 2015 professional edition or other edition, the entire contents of which is incorporated by reference. Moreover, the user can view information related to tests and procedures performed on the patient based on an ICD code. Other clinical vocabularies such as Systematized Nomenclature of Medicine (hereinafter "SNOMED codes") can be used in other embodiments as the system is not limited.

In some embodiments, the user can compare patient clinical information, such as labs and vitals using the medical records dashboard 400, before and after a selected medication has been prescribed or a procedure has been performed to better understand the effect of the medication or procedure on the patient. Similarly, in other embodiments, the user can examine how the current patient compares against other patients in the practice and population in general using the medical records dashboard 400 to better understand outcomes.

As depicted in FIGS. 4A-4D, in some embodiments, medical procedures performed (including any of the aforementioned medical imaging procedures) that have been billed and claimed can be viewed or accessed by a user within any of the "OCT" column 850 (split as an "OD" column 855 and "OS" column 860), an "FA" column 870 (split as an "OD" column 872 and "OS" column 874), and/or "ICG" column 880 (split as "OD" column 882 and "OS" column 884).

Referring back to FIG. 4C, the information columns 800 can include a photo column 890 configured to enable a user to access any photographic images of the patients eyes including optical and auto-fluorescent images of the eyes ("OU" column 892 and "AF" column 894). In some embodiments, if visual function tests were performed, information can be viewed or accessed in the visual field "VF" column 900 (including an "OD" column 910, "OS" column 920, and/or "OU" column 930). Some embodiments also include an extended ophthalmology column 1000 (including "OD" column 1050 and "OS" column 1070), and a visual acuity column ("VA" column 1100, including "OD" column 1150, and "OS" column 1170). In some embodiments, as described earlier, other details of various tests, procedures or services can be viewed or accessed in the other column 1200. Further, information associated with any of the user-accessible tests, procedures or services or other notes provided by the user and/or medical care provider can be viewed or accessed in the notes column 1300 using one or more notes access icons/buttons 1350 and/or by viewing a note entry 1375 (e.g., and/or any note entered using the note entry window 1375 . . . . The functionality of the notes column 1300 is further discussed below with reference to FIG. 5B). In accordance with embodiments of the present principles, the information can be auto-populated into the medical records dashboard 400 or into EMR plan pages as described above with respect to different embodiments. That is, as described above, various data fields/entries of the medical records dashboard 400 of the Data Command center 001 of, for example, FIG. 1, can be auto-populated via an electronic dataflow established between the Data Command center 001 and one or more computer systems of servers that comprise patient information (e.g., such as electronic medical records). The dataflow to and from the medical records dashboard 400 can comprise a two-way flow from the source of patient data to the Data Command center 001, and from the Data Command center 001 to the data source.

In some embodiments, the medical records dashboard 400 can include visual cues, icons, or markers representing and/or enabling access to detailed information related to medical services, procedures or tests provided to the patient. Further, by employing data visualization techniques, a user's eye can be trained to quickly identify these icons or markers and increase the efficiency of user accessing key medical indicators such as test results and surgical histories. For example, in some embodiments, medical services, procedures or tests performed or provided can be assigned a visual code, icon, or graphical marker. For example, the embodiment of the medical records dashboard 400 of FIG. 4B depicts visual cues, icons, or markers 885 representing medical services, procedures or tests performed or provided to a patient. In some embodiments, the information columns 800 within the display window 500 can include at least one "test done, no image attached" icon 885a, one or more "see image in order viewer" icon 885b, at least one "view order interpretation" icon 885c, and/or at least one "procedure billed or claims made" icon 885d, where an appearance in the medical records dashboard 400 can indicate that a claim was made, and a change in color or other method (italics, bold, etc.) can represent whether the bill was paid. Further, FIG. 4D depicts another example of "test done, no image attached" icon 885a, "see image in order viewer" icon 885b, "view order interpretation" icon 885c, and "procedure billed or claims made" icon 885d, in which an appearance in the medical records dashboard 400 represents a claim was made, and a change in color or other notification method can represent whether the bill was paid. Data visualization icons and markers located in the medical records dashboard 400 can be used to quickly identify billing or coding errors by enabling a user to determine inconsistencies among various entries in the medical records dashboard 400, and thus can empower the physician to be proactive and thorough in areas of compliance with insurance guidelines. The use of these icons to identify potential errors in coding can provide an additional level of protection and proofing to reduce and prevent potential billing and/or malpractice errors.

Figure 5A:
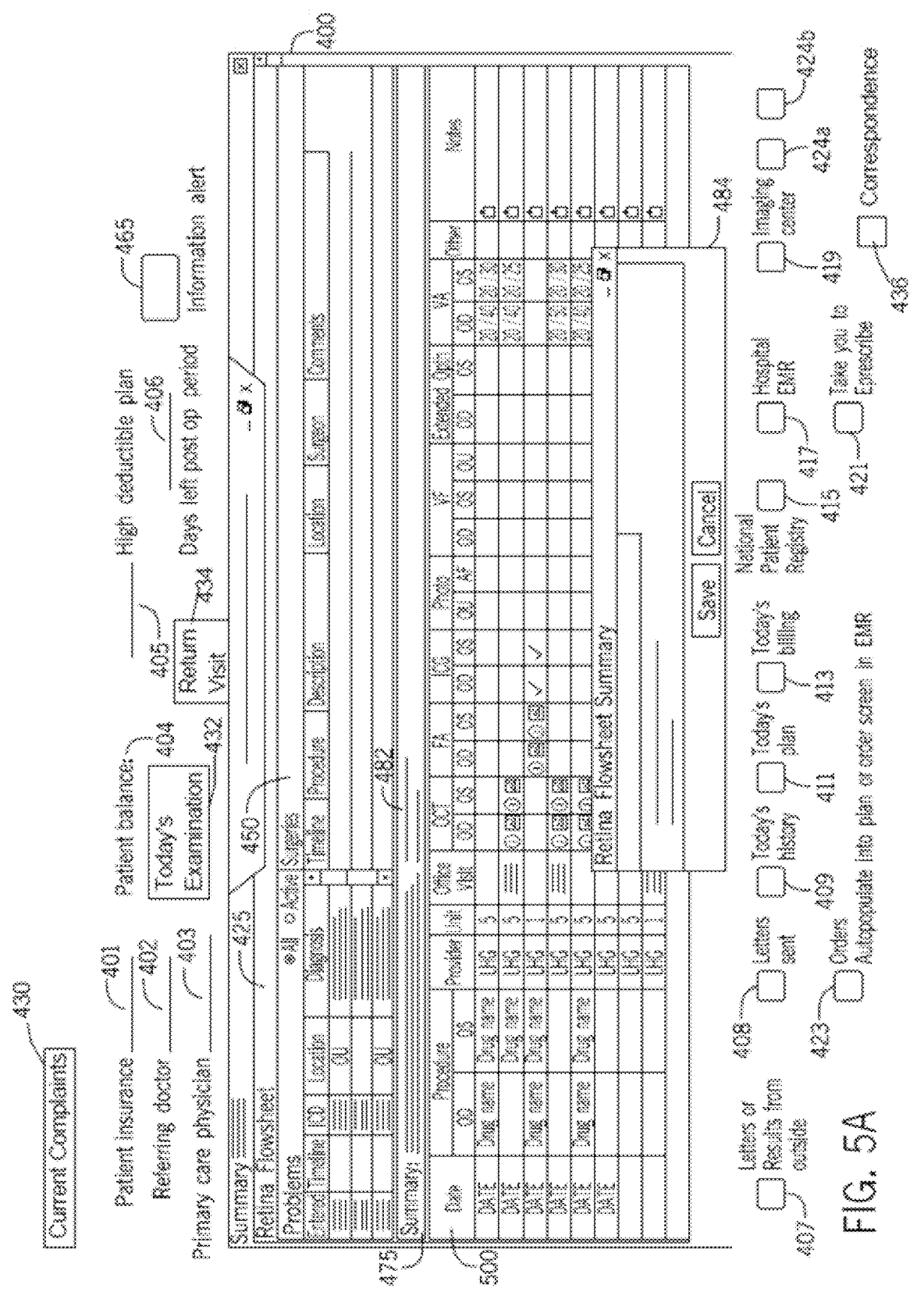

In some embodiments, the medical records dashboard 400 can provide a text summary of any entry within the medical records dashboard 400. As described earlier, the summary window 475 can enable a user to view and edit summary information related to the patient, any details of care provided to the patient, and/or any medical diagnosis information prepared by a medical practitioner. In some embodiments, the user can add and/or edit the summary information. For example, FIG. 5A depicts the medical records dashboard 400 including a medical summary update process in accordance with some embodiments of the present principles. In the embodiment depicted in FIG. 5A, the medical records dashboard 400, including the problems window 425, surgeries window 450, summary window 475, and command center visual display window 500, can further include summary comments 482 that can be entered, updated, expanded using the summary input window 484. In some embodiments, a user can enter information within the summary input window 484 for entry into the summary window 475.

Figure 5B:
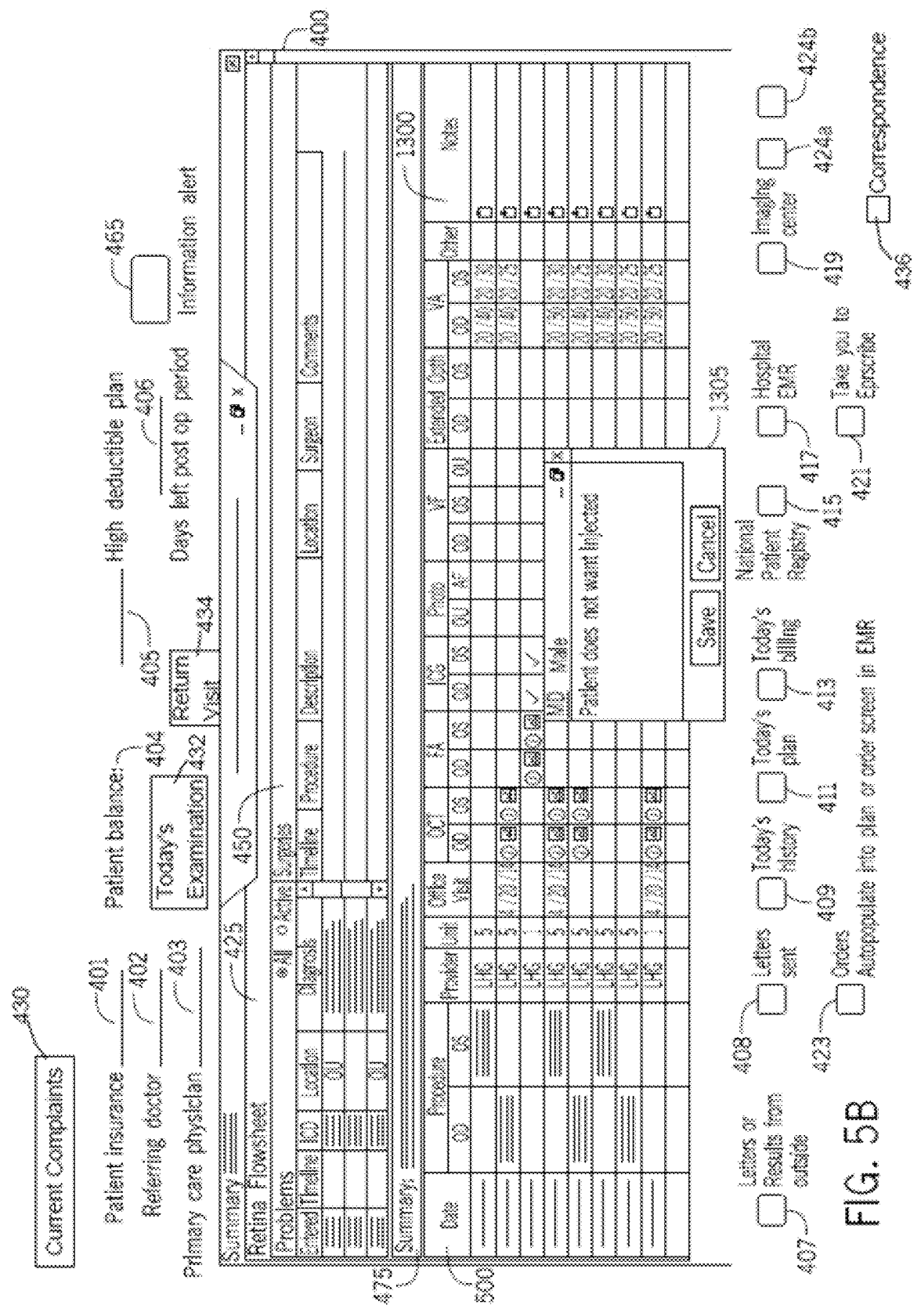

FIG. 5B depicts a portion of the medical records dashboard 400 including a notes update procedure in accordance with an embodiment of the present principles. For example, using a notes update procedure, a user can add or update information associated with any of the user-accessible tests, procedures or services or other notes provided by the user and/or medical care provider in the notes column 1300. As depicted in the embodiment of FIG. 5B, the medical records dashboard 400 can include the problems window 425, the surgeries window 450, and the summary window 475, and the visual display window 500 of with notes column 1300 of the medical records dashboard 400 can be updated with one or more notes using the note entry window 1305.

In some embodiments, placement or viewing functions of the medical records dashboard 400 can be toggled using a left or right mouse click function. For example, in some embodiments, following an initial impression or diagnosis, a right click can bring up a note function (e.g., through note entry window 1305), and/or a left click can bring up the summary function (e.g., through summary window 475 as summary comments 482).

Figure 6:
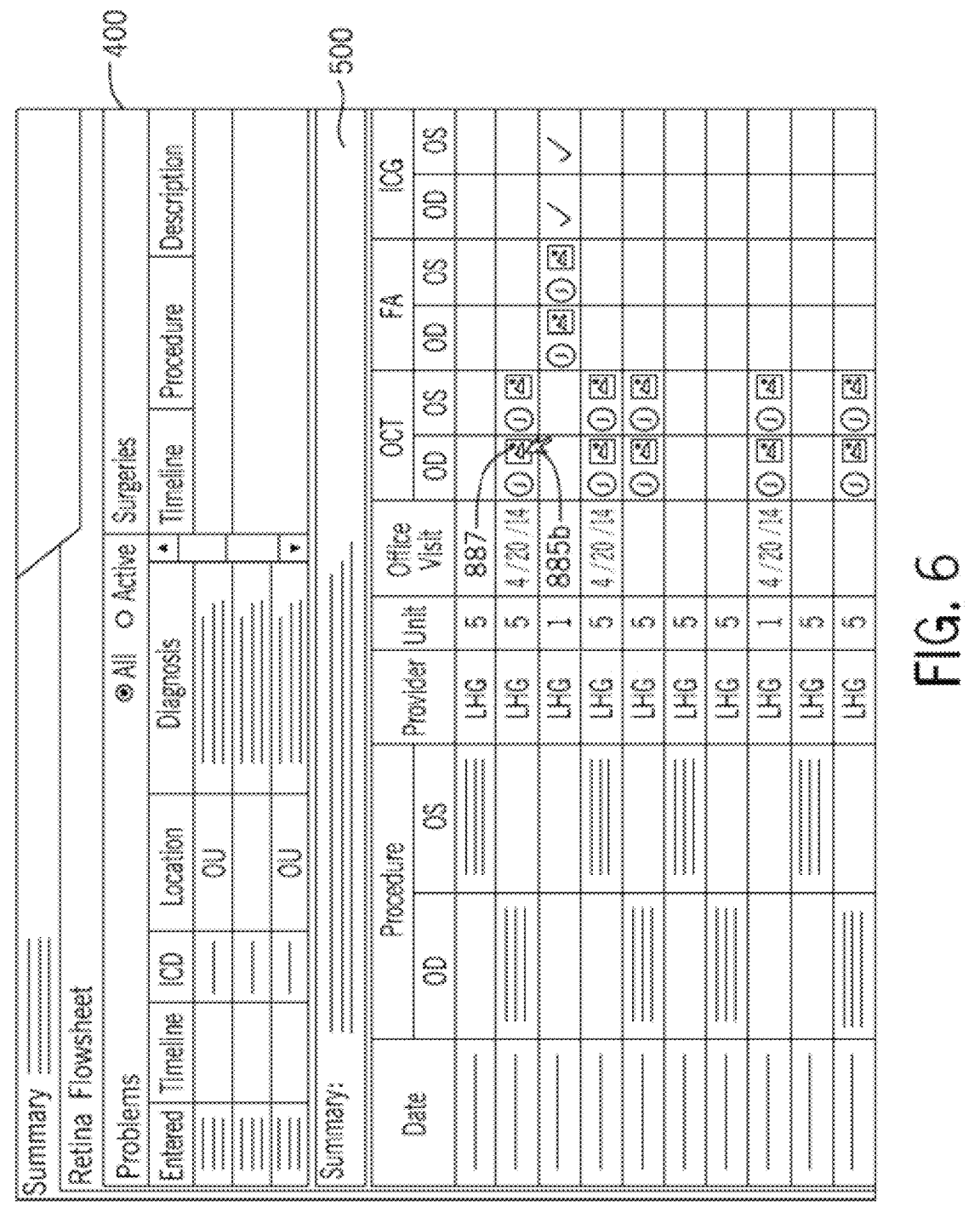

Referring to at least FIG. 4B, in some embodiments, a user can access underlying information linked to visual cues, icons, or markers 885 by, for example, using a single click or mouse-over. That is, in accordance with the present principles, in some embodiments a user can use the visual display window 500 of the medical records dashboard 400 to access and view any information auto-populated within the visual display window 500 and/or other windows or sub-windows of the medical records dashboard 400. For example, FIG. 6 depicts a user record access process of the medical records dashboard 400 in accordance with an embodiment of the present principles. In some embodiments, a user action 887 (depicting a user click or mouse-over of a cursor) can enable a user to access and view information (in this example, information linked to "see image in order viewer" icon 885b). In some further embodiments, a user can use a single click of or mouse-over of a portion of the medical records dashboard 400 to access and view any information within any portion of the medical records dashboard 400. Further, in some embodiments, a user can use left and right mouse clicks to navigate from one portion of the medical records dashboard 400 to another. Furthermore, in some embodiments, a right-click mouse function can be used to bring up and update a an portion of the medical records dashboard 400 and/or display any important information in the medical record dashboard 400, and a left-click can bring the user back to another portion of the medical records dashboard 400.

Figure 7:
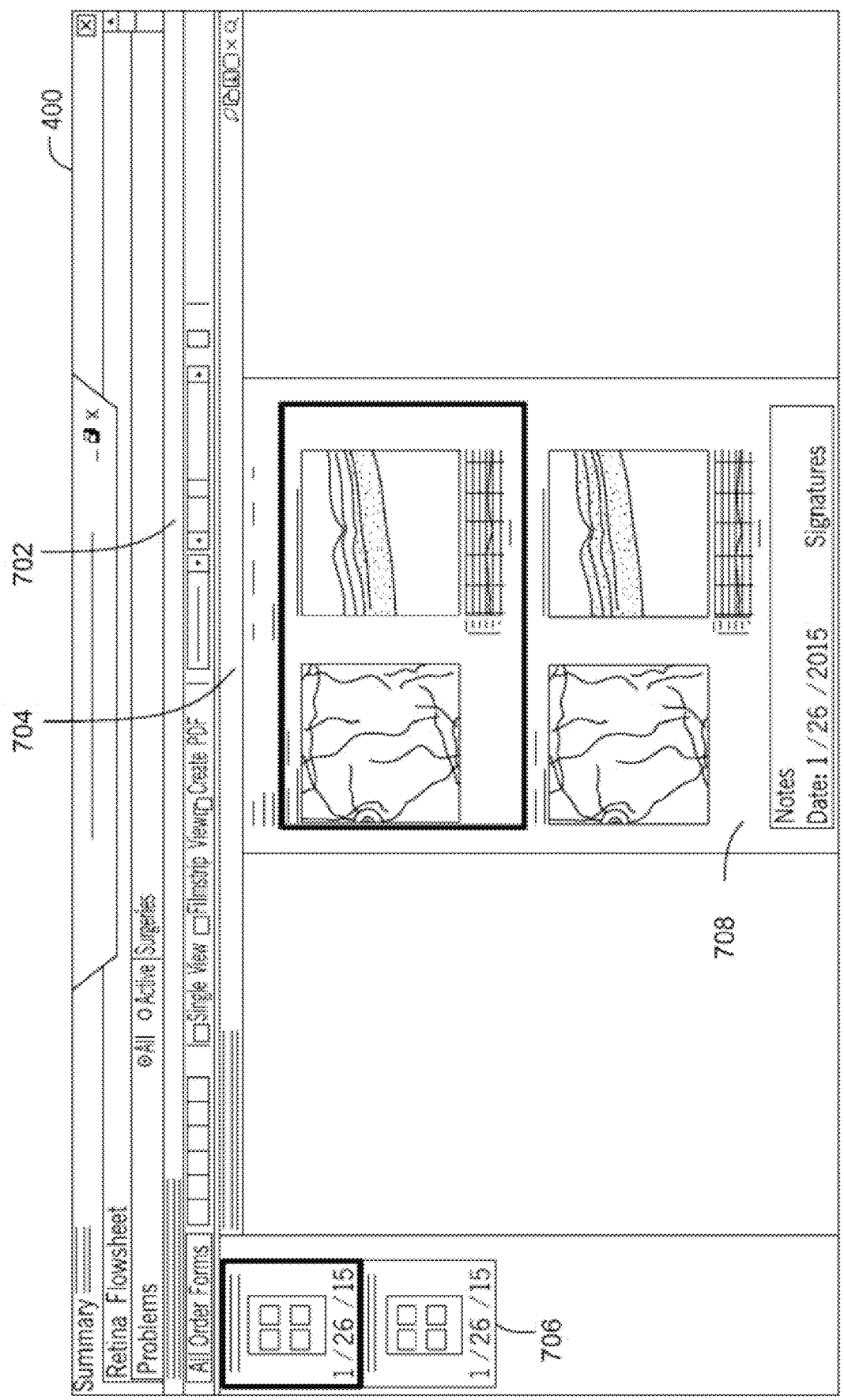
FIG. 7 depicts a medical records access window of the medical records dashboard in accordance with an embodiment of the present principles.

In some embodiments, the Data Command center 001 via the medical records dashboard 400 can display at least one medical record as a result of the user action 887. For example, FIG. 7 depicts a medical records access window 702 of the medical records dashboard 400 in accordance with an embodiment of the present principles. In some embodiments, the user's action (represented by user action 887) can cause a display of the medical record access window 702 including a medical record display 704. Further, in some embodiments, at least one medical record 708 can be selected from the medical record list 706 for viewing in the medical record display 704. As illustrated in FIG. 7, in some embodiments, the at least one medical record 708 can comprise an image or photograph such as an optical and/or fluorescein angiogram image. In other embodiments, the at least one medical record 708 can comprise an X-ray image. In some further embodiments, the at least one medical record 708 can include an MRI scan or any report or anything ordered or performed by medical care providers. In some embodiments, the at least one medical record 708 can comprise one or more dictated letters from the user or another medical care provider. Further, in some embodiments, the at least one medical record 708 can comprise a record or any portion of a correspondence from another medical care provider.

A unique aspect of the medical records dashboard 400 of the Data Command center 001 in accordance with the present principles is that so much relevant patient information can be viewed in context to the procedures, the clinical information and/or the medical services provided over time while having direct one click access to any image and diagnostic test or plan. In addition, in embodiments of the present principles all of the patient studies can be accessed in context of all other patient data.

In some embodiments, images related to patient treatment can be viewed as thumbnails in one or more windows being visible and accessible along with at least portions of all other data available on the medical records dashboard 400. In some embodiments, a user is able to manipulate and modify an image with the ability to store and recall the modified image. For example, a user, while looking at an image in context, can mark and make notations, draw on the image. Such modifications can be stored with the image or with a copy of the image.

In some embodiments, thumbnails of respective images can be displayed with an ability to see the full-size image including relevant information. For example, in some embodiments, thumbnails can be displayed across the bottom of a display of all images in a column of the medical records dashboard 400, one per image, such that a user is able to pull up all visual fields of a column, such as the OCT column. Further embodiments describing the display of patient care related images are described further below. In accordance with the present principles, what is critical is not that the Data Command center 001 via the medical records dashboard 400 can display images related to patient care, but instead that all of the images can be looked at in context with clinical and exam findings and or procedural information and dates of other medical services lined up in an intuitive way that enables a user to quickly decide which image or test to review, and in some embodiments, receive guidance from the Data Command center 001 on how to proceed with treatment using various tools and functionality of the Data Command center 001 described herein.

In some embodiments, a user is able to assign a respective icon for accessing and representing images in the medical records dashboard 400. In some such embodiments, the assigned icon can visually represent information related to the image, including whether or not the image indicates that a patient's condition has gotten better, worse or has remained the same.

In some embodiments, the Data Command center 001 via the medical records dashboard 400 can enable a user to access underlying information linked or related to diagnostic codes listed in the medical records dashboard 400. In some embodiments the Data Command center 001 via the medical records dashboard 400 can enable a user to access underlying information linked or related to billing codes. For example, in some embodiments, using a single click or mouse-over, a user can use information made available via the visual display window 500 of the medical records dashboard 400 to access and view any information related to diagnostic and/or billing codes. In some embodiments, the diagnostic and/or billing code information and payment history can be displayed in a separate document or window. In some other embodiments, diagnostic and/or billing code information can be display overlaid onto the medical records dashboard 400 (e.g., as a pop-up window or transient text and/or graphics).

With reference to FIG. 7, in some embodiments, at least one medical record 708 can comprise a transition of care document (hereinafter "CCD"). In some embodiments, the Data Command center 001 via the medical records dashboard 400 can be configured to receive one or more CCDs from one or more medical care providers for display to the user. In some embodiments, the Data Command center 001 via the medical records dashboard 400 can be configured to extract information from the CCD for display to the user. For example, in some embodiments, information from a received CCD can be extracted and used to populate one or more data columns or fields of the medical records dashboard 400 and/or one or more linked data columns or fields of the medical records dashboard 400. In some embodiments, the Data Command center 001 via the medical records dashboard 400 can be configured to receive direct messaging information exchange with other healthcare organizations such as IHE profiles, CDA and CCD, NwHIN Direct, HL7v2, HL7v3, DICOM, X12, ITK (UK), DMP (France), and NEHTA (Australia), etc. For example, in some embodiments, the integration module 002 of the Data Command center 001 can include an HL7 message router and schemas for exchange of direct messages including a graphical editor for transforming messages and data.

Figure 8:
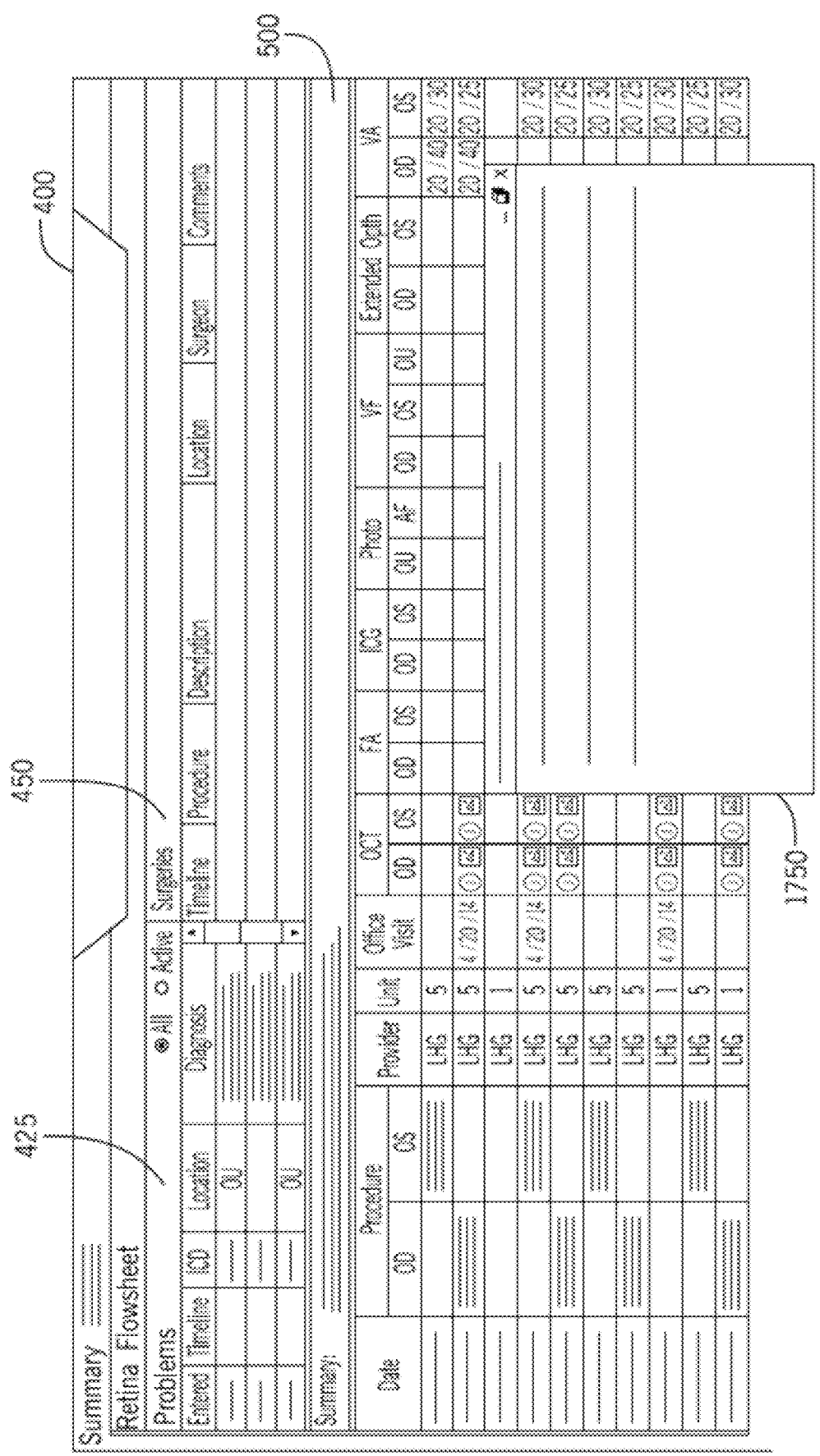
FIG. 8 depicts a medical records and diagnosis update process of the medical records dashboard in accordance with an embodiment of the present principles.

In some embodiments of the present principles, a user via the medical records dashboard 400 of the Data Command center 001 can retrieve and/or update information related to a medical diagnosis. For example, FIG. 8 depicts a medical records and diagnosis update process of the medical records dashboard in accordance with an embodiment of the present principles. In some embodiments, the medical records dashboard 400 including problems window 425, surgeries window 450, summary window 475, and command center visual display window 500 can include an option to enable a user to update or enter at least one medical diagnosis using a medical record/diagnosis window 1450. In some embodiments, multiple medical diagnoses can be provided or updated by a user. In some embodiments, the user providing the medical diagnosis can be any medical practitioner providing the service or procedure to the patient. In some other embodiments, the medical record/diagnosis window 1450 can be updated by a user other than the medical practitioner providing the service or procedure to the patient.

Further, in some embodiments, information can also be auto-populated into the EMR plan pages. A Data Command Center in accordance with the present principles via the medical records dashboard 400 can auto-populate various data fields related to information in any one of the problems window 425, surgeries window 450, summary window 475, and record/diagnosis window 1450 via an electronic dataflow established between the Data Command Center and one or more computer systems of servers that comprise patient information (e.g., such as electronic medical records). The dataflow can comprise a two-way flow from the source of patient data to the Data Command Center, and from the Data Command Center to the source.

Figure 9:
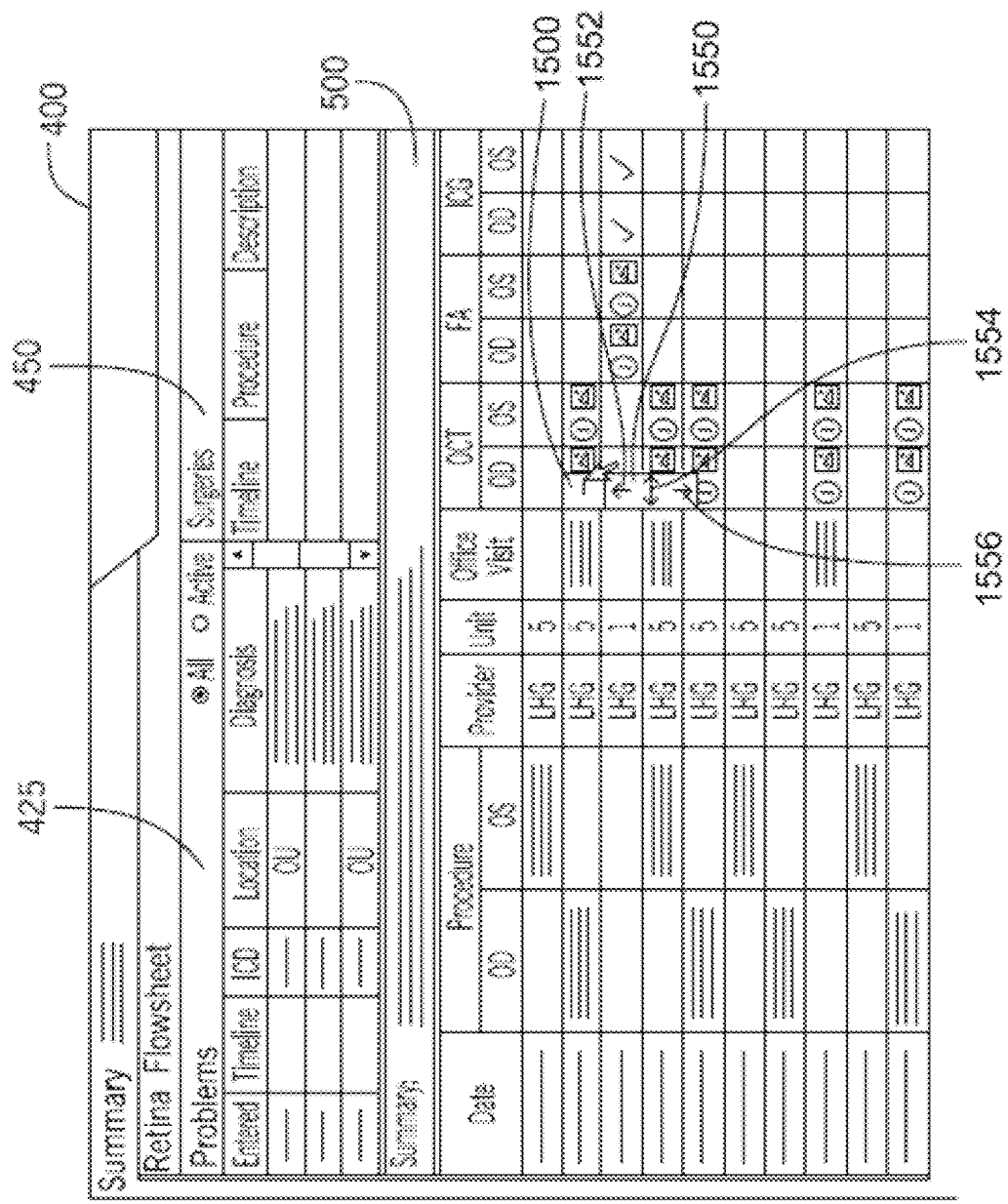
FIG. 9 depicts a medical record update marker process of the medical records dashboard in accordance with an embodiment of the present principles.

In some embodiments, the Data Command center 001 via the medical records dashboard 400 can enable a user to update information displayed in the visual display window 500. For example, in some embodiments, a user can update information related to a medical diagnosis and/or information related to a medical test or other service or procedure. For example, FIG. 9 depicts a medical record update marker process of the medical records dashboard in accordance with an embodiment of the present principles. That is, in FIG. 9 the medical records dashboard 400, including problems window 425, surgeries window 450, and summary window 475 is depicted with a record update marker 1500 being accessed by a user and displaying an update marker selection tab 1550. In some embodiments, the update marker selection tab 1550 can include a user-selectable marker or icon. For example, in some embodiments, update marker selection tab 1550 can include a selectable diagnosis indicator 1552, a selectable diagnosis indicator 1554, and/or a selectable diagnosis indicator 1556. In some embodiments, the selectable diagnosis indicators 1552, 1554, 1556 can provide a graphical representation of a medical diagnosis, outcome, or test. For example, in some embodiments, the diagnosis indicators 1552, 1554, 1556 can provide a visual representation of an improvement of a medical problem, disease, or symptom, or a worsening of a medical problem, disease, or symptom. Further, in some embodiments, the diagnosis indicators 1552, 1554, 1556 can provide a visual representation of a medical problem, disease, or symptom that is stable or substantially unchanged. In some embodiments, the diagnosis indicators 1552, 1554, 1556 can provide a visual representation directly related to one or more variables of a physical test. For example, in the field of ophthalmology, some imaging tests can provide an analysis of the thickness of the retina related to an eye disease such as macular degeneration. In some embodiments, an increase in thickness can represent a worsening of the condition, whereas a decrease in thickness can represent an improvement. A stable or unchanged thickness can indicate the disease is responding to treatment or is in remission. Further, by using data visualization techniques such as by using a color change or other method (e.g., such as using italics, bold text, and/or underlined text), a particular important change in a test can be marked for internal reference alerting a physician to the tests or procedures that are important and to take note for future reference. Further, in some embodiments, the diagnosis indicators 1552, 1554, 1556 can comprise a color and/or graphical change providing a visual representation of items billed, items not billed, or tests needing reports or interpretations are required. A color change or data visualization method (e.g., such as using italics, bold text, and/or underlined text) can also tell a physician if a test or procedure was billed, rejected, or if an interpretation needs to be made.

As an example embodiment, the diagnosis indicators 1552, 1554, 1556 can provide a visual representation of the status of a patient with an eye disease such as macular degeneration. For example, in some embodiments, the diagnosis indicators 1552, 1554, 1556 can be selected from the update marker selection tab 1550 when the user intends to indicate a worsening of the condition (e.g., where the thickness of the retina is increasing). In some embodiments, any of the diagnosis indicators 1552, 1554, 1556 can be color-coded to represent a status or provide a visual indicator of a medical condition, test, or diagnosis linked to the diagnosis indicators 1550. For example, in some embodiments, the diagnosis indicator 1552 can be color coded red and the diagnosis indicator 1556 can be color-coded green. Further, the diagnosis indicator 1554 can be color-coded blue or black. In some other embodiments, the diagnosis indicator 1552 can be color coded green and the diagnosis indicator 1556 can be color-coded red. In other embodiments, other graphical markers or icons can be used, and/or other colors can be used to differentiate the diagnosis indicators 1552, 1554, 1556. Further, in some embodiments, in addition to or in place of using a color differentiation between the diagnosis indicators 1552, 1554, 1556, one or more of the diagnosis indicators 1552, 1554, 1556 can flash or pulsate.

Figure 10:
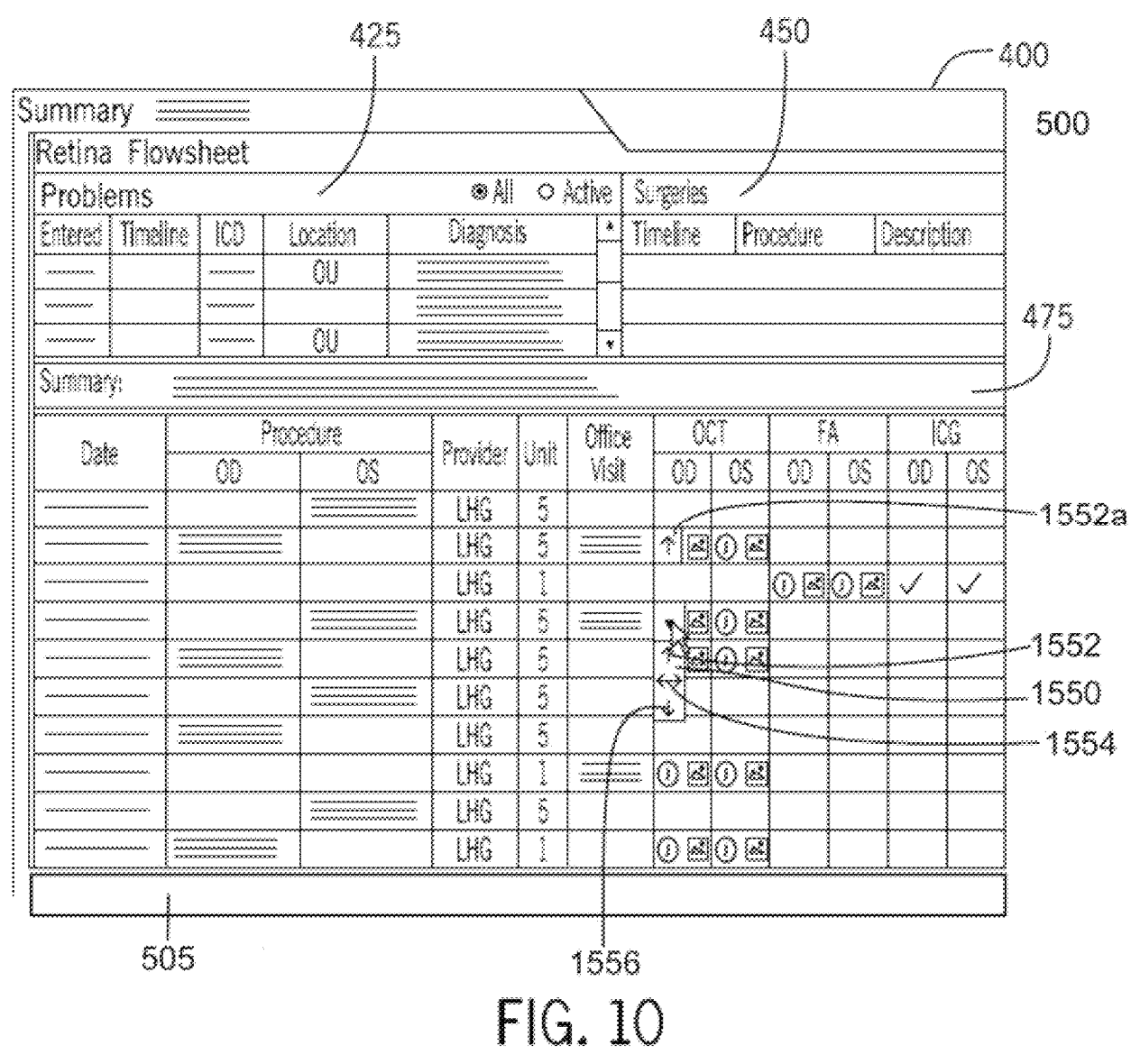

In some embodiments, the Data Command center 001 via a medical records dashboard of the present principles, such as the medical records dashboard 400, can enable a user to provide a plurality of updates to information displayed in the visual display window 500. For example, in some embodiments, a user can update information related to a medical diagnosis and/or information related to a medical test or other service or procedure, and subsequently provide further updates to the same information or to other information. For example, FIG. 10 depicts a medical record update marker process of the medical records dashboard 400 in accordance with an embodiment of the present principles. The embodiment of the medical records dashboard 400 of FIG. 10 includes a problems window 425, surgeries window 450, summary window 475, and command center visual display window 500. The command center visual display window 500 depicts diagnosis indicator 1552a representing previously updated information. The visual display window 500 also illustrates a user updating information with a process described above using the update marker selection tab 1550 comprising a selection of diagnosis indicator 1552, diagnosis indicator 1554, or diagnosis indicator 1556. In some embodiments, the diagnosis indicator 1156 can be modified to be indicative of updated information or status of a patient and/or a patient's disease, test, or medical condition. Further, any ICD, SNOMED or similar code can be inserted.

In addition, FIG. 10 illustrates a portion of the medical records dashboard 400 including a scrolled display in accordance with some embodiments. In some embodiments, the medical records dashboard 400 including problems window 425, surgeries window 450, summary window 475 can include a command center visual display window 500 that comprises a scroll display 505. In some embodiments, any information displayed in the command center visual display window 500 can be scrolled by the user to bring non-visible portions of the command center visual display window 500 into view. Such capability can enable the user to view the entire history of the patient independent of the number of years of history that is on record.

Figure 11:
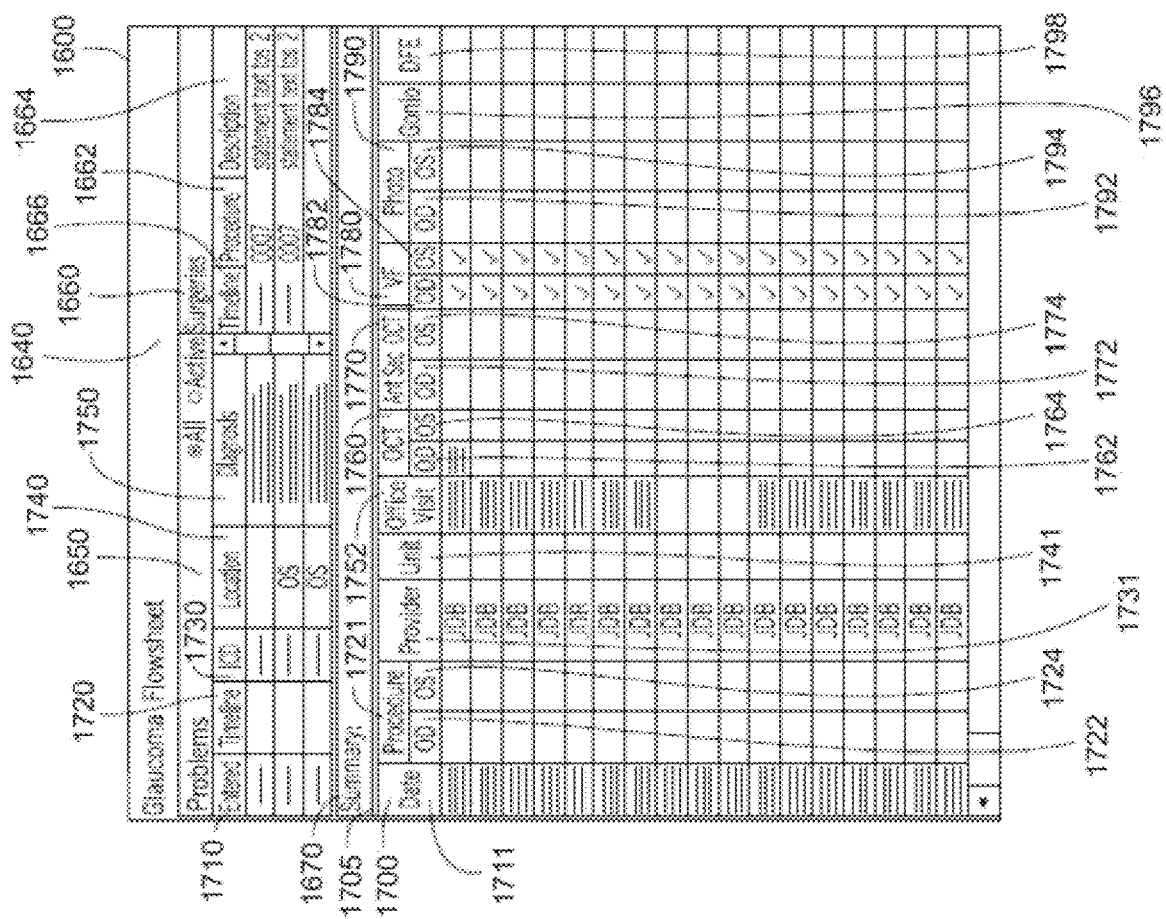
FIG. 11 depicts a portion of a medical records dashboard in accordance with another embodiment of the present principles.

FIG. 11 depicts a portion of a medical records dashboard 1600 in accordance with another embodiment of the present principles. In some embodiments, the medical records dashboard 1600 can display data from one or more medical records, and/or track medical procedures and services based on claims made or billing signed off by a physician for one or more delivered medical procedures or services. Further, in some embodiments, the medical records dashboard 1600 can be auto-populated as a function of claims made or billing signed off by a physician, auto-populated from any portion of a selected chart. In this instance, any data displayed within the medical records dashboard 1600 can be derived from one or more claim records that have been billed for one or more procedures or services have previously been provided to the patient. In reference to the medical records dashboard 1600 and/or the previously described medical records dashboard 400, in some embodiments, auto-populating visits by actual claims made or billings signed off by a physician, by definition occurs after the visit with a patient.

In some embodiments, the Data Command Center of the present principles can auto-populate some information of the medical records dashboard at the time the patient is seen, or shortly thereafter, or even before in preparation for a visit (i.e., lab results), so that even if a patient is not seen on a particular day, the user (e.g., medical care provider) can view the displayed information in the table for information. For example, in some embodiments, information related to vision can be made with the current date at the time patient is seen. In some embodiments, a user or user's assistant can update the Data Command Center with medical tests or test results (e.g., a vision test) as they are performed or shortly thereafter (i.e., on the same day). In this example, this information can immediately trigger the current date and auto-populate the vision column. This information can then be immediately viewed by a user and/or medical care provider and can be updated with notes or comments or other information as the user and/or medical care provider is attending to the patient. Further, after the claim has been made for any diagnostic tests or examinations or procedures that have not yet been billed, the date will then auto-populate in the future with the other related columns. In some embodiments, while examining a patient, important information and/or certain parameters that are critical to follow can be immediately updated to the Data Command Center. Using these procedures, the Data Command Center of the present principles can enable a medical care provider to review the patient's medical history, treatment history, and instantly see items of importance on the day they're examining a patient. For example, the user and/or medical care provider can be enabled by the Data Command Center, on the day the patient is examined, to review information such as a vision or glaucoma table, intraocular pressure, blood pressure, blood sugar, etc. When billing claims are made, further information is filled to complete the billed claims record. As a further example, a patient may be seen a few days apart and the diagnostic tests etc. and claims have not yet been made, however the Data Command Center can be configured to show that the patient was seen that day (e.g., with a vision, pressure test, etc.), and the Data Command Center can enable a user (such as a physician) to interpret and/or add special notes on the day they see a patient or before they see the patient rather than waiting to make some notes when a claim is actually generated.

If a medical office wishes to communicate results or a test (e.g., a pathology result or test) to a user, in some embodiments, a blinking cursor can appear to alert the user. Also any written or typed correspondence or any links to dictated information using voice recognition can be coupled to or integrated with a medical records dashboard via the Data Command Center of the present principles. For example, in some embodiments, the integration module 002 of the Data Command center 001 of FIG. 1 can integrate such information into the medical records dashboard. In some embodiments, information can be auto-populated into the medical records dashboard with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, a summary section of a medical records dashboard can be constantly fluid, and can be changed at every visit rather than being written to an unchangeable document or file (e.g., such as a PDF). Any patient data that is inputted, received, analyzed, or created can be auto-populated into any portion of a medical records dashboard. The Data Command Center can auto-populate in a one-way or two-way direction in various data fields related to information in any patient information via an electronic dataflow established between the Data Command Center and one or more computer systems of servers that comprise patient information (e.g., such as electronic medical records). The dataflow can comprise a two-way flow from the source of patient data to the Data Command Center, and from the Data Command Center to the source including another electronic system or server, or another user, observer, or other 3rd party.

By following a patient on the day of delivery (e.g., for a vision intraocular pressure or anything else) the Data Command Center can enable the user and/or medical care provider via the medical records dashboard to see the diagnostic test on same day even though it has not been billed. Further, this procedure can enable the medical care provider to optionally add a note and allow free hand typing at the end of the line.

In some embodiments, medical information populated within medical records dashboard (e.g., shown as visual cues, icons, or markers 885 representing medical services, procedures or tests performed or provided to the patient) can include a visual marker such as a red dot. In some embodiments, the Data Command Center can display the red dot until a claim is actually made at which time the Data Command Center can display a green dot (i.e., the Data Command Center can convert the red dot to a green dot). In some embodiments, by clicking on the dot, the user can toggle between the payment screen and the command center visual display window 500, 1700. This can allow medical care providers to improve patient care, to review the actual picture of a diagnostic test that is displayed within the command center visual display window 500, 1700, to review other diagnostic tests results, and to compare to what happened on other days. In some embodiments, at any time, a medical care provider can click on the dot to access a display where the claim is billed, and any payment that was made can be displayed. This process can help to reduce medical errors enabling medical care providers to quickly review the billings and claims made or billings signed off by a physician and payment portions of the Data Command Center. Further, this procedure serves as an additional tool to minimize coding, compliance with insurance guidelines, and medical treatment errors, as the Data Command Center can provide a quick reference tool that can pull all critical medical and procedure data from the patients EMR chart into a concise and clear table.

In some embodiments, a medical records dashboard of the present principles can display information related to medical procedures or services in relation to care of a patient with glaucoma. In some embodiments, the medical records dashboard can display various windows and sub-windows based on a user preference and/or current or previous user interaction with the medical records dashboard. As depicted in FIG. 11, in some embodiments a medical records dashboard 1600 can include information columns 1640 including a problems window 1650 and/or a surgeries window 1660 where information related to a patient's medical problems and surgeries can be displayed. In some embodiments, the medical records dashboard 1600 can include a summary window 1670 enabling a user to view and edit summary information related to the patient, any details of care provided to the patient, and/or and any medical diagnosis information prepared by a medical practitioner. Further, the medical records dashboard 1600 can also display detailed information related to any medical procedures or services provided to the patient, including procedures or services that are auto-populated by claims made or billing signed off by a physician as detailed above or other method. For example, in some embodiments, the medical records dashboard 1600 can display a visual display window 1700 including a plurality of information columns 1705. In some embodiments, the visual display window 1700 can be scrolled by the user to display other portions of the visual display window 500.

In some embodiments, the medical records dashboards of the present principles can also display detailed information related to notification of payment of any medical procedures or services provided to the patient, including procedures or services that are auto-populated by claims made or billing signed off by a physician as detailed above or other method. Moreover, the medical records dashboards can enable a user to access and/or track the status of the billing and payment process at any point in time. For example, in some embodiments, the medical records dashboards can access and view any patient encounter form (i.e. a superbill), any claims made to a clearing house, any updates on accepted or rejected bills from the clearing house, any claims made to an insurance company, and/or any payments received for any claims made.

As depicted in FIG. 11, in some embodiments of a medical records dashboard, the problems window 1650 can include a date and time information in entered date column 1711, a timeline column 1720, an "ICD" column 1730 for ICD code information, location of the problem or disorder (shown as "OD", "OS", "OU" identifying right eye, left eye, both eyes) (column 1740), and a diagnosis column 1750 for detailing information related to an initial diagnosis or final diagnosis of a patients problem or disorder. Further, the surgeries window 1660 can include information related to services or procedures were provided to the patient (procedure columns 1662), a description of the services or procedures performed (description columns 1664), and when the services or procedures were provided to the patient (shown as timeline columns 1666), and can include a surgical report that can be brought up and viewed by the user.

Referring to the visual display window 1700 of the medical records dashboard 1600 of FIG. 11, the information columns 1705 can include a date column 1711, and a procedure column 1721 illustrating or providing access to information detailing one or more procedures performed on the patient. Further, the procedure column 1721 can include an "OD" column 1722, and "OS" column 1724 providing right and left eye procedure information. In some embodiments, information related to the medical care provider, location where the procedure was performed, and office visit information can be provided to the user in the provider column 1731, and unit column 1741, and office visit column 1752. In some embodiments, the visual display window 1700 can enable a user to view information related to tests and procedures performed on the patient including, but not limited to one or more medical imaging procedures such as an optical coherence tomography ("OCT"), or fluorescein angiography ("FA"), and/or indocyanine green chorioangiography ("ICG"). In some embodiments, medical procedures performed (including any of the aforementioned medical imaging procedures) that have been billed and claimed can be viewed or accessed by a user within any of the "OCT" column 1760 (shown split as an "OD" column 1762 and "OS" column 1764), an "Ant Seg OCT" column 1770 (split as an "OD" column 1772 and "OS" column 1774).

In some embodiments, if visual function tests were performed, information can be viewed or accessed in the "VF" column 1780 (including an "OD" column 1782, and/or an "OS" column 1784. Some embodiments include a photo column 1790 configured to enable a user to access any photographic images of the patient's eyes including optical and/or auto-fluorescent images of the eyes ("OD" column 1792 and "OS" column 1794). Further, the embodiment of the medical records dashboard 1600 of FIG. 11 includes a Gonio column 1796 providing access to gonioscopy data and/or information related to a dilated fundus examination ("DFE" column 1798). In some embodiments, the surgeries window 1660, can include a location column, a surgeon column, and a comments column (not shown).

Figure 12:
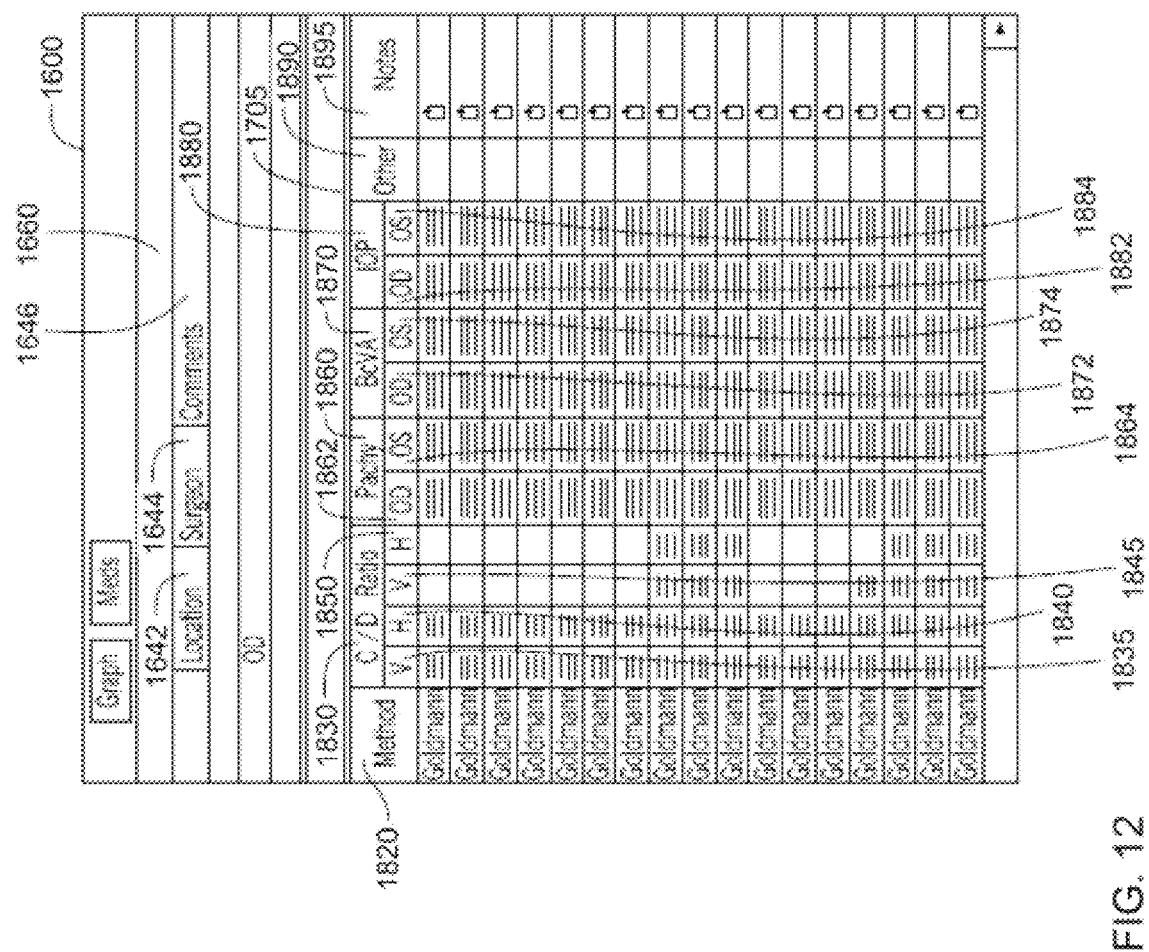
FIG. 12 depicts a portion of the medical records dashboard of FIG. 11 in accordance with an embodiment of the present principles.

In some embodiments, the visual display window can enable a user to view information related to tests and procedures performed on the patient including a cup-to-disc ratio ("C/D") to assess the progression of glaucoma, Pachymetry data ("Pachy"), refraction test information such as best-corrected visual acuity ("BCVA"), and/or intraocular pressure (IOP) data. For example, FIG. 12 depicts a portion of the medical records dashboard 1600 of FIG. 11 including column 1820, "C/D ratio" column 1830, "Pachy" columns 1860, "BcVA" columns 1870, and "TOP" columns 1880. In some embodiments, the "C/D ratio" column 1830 includes "V" column 1835, "H" column 1840, "V" column 1850, and "H" column 1850. Further, in some embodiments, the "Pachy" columns 1860 includes "OD" column 1862, and "OS" column 1864. In some embodiments, the "BcVA" columns 1870 includes "OD" columns 1872, and "OS" columns 1874. Some embodiments include "IOP" columns 1880 including "OD" columns 1882, and "OS" columns 1884. In some embodiments, other columns 1890 can be used to add additional test information. Further, the visual display window 1700 can also include a notes column 1895 for accessing and updating notes related to tests and medical diagnosis. In some embodiments, the tracking display window 1700 can be updated with comments and notes as described earlier.

In some embodiments, the Data Command Center can display and auto-populate a medical records dashboard of the present principles, such as the medical records dashboard 400 and/or the medical records dashboard 1600, with more than one patient information. For example, in some embodiments, any windows, sections, or columns of the medical records dashboard can display information related to a plurality of patients. Any patient data that is inputted, received, analyzed, or created can be auto-populated into any portion of the dashboard, where the Data Command Center can auto-populate in either a one-way or a two-way direction. Thus, data fields related to information in any patient information can be communicated via an electronic dataflow established between the Data Command Center and one or more computer systems of servers comprising patient information (e.g., such as electronic medical records). Further, in some embodiments, any information displayed by Data Command Center can display and auto-populate the medical records dashboard as a function of patients seen during a specified time period. In some other embodiments, the Data Command Center can display and auto-populate the medical records dashboard as a function of a specified disease and/or diagnosis. For example, in some embodiments, the Data Command Center can display and auto-populate the medical records dashboard as a function of a diagnosis or procedure or prescribed medication or lab or imaging test from input received from a physician or other medical practitioner or provider. For instance, every patient who has the diagnosis of diabetes with their name and the date last scene is auto-populated. Certain parameters that may need to be followed by the user from all of their patients with this condition can be auto-populated. For example, in the case of patients with diabetes, parameters can include how often they've missed appointments, blood sugar, hemoglobin A1C, medications, major new medical complications such as heart attack, stroke, amputations, blindness, each of which can be auto-populated and followed to enable the user to see how all their patients are doing. In some embodiments, input and the ability to display data can be based on single values or on complex multi-variate input (i.e. patients with diabetes, taking metformin and seen by the practice in the last 30 days).

In some embodiments, a user(s) can receive, via the medical records dashboard, a daily report on all the patients they have seen, what the diagnosis codes are and what CPT, ICD, or office visit billing codes were done whether they have been billed or not. In some embodiments, the user can view a report of patients for a specific day or week based on appointments or other data such as referrals. With this functionality, at the end of the day physicians can see all of their activity or the practice's activity on the medical records dashboard of the present principles and using data visualization techniques can realize what activity still needs to be completed or was not entered properly. The user can then review the same information in a few days' time and weeks or months later to ensure that the proper billing and collections has occurred. Additionally, the medical records dashboard enables direct one click access to underlying data, so without leaving the screen, providers can make medical decisions. For instance, an icon displayed on the medical records dashboard can represent that a test was performed on a particular patient or group of patients and that test can be directly accessed by activating that icon. If more information is needed, the entire individual flowsheet of the patient can be, with no more than one click, brought up, decisions made, and then with one click, return to viewing the entire medical records dashboard.

In some embodiments, two monitors can be implemented during which a first monitor can display the medical records dashboard and the second monitor, controlled by the first, can display the data from a selected patient. In such embodiments, even a single click to return to the medical records dashboard is not needed as information can be displayed on both monitors at once. In some embodiments, a portion or all of the data of a medical records dashboard, as well as the diagnostic tests, can be sent to a patient portal, to an email server, and/or as a fax. Further, in some embodiments, a user can be alerted via the medical records dashboard, when claims are sent out for payment and when claims are actually paid. For example, in some embodiments, the above described methods of display can provide a mechanism for displaying payments to the user, and if claims are being made for each patient seen in any particular day, week or month.

In some embodiments, any report, note, letter, referral or diagnostic test can be sent from a medical records dashboard of the present principles to an EMR, patient portal, a messaging platform to an email server, and/or as a fax. Messages can be transmitted to a patient or another practice focused on appointment reminders, medication prescriptions and/or refills, and good care management guidelines. It should be recognized that data interoperability and messaging are not limited to the examples provided but apply to any information within the Data Command Center.

Figure 13:
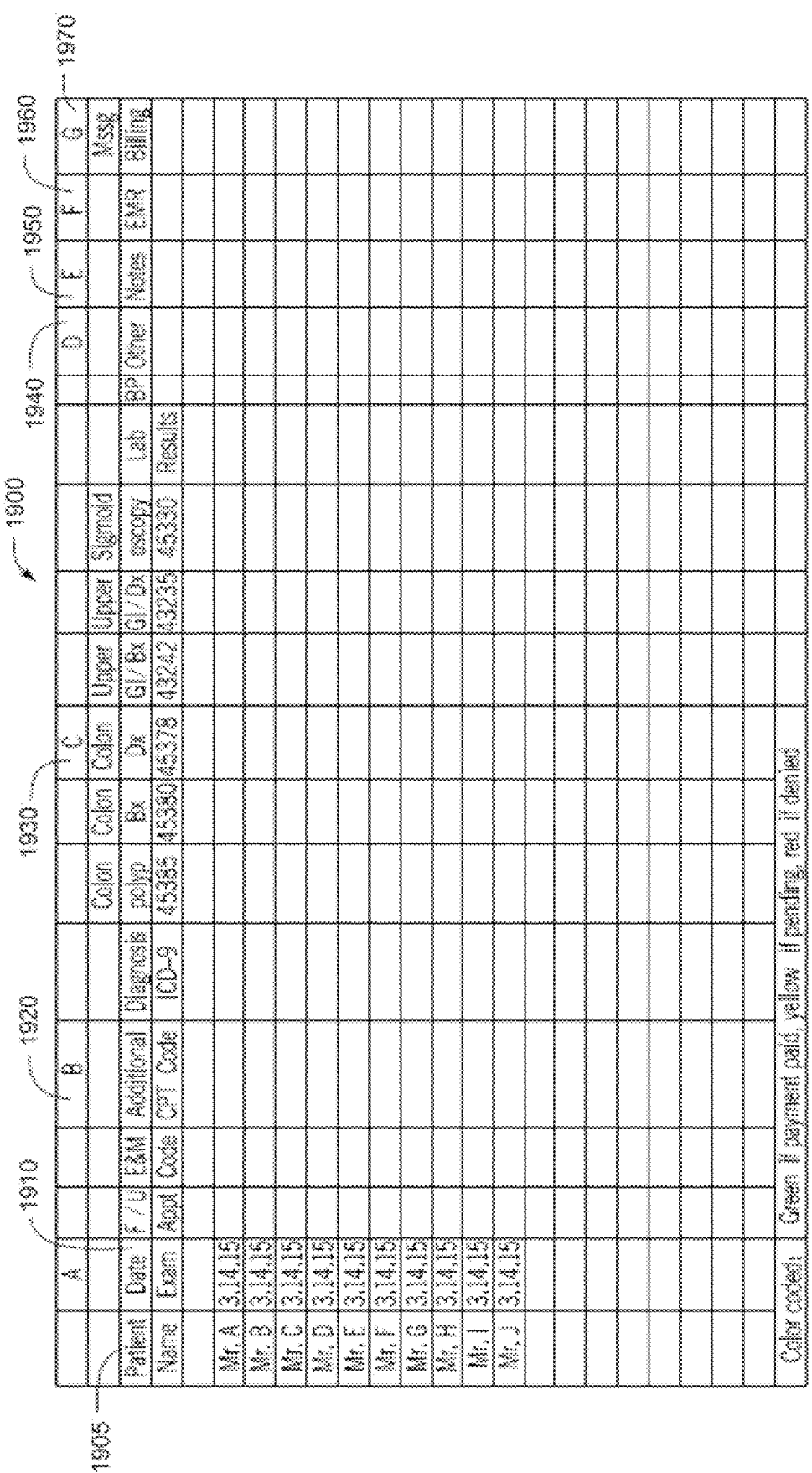
FIG. 13 depicts a portion of a medical records dashboard configured for display as a function of disease or patient in accordance with another embodiment of the present principles.

FIG. 13 depicts a portion of a medical records dashboard 1900 configured for display as a function of disease or patient in accordance with another embodiment of the present principles. In some embodiments, the medical records dashboard can be displayed overlaid on a previously viewed dashboard such as the medical records dashboard. For example, in some embodiments, the medical records dashboard can be displayed in the visual display window 500. In other embodiments, the medical records dashboards can be displayed independently from the medical records dashboard, and the user can toggle a display of any of the medical records dashboards.

The medical records dashboard 1900 of FIG. 13 provides a list of patients 1905, and within column 1910, an entire day of patients listed by date or by insurance coverage can be provided or the list can comprise a single patient with multiple visits. For example, in some embodiments, within column 1920 of the medical records dashboard 1900, an office visit and any items billed for a routine examination day and any other CPT codes billed that day can be displayed. In some embodiments, some specialties will have many CPT codes during an office visit (e.g. Ophthalmologists), whereas others (e.g., Gastroenterologists) can have four during an office visit. In some embodiments, column 1930 of the medical records dashboard 1900 can include the procedures that a physician can perform and are usually not on the same day as the exam (these can be GI physician examples). In some further embodiments, the column 1940 of the medical records dashboard 1900 can include various important parameters that can be followed for a specific patient. Some embodiments of a medical records dashboard, such as the medical records dashboard 1900, include column 1950 that enables a physician to write notes about patient care issues and column 1960, which enables a user to access that patient's personal EMR or review table and can also send a message to the patient. In some embodiments, the column 1970 of the medical records dashboard 1900 can enable a user access to the charge payment history of the patient and also enable a message to be sent to the billing department from this table. In some embodiments, columns can be reconfigured such that all patients with a particular insurance company that have a particular diagnosis on any given date or over a prolonged period of time can have tests and procedure results, as well as payments compared, allowing on one screen anyone to rapidly move through this visual display system to enable rapid comparison of results and potential payment anomalies for the same insurance company for the same CPT codes but perhaps different ICD9 or 10 diagnosis and to see if there is a mismatch (e.g., through the use of artificial intelligence systems discovering insurance payment irregularities). In some embodiments, columns 1920, 1930 of the medical records dashboard 1900 can be colored 'black' when a claim is made, and can be colored 'green' if paid, and can be colored 'yellow' if a payment is pending, and can be colored 'red' if payment denied by one rendition, e.g., physician reconciliation report of messages sent individuals for follow up, and/or a report of all the message activity from any given day.

Figure 14:
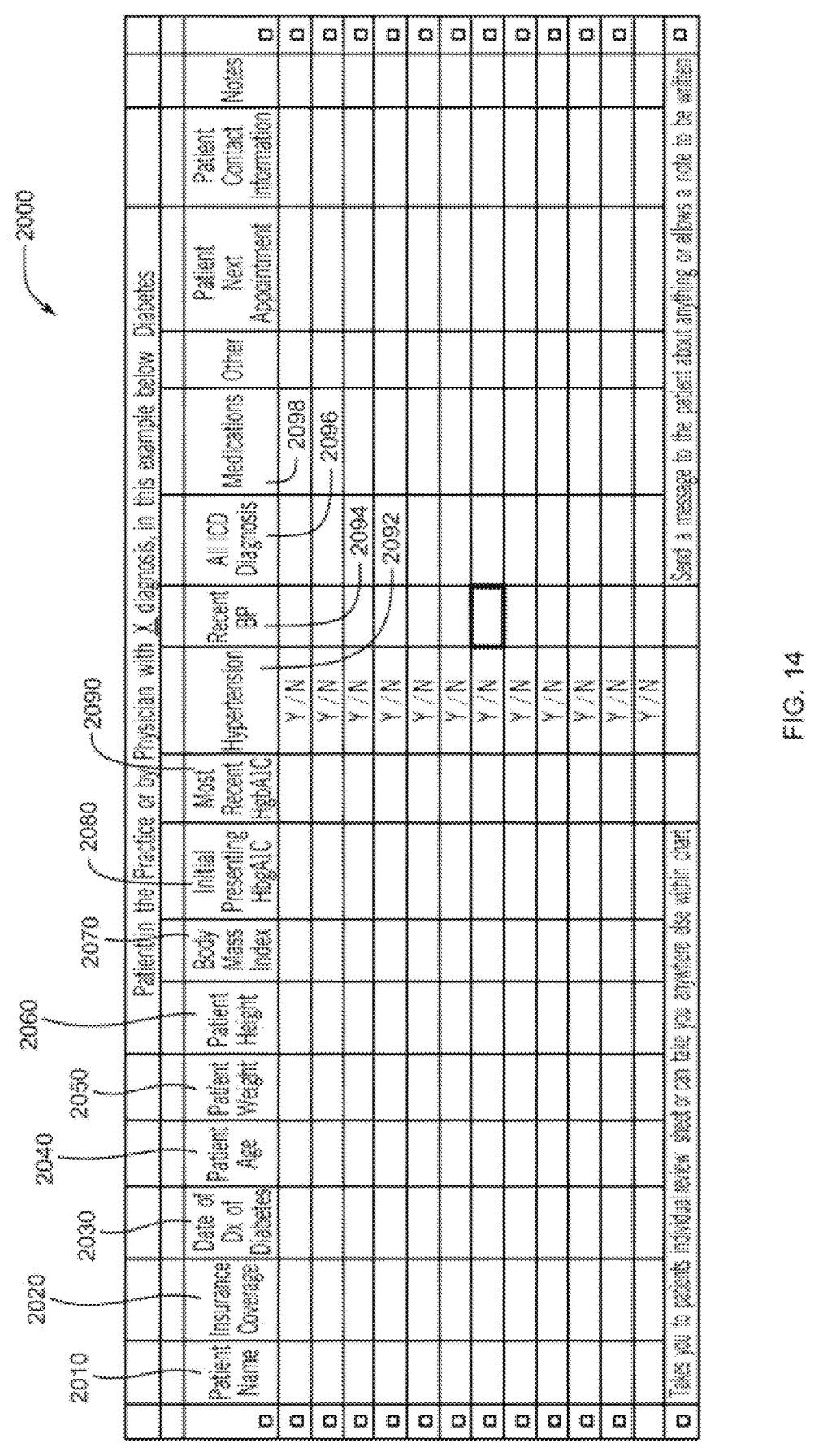

FIG. 14 depicts a portion of a medical records dashboard 2000 configured for display as a function of disease of a patient and specifically configured to display data related to patients with diabetes in accordance with another embodiment of the present principles. In the medical records dashboard 2000, the display for patients 2010 can include a variety of medical, billing, and insurance related information. FIG. 14 illustrates a portion of a medical records dashboard for display as a function of patients with a specific disease ICD, such that many patients may be compared at the same time, which can be useful for clinical research or for tracking clinical outcomes. The embodiment of FIG. 14 tracks all patients in a practice or a subset of patients and can compare, for example, particular diagnostic test results in patients with a particular condition, the results of a particular medication, how all the patients did who received a particular intraocular lens into the eye, etc. The information is put into each individual patient's table, but all patients with that issue can also be called up on a single table such as illustrated in FIG. 14. In some embodiments, such functionality can compile and compare all patients with a particular insurance company that have a particular diagnosis and compare tests and procedure results, as well as payments, allowing a user on one screen to rapidly see results, changes, patterns and payment anomalies. This feature also allows the extraction of patients with similar conditions for referrals and clinical research, batch generation for cross-referrals (e.g. optometry for an ophthalmologist), etc. In some embodiments, the medical records dashboard 2000 can be displayed as shown or can be sorted based on any of the data columns. For example, the patients 2010 can be shown including information displaying insurance coverage 2020, date of diagnosis of diabetes 2030, the patient's age 2040, the patient's weight 2050, the patient's height 2060, the body mass index 2070, the initial presenting HbgA1C 2080, the most recent HbgA1C 2090, the hypertension status 2092, the recent blood pressure 2094, the All ICD diagnosis 2096 and the current or past medications 2098. In some embodiments, the medical records dashboard 2000 can be reconfigured to display patients 2010 sorted by any of the columns 2020, 2030, 2040, 2050, 2060, 2070, 2080, 2090, 2092, 2094, 2096, 2098.

The medical records dashboard 2000 of FIG. 14 enables a user to present on one display everything the physician has done in a particular time frame, such as a day. For instance, a line of information for the information entered into the chart for every patient for today's visit, can be presented in the dashboard 2000. Whatever the user records, like the patient's vision and any diagnostic tests or laser procedures or injections in the eyes that were actually done that day, can be displayed on the medical records dashboard 2000 for interpretation. A medical records dashboard of the present principles can also enable a user to configure follow-up enabling a user to check again (e.g. 48 hours later) when everything for that day should have already been billed or 60 days later when everything is paid and all dates queried can be compared. Also, the user is able to review all patients having a common insurance carrier to facilitate satisfactory payments from the insurance company.

In some embodiments, a Data Command Center of the present principles can enable an addition of a date alert or self-destruction of any information or data entered or auto-populated in the medical records dashboard 400. For example, in some embodiments, any message, or note, or summary, or any medical data can include a date alert and/or a self-destruct function that can remove and/or delete information from the medical records dashboard 400. In other embodiments, the historical date and/or an alert or warning can be provided with any auto-populated or user-summoned information to assist the user with an assignment of relevancy to any data being reviewed prior to, during, or after a patient visit or examination. In some embodiments, this feature can optimize the standard of care being delivered by the user. For instance, this feature can help monitor preferred practice patterns or serve as a reminder on information needed for clinical review.

In some embodiments, a Data Command Center of the present principles enables the prioritization of relevant data in at least portions, columns and rows of a medical records dashboard, while minimizing less important values. This functionality enables a user to focus on the most important data pertinent to the current use case (i.e., with a patient that has a certain diagnosis, several preferred diagnostic test results and data are germane). In some embodiments, such display capabilities can be applied to data that originates from additional users/EHR deemed important and which can be rendered in chronological order. Utilizing Artificial Intelligence (AI), Natural Language Processing (NLP), and/or conventional business logic, a Data Command Center of the present principles can programmatically filter out unnecessary information and queries for display.

In some embodiments, a medical records dashboard of the present principles can be configured based on key events, results, date/time, and/or logical parameters which can include, but are not limited to Diagnoses, Medication Start/End Dates, Allergy Start/End Dates, Billing History, Demographic Data, Observations/Plans, and Life Events. In accordance with the present principles, the format and display of rendered data in the medical records dashboard will make maximum usage of space by shrinking less relevant rows, auto-sizing of columns, and automatically collapsing less relevant data. The intention of this functionality is to provide the most efficient view in the medical records dashboard of relevant data, while not overloading the provider with information not germane to the current configuration. An example would be if a patient has glaucoma, there are specific columns in the medical records dashboard that are highly important to monitoring the chronic condition but some which have no relevance. In this example, the patient that has a diagnosis of glaucoma will have Intra-Ocular Pressure (IOP), Glaucoma medications, etc. displayed prominently while the other less relevant columns are masked.

In some embodiments, the Rules module 004 of the Data Command Center of the present principles can include a Flowsheet Editor Interface that provides a method by which a user/medical care provider can configure the formatting and display of data intended for the medical records dashboard. This simplified interface editor embodies "What You See Is What You Get" (WYSIWYG) methodology, in some embodiments including drag and drop of Flowsheet elements. Upon completion of a Template for the medical records dashboard, associated parameters can be defined. The Flowsheet Editor enables a user to define how columns and rows will be displayed in the medical records dashboard. While users have the ability to only view predefined data, filtered data may trigger a rule to display in lieu of predefined filters. Preconditioned upon required contract/agreement between users, data can display from multiple, disparate sources to display continuity of care.

In some embodiments, the Flowsheet Editor Interface of the Data Command Center also enables an end-user to configure how summary rows are presented within the medical records dashboard. A user can choose to discard certain edge-cases from the summary calculation, take the highest and lowest values, take an average, or some other logical calculation to determine how the individual columns summary row data presents itself. In addition to enabling changes which reflect the display of the data, it is possible for the user to program alerts and auto-tasks which are sent as a result of the rule threshold being exceeded. For example, if a user/medical care provider determines that a new alert rule must be created, they are able to select the column, or columns, apply logical rules to the column or columns being analyzed, and set the task associated with rule which will be sent to the user-defined staff member or groups of staff members. As another example, a user can choose to add a new alert for those patients which have a diagnosis of Glaucoma and have not had a required diagnostic test, a Visual Field, in 365 days. The user is then able to set a task that will be sent to staff to schedule the diagnostic test that will automatically be sent when the system and user-defined auto task and alerts are processed. The editor interface also enables a user to configure a manner in which the alert is displayed in the medical records dashboard. For example, a user can set the display of an alert to any of the following, but not limited to, headers, within the rows and columns of the flowsheet, on the patient demographic panel, etc.

Pre-defined display rules can override a user-defined configuration of a medical records dashboard when the rule is prioritized, in some embodiments, for patient safety reasons. These overrides can display information regarding a subject visit in a prominent color. For example, if a patient had recently found out that she was pregnant, it becomes very important that she does not have certain diagnostic tests performed as such tests can endanger the viability/health of the fetus. For example, a Fluorescein Angiogram should not be performed on a patient to monitor the progress of a patient if she is pregnant. Due to the potential life altering consequences, the Data Command Center, through the use of, for example AI, is smart enough to override a medical records dashboard template, and prominently display the visit from the OBGYN on the medical records dashboard, in an instance in which the patient was confirmed to be pregnant.

Figure 15:
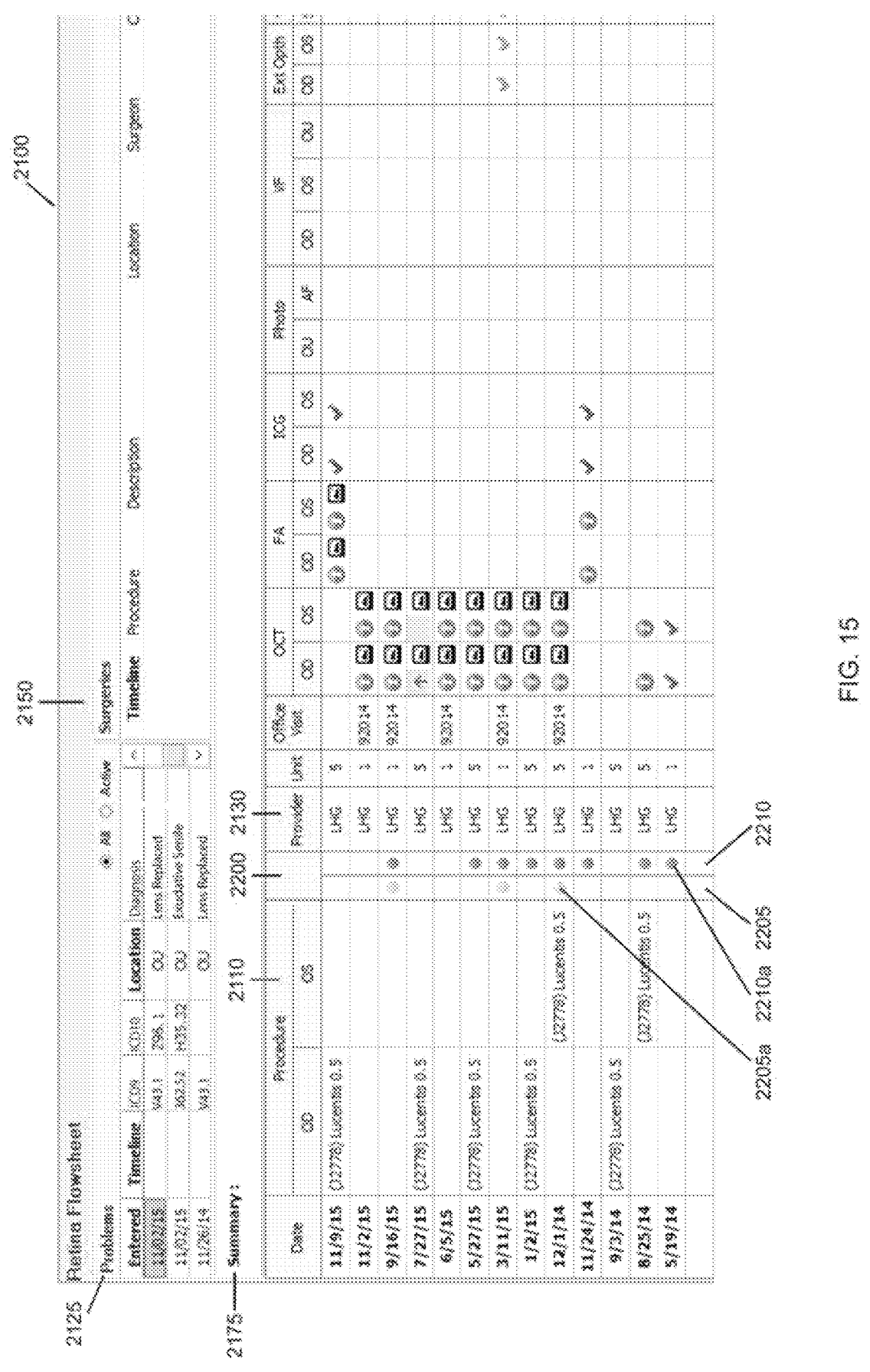

In some embodiments, a Data Command Center of the present principles can enable a user to access a detailed ledger comprising patient financial information from a medical records dashboard. In some embodiments, the medical records dashboard can include at least one visual indication of a payment for services provided, where detailed information of the charges, payments, write-offs, adjustments, and balances can be accessed and displayed. For example, FIG. 15 depicts an embodiment of a medical records dashboard 2100 which can be displayed following a user's selection of at least one medical records dashboard from the medical records dashboard selection window in accordance with another embodiment of the present principles. For example, in some embodiments, the user can make a selection of "Retina Flowsheet" to access and/or launch the medical records dashboard 2100. In some embodiments, the medical records dashboard 2100 can include a display of data from one or more medical records and can track medical procedures and services based on claims made or billing signed off by a physician for one or more delivered medical procedures or services. Some embodiments include a Data Command Center that can dynamically link to various external databases comprising patient information that can be displayed in the medical records dashboard 2100. For example, in some embodiments, the Data Command Center can function as a portal to patient information prepared by the user or patient information from other sources. Further, in some embodiments, the medical records dashboard 2100 can be auto-populated as a function of claims made or billing signed off by a physician. In this instance, any data displayed within the medical records dashboard 2100 is derived from one or more claim records that have been billed for one or more procedures or services have previously been provided to the patient. In some other embodiments, auto-population can be enabled in both directions interacting as a switchboard between the entire EMR and the medical records dashboard 2100.

In some embodiments, the medical records dashboard 2100 can display information related to medical procedures or services in relation to retinal eye care of a patient. In other embodiments, a medical records dashboard can display information related to medical procedures or services in relation to any kind of medical care of a patient. In some embodiments, the medical records dashboard 2100 can display various windows and sub-windows based on a user preference and/or current or previous user interaction with the medical records dashboard 2100. For example, in some embodiments, the medical records dashboard 2100 can display a problems window 2125 and/or a surgeries window 2150 where information related to a patient's medical problems and surgeries can be displayed.

In some embodiments, the medical records dashboard 2100 of FIG. 15 can display information including components where there is a summary of the patient's problem list in which a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical records dashboard 2100 can be constantly fluid and can be changed at every visit rather than being written to an unchangeable document or file (e.g., such as a PDF). For example and as depicted in FIG. 15, the medical records dashboard 2100 can include a summary window enabling a user to view and edit summary information related to the patient, any details of care provided to the patient, and/or and any medical diagnosis information prepared by a medical practitioner. Further, the medical records dashboard 2100 can also display detailed information related to any medical procedures or services provided to the patient, including procedures or services that are auto-populated by claims made, or billings or payments including billing signed off by a physician as detailed above. Additionally, all of the features of the previously described medical records dashboards of the present principles can be provided in the medical records dashboard 2100.

Some additional features of a medical records dashboard of the present principles, such as the medical records dashboard 2100 of FIG. 15, include displaying at least one visual indication of a payment for services provided. Further, the user can be provided with access to a detailed ledger comprising financial information related to one or more procedures. For example and as depicted in FIG. 15, the medical records dashboard 2100 can comprise a payment indicator column 2200 including one or more indicator and/or access icons. For example, in some embodiments, the payment indicator column 2200 can comprise a column or columns 2205/2210 that can be populated with one or more indicator or access icons 2205a/2210a. In some embodiments, the one or more indicator or access icons can comprise icons of color such as yellow or green to indicate a status of payment. The payment indicator column 2200 can be located anywhere on the of the medical records dashboard 2100. In the embodiment of FIG. 15, the payment indicator column 2200 is positioned between the procedure column 2110, illustrating or providing access to information detailing one or more procedures performed on the patient and information related to the medical care provider, and the provider column 2130, that can display the location where the procedure was performed, and office visit information.

Figure 16:
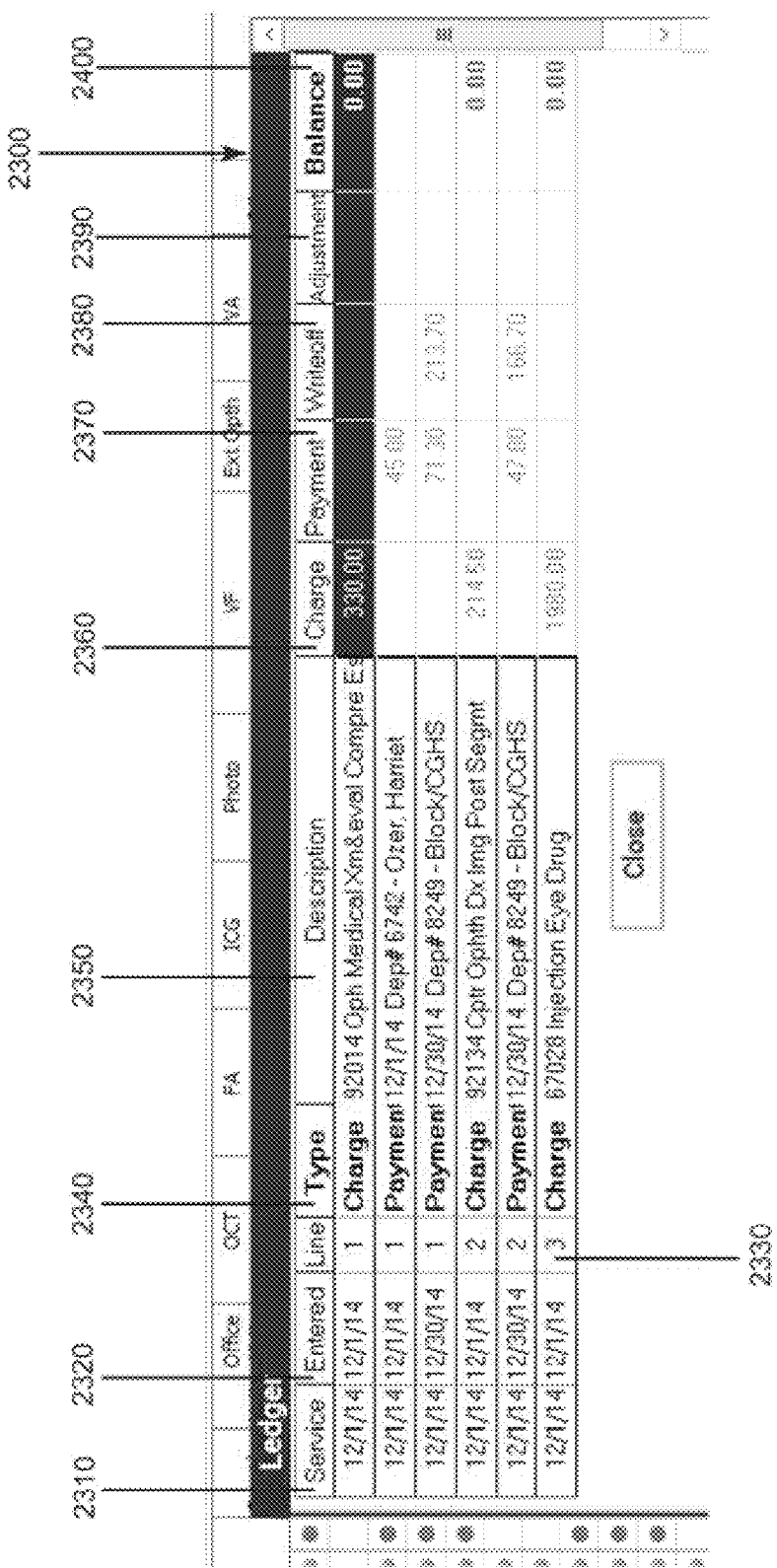
FIG. 16 depicts a ledger window accessible from the medical records dashboard of FIG. 15 in accordance with an embodiment of the present principles.

In some embodiments, one or more of the icons of the payment indicator column 2200 can be accessed by the user to initiate the display of more detailed financial information. For example, FIG. 16 depicts a ledger window 2300 accessible from the medical records dashboard 2100 of FIG. 15 in accordance with an embodiment of the present principles. In some embodiments, the Data Command Center of the present principles can display the ledger window 2300 overlaid onto the medical records dashboard 2100. In other embodiments, the ledger window 2300 can be displayed in place of the medical records dashboard 2100. In other embodiments, the ledger window 2300 can be displayed with the medical records dashboard 2100. In some embodiments, the ledger window 2300 can include information processed by the Data Command Center, which includes information related to the date of procedure, description of the procedure, dates entered, a charge type, etc. For example and as depicted in the embodiment of FIG. 16, the ledger window 2300 can include the service to column 2310, entered column 2320, line column 2330, type column 2340, and description column 2350. Further, in some embodiments, the ledger window 2300 can include information related to payments and billing. For example, in some embodiments, the ledger window 2300 can include a display of a charge column 2360, payment column 2370, write-off column 2380, adjustment column 2390, and a balance column 2400. In some embodiments, the user can close the ledger window 2300 and return to the medical records dashboard 2100 at any time. In other embodiments, more than one ledger window 2300 can be displayed based on selections made by the user in the medical records dashboard 2100.

Figure 17:
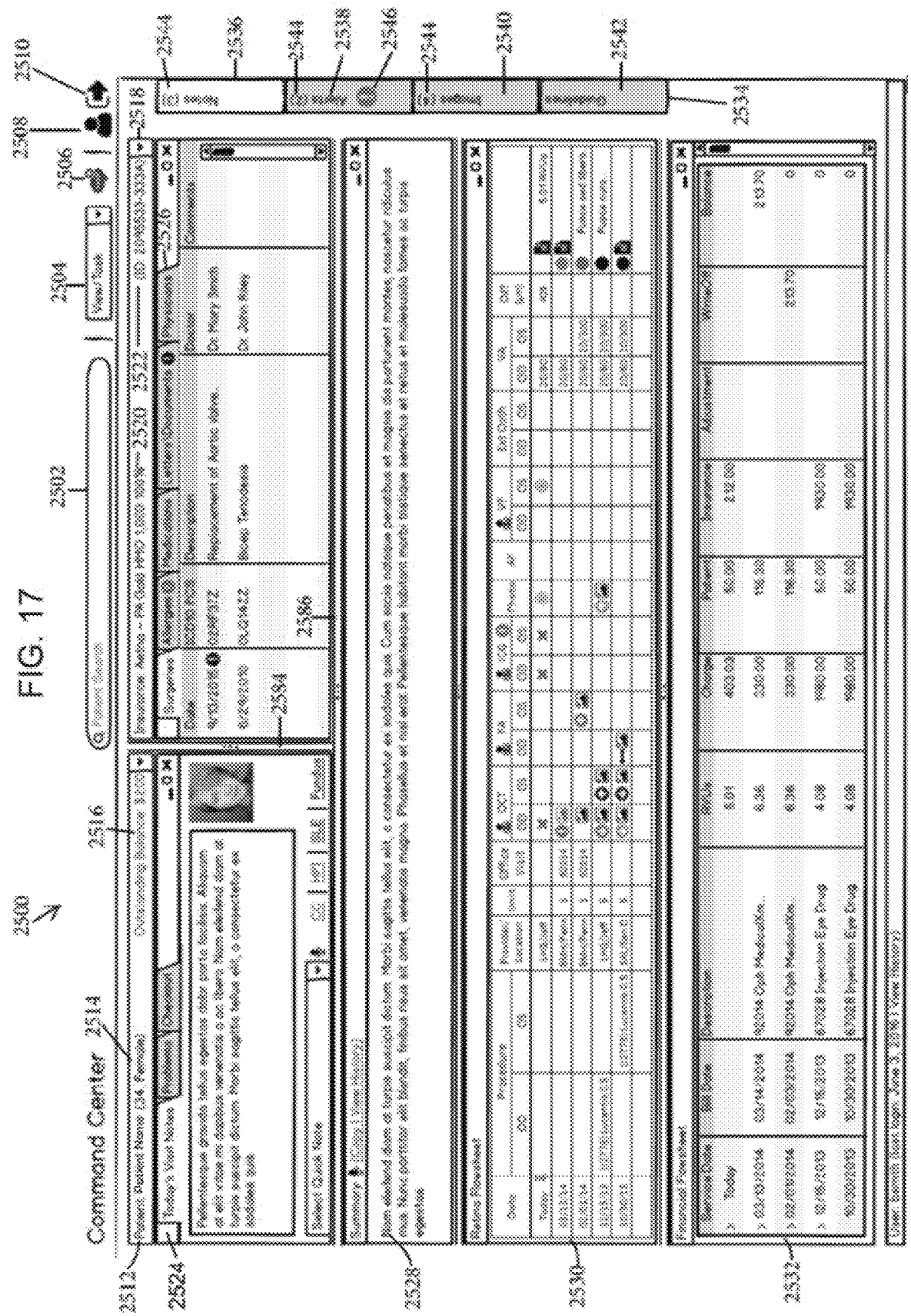
FIG. 17 depicts an embodiment of a Data Command Center menu including a medical records dashboard implemented as a data interface to a medical record system in accordance with an embodiment of the present principles.

FIG. 17 depicts an embodiment of a Data Command Center menu 2500 including a medical records dashboard 2530 implemented as a data interface to a medical record system in accordance with an embodiment of the present principles. The Data Command Center menu 2500 in the embodiment of FIG. 17 is designed to interact with a conventional EMR system although, as noted above, the Data Command Center menu 2500 of FIG. 17 can be used with other large data systems to present data to users in a meaningful way. In addition, the exemplary embodiment illustrates a Data Command Center menu 2500 for implementation in an Ophthalmology practice. Those skilled in the art will appreciate that the interface can be readily configured for other medical specialties. The Data Command Center menu 2500 is able to display data from multiple data sources in multiple different panels on a single interface. In the exemplary embodiment of FIG. 17, the Data Command Center menu 2500 provides a comprehensive overview of the patient's clinical and financial history as well as providing a means to quickly order tests while retaining the ability to see previous medical history. Clinical and insurance guidelines as well as preferred practices can be quickly accessible based on the patient's conditions, medications and procedures so that a medical care provider/user can readily provide optimal care and be compliant with medical and billing requirements. The medical care provider thus becomes a part of revenue cycle management for each patient in the medical care provider's practice.

A Data Command Center and medical records dashboard in accordance with the present principles can incorporate self-deleting staff messages that are presented to the Data Command Center. For example, a staff person can send a message about a patient to the medical care provider that appears in a display window in either of the Data Command Center menu 2500 and the medical records dashboard 2530 with a message such as "the patient has been waiting over an hour and is upset" or the "patient has previously filed a malpractice complaint" that do not become part of the patient's medical record. The message can be programmed to be deleted once the patient's visit is billed.

As depicted in the embodiment of FIG. 17, a user has the ability to search for patients at 2502, select different views of the data at 2504, add sticky notes at 2506, access user information at 2508, and logout at 2510. Immediately below that on the upper left-hand side of the Data Command Center menu 2500 is the Patient Information Bar 2512, which contains the patient's identifying information 2514 so the user knows they are looking at the correct patient record. The Patient Information Bar 2512 also notifies the user of patient's outstanding balance 2516. To the right of the Patient Information Bar 2512 is the Patient Insurance Bar 2518, which provides the patient's insurance information 2520, including the ID number 2522 for the patient's primary insurance. Below the Patient Information Bar 2512 is a collection of tabs 2524 displaying different sets of information about the selected patient. A different collection of tabs 2526 is found underneath the Patient Insurance Bar 2518. Under tabs 2524 is the Summary panel 2528 where the user can enter notes about the patient (e.g. patient did not show up for missed appointments).

The medical records dashboard 2530 (illustratively depicted as a Retina Flowsheet), is an encounter driven panel that summarizes key clinical and financial information in chronological or reverse chronological order at a glance, allows the user to order new Procedures and Imaging tests, and provides assistance complying with insurance regulations, as will be described in more detail below. Below the medical records dashboard 2530 is the Financial Flowsheet 2532 providing a summary of the financial information related to the patient and this is adapted to provide the user with the ability to drill down into individual transactions. On the right side of the medical Data Command Center menu 2500 are a series of vertical tabs 2534 that when individually clicked slide out to provide more information to the user. The Notes Tab 2536 expands to display patient notes, while the Alerts Tab 2538 expands to display patient alerts (e.g. patient's chart was requested by insurance company or sent for a second opinion). The Images Tab 2540 expands to display images for the patient and the Guidelines Tab 2542 expands to display clinical practice and insurance guidelines along with preferred practice patterns where applicable. On each tab, displayed next to the tab title is the count of the new items 2544 since the last time the user accessed the patient record. Once the tab is expanded, the new count will be removed because the user has seen the information. If important or critical data exists within the tab, a special alert icon 2546 is displayed on the tab (describe modules and details of this function). Once viewed, the alert icon 2546 is removed. As will become apparent from the following description, the layout of the Data Command Center menu 2500 permits access by the user to all of the relevant information within one click of the mouse and without having to steer to other screens that would take the user away from the Data Command Center menu 2500. For example, the information is either available in a display window, behind a tab, or available via a pop-up window; accordingly, the user does not have to leave the display screen to access the information (describe modules and details of this function).

Figure 18:
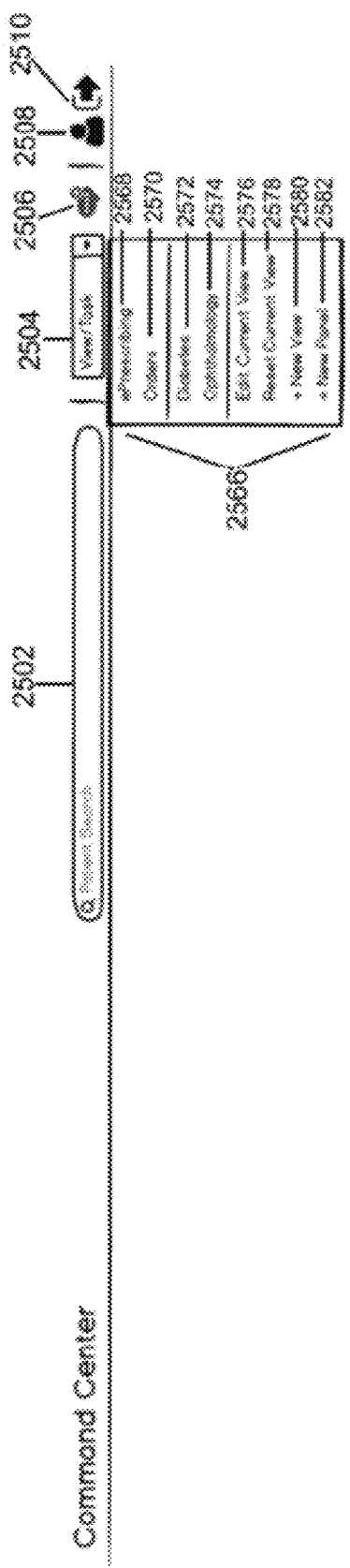
FIG. 18 depicts an embodiment of a User View control panel that can be part of the View/Task menu of the medical records dashboard of the Data Command menu of the embodiment of FIG. 17 in accordance with an embodiment of the present principles.

FIG. 18 depicts a USer View control panel 2566 that can be part of the View/Task menu 2504 of the medical records dashboard of the Data Command menu of the embodiment of FIG. 17 in accordance with an embodiment of the present principles. The user View control panel 2566 of FIG. 18 displays views for selection by the user. As illustrated, the user can select one of several Views 2568-2574. Views ePrescribing 2568 and Orders 2570 are examples of task-based views, while Diabetes 2572 and Ophthalmology 2574 are examples of condition or specialty specific views. In an exemplary embodiment, the system has several pre-configured views but more can be added over time by deploying new versions of the system or by user modification. The user can edit the Current View 2576, Reset the Current View 2578 to its default configuration, create a new View 2580, or create a new Panel 2582. If the user selects a new view from options 2568-2574, the screen layout is changed to reflect the selected view for the current patient. (describe modules and details of this function). Referring back to FIG. 17, it should be noted the dimensions of the different panels can be resized by changing the location of the vertical sliders 2584 and horizontal sliders 2586. This enables the user to control how space/area on the display is used for each panel. As the user adjusts the sliders 2584 and 2586, the dimensions are remembered so when the user returns to the view at a later time the system remembers the dimensions. The user also can reset the view to its default dimensions by clicking the Reset Current View 2578 option in the view control panel 2566. The entire view also resizes based on the dimensions of the user's monitor and the size of the browser display.

Figure 19:
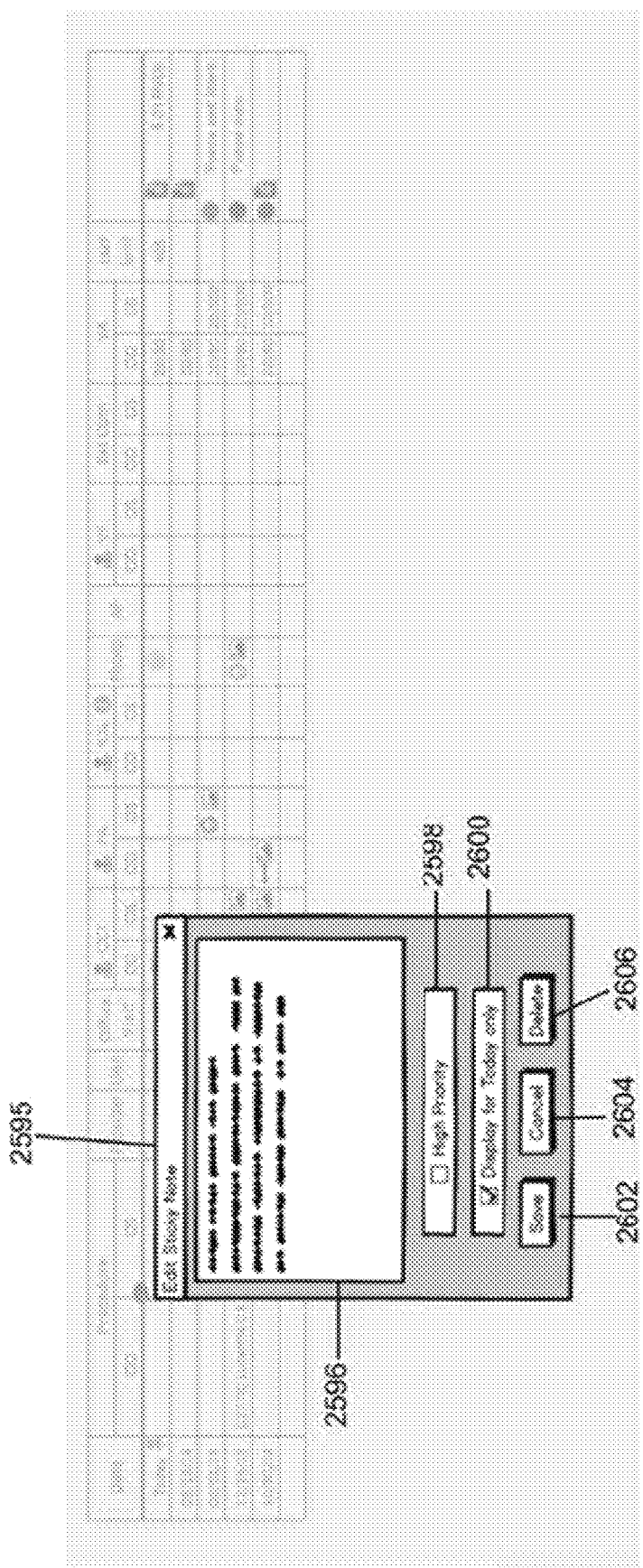
FIG. 19 depicts an embodiment sticky note panel of the Data Command Center menu of FIG. 17, which is activated when the add sticky notes icon in FIG. 17 is selected in accordance with an embodiment of the present principles.

FIG. 19 depicts a sticky note panel 2595 of the Data Command Center menu 2500 of FIG. 17, which is activated when the add sticky notes icon 2506 in FIG. 17 is selected in accordance with an embodiment of the present principles. As illustrated, the user may click and drag the icon 2506 to any location on the page and drop it where they want it placed. This allows the user to place the note in context of the information to which it refers. The icon 2506 then stays in place and is associated with dynamic data until deleted by a user or it expires based on the note settings. (describe modules and details of this function). When the icon 2506 is placed, the Edit Sticky Note control panel 2595 is displayed. The Edit Sticky Note control panel 2595 can also be displayed if a user selects the icon 2506. Once the Edit Sticky Note control panel 2595 is opened, the user can enter a note in field 2596, select if the note is high priority 2598, select if the note should only be displayed today 2600, in which case after the date it is entered the note will no longer display. The user can save the note by clicking the Save Button 2602 or cancel the action by clicking the Cancel Button 2604. The user can delete the note by clicking the Delete button 2606 at which point the action is confirmed before deleting. When a user moves the mouse over the note icon 2506, the note text is displayed next to it in a tooltip. The note icon is colored, e.g., black if it is not high priority and, e.g., red if it is high priority or can flash or be highlighted in any other manner. All deleted or expired Sticky Notes along with the location and duration where they are displayed can be preserved for purposes of legal discovery but may not be accessible to the user as a general practice.

Referring back to FIG. 17, when the user selects the user profile icon 2508, a panel (not shown) is presented to enable the user to edit typical user information including their name, address, phone numbers, email address and password. The user can also select their preferred email or phone number or other method for communications sent by the Data Command Center of the present principles. When the user selects the Logout icon 2510, if any data is not saved, the user can be prompted to save data before closing the system. If the user answers positively that they want to save unsaved data, the user is not logged out. Once all data is saved, the user is prompted to confirm their desire to logout. If confirmed, the user is logged out.

The Patient Information Bar 2512 illustrated in FIG. 17 displays high level information about the patient. The user can click on the Patient Information Bar 2512 and the Patient Information Panel 2610 shown in FIG. 20 is displayed underneath the Patient Information Bar 2512. Clicking the bar a second time or anywhere else on the page will close the Patient Information Panel 2610. The Patient Information Panel 2610 contains the patient's date of birth 2612, race 2614, phone number 2616, the date when the patient was first seen 2618, the referring physician 2620, and interesting facts to remember 2622. Information in the Patient Information Panel 2610 can be edited in place by clicking on the item to be changed. When clicked, the field will change to a text field allowing the value to be changed with a Save button displayed next to it (not depicted). Clicking Save will save the data. Clicking a Cancel button (not shown) will not save the data leaving the value unchanged and the control will revert to static text. Below these fields is a Revenue Summary 2624 for the patient. The Revenue Summary 2624 displays patient totals for each year 2626 as well as grand totals 2628 for the total amount billed 2630, amount paid by insurance 2632, amount paid by the patient 2634, amount written off 2636, and the adjustments 2638 for each year.

Figure 21:
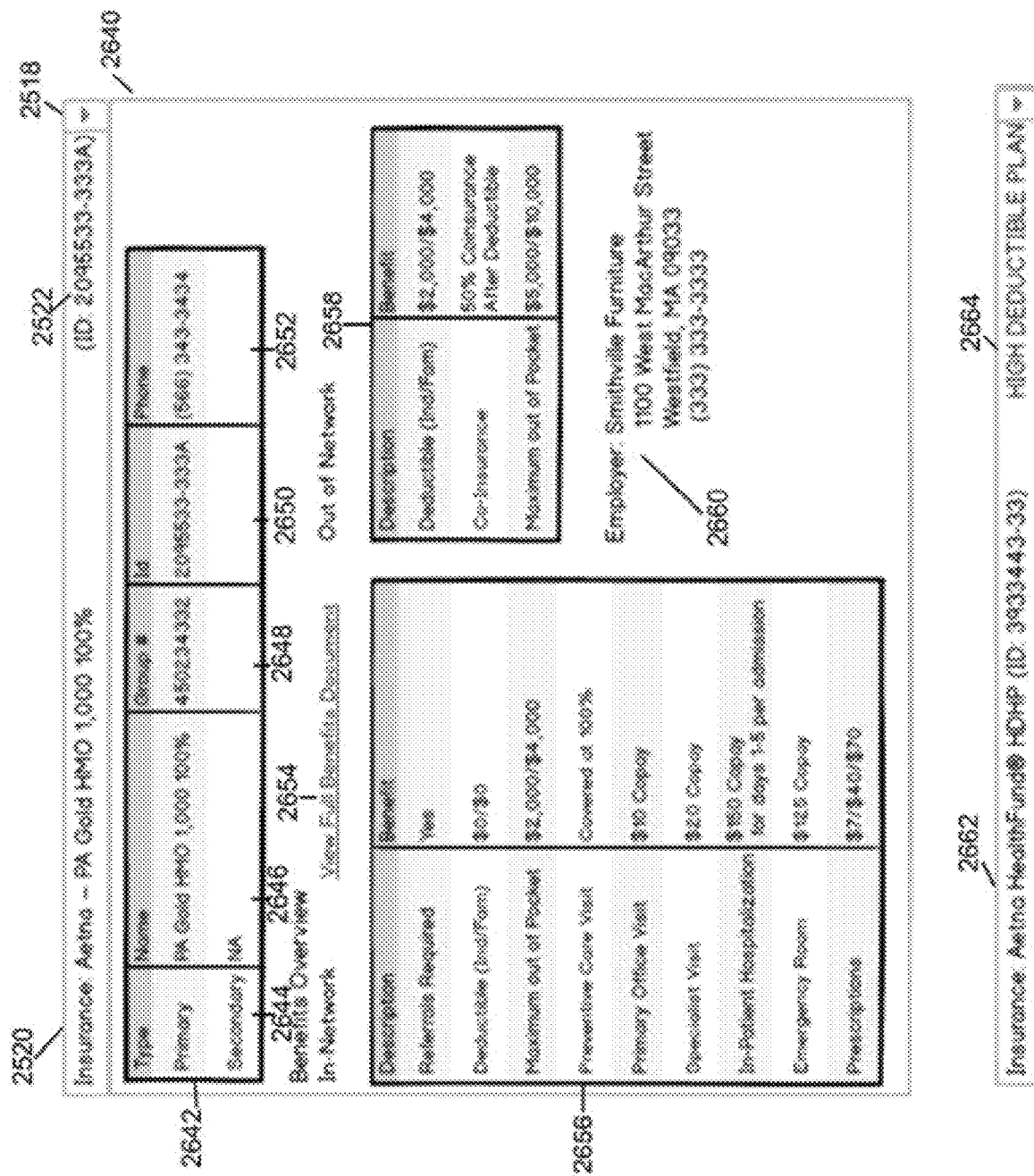
FIG. 21 depicts an embodiment of a Patient Insurance Panel of the Data Command Center menu, which can be activated when the Patient Insurance Bar is selected in accordance with an embodiment of the present principles.

To the right of the Patient Information Bar 2512 in FIG. 17 is the Patient Insurance Bar 2518. The user can click on the bar and the Patient Insurance Panel 2640 illustrated FIG. 21 is displayed underneath the Patient Insurance Bar 2518. Clicking the Patient Insurance Bar 2518 a second time or anywhere else on the page will close the Patient Insurance Panel 2640. The Patient Insurance Panel 2640 contains information about the patient's insurance 2642 including the type 2644, name 2646, group number 2648, insurance ID number 2650, and phone number 2652 for each insurance company. A link to the patient's benefit document 2654 is provided as well as an overview of the patient's in-network benefits 2656 and out of network benefits 2658 as provided by the patient's insurance company. The values illustrated as 2656 and 2658 are provided for example purposes and will vary based on the data provided by insurance companies. The patient's employer's address and contact information 2660 is also displayed for convenience. Item 2662 displays an alternative embodiment of the Patient Insurance Bar 2520. In this case, the patient has a high deductible plan and this fact is displayed at 2664 in red in the Patient Insurance Bar 2520 to be sure the physician is aware that, in this case, the patient has a high deductible plan.

Figure 22A:
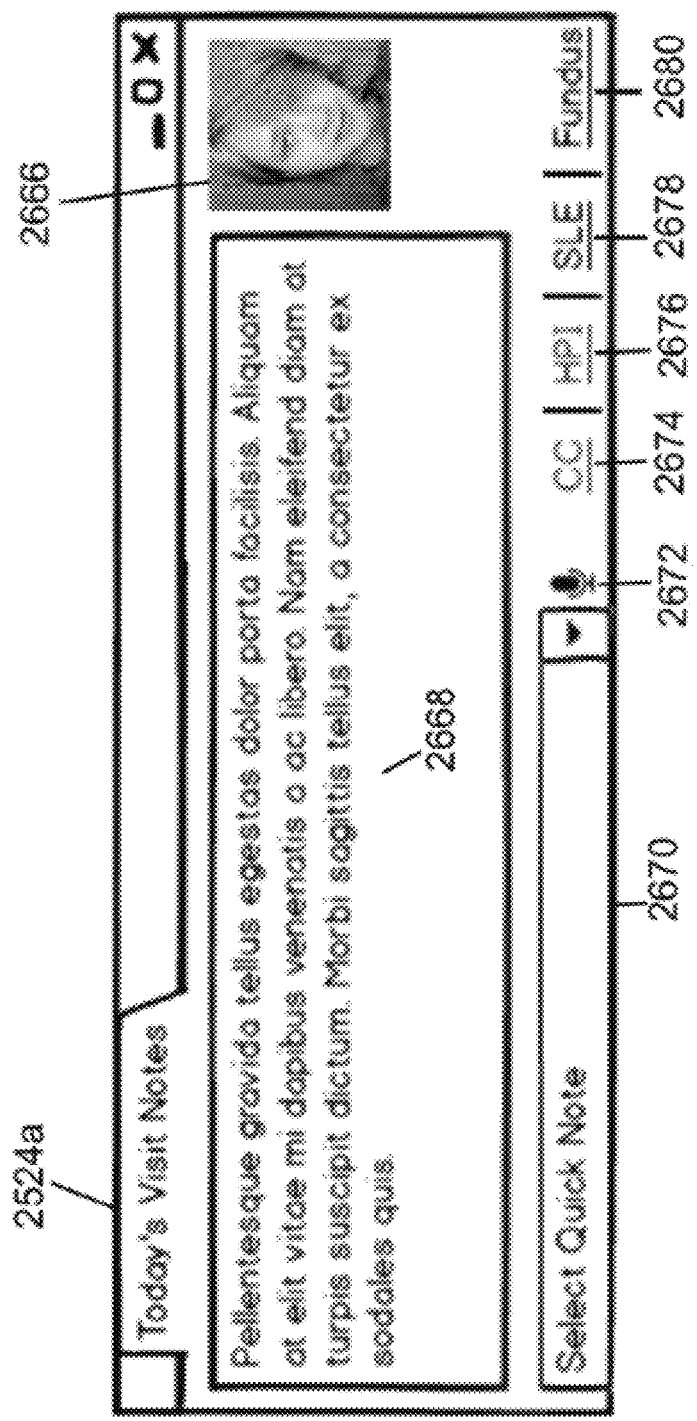
FIG. 22A depicts an embodiment of a Today's Visit Notes tab of the Data Command Center menu in accordance with an embodiment of the present principles.

FIG. 22A depicts an embodiment of a Today's Visit Notes tab 2524a of the Data Command Center menu 2500 in accordance with an embodiment of the present principles. The Today's Visit Notes tab 2524a as illustrated in FIG. 22A contains elements related to capturing information about notes specific to today's visit. The tab 2524 contains a photo 2666 of the patient, free form text notes 2668, a control allowing the user to select pre-configured notes 2670, an icon 2672 that triggers a dictation feature allowing text entry into free form text notes 2668 via voice recognition, and a set of links 2674-2680 that are reminders to complete important aspects of an encounter in the EMR. The patient image 2666 is imported from the EMR and text notes 2668 can also be imported from the EMR through the Command Center CCOW Implementation described below. Items 2674-2680 display the status of the chief compliant (CC) 2674, history of present illness (HPI) 2676, slit lamp exam (SLE) 2678, and Fundus photograph 2680. This status is also provided to the Command Center via the CCOW implementation. Items 2674-2680 are displayed in red until complete at which time they are displayed in black. Based on EMR access and functionality, items 2674-2680 are links back to the specific area in the EMR. In an exemplary embodiment, the physician may dictate or type notes into the Today's Visit Notes tab 2524a that automatically generates a letter to a referring physician or another physician alerting that physician about something important in the patient's medical history. Beneficially, the referring letter may be generated while the patient's medical history is on the display screen in the Data Command Center interface.

Embodiments of the present principles can further include a Problems tab, which displays a patient's problem list as imported from the EMR. The following fields can be displayed, including but not limited to; date entered, associated ICD10 code, body location, and diagnosis. The user can manually order the list in order of severity or importance by clicking and dragging the rows. A Sort by Date can sort the list in reverse chronological order and Sort by Importance can sort the list using the user's manual ordering. If the user has not adjusted the order of Problems, it will display in reverse chronological order. A default sort order can be by date, but, in some embodiments, the user's last selection is remembered and automatically selected when the user returns to the application.

Embodiments of the present principles can further include a Checkout tab used to determine when a patient should return to the practice. This can also be used for a return visit to a shared physician's office which would then also in some embodiments populate a shared care medical table that can be given to a patient for a future reminder of appointment. The Checkout tab can be configured to display a recommended clinical guideline based on Clinical Decision Support algorithms of the Data Command Center. A user can select a count and a period to generate a time period in which the patient should return. A search feature can implement basic type-ahead search and results listing enabling the user to select an item. In the case of either the search or a drop-down menu the selected item can be listed underneath. The user has the ability to delete the item by clicking an associated delete icon. The user can also enter a free form text note or use dictation by selecting a dictation icon 2702. When complete, the user can click a Save button to save the Checkout information and send it to the EMR or clear the information by clicking a Clear button.

Figure 22B:
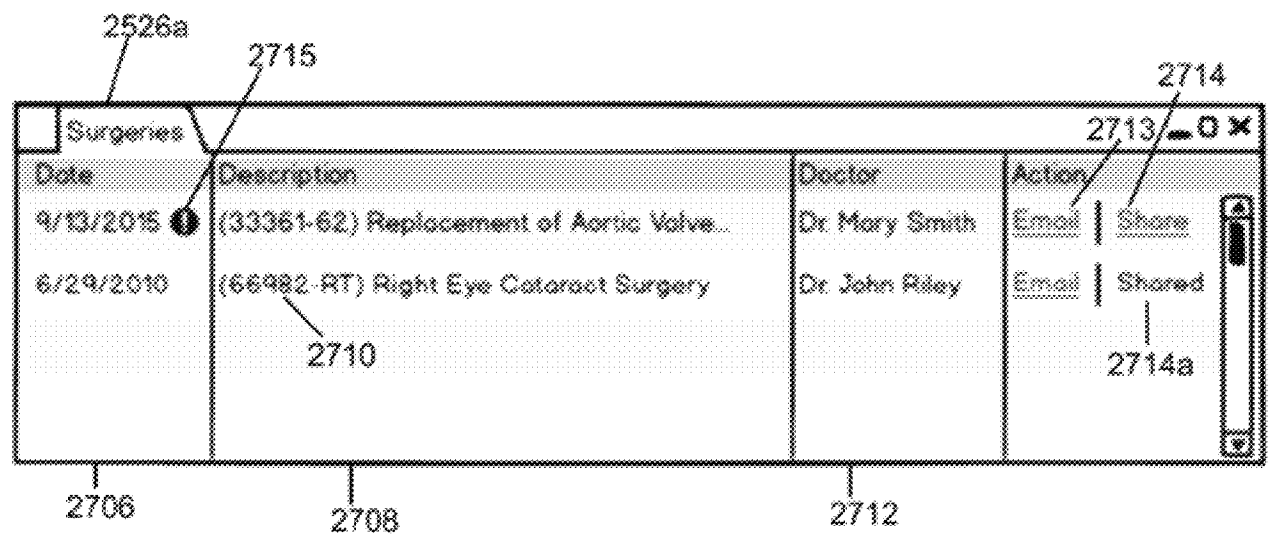

FIG. 22B depicts an embodiment of a Surgeries tab of a medical records dashboard of a Data Command Center in accordance with an embodiment of the present principles. The Surgeries tab 2526a as illustrated in FIG. 22B displays information about the patient's surgeries. The Surgeries tab 2526a displays the date of surgery 2706, the description 2708 including the billing (ICD10) code 2710, the primary physician 2712, and several actions including the ability to email 2713 or share 2714 the patient record with another physician. The shared notation 2714a signifies that the patient record has already been shared with the other physician. A notes column (not shown) displays the first few characters or words based on available space of an associated note. Moving the mouse over the specific note displays it in a pop up. In the case of some surgeries, a hospital or physician will not be paid if readmitted in 30 days. In these cases, if a surgery has been performed in the last 30 days a black circle with an exclamation point 2715 can be displayed next to the date. Moving the mouse over the icon displays a message stating how many days are left until the patient can be readmitted. An associated note can also indicate that the patient is participating in a capitated plan where anything the physician orders for the patient will not be reimbursed.

When a patient record is shared with another medical professional, if the professional does not have access to the D at a Command Center of the present principles, the other medical professional can receive an email to register for access to the Data Command Center. In some embodiments, if the professional does have an account but a new patient is being shared, the physician can receive an email notification. The new external user will only have access to the specific patients that are shared. Such sharing of patient medical records amongst the patient's physicians better enables the physicians to work together to follow preferred practice patterns for patient treatment as may be required by insurance companies and/or the government. This process is particularly helpful for managing patients with certain chronic diseases like diabetes in which a nephrologist, podiatrist, ophthalmologist, endocrinologist, and family physician need to see each other's results. Another example is shared care before and after cataract surgery where optometrists and ophthalmologist need to see each other's results.

Figure 23:
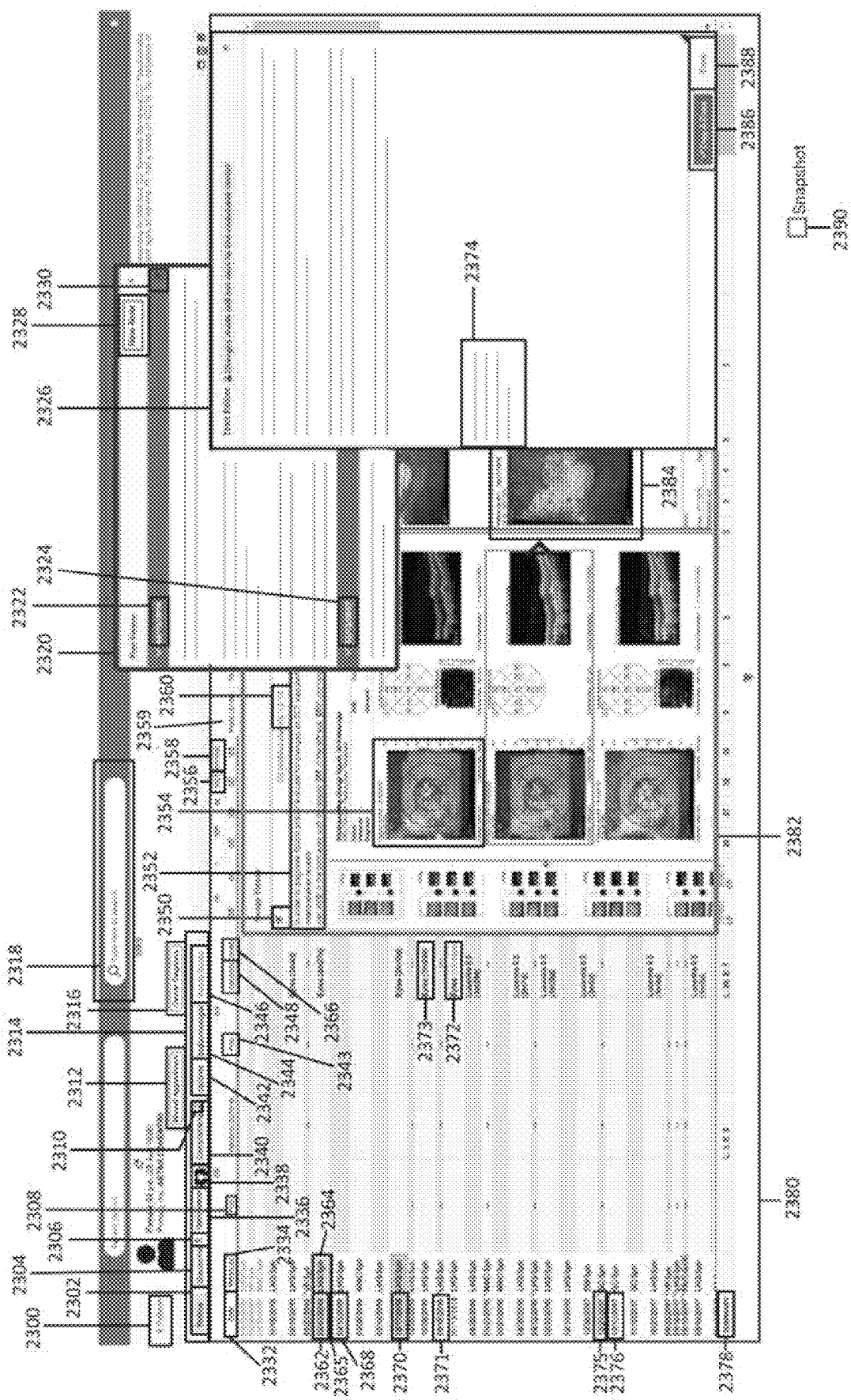
FIG. 23 depicts an embodiment of a medical records dashboard in accordance with another embodiment of the present principles.

FIG. 23 depicts an embodiment of a medical records dashboard in accordance with another embodiment of the present principles. In accordance with the present principles, the medical records dashboard of FIG. 23 is intended to provide and display to a user/medical care provider with all patient data/information necessary to perform accurate and efficient patient care using a single display. In the embodiment of the medical records dashboard of FIG. 23, panels 2380, 2382, 2326, 2320, and 2314 are some examples of different panels that can be moved around, toggled, simultaneously active (i.e., information from each panel can be assessed interchangeably without changing views) and displayed while critical information is viewed. In each column, what is an important data element over time can be followed as noted in column 2332. This enables a user to view the information vital to evaluation of their patients. In addition, in some embodiments, the medical records dashboard of FIG. 23 enables, direct access to patient data/information (no more than one click, one hover or selected directly in any manner). Some embodiments enable toggling by a mechanism such as alt-tab to gain access to underlying patient data/information or associated screen, tab or window. A user/medical care provider is able to decide what is important to pull up, directly to view, and can move the separate windows or other pop-ups out of the way to view important patient data/information underneath. In one embodiment, a Rules module, such as the Rules module 004 of the Data Command center 001 of FIG. 1, can be configured to know what information for the patient is important, what information must not be blocked, and when information is directly clicked and displayed, enables the movement of a needed columns into a set area on the screen where critical information remains in view. In the embodiment of FIG. 23, an example of two data sets that remain in view is depicted by column 2332, which includes the date of service when an encounter occurred with a patient, and column 2334, which displays the provider and location of encounter. In the embodiment of the medical records dashboard of FIG. 23, all of the other columns, such as column 2348, which depicts injections performed on a patient and/or procedures column 2308 can be moved or at least partially covered from display.

Alternatively or in addition, in some embodiments none of the patient data/information is completely blocked from view through the use of transparency viewing. In FIG. 23, block 2354 displays an image of an OCT that displays to a user/medical care provider if injections of the left eye are working. In the embodiment of the medical records dashboard of FIG. 23, column 2348 is viewed, not blocked, so the user can correlate when the injection (or any procedure of clinical information or diagnostic test) was performed and how it relates to the information that was pulled up, with direct access to any additional information. In some embodiments of a medical records dashboard of the preset principles, columns/windows/pop-ups of interest to a user can be moved to another portion of the medical records dashboard where no patient data/information or patient data/information of little or no interest to a user, exists. For example, if the user would also like to compare OCT data (2356) and in particular the left eye, as this example shows injections of certain medications (i.e. Eylea, Lucentis) and column 2348 over time, the user could simply drag 2356 or just 2358 (left eye) over to column 2308, because no data is present in that area of the medical records dashboard. Now all in one view and in a particular section of the medical records dashboard, exists all information that user would need to compare OCTs (2356) over time with injections (2348). In another example, when an OCT of left eye (2359) is being compared to when an injection is done in the left eye 2348, then 2359 (OS), can be moved, dragged or automatically be placed in location for example next to or in place of 2343. A user remains in control and able to move items out of view and by activating icon 2390 can take a snapshot (record) of a current arrangement of the medical records dashboard such that a record of the arrangement can be stored.

Simultaneously, a medical records dashboard of the present principles enables a user/medical care provider to recall and view plans of the past by activating a plan or A&P column or a particular plan in a column. The medical records dashboard of FIG. 23 enables current and past plans to be simultaneously displayed. As such, in context, a new note could be created in block 2328. A medical records dashboard of the present principles, such as the medical records dashboard of FIG. 23, enables images, procedures, dates of service, plan, or any other patient-related data/information, such as clinical measurement, i.e. VA (vision OD 3005—right or OS 3006—left), to be compared in context. By way of example, how a treatment is working as measured by an image, clinical parameter, or any other related data set can be interpreted and noted in the medical records dashboard in at least block 2352, which can be a new interpretation and can be edited by activating icon 2350. In one embodiment a plan viewer can be accessed by activating block 2328 and a new note or the editing of an old exiting note 2330 can be accomplished via a text editor window 2326. In the embodiment of the medical records dashboard of FIG. 23, a user/medical record provider is enabled to type or dictate a note 2374 accurately while relevant information is viewed in for example a window. Although in the embodiment of FIG. 23 the medical records dashboard only provides a user/medical care provider one means for editing notes, in some embodiments, a medical records dashboard of the present principles can provide a user/medical care provider many ways to edit notes.

In the medical records dashboard of FIG. 23, panel 2314 enables a user/medical care provider to select to view patient-related data/information from a number of different health care providers, such that patient-related data/information from every medical care provider that has ever cared for a patient can be viewed by, for example, all other specialties who provide care for that patient. For example in FIG. 23, a user/medical care provider can select to see patient care data/information related to a retina specialist 2302 and/or a glaucoma specialist 2304. In some embodiments, sharing of patient-related data/information from other users/medical care providers can require permission from at least one of the patient and the other user/medical care provider.

In the medical records dashboard of FIG. 23, the panel arranges patient data/information displayed in rows and columns. Users/medical care providers can have dashboards that are similar in display because the users/medical care providers charge, order, or perform similar CPT codes and often treat similar ICD diagnostic codes. Type of eye doctors are listed in order in this example # 2302 (retina), 2304 (glaucoma), 2336 (optometrist), and 2340 comprehensive eye doctor.

In the embodiment of the medical records dashboard of FIG. 23, the different users/medical care providers can let all the other providers know something is important by highlighting the tab 2302, 2304, 2342, 2344, and 2346 in the medical records dashboard view of other users/medical care providers. In such embodiments, a user/medical care provider is able to hover or otherwise active the highlighted tab to bring into view a message 2312 that can detail an important aspect of patient care for the corresponding other user/medical care provider. As depicted in FIG. 23, a current user/medical care provider is alerted that a patient has missed appointments with a corresponding user/medical care provider. In another example, a tab to a family doctor 2346 could light up or blink or in any way get a user's attention to indicate that an event is particularly important. In another example and as depicted in FIG. 23, when activated by a user/medical care provider, over a blinking endocrinologists tab 2344 can appear an alert window 2316 that can inform a user/medical care provider that a patient has received a diagnosis of cancer. In some embodiments, such important messages can be caused to display without requiring a user to activate or hover over a blinking or colored specialist tab.

There are situations where doctors, even if in separate practices and separate specialties, what they do can impact what another doctor does. By way of example, a retina surgeon injects many times in an eye, up to 12 times a year. But, clearly, if a family doctor discovers cancer that might change the frequency a retina doctor may want to inject. If a patient has a stroke, there are some research studies that suggest the medication that one doctor is using, in this case displayed 2348 injections in the eye, by a retina surgeon might increase the risk of another stroke. In some embodiments, a Rules module of the present principles, such as the Rules module 004 of the Data Command center 001 of FIG. 1, is configured to recognize such situations in which treatment by one doctor can effect a treatment by another doctor and, in such instances, the Rules module 004 is configured to generate an alert to be displayed to all users/medica care providers of such situations.

There are many different ways that embodiments of a medical records dashboard of the present principles can display important information. By way of another example, at any time, if an important event occurs in any encounter of any provider, the information can be inserted into a row in chronological order, where it makes sense, to show on a timeline that the event occurred. So, if it was discovered that the patient had a stroke on May 25, 2019, as depicted by number 2362 in FIG. 23, the initials of a caring provider can be displayed under the provider instead of a current provider as depicted in FIG. 23 by 2362 marked as 2364. The difference between providers can be highlighted in many different ways. If it's a provider that is not normally on a row on clinical panel 2380 or for example in this case, illustrated as an example of a retina doctor provider, then this new provider with a row can be highlighted or be a smaller row or a larger row. Also, instead of having the normal information in columns, because the other provider might not perform similar CPTs, instead in some embodiments there can be displayed, at the end of the row in a specially designated area for outside attachments or notes, information and it can be identified if the information is from a different provider.

In the embodiment of the medical records dashboard of FIG. 23, 2306 can include financial data, and in this example shows '$' sign. In such embodiments, access to financial data can be limited to only user/medical care providers credentialed to have access for instance only the users/medical care providers and colleagues in their practice can have access. In the embodiment of FIG. 23, icon 2338 can be activated to enable access to financial data to different users/medical care providers. For example, in FIG. 23 2336 is an example of an optometrist and 2338 depicts an icon with appearance of two faces which can represent sharing access.

In the embodiment of the medical records dashboard of FIG. 23, the glaucoma specialists has 2306 next to it, which can be used to launch a revenue cycle management (RCM), which is just one mechanism that any user/medical care provider can use to get more information in regards to their own practice's billing or any other information. By way of example, in the embodiment of FIG. 23, activating icon 2306 can enable access to a user/medical care provider to cost, charges, any financial information payments, rejections, to which the user/medical care provider has access. In one embodiment, the financial information can comprise a mirror-image of the clinical dashboard, so a doctor, by toggling back and forth, a transparency or overlay can be used to determine what was charged, paid, rejected, or authorized for every service performed. Alternatively or in addition, clicking on RCM on the same view or on the same scanning screen the information that is financial in nature can be displayed under, over, above, or superimposed, similar to transparent paper, with one embodiment, the billing function, being behind or lighter and clinical being darker or vice versa. In some embodiments, each row of panel 104 can have 2306 or 2338 next to every one of the tabs (actionable dashboards of different providers).

In some embodiments of the present principles, a user of a medical records dashboard is identified upon use. For example, in some embodiments, a user/medical care provider is required to provide identifying information when the user/medical care provider wants to use a medical records dashboard of the present principles. In some embodiments, a user/medical care provider can provide predetermined configuration information to identify how a medical records dashboard should be displayed for that particular user. For example, in some embodiments a Rules module, such as the Rules module 004 of the Data Command center 001 of FIG. 1 can have access to configuration information for a medical records dashboard provided by a user. In such embodiments, the Rules module 004 can be configured to arrange and cause a display of the medical records dashboard in accordance with the predetermined configuration information provided by the user, for example, upon initiation of the medical records dashboard by the user.

Alternatively or in addition, in some embodiments, a user/medical care provider can drag and drop portions of a medical records dashboard to arrange the medical records dashboard into an arrangement that is best for the user and/or the user's practice or in some embodiments, into an arrangement that is best for a particular patient. For example, an eye doctors might care more about a condition like diabetes, so any doctor that takes care of diabetes, endocrinologists, family doctors, kidney specialists, urologists tend to have more patients and procedures related to diabetes than other specialists, like a radiologist.

In the embodiment of the medical records dashboard of FIG. 23, when a user selects 2330, window 2374 is displayed for inserting notes, which can then be saved or closed by selecting 2386, or just closed by selecting 2388.

Tab 2348 of FIG. 23 is a tab for providing a user information regarding injections given to a patient, and tab 2366 of FIG. 23 can provide quick information about the injections including a number of injection or a type of the injections. In FIG. 23, 2372 depicts the identification of an example of an Eylea injection having been performed on Jul. 13, 2018, and it is red but can be highlighted in many different ways. In 2372 adjacent to Eylea it says 15 days which in this example count from the last time an injection in the eye was done. In the embodiment of FIG. 23, the medical records dashboard depicts that Lucentis was injected Jun. 28, 2018 which is only days earlier from a Jul. 13, 2018 injection of Eylea and the column counts in the embodiment from one to the other. In some instances, procedures of Eylea or Lucentis injections are allowed only every 28 days from each other. In embodiments of the present principles, a Rules module, such as the Rules module 004 of the Data Command center 001 of FIG. 1, can be configured to have access to information, including but not limited to, rules regarding how frequent or far apart medications can be given, and in some embodiments, the Rules module 004 is configured to cause the display of an alert if a user/medical care provider is attempting to order a procedure improperly or if procedures have already been performed improperly.

In the embodiment of FIG. 23, the panel can be used to display diagnostic test and images. In the embodiment of FIG. 23, when tab 2350 is selected an interpretation panel 2352 is opened, which can display notes of an interpretation of patient care that could be actually written on the day of treatment. Element 2354 of FIG. 23 is an image of a test performed on the patient.

In some embodiments, image icons, representative of results of test performed on a patient, can be selected to cause a display of an underlying corresponding image, such that a user/medical care provider can, in context, make a determination of the test and see the actual test while knowing whether there was a procedure or in this example a medication injection done, as depicted in 2366.

The embodiment of the medical records dashboard of the present principles of FIG. 23 illustratively includes a search box 2318. The search box of the medical records dashboard of FIG. 23 can be used to search for a doctor, a date, an image, particular procedures, a particular diagnosis, payment rejections and payments and substantially any other patient related data/information related to the medical records dashboard. In some embodiment, the medical records dashboard can instantly reconfigure based on what is searched and can be configured to display only the portions of the medical records dashboard for which search results are returned. Combinations of queries can be searched. For instance, show only the rows and dates of service with the diagnosis of diabetes that had injections of a particular medication, column 2348. Instantly, only the rows with injections with the patient having a diagnosis of a certain ICD like diabetes or if comparing a particular diagnostic test with a procedure and trying to correlate it, along with a clinical finding, the user could search "show me only the rows and dates of service where the vision was between 20/20 and 20/80" or "the pressure of 16 to 20 that also had the same date of service, a procedure in 2348 of Eylea and also had an OCT. The patient data/information associated with the medical records dashboard can then be searched and in some embodiments, only rows and columns of the medical records dashboard related to the search can be searched.

Figure 24:
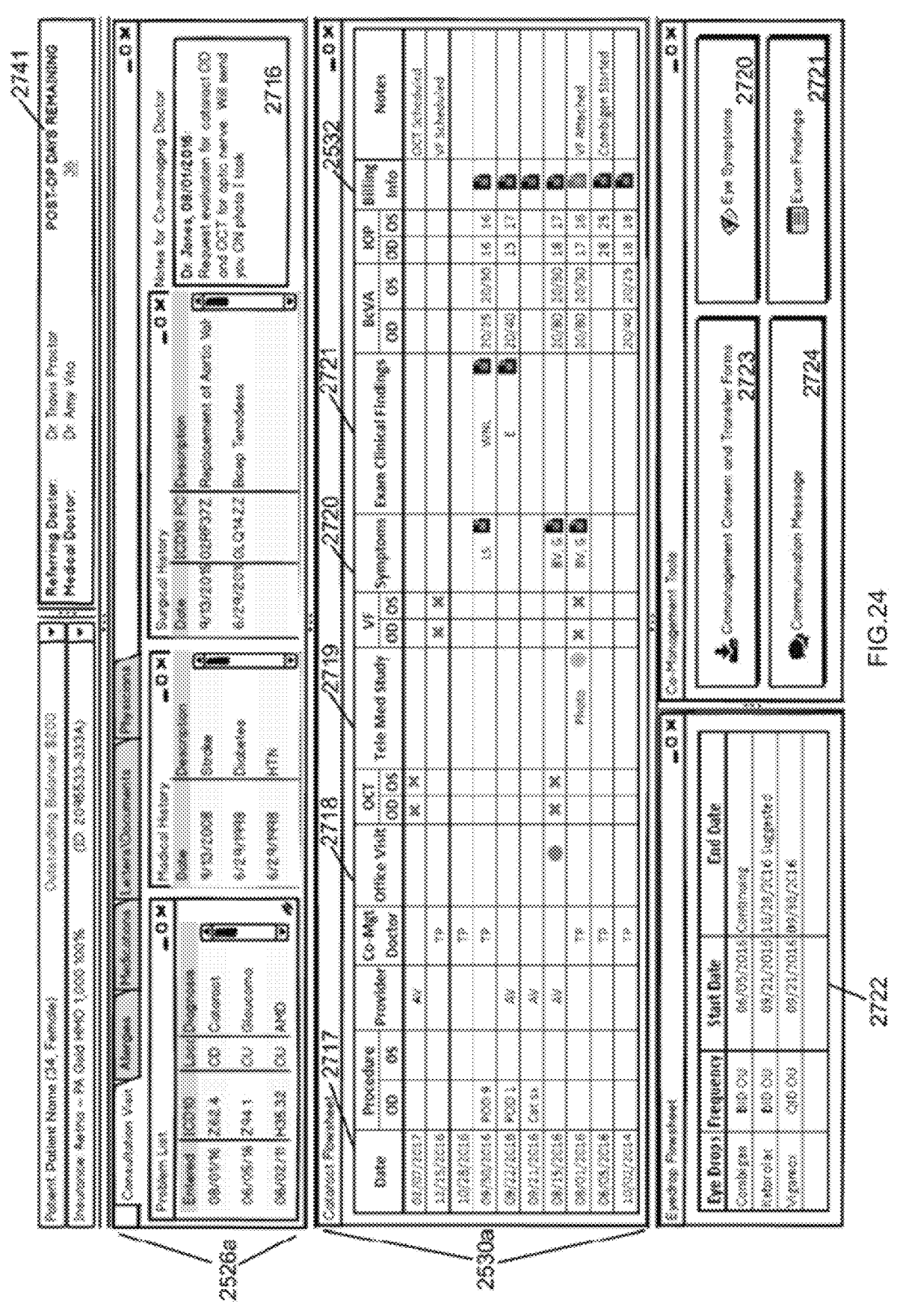

FIG. 24 depicts an embodiment of a co-managed medical records dashboard in the Data Command Center of the present principles in accordance with one embodiment. In the embodiment of FIG. 24, an optometrist and an ophthalmologist share (co-manage) a patient's cataract surgery then share treatment of the patient's glaucoma. A notes field 2716 in the Consultation Visit 2526*a* panel presents a mechanism to facilitate contextual content surrounding the co-managed procedure(s). A Cataract Flowsheet 2530*a* (purpose optimized dynamic panel) is presented with structured data elements designed to facilitate the identified procedure as conducted by multiple care givers. The Cataract Flowsheet 2530*a* (purpose optimized dynamic panel) is presented with structured data elements designed to facilitate the identified procedure as conducted by multiple care givers. The Cataract Flowsheet 2530*a* is arranged by interaction dates 2717 and tracks office visits 2718 (both scheduled and realized) including sending reminders to patients and alerts when an appointment is missed (not shown), provides means to review and issue concurrence or dissent with diagnostic tests 2719, a summary of symptoms 2720, and a summary of exam findings 2721. The Data Command Center keeps track of appointments between comanaging providers and when an appointment is not kept. The Data Command Center enables messaging to both providers as well as reminders through patient portal for patient to schedule appointment. (describe modules and details of this function). Where available, billing summaries 2532 are presented in the Cataract Flowsheet 2530*a* as well. Clicking the billing summary 2532 can open a new billing window to show billing details. Eye drops after cataract surgery and/or glaucoma treatment can be tracked on the Eye Drop Flowsheet 2722 (another purpose optimized dynamic panel).

In the embodiment of FIG. 24, there is panel of co-management tools that provide the user with a means to download relevant forms 2723, and to send direct messages to the co-managing physician using button 2724 to access a co-management message center. An indication of the number of postop days remaining 2741 may also be provided. All financial data in the system, including costs to patient, is compartmentalized such that no user can see financial details for users or organizations not authorized in accordance with applicable policies and law. In addition, any rows and columns of information can be programmed to include or exclude those data fields from either provider.

To co-manage a patient using the interface embodiment illustrated in FIG. 24, when a referring medical care provider outside the practice wants a consultation, he or she can connect to the practice they are referring to and send information by opening the Cataract Flowsheet 2530*a*. The referring physician can manually insert or auto-populate information from any previous visit of the patient and provide an annotation 2717 giving the reason for the consultation. When the receiving consultation medical care provider examines the patient, the Cataract Flowsheet 2530*a* is auto-populated with the medical care provider's findings. Co-management forms can be downloaded from the table at 2718 either at the time of the referral or after the consulting medical care provider fills out the paperwork and the patient signs a consent form by selecting co-management forms or by visiting the referring medical care provider's website. A message is sent to the referring medical care provider to open the Cataract Flowsheet 2530*a* and the consent or other forms can be clicked upon and the referring medical care provider can read or sign any forms needed. The "co-management consent" can change color or be distinguished in some other fashion when received back from the referring physician. Every time the surgeon sees the patient, the Cataract Flowsheet 2530a automatically includes the date and findings. Then, post-operatively the co-managing physician, or consultation physician or optometrist, when they see the patient in their office, auto-populates or fills out on the Cataract Flowsheet 2530a and shares any results.

In the embodiment of FIG. 24, notes may be communicated between the medical care provider by selecting "communication message" 2724 to determine if there is any information that needs to be shared for office visits. The date column 2719 and office visit column 2720 are tied together. Some of the columns are left blank until the patient actually shows up for a future visit. For instance, after a surgery or consultation, the consulting medical care provider, just as they would normally give an appointment card to a patient can actually give a co-management medical summary table where it shows the date of the future appointment at the referring or sharing medical care provider's office, and when that date arrives the patient is seen and everything is auto populated so the surgeon can see the results that the co-managing medical care provider found. The findings are auto populated by the optometrist/referring medical care provider/co-managing sharing medical care provider. If the appointment date is missed, the table can link up with the missing ticket report or send an alert to the patient themselves, the surgeon, the referring medical care provider, business managers or anyone else as appropriate.

In accordance with the present principles, shared medical care may be provided in management of common eye conditions besides cataracts, such as glaucoma. For example, an optometrist/general ophthalmologist can manage interval visits after the glaucoma specialist establishes a plan of care. That is, after initial consultation, the plan can be shared with the referring or co-managing medical care provider. At a subsequent examination, the referring medical care provider accesses patient data, executes the plan and enters the data into a Cataract Flowsheet and/or a Glaucoma Flowsheet. An alert can then be sent to the glaucoma specialist confirming that the action plan is being carried out. This facilitates can care for the patient according to the plan. The glaucoma specialist can follow up every year or two while sharing interval visits with the referring optometrist/general ophthalmologist. Multiple benefits of the concepts of the present principles include excellent care, appropriate supervision, reduced cost, improved quality of care of the patient without undue distance traveled. At any point of execution of the treatment plan, treatment can be altered based on clinical data available to the patient, glaucoma specialist as well as the referring medical care provider at all times. Of course, other fields of medicine and industry have similar examples. For example, orthopedic surgeons share care with podiatrists and family physicians share care with all medical specialists. A prime example is shared care with multiple healthcare providers caring for a patient with a chronic disease, state such as diabetes. One patient can have an eye doctor, podiatrist, primary care doctor, endocrinologist, nephrologist, dietician, exercise physiologist, all who need to share care. Different medical care providers can order the same or different tests. If they are in separate health systems, they may not know each other's diagnostic tests, but through the shared medical records dashboard of the present principles, medical care providers can avoid duplication of ordering tests, thereby, reducing costs and delivering better care. In some embodiments, different practices can identify what is important for them to know about a patient and information from the various respective medical records dashboards can be combined so that the identified important information can populate into a single dashboard.

For instance, a general ophthalmologist can have a complex case, for instance neovascular glaucoma, which can sometimes be associated with carotid disease. In some instances the ophthalmologist can send the patient to a glaucoma surgeon. In some embodiments, the pertinent portions of the medical records dashboard of the general ophthalmologist's can be displayed to the glaucoma surgeon, who now has the necessary information to care for the patient. The general ophthalmologist's medical records dashboard can be automatically populated to include the encounters between the patient(s) and the general ophthalmologist, so that medical care providers can, in real time, see what the changes in the patient's treatment are made. In some embodiments, other specialist can become involved in the treatment of a patient and can also have respective medical records dashboards that can share information with some or all of the other medical records dashboards of already involved medical care providers.

In addition, embodiments of the present principles as described above can be implemented to track laboratory tests. For example, every day a family physician and the patients they see can schedule radiological or diagnostic tests to be performed on a patient. A difficulty arises in keeping track of all the different referrals and/or the medications that are prescribed. A medical records dashboard of a Data Command Center of the present principles is able to keep track of every single diagnostic test, medication, or consultation that medical care providers prescribe. Using a medical records dashboard of the present principles, a medical care provider can sort a patient's medical history by date ordered, date performed, or by patient. The results can be automatically collated in rows and columns or in other orientations on a single display. As a patient's laboratory results come back, an entire group of patients that were seen in any time period or for a particular diagnostic test can be displayed in red on a medical records dashboard until the results are received. Upon receiving the test results, the test results can turn another color to indicate the receipt of the results. In such a way, a medical care provider is able to track all of their practice's patients and what the results are, when they are received. In some embodiments, a medical care provider can be alerted to abnormal results.

In embodiments in which the Data Command Center of the present principles, such as the Data Command center 001 of FIG. 1, enables the Co-Management of patient information available via a medical records dashboard of the present principles and as described above, Co-Management is meant to refer to referrals, transfers of care, and any instance of the sharing of patient data either unidirectionally, bidirectionally, or multi-directionally between a Data Command Center of the present principles and any source of patient data and the management of such data via, for example, a medical records dashboard in accordance with the present principles. In some embodiments, a Co-Management process of the present principles can be accessed utilizing a button, keystroke, or series of keystrokes, to initiate the Co-Management workflow.

In some embodiments, upon initiation of a Co-Management process of the present principles, a user can be given the option (i.e., via a prompt on a display) to select a predetermined template for performing Co-Management, to select to determine a custom configuration for performing Co-Management, or to select a hybrid configuration for performing Co-Management. For example, in some embodiments, a template or set of templates can be preconfigured and stored and accessible to at least one of the Rules module 004 and the Display module 006 of the Data Command center 001 for configuring the medical records dashboard and displaying the medical records dashboard in accordance with a selected, preconfigured template. In some embodiments, a predetermined templates can be preconfigured based upon conditions including but not limited to a specialty of at least one medical care provider/user, practice location of at least one medical care provider/user, the identity of at least one medical care provider/user and/or at least one patient, at least one patient's conditions, procedures performed on at least one patient, risk factors for at least one patient, diagnostic results of at least one patient, future orders for at least one patient, future appointments for at least one patient, data values recorded for at least one patient, data values not recorded for at least one patient, calculated data values for at least one patient and absolute values for display. That is in some embodiments, portions, columns, and/or rows of a medical records dashboard to be displayed or hidden can be determined based on a selected preconfigured template of a Co-Management process in accordance with the present principles.

Figure 25:
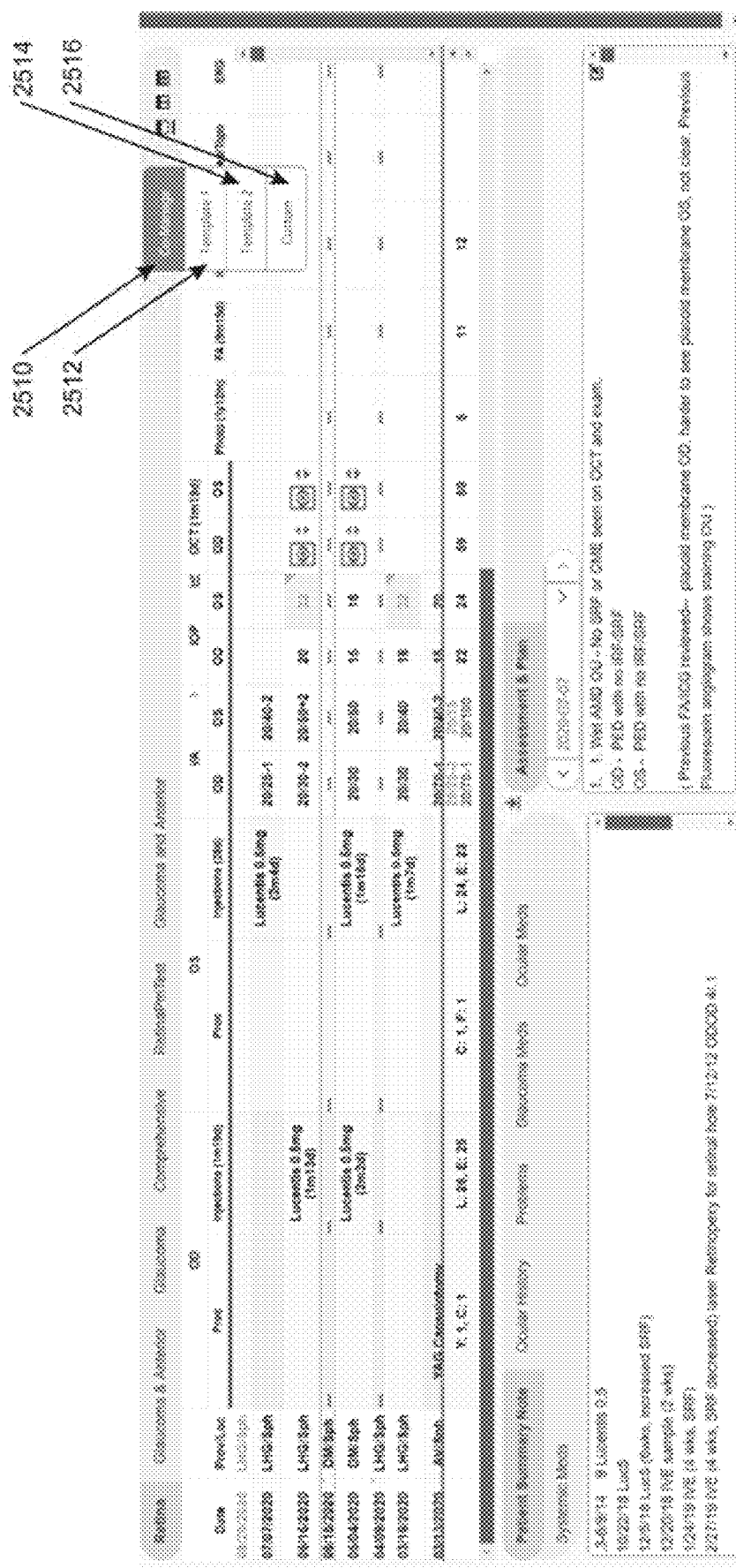
FIG. 25 depicts a medical records dashboard including an ability to launch a Co-Management process in accordance with an embodiment the present principles.

Alternatively or in addition, in some embodiments portions, columns, and/or rows of a medical records dashboard to be displayed or hidden can be determined based on a custom template of a Co-Management process in accordance with the present principles. In some embodiments a Co-management template of the present principles can be determined using, for example, a user interface of the computing device 200 of FIGS. 1 and 2. That is, in some embodiments a user interface can be implemented to create a custom Co-Management template in accordance with the present principles. For example, FIG. 25 depicts a medical records dashboard including an ability to launch a Co-Management process in accordance with an embodiment the present principles. In the embodiment of FIG. 25, the medical records dashboard includes a Con-Manage icon/button 2510 for launching a Co-Management process. Upon selection of the Co-Manage icon/button 2510, a menu is displayed on the medical records dashboard enabling a user to select between preconfigured templates, illustratively preconfigured template 1, 2512, and preconfigured template 2, 2514. In the embodiment of FIG. 25, the displayed menu further enables a user to select the ability to create a custom template 2516.

Figure 26:
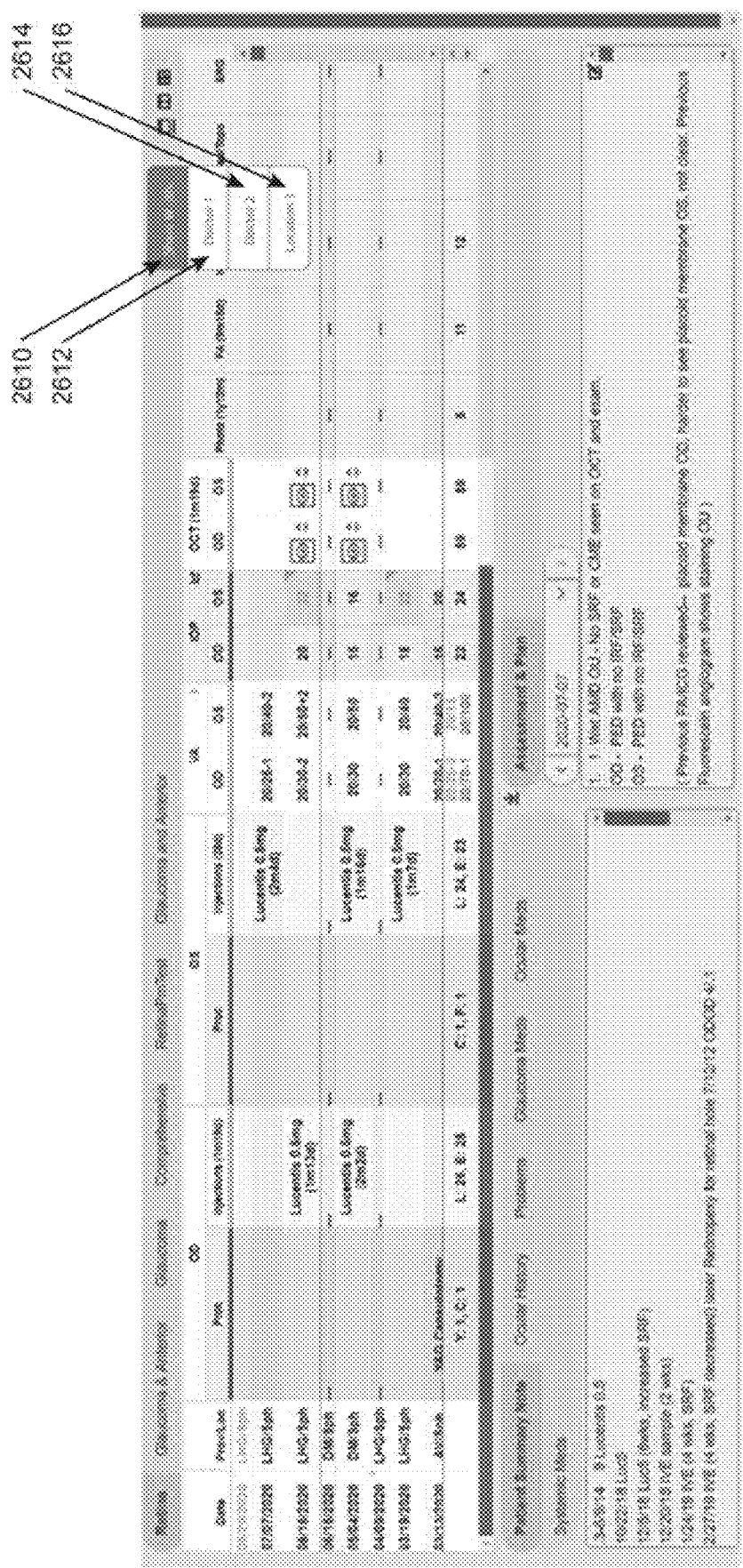
FIG. 26 depicts a medical records dashboard including a custom template creation process for co-management in accordance with an embodiment of the present principles.

Upon selection by a user of the custom template 2516, a process is initiated that, in some embodiments, enables a user to select portions, columns and/or rows of the medical records dashboard to display or hide. For example, FIG. 26 depicts a medical records dashboard including a custom template creation process for co-management in accordance with an embodiment of the present principles. In the embodiment depicted in FIG. 26, a user is given the ability to select, for example using a user interface (i.e., mouse, keyboard, etc.), portions, columns, and/or rows of the medical records dashboard to be accessible to (i.e., displayed to) a shared user(s) of a Data Command Center of the present principles, such as the Data Command center 001 depicted in FIG. 1, via a medical records dashboard in accordance with an embodiment of the present principles. Alternatively, a user can select, via the process described above, portions, columns, and/or rows of the medical records dashboard to be hidden from (i.e., not displayed to) a shared user(s) of the Data Command Center.

In some embodiments, information regarding preconfigured templates and custom templates for a Co-Management process in accordance with the present principles can be associated with at least one of the Rules module 004 and the Display module 006 of the Data Command center 001 of FIG. 1. For example, in some embodiments, information regarding preconfigured templates can be stored in a storage means accessible to the Rules module 004. As such, during a Co-Management process in accordance with the present principles, when a preconfigured template is selected by a user, the Rules module 004 can configure what portions, columns, and/or rows of the medical records dashboard are to be hidden or displayed based on the preconfigured template selected by the user. Such information can then be made available to the Display module 006, which causes the display or lack of display of portions, columns, and/or rows of the medical records dashboard based on the determinations and information associated with a selected, preconfigured template.

In some embodiments in which a user selects to create a custom template, upon selection of the creation of a custom template, the Rules module 004 can initiate a process, for example as described above with reference to FIG. 26, for enabling a user(s) to select to which to portions, columns, and/or rows of the medical records dashboard a user(s) is to be allowed or denied access. In some embodiments the Rules module 004 stores such custom template configuration selected by the user(s) in a storage means accessible to the Rules module 004 and the Display module 006. Upon creation of a custom template for Co-Management in accordance with the present principles, the Display module 006 can cause the display or lack of display of portions, columns, and/or rows of the medical records dashboard based on the determinations and information associated with a created, custom template.

In addition to the selection of a preconfigured template, for example preconfigured template 1, 2512, and preconfigured template 2, 2514, and/or the creation of a custom template, for example custom template 8716, in some embodiments, a Data Command Center of the present principles, such as the Data Command Center 100 depicted in FIG. 1, via a medical records dashboard, can enable a user(s) to select parameters that decide to whom/what/where to enable access or deny access to portions, columns, and/or rows of the medical records dashboard. For example, in the embodiment of FIG. 26 the medical records dashboard comprises a Share With menu 2610 enabling a user(s) to select to whom/what to enable access or deny access to portions, columns, and/or rows of the medical records dashboard. In some embodiments, the Share With menu 2610 can include predetermined selections such as a first doctor, Doctor 1 2612, a second doctor, Doctor 2 2614, and a location, such as the location of a medical practice, Location 1 2616. Alternatively or in addition, in some embodiments the medical records dashboard can enable a user(s) to input identifying information including but not limited to a specialty of at least one medical care provider/user, practice location of at least one medical care provider/user, the identity of at least one medical care provider/user and/or at least one patient, at least one patient's conditions, procedures performed on at least one patient, risk factors for at least one patient, diagnostic results of at least one patient, future orders for at least one patient, future appointments for at least one patient, data values recorded for at least one patient, data values not recorded for at least one patient, calculated data values for at least one patient and absolute values for display to identify to whom/what to enable access or deny access to portions, columns, and/or rows of the medical records dashboard.

Figure 27:
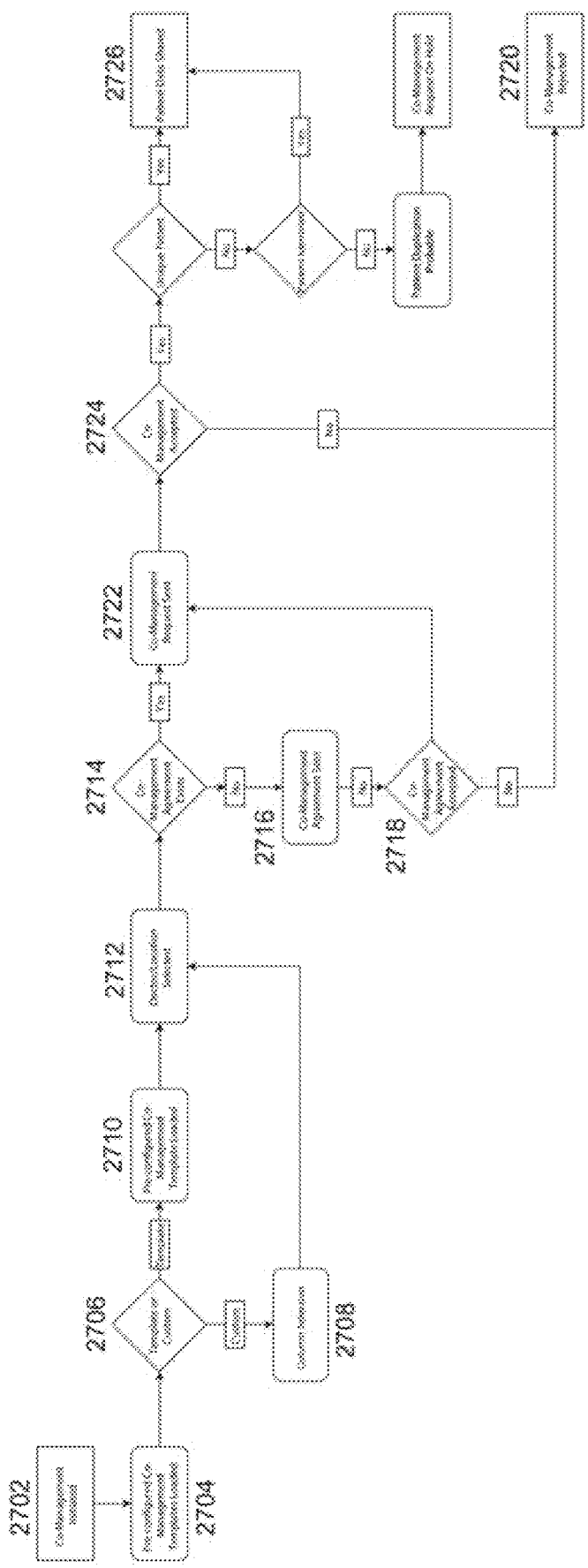
FIG. 27 depicts a workflow diagram of a Co-Management process in accordance with an embodiment of the present principles.

FIG. 27 depicts a workflow diagram of a Co-Management process in accordance with an embodiment of the present principles. In the embodiment of FIG. 27, the Co-Management process is initiated at 2702. At 2704 preconfigured Co-Management templates are all loaded. A selection is then made by a user(s) to use a pre-configured template(s) or to use the Custom option to create a Custom Co-Management configuration at 2706. If a user selects to use a pre-configured template, the selected pre-configured template is loaded at 2708. If a user selects to create a Custom Co-Management configuration, user selections for creating the Custom Co-Management configuration and determining which portions, columns, and/or rows of the medical records dashboard to which to grant or deny access are made at 2710. In the embodiment of FIG. 27, at 2712, a user selects select to whom/what/where to enable access or deny access to portions, columns, and/or rows of the medical records dashboard.

At 2714 it is determined if a Co-Management agreement exists. If no Co-Management agreement exists a Co-Management agreement is communicated to at least one other user at 2716. At 2718 it is determined if the communicated Co-Management agreement was accepted by another user. If the communicated Co-Management agreement was not accepted by another user, the Co-Management agreement is cancelled at 2720. If at 2718 it is determined that the communicated Co-Management agreement was accepted by at least one other user, a Co-Management request is communicated to an accepting user at 2722.

Referring back to 2714, if it is determined that a Co-Management agreement does exist, the process also proceeds to 2722 during which a Co-Management request is communicated to at least one user with which the Co-Management agreement exists. At 2724 it is determined if the Co-Management request was accepted. If at 2722 it is determined that the Co-Management agreement is not accepted, the Co-Management agreement is cancelled at 2720. If at 2722 it is determined that the Co-Management request has been accepted by at least one user, the patient data is shared at 2726 in the medical records dashboard in accordance with the pre-configured template selected or the custom configuration created and the whom/what/where selections made by a user(s).

Figure 28:
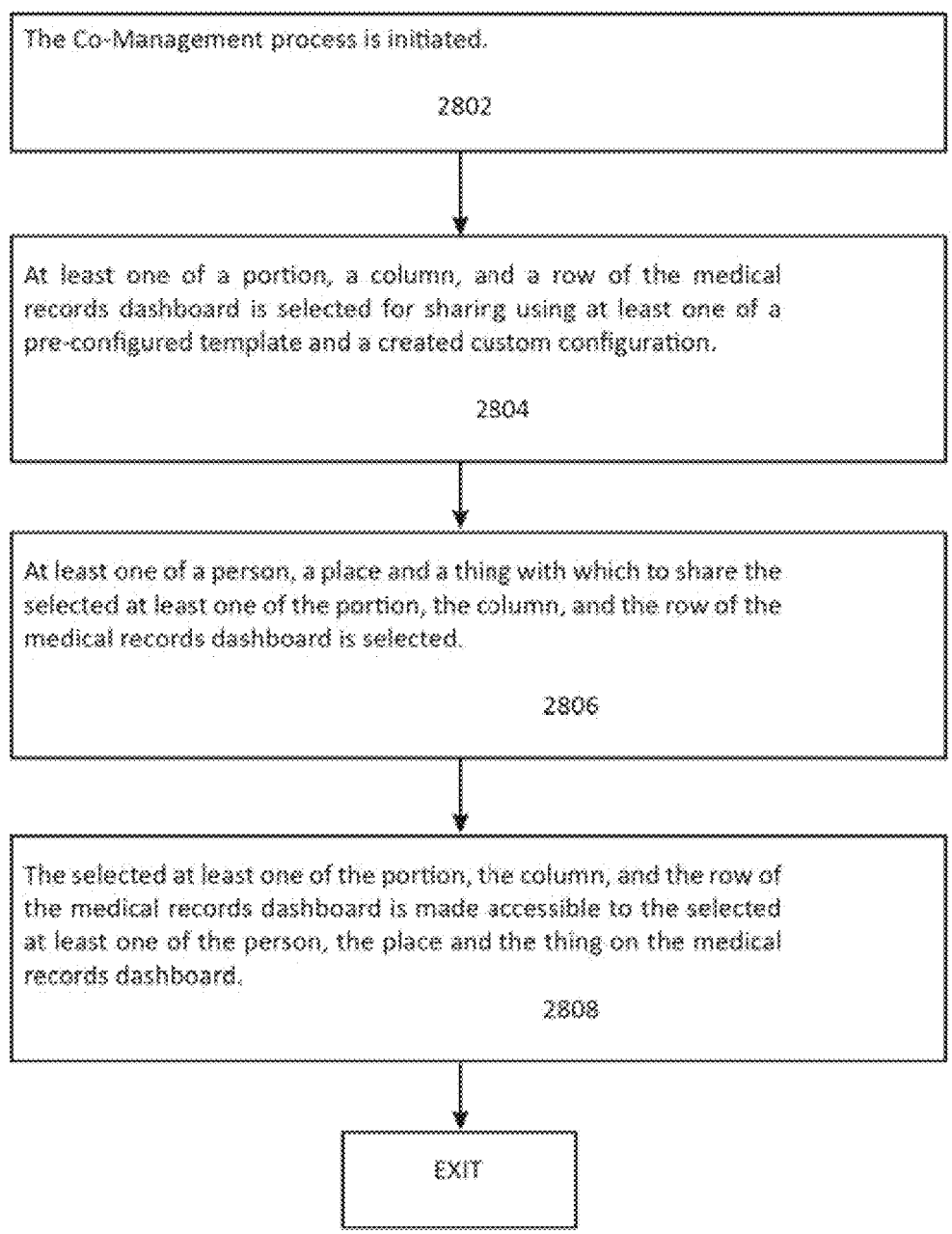
FIG. 28 depicts a flow diagram of a method for Co-Management of patient information in a medical records dashboard in accordance with an embodiment of the present principles.

FIG. 28 depicts a flow diagram of a method for Co-Management of patient information in a medical records dashboard in accordance with an embodiment of the present principles. In the embodiment of FIG. 28, the method begins at 2802 during which the Co-Management process is initiated. For example and as described above, in some embodiments the medical records dashboard can include a Co-Management icon/button for initiating a Co-Management process in accordance with the present principles. The method can proceed to 2804.

At 2804, at least one of a portion, a column, and a row of the medical records dashboard is selected for sharing using at least one of a pre-configured template and a created custom configuration. The method can proceed to 2806.

At 2806, at least one of a person, a place and a thing with which to share the selected at least one of the portion, the column, and the row of the medical records dashboard is selected.

At 2808, the selected at least one of the portion, the column, and the row of the medical records dashboard is made accessible to the selected at least one of the person, the place and the thing on the medical records dashboard. The method can then be exited.

In some embodiments, the Co-Management Workflow can exist in a single, unidirectional state, whereby the party that initiates the Co-Management request shares data with the recipient, but the recipient does not reciprocate sharing of patient data. In another embodiment, the party that initiates the Co-Management request shares patient data with the recipient, and the recipient initiates a Co-Management request to the party that initiated the initial request, thus data is shared bidirectionally. In another embodiment, several parties initiate Co-Management requests, and each party shares data with each other party, in a multi-directional state. At any point, a Co-Management participant my opt to no longer share data with one or more recipients, at which point data sharing and the Co-Management workflow reaches a logical end.

In some embodiments, upon initiation of Co-Management, a record of the Co-Managed patient is recorded, including all relevant Patient Identifiers from all parties involved in Co-Management. Alternatively or in addition, upon initiation of Co-Management, shared configurations are recorded. Shared configurations can be used to determine what data from each party can be viewed within a recipient's medical records dashboard in accordance with the present principles.

In some embodiments, a source of patient data can exist within storage means associated with respective Data Command Centers of users participating in the Co-Management of the present principles. In such embodiments, shared data can consist of a series of links or cached data in the respective Co-Management databases. Links or cached data can be updated upon any change in source. Additionally in some embodiments, data can be recorded within a Co-Management database as well as a database/storage means associated with a participating user's respective Data Command Center, the data including, but not limited to, audit logs of Co-Management Workflow interactions, Messaging between users, file and document sharing between users, and notifications and/or triggers for automated tasks. It should be noted that, in some embodiments, a Co-Management Workflow in accordance with the present principles can be non-linear, can be automated in whole or in individual or groups of steps, and algorithms can intelligently update, flag, or otherwise override certain steps of the Co-Management Workflow.

In one example of a Co-Management Workflow in accordance with the present principles, a primary care physician (PCP) can initiate the Co-Management Workflow for a single patient having multiple Specialists. Each Co-Managing Specialist can opt to Co-Manage with one of more PCPs and Specialists. In some embodiments, the Co-Managed patient data would not be shared further than one logical step, thus a PCP can share their patient data with Specialist 1, who then shares their patient data with Specialist 2, but the PCP's patient data would not be shared with Specialist 2 unless the PCP takes action to initiate Co-Management with Specialist 2.

In a second example, a doctor can initiate a Co-Management Workflow of the present principles with a patient during a Transfer of Care, in which case, the patient's data is shared unidirectionally, and the recipient is not expected to share data back with the initiating doctor, nor is there an expectation that the patient would return to the transferring doctor.

In a third example of a Co-Management Workflow of the present principles and with the context of a hospital and several physicians, as is normally the case in patient care, any number of Co-Management Agreements and Workflows can be in place to allow for patient data sharing between any to all recipients of a Co-Management Request. This configuration can include unidirectional sharing, bidirectional sharing, and multi-directional sharing of patient data in accordance with the present principles.

In co-management, where different practices share information about the same patient, it is critical to identify that the patient that is being shared is in fact the same person. There can be dozens of John Smiths and systems cross-reference by looking at the last name, the age, the gender, the zip code and perhaps the home address. But still, there can be confusion between patients. In medicine you can take no chances that you confuse one patient with the other and when patients travel from different offices or different EMRs and computer systems, the possibility of confusion is present.

In some embodiments, the Data Command Center of the present principles, such as the Data Command center 001 of FIG. 1, enables unique patient identification by incorporating patient medical history information. Current methods for identifying patients include matching Social Security Numbers (SSN) and Driver's License Numbers, where available. However, as privacy became more of a concern in the modern digital age, such data is becoming less available to medical care providers and their Practices. In addition, other methods for identifying patients can include identifying patients via First Name, Middle Name or Initial, Last Name, Age, Sex, Address, City, State, and Zip Code. Such information, however, is subject to flaws of human error, such as typos, human choice, such as a patient offering a nickname instead of the accurate name on a birth certificate or other identification. In addition, even having accurate patient information, it can still be difficult to distinguish between two people having the same name. Using such current methods, multiple systems are only able to match patients whose information is listed exactly the same in the multiple systems, a limitation which requires human intervention and prevents full automation of the process.

A subset of data exists within the Medical Community, as mandated by Meaningful Use 2014 and 2015 EHR Certification requirements specified in 45 CFR § 170.102, known as the Common Clinical Data Set (CCDS). The CCDS consists of patient information including, Patient Name, Sex, Date of birth, Race, Ethnicity, Preferred language, Smoking status, Medical Problems, Medications being taken, Medication allergies, Laboratory test(s) having been performed on the patient, values of the Laboratory result(s), Vital signs, Procedures, Care team member(s), Immunizations, Unique device identifier(s) for a patient's implantable device(s), Assessment and plan of treatment, Treatment Goals, Health concerns and the like.

CCDS was developed to encourage interoperability through the exchange of a common data set and is routinely shared between practices by means of the Direct Messaging Exchange, a secure messaging system by which Continuity of Care Document (CCD) or other document conforming to the Clinical Document Architecture (CDA) as defined in the 2014 and 2015 Certified EHR requirements. This is the current standard for Clinical Data transport between EHRs, thus between practices. The future requirement, Fast Healthcare Interoperability Resources (FHIR), expands on the clinical data set to include more discrete data points.

In accordance the present principles, the inventors propose to incorporate such additional data, such as the data supplied through the CCDS, to accurately identify unique patients using a combination of techniques including but not limited to a Common PII Matching technique, a Problems, Allergies, and Medications technique, a Doctors, Locations, and Procedures technique, and CCDS data technique.

In a Common PII Matching technique, none of the PII data may be valid given name changes, nicknames, and misspellings, as well as marriage and legal name changes, addresses and phone numbers change over time, and the increasing reluctance of patient and practice alike to maintain or share key identification numbers. At best, every data point would need to match exactly to ensure the closest match, but can still fall short in the cases of same names such as in the case of George Forman's eight sons all named George Edward Foreman, if date of birth and suffix data was not present. Twins could make identification even more difficult. As evident, the Common PII Matching technique may not be reliable on its own for identifying unique patients.

In a Problems, Allergies, and Medications technique, a commonly shared data set which includes key conditions (Problems), allergies to certain medicines (Allergies), and specific medications (Medications), is compared to determine a profile of a patient which offers an additional level of accuracy by taking a loose match from PII and determining if that patient also has the same list of Medical Problems, Allergies, and Medications in a system for comparison. The likelihood that two people within similar PII, or lacking key aspects of PII, would also share the same Problems, Allergies, and Medications is a significant reduction in ambiguity. For instance, George Foreman's 3rd son may share certain genetic predispositions to Medical Problems and even share Allergies with a $1^{st}$ son, but the likelihood that George Foreman's two sons would have been prescribed the same exact Medications for these and any other Problems they have is minimal.

In a Doctors, Locations, and Procedures technique, information from a document complying with the CCDA can be used for identifying a unique patient. For example, each CCD, or document complying with the CCDA, is required to have specific information in the Header of the document denoting the Care Provider, Date, and Location. The body of the document contains Procedures and relative Dates. The high accuracy enabled when comparing patients' Doctors, Locations, and Procedures is a product of the inability for a Doctor to see more than one patient at the exact same time, the unlikelihood of that even if the doctor saw more than one patient at the same time, and at the same location, the Doctor still would have little ability to perform the same procedure at the same time on more than one patient.

In a CCDS data technique, additional Data from the CCDS, when available, offers increased accuracy in patient identification and matching. That is, comparing patient information including at least Patient Name, Sex, Date of birth, Race, Ethnicity, Preferred language, Smoking status, Medical Problems, Medications being taken, Medication allergies, Laboratory test(s) having been performed on the patient, values of the Laboratory result(s), Vital signs, Procedures, Care team member(s), Immunizations, Unique device identifier(s) for a patient's implantable device(s), Assessment and plan of treatment, Treatment Goals, Health concerns and the like, among different patients, greatly increases the accuracy of unique patient identification.

In some embodiments of a Unique Patient Identification method of a Data Command Center in accordance with the present principles, a Unique Patient Identification algorithm collects every available Identification Point, validates the points for presence of data, and assigns each Identification point a level of accuracy as it pertains to Patient Matching. Presence of data points with High Accuracy are prioritized and validated. Each Exact match is scored for accuracy. Each Likely Match is appropriately scored for accuracy. Each data point with no matching counterpart is negatively scored. Presence of data points with Moderate Accuracy are then prioritized and validated. Each Exact match is scored for accuracy. Each Likely Match is appropriately scored for accuracy. Each data point with no matching counterpart is negatively scored. Moderate accuracy data points are scored lower than High accuracy data points. Presence of data points with Low Accuracy are then prioritized and validated. Each Exact match is scored for accuracy. Each Likely Match is appropriately scored for accuracy. Each data point with no matching counterpart is negatively scored. Low accuracy data points are score lower than Moderate accuracy data points.

Upon gathering and analyzing all available data for Unique Patient Identification, scores are tallied and compared to an acceptable Matching Threshold. In some embodiments of the present principles, the Matching Threshold is configured to clearly exceed a matching accuracy of current patient identification techniques with the inclusion of far more points of identification to compare. In some embodiments, the matching of the present principles can occur without the requirement of matching on current PII data. For example, George Edward Foreman IV may have been staying with a friend in Florida when he visited a doctor. Not wanting to be identified as the son of the famous boxer, he purposely listed his name as G. Foreman and address as the place he was staying. Date of birth may have been left blank. A positive identification can still be made, in accordance with the present principles, if the clinical data supplied matches with a high enough degree of accuracy clinical data stored for George Edward Foreman IV, such as the unique identifier on his knee replacement or the fact that a large number of Doctors, Locations, Procedures, Problems, Allergies, Medications, and Lab Results are found to be matching, while the name, address, and date of birth have non-matching counterparts.

A Unique Patient Identification algorithm of the present principles can reach a logical end when a positive match is determined, or no positive match can be made. In some embodiments, should no positive match be made, the patient and possible matches can be flagged for human intervention.

Figure 29:
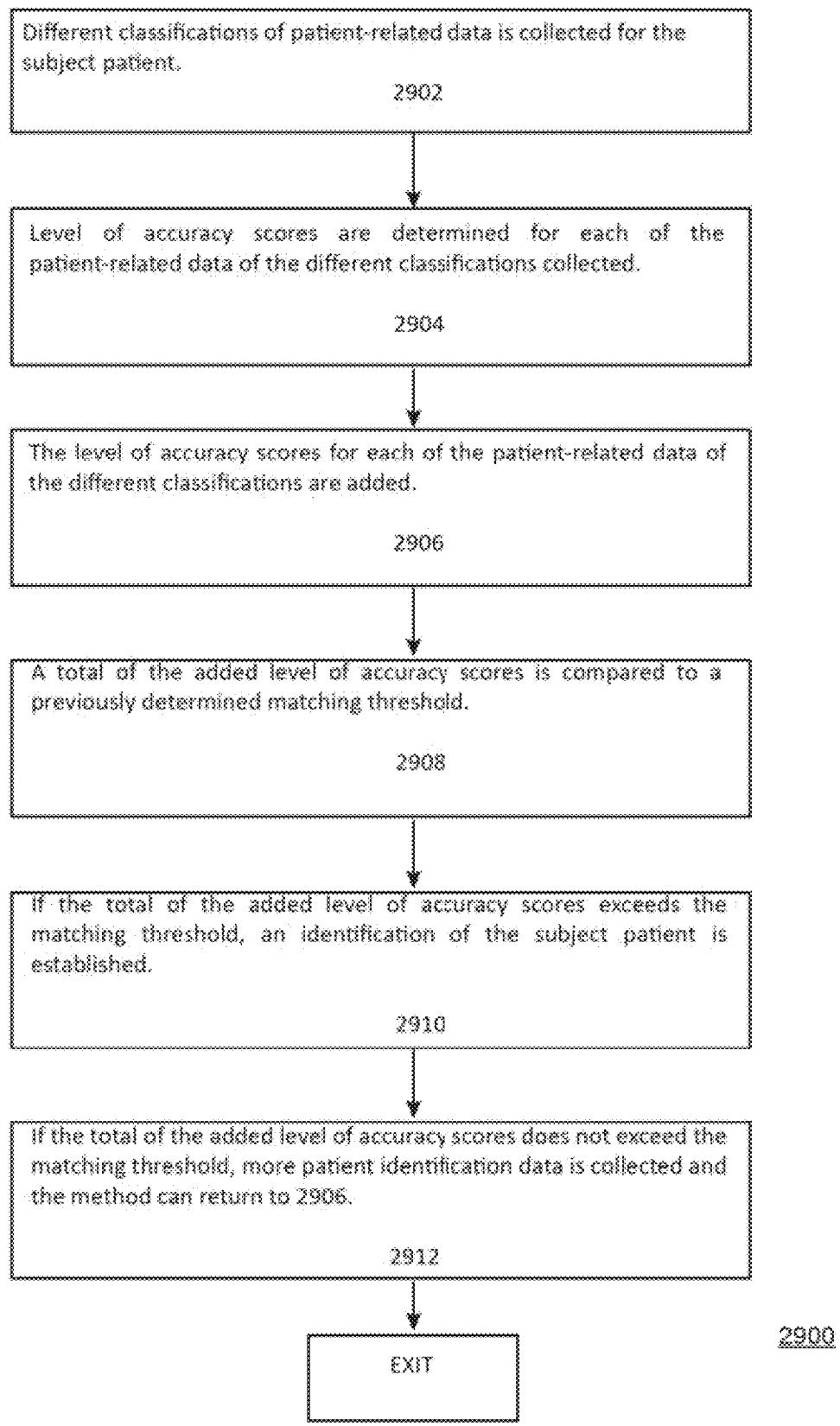
FIG. 29 depicts a flow diagram of a method for Unique Patient Identification in a Data Command Center in accordance with an embodiment of the present principles.

FIG. 29 depicts a flow diagram of a method for Unique Patient Identification for a subject patient in a Data Command Center including patient-related data received or derived from at least one patient database in accordance with an embodiment of the present principles. The method 2900 of FIG. 29 illustratively begins at 2902 during which different classifications of patient-related data is collected for the subject patient. For example and as described above, in some embodiments, data from the Common Clinical Data Set and other sources can be collected to be used in patient identification techniques of the present principles. The method 2900 can proceed to 2904.

At 2904, level of accuracy scores are given for each of the patient-related data of the different classifications collected. The method 2900 can proceed to 2906.

At 2906, the level of accuracy scores for each of the patient-related data of the different classifications are added. The method 2900 can proceed to 2908.

At 2908, a total of the added level of accuracy scores is compared to a previously determined matching threshold. The method 2900 can proceed to 2910.

At 2910, if the total of the added level of accuracy scores exceeds the matching threshold, an identification of the subject patient is established. The method 2900 can proceed to 2912.

At 2912, if the total of the added level of accuracy scores does not exceed the matching threshold, more patient identification data is collected and the method 2900 can return to 2906. The method 2900 can then be exited.

It is critical for a medical care provider to know what medications a patient has ever taken or is currently taking, what the frequency is, why the medication was taken or discontinued and reasons for switching to another medication. There is currently no medication management tool that visually correlates the clinical parameters or disease state findings that the medication is prescribed to have an impact on. A Data Command Center of the present principles via at least one of a medical records dashboard and a Medications Management chart or tool in accordance with the present principles enables a user to correlate frequency, amount and types of medications taken to enable the user to visualize how that medication affects the parameters reviewing modulation such as blood pressure, eye pressure, weight, heart rate, etc. and corresponding it to when the medications were taken to see if there is a cause and effect. There is no system that can also correlate and display on a view surgical intervention, an injection or any other intervention and see how these additional factors correlate with timing of medication taken and how all this impacts clinical finding, measurements, disease progression and symptoms. A Data Command Center of the present principles enables a user to visually correlate diagnostic tests and images that may show how all these treatment modalities result in changes or lack thereof on lab results, imaging, etc. For example and as enabled by embodiments of the present principles, if a patient is being treated for cancer and chemotherapeutic medication can be seen with direct access on one screen with x-rays taken over time showing changes in size of a tumor or mass along with the labs or clinical symptom changes all in context of when surgical or radiation therapy intervention was performed, enables medical care providers to efficiently and accurately make medical decisions.

Embodiments of a Data Command Center of the present principles can also be linked to a Pharmaceutical system or other provider of prescribed medication (i.e., E-prescribe or a similar system) such that a medical care provider is enabled to accurately track when medication was actually received by a patient. It can be very difficult if not impossible with current systems for a medical care provider to know when a medication was actually received by a patient. That is, medical care providers often rely on scribes to write prescriptions and when patients call to refill the medication, often it is not the medical care provider who prescribes the refills of medication but an assistant who does so. Even further, just because a medical care provider orders a drug for a patient that does not mean the patient actually went and got it filled or that the medication was taken as prescribed. To further complicate matter, patients can be given different medication than prescribed by the medical care provider because a generic drug instead of a brand drug could have been given.

Embodiments of a Data Command Center of the present principles can also be linked to home monitoring devices or system for being able to more accurately determine when medication was actually taken by a patient. That is, just because medications are prescribed and received by a patient does not mean that the patient has started taking the medication or even taking it as prescribed. A patient may also misunderstand what the doctor actually wants the patient to do and is actually taking the medication incorrectly. Embodiments of a Data Command Center via, for example, a medical records dashboard of the present principles enable medical care providers to more accurately track medications and how they are being taken by patients, which improves quality of care. More specifically, in accordance with the present principles, a medical care provider is enabled to visualize the medications, the start and stop dates, reasons for discontinuation, and is enabled to manage and change the display based on reality they confirm with the patient at point of care and via the pharmaceutical and home monitoring devices that can be linked into the Data Command Center of the present principles.

As described above, embodiments of a Data Command Center via, for example, at least one of a medical records dashboard and a Medication Management chart/tool of the present principles enables medical care providers to more accurately track medications and dates associated with the medications, for example in rows and columns. In some embodiments a Data Command Center via, for example, at least one of a medical records dashboard and a Medication Management chart/tool of the present principles can display tracked medication information in graph form. In some embodiments, each medication or class of medications associated with a patient can be represented by a bar graph or a linear graph or other visual method or means that in either the vertical direction or in a horizontal direction the doctor can visualize the actual start and stop dates of all relevant medications for a patient, which can all be seen simultaneously with any other relevant data that the medications can impact. More specifically, in some embodiments, a Data Command Center in accordance with the present principles, such as the Data Command center 001 of FIG. 1, can further include the ability to intelligently display medications in context (referred to by the inventors in some embodiments as Medication Management), by grouping, categorizing, expanding, contracting, displaying, hiding, and highlighting or flagging medications to visually present medications to a user of the Data Command Center (e.g., medical care provider) in a medical records dashboard in a manner that makes such medication more easily identifiable by the user. In one embodiment, Medication Management exists as a series of intelligent vertical columns representing individual medications, classes of medications, categories of medications, or logical groupings of medications, differentiating medications by color or combinations of colors, symbols, and/or text, graphing start and stop dates and times or individual doses correlated to relevant values and relevant events. In accordance with the present principles, graphical differentiation between medications can consist of individual colors for individual medications, combinations of colors for medications including more than one component, or complex graphical representations. In some embodiments, color standards, such as defined by the American Academy of Ophthalmology, can be used for color coding the medications and/or custom colors can be used. For example, in ophthalmology and with respect to eye care, medications have been assigned in the industry to have a certain color on the eye drop bottle or cap. In some embodiments, these colors can be displayed allowing recognition by the user of the class of medication. For instance, yellow is a beta blocker one of which is Timoptic. In accordance with the present principles, medical care providers who have memorized the color caps can instantly recognize, by viewing a medical records dashboard of the present principles, the class of medication without even seeing the name.

Figure 30:
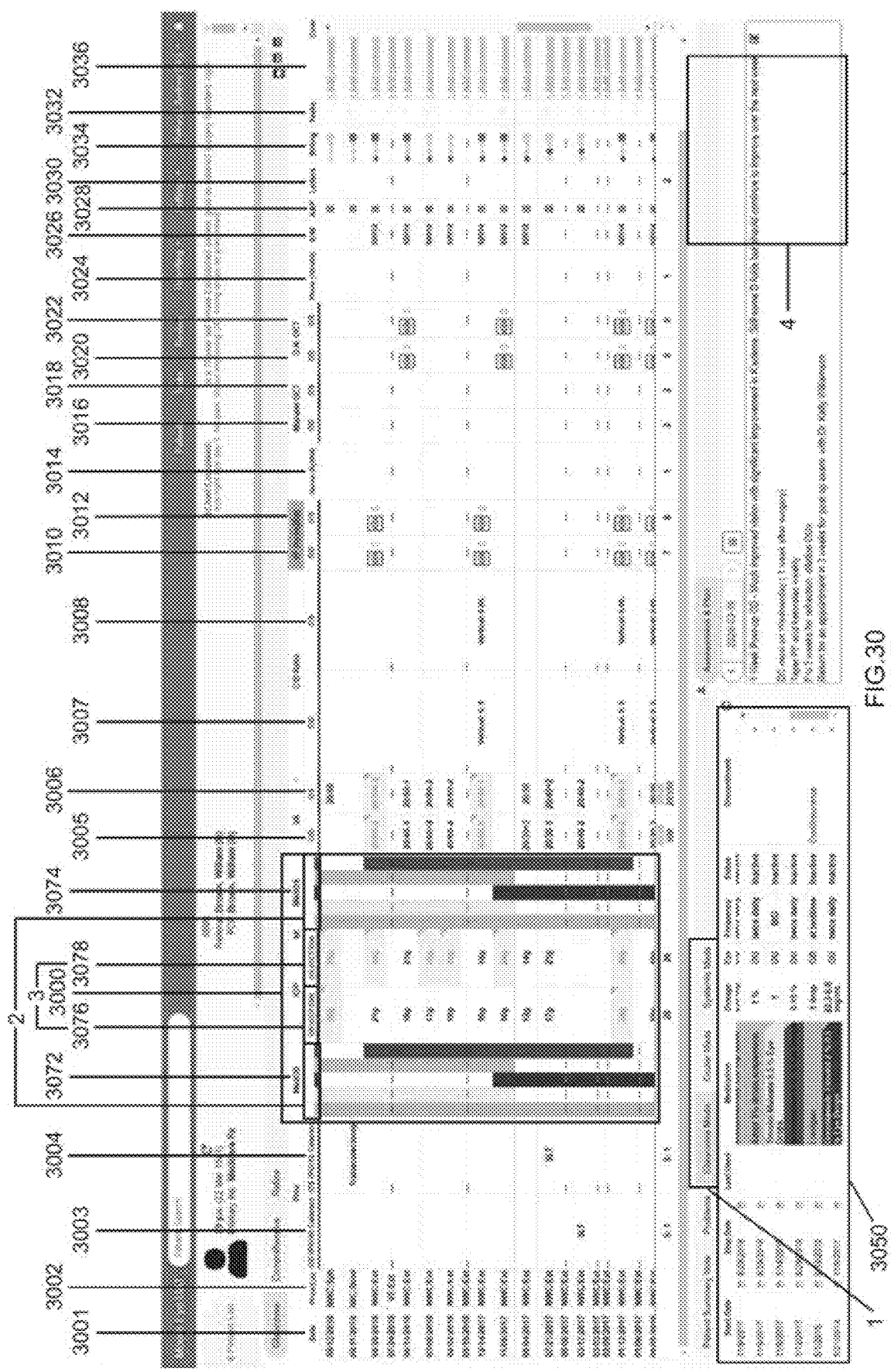
FIG. 30 depicts a first embodiment of a Medication Management chart that can be displayed in at least a portion of a medical records dashboard of the present principles in accordance with one embodiment.

For example, FIG. 30 depicts a first embodiment of a Medication Management chart 3000 that can be displayed in at least a portion of a medical records dashboard of the present principles in accordance with one embodiment. The medical records dashboard of FIG. 30 illustratively comprises a patients Glaucoma chart including a date column 3001, a Provider/Location column 3000, a Procedures column for a right eye 3003 and for a left eye 3004, the Medications Management Chart 3000, a VA column for the right eye 3005 and for the left eye 3006, a C/D Ratio column for the right eye 3007 and for the left eye 3008, a VF column for the right eye 3010 and for the left eye 3012 including a Gonio column 3014, a Macular OCT column for the right eye 3016 and for the left eye 3018, an O.N. OCT column for the right eye 3020 and for the left eye 3022, a Photo column 3024, an E/M column 3026, an A&P column 3028, a Letters column 3030, a Tasks column 3032, a Billing column 3034, and a Comments column 3036 all arranged to depict information in rows of the medical records dashboard of FIG. 30 by date.

The Medications Management Chart 3000 of FIG. 30 includes a Medication column for the right eye 3072 and the left eye 3074, illustratively on either side of an IOP column for a right eye 3076 and the left eye 3078. all arranged to depict information in rows of the medical records dashboard by date. In the Medications Management Chart 300 of FIG. 30, the Medication column for the right eye 3072 and the left eye 3074 are illustratively separated into sections for separately displaying bars for each of a plurality of available medications. The embodiment of FIG. 30 depicts an example of a medical records dashboard including medication management in the field of eye care, however embodiments of the present principles can be applied to substantially any medical specialty and the like.

In the embodiment of FIG. 30, the pressure of each eye of a patient is measured from 0 to 50. In addition, each of the medications taken associated with each respective eye of the patient are depicted in bar graph form and distinguished by color according to the dates taken. In the embodiment of the medical records dashboard of FIG. 30, the color bars representing the medications administered to the patient are displayed adjacent to respective pressure data points for each eye according to a date administered to allow the user to directly correlate the effect of the medication on a respective eye. In the embodiment of FIG. 30, section #2 depicts the medication bar graphs, section #3 depicts clinical measurements of eye pressures that are affected by the medications, and window #4 depicts an ordering panel enabling the ordering of medication through, for example, E-prescribe, DoctorFirst, or other methods. In the embodiment of FIG. 30, window #1 depicts an embodiment and location of a control panel 3050 of the medical records dashboard, which identifies which medications are represented by which colors and identified a dosage, a frequency and a status of the medications being administered to a patient.

For example, FIG. 31 depicts an embodiment of the control panel #1 of the Medication Management chart of FIG. 30 in accordance with an embodiment of the present principles. The control panel of FIG. 31 illustratively includes a Start Date Column 3110 depicting a start date of a medication in a respective row, a Stop Date Column 3120 depicting a stop date (if any) of the medication in the respective row, a Last Column 3130 depicting a date when the medication in the respective row was last taken, a Medications Column 3140 depicting medications taken by the patient, a Dosage Column 3150 depicting a dosage amount of the medication taken by the patient, a Location Column 3160 indicating in what part of the patient's body the medication was applied, a Frequency Column 3170 indicating how often the medication is being applied, a Status Column 3180 depicting if the medications are or are not currently being applied, and a Discontinued Column 3190 depicting a reason for discontinuance of the medication (if a reasons exists). As depicted in FIG. 31, in accordance with some embodiments of the present principles, the Medications Column 3140 can be color coded such that each medication comprises a respective color.

Figure 32:
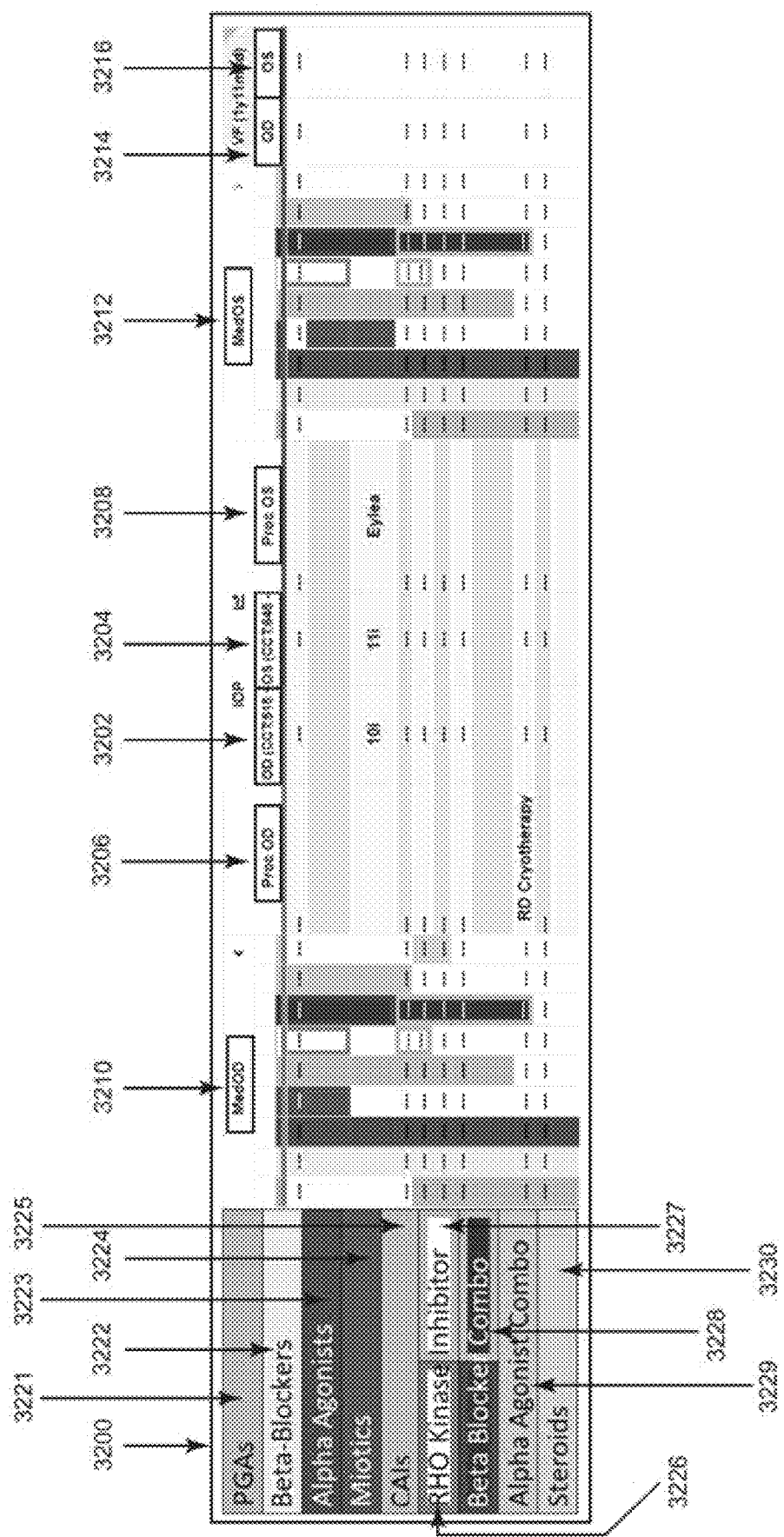
FIG. 32 depicts a Medication Management Chart that can be displayed as part of a medical records dashboard or as a stand-alone Medication Management tool in accordance with an embodiment of the present principles.

For example, FIG. 32 depicts a Medication Management Chart 3200 that can be displayed as part of a medical records dashboard or as a stand-alone Medication Management tool in accordance with an embodiment of the present principles. In the embodiment of FIG. 32, the Medication Management Chart 3200 includes a center section including respective columns depicting an intraocular pressure (IOP) for a patient's right eye 3202 and an intraocular pressure (IOP) for the patient's left eye 3204 on various different dates. In FIG. 32, next to the respective pressure columns for the patient's right eye 3202 and the patient's left eye are respective columns depicting respective procedures performed on the patient's right eye 3206 and the patient's left eye 3208 on the different dates. The Medication Management Chart 3200 of FIG. 32 further includes respective columns depicting respective medications administered to the patient right eye 3210 and the patient's left eye 3212 on the different dates. The Medication Management Chart 3200 of FIG. 32 further includes a visual field (VF) column for the right eye 3214 and a VF column for the left eye 3216.

The Medication Management Chart 3200 of FIG. 32 further illustratively includes a color-coded key identifying medications present in the Medication Management Chart 3200. In the embodiment of FIG. 32, medications administered to the patient's eyes include PGAs 3221, Beta-Blockers 3222, Alpha Agonists 3223, Miotics 3224, CAIs 3225, Rho Kinase 3226 and Inhibitor 3227, Beha-Blocker Combo 3228, Alpha Agonist Combo 3229, and Steroids 3230. As depicted in the Medication Management Chart 3200 of FIG. 32, in some embodiments, combinations of drugs can exist and can be depicted as a combination of the colors of the drugs that make-up the drug combination. Although in the embodiment of FIG. 32, the Medication Management Chart 3200 illustratively comprises a color-coded key for identifying the medications, in other embodiments of a Medication Management Chart of the present principles, a color-coded key does not have to be included. In addition, although in the embodiment of the present principles depicted in FIG. 32, the Medication Management Chart 3200 depicts a combination of drugs as a bar having one color representing a first drug and a box around the bar in a second color representing a second drug of the combination, in some embodiments a drug combination can be represented using a cross-hatch method, in which stripes in a bar are a first color representing a first drug and the rest of the bar is as second color representing the second drug of the combination. In accordance with the present principles, a drug combination can include more than two drugs and drugs and drug combinations can be represented by assigning a color to each drug and if a medication has more than one drug in it then all colors can be displayed by any means in, on or around the bar representing that medication.

Figure 33A:
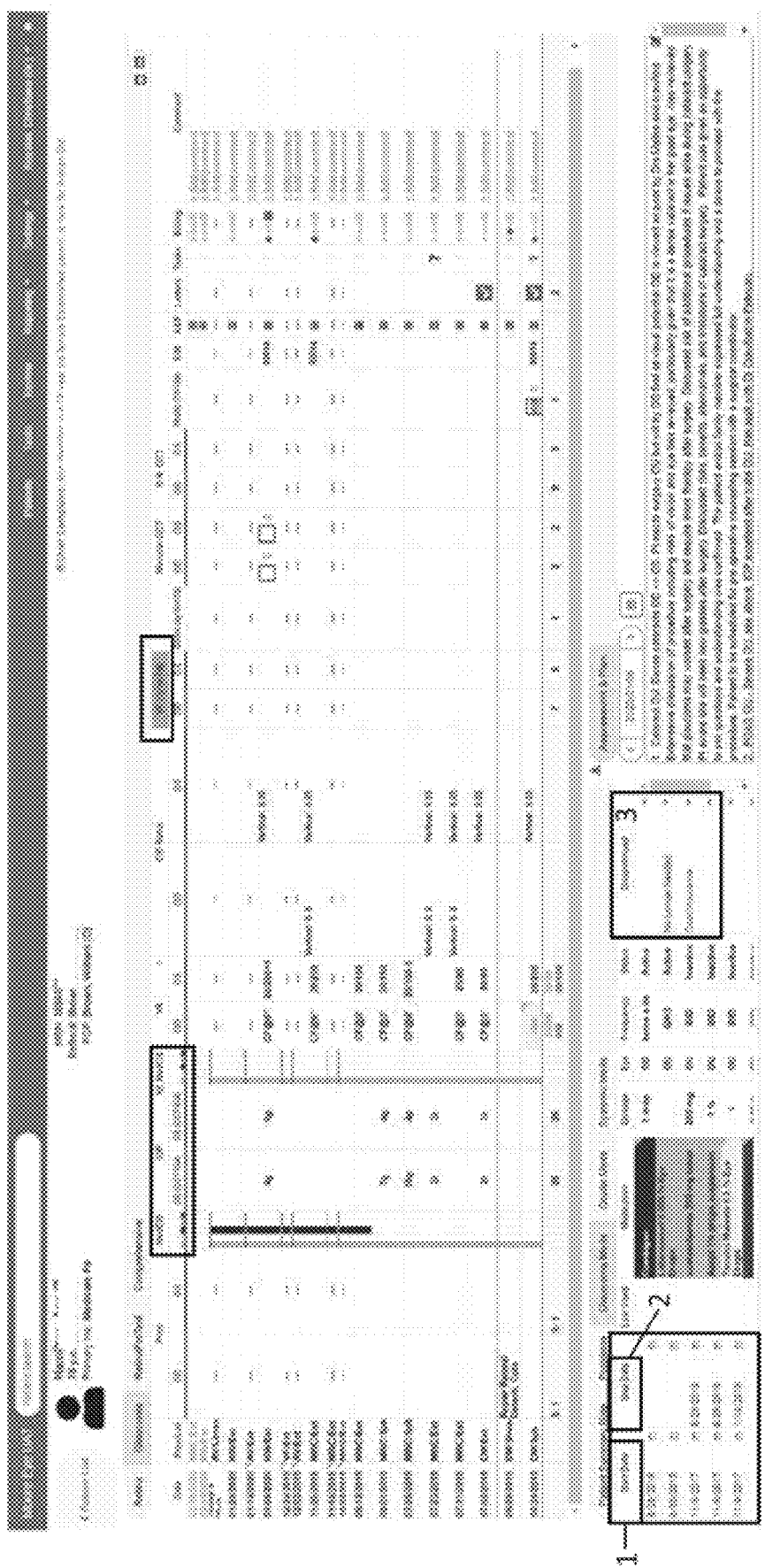
FIG. 33A depicts an example of how the Control Panel #1 of FIG. 30 can be implemented by a user to identify start and stop dates for the various medications taken by a user in accordance with an embodiment of the present principles.

FIGS. 33A-33I depict embodiments of a Medication Management Chart having different features in accordance with the present principles and will be described with reference to the medical records dashboard and the Medications Management Chart 3000 of FIG. 30. FIG. 33A depicts an example of how the Control Panel #1 of FIG. 30 can be implemented by a user to identify start and stop dates for the various medications taken by a user in accordance with an embodiment of the present principles. FIG. 33A further depicts how section 2 of the Control Panel #1 can be implemented to identify and assign colors for the medications and section 3 of the Control Panel #1 can be implemented to note reasons for a patient discontinuing a medication.

Figure 33B:
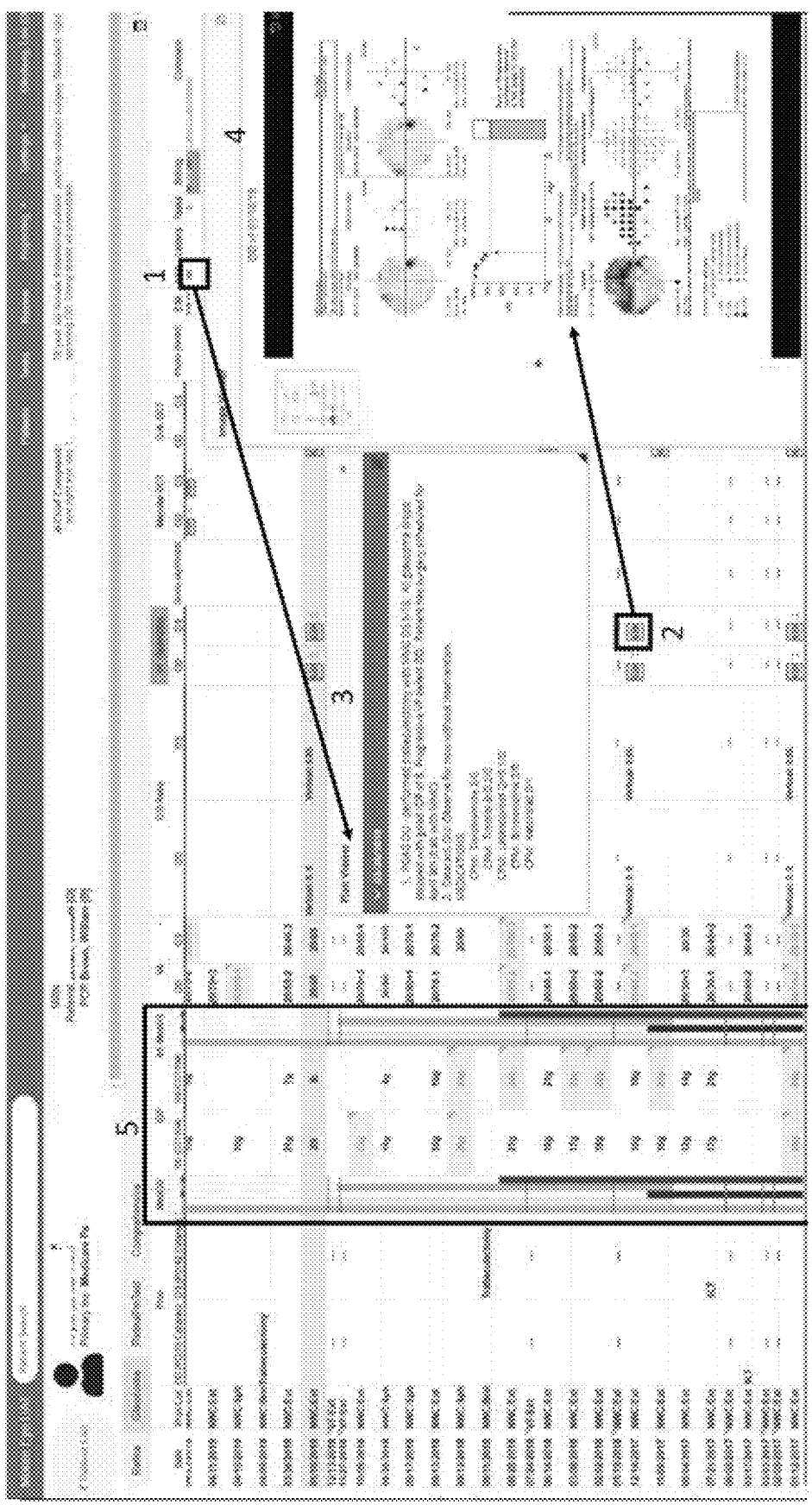
FIG. 33B depicts an embodiment of a Medication Management Chart in which icons can be activated to bring up additional information in accordance with an embodiment of the present principles.

FIG. 33B depicts an embodiment of a Medication Management Chart in which icons can be activated to bring up additional information in accordance with an embodiment of the present principles. In FIG. 33B, element 1 depicts how by clicking on a column heading, information available under the column heading, such as a note inserted by a user, can be accessed, for example, in a pop-up window, element 3. In FIG. 33B, a note regarding a treatment plan for the patient was accessed via a pop-up window (element 3) when an icon under the column heading was activated. As depicted in the embodiment of FIG. 33B, the column heading can contain an icon indicating that a note exists. Element 2 of FIG. 33B depicts an icon in the OS column of the VF column that when activated can cause a display of a pop-up window (element 4), which displays a visual field image performed on the patient's left eye. Element 5 of FIG. 33B depicts how all of the medications being taken by a patient can be simultaneously displayed using bar graphs and color coding of the present principles.

Figure 33C:
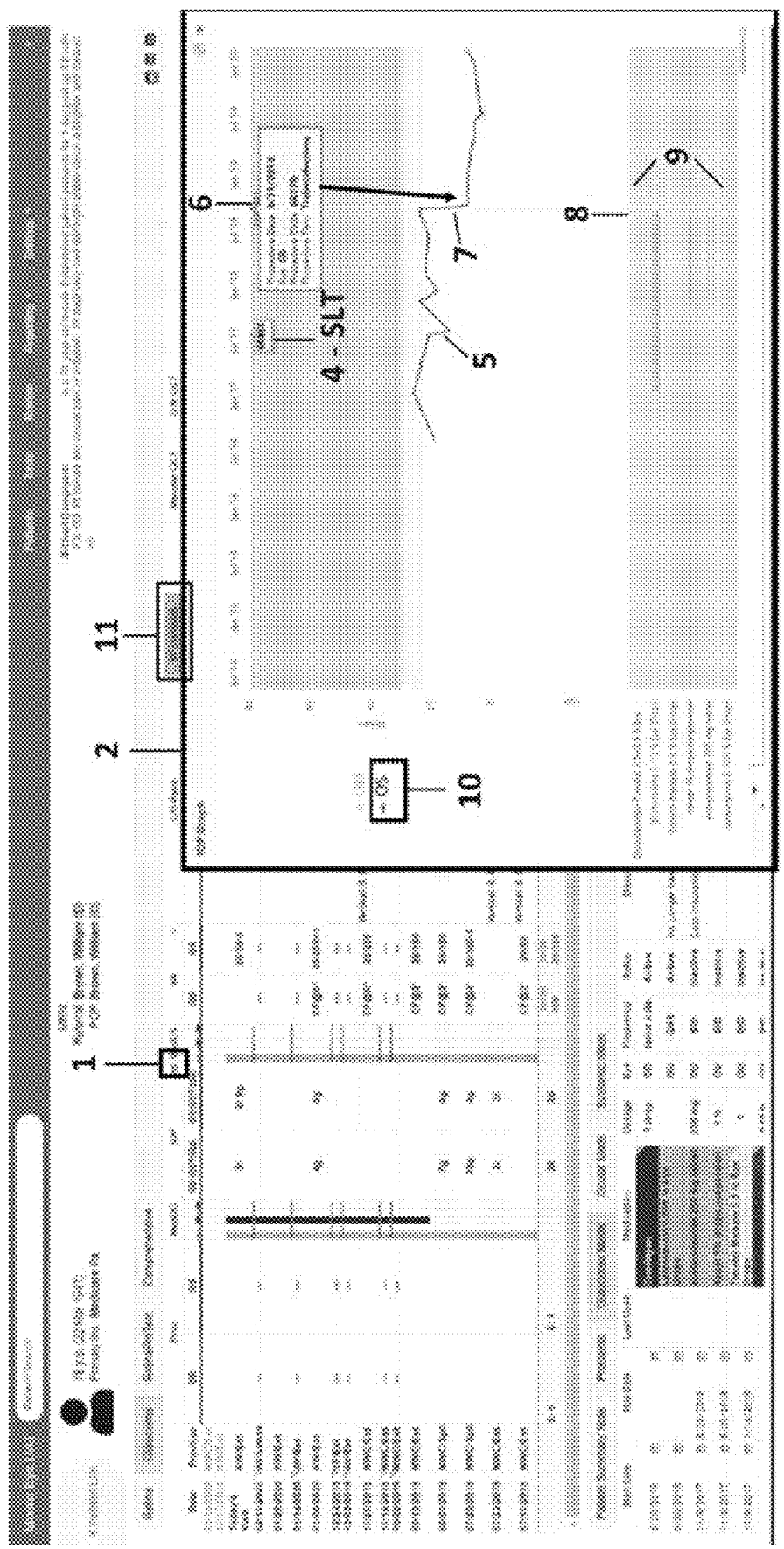
FIG. 33C depicts another embodiment of a Medication Management Chart in which icons can be activated to bring up additional information in accordance with another embodiment of the present principles.

FIG. 33C depicts another embodiment of a Medication Management Chart in which icons can be activated to bring up additional information in accordance with another embodiment of the present principles. In FIG. 33C, element 1 depicts how activating an icon in, for example, a column heading of the Medications Management chart can cause a display of a pop-up window (element 2), which in some embodiments can display another embodiment of a Medication Management chart which displays mediations using horizontal lines and correlates patient well-being data/information (i.e., intraocular pressure) with events that occurred to the patient that would affect the patient's well-being (i.e., the application of medications, surgery, etc.) and with a medication timeline (described in greater detail with respect to FIG. 34). As depicted in FIG. 33C, using such Medication Management charts of the present principles, a user can make a reasoned estimation of what caused a decline or an improvement in the patient's well-being. As further depicted in FIG. 33C, a user can select to display information for one eye at a time or for both eyes simultaneously.

Figure 33D:
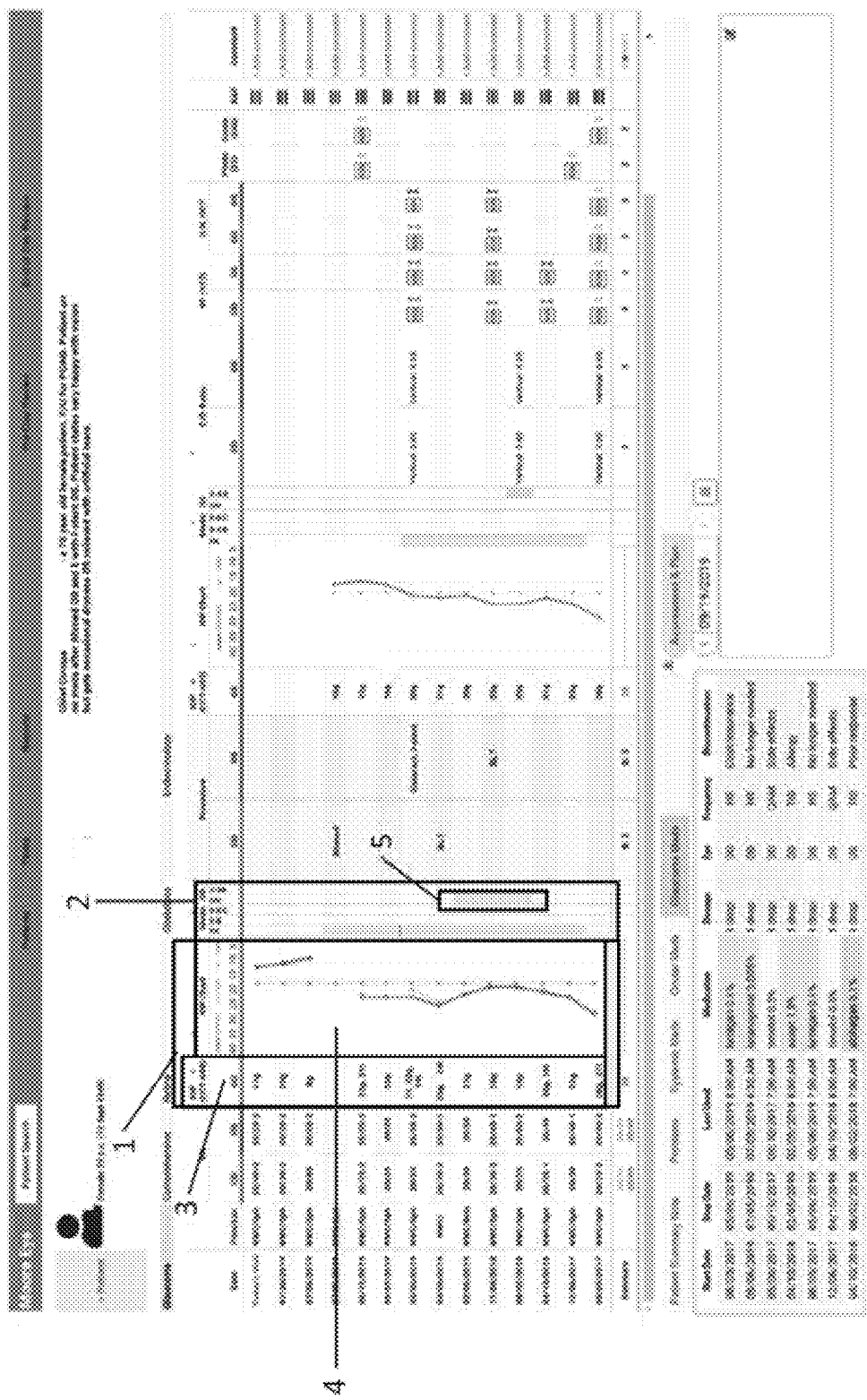
FIG. 33D depicts an embodiment of the Medication Management Chart in which intraocular pressure, in addition to being listed by number, is also displayed as a vertical line graph, for example as depicted by element 1 in accordance with an embodiment of the present principles.

FIG. 33D depicts an embodiment of the Medication Management Chart in which intraocular pressure, in addition to being listed by number, is also displayed as a vertical line graph, for example as depicted by element 1 in accordance with an embodiment of the present principles. In the embodiment of FIG. 33D, element 2 displays bar graphs of the medications being taken by the patient. element 3 of FIG. 33D depicts values of intraocular pressures of a right eye and element 4 displays the corresponding vertical line graphs of the values pointed out by element 3.

Figure 33E:
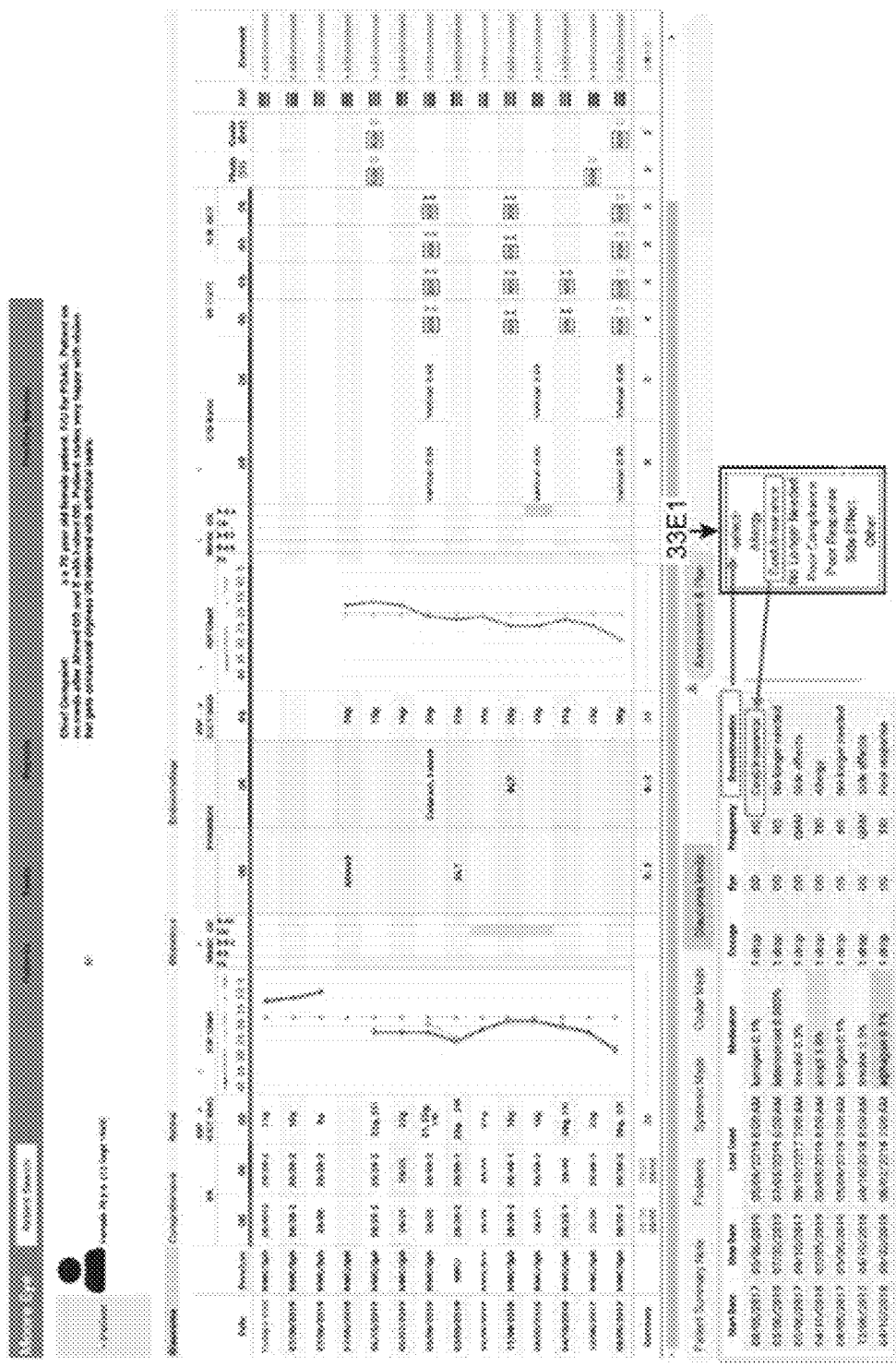
FIG. 33E depicts an embodiment of the Medication Management Chart of FIG. 33D in which the control panel can be used to input a reason that a medication has been started or stopped in accordance with an embodiment of the present principles.

FIG. 33E depicts an embodiment of the Medication Management Chart of FIG. 33D in which the control panel can be used to input a reason that a medication has been started or stopped in accordance with an embodiment of the present principles. In the embodiment of FIG. 33E, a drop down menu 33E1 can be used to enable a user to select a reason that a medication has been started or stopped.

Figure 33F:
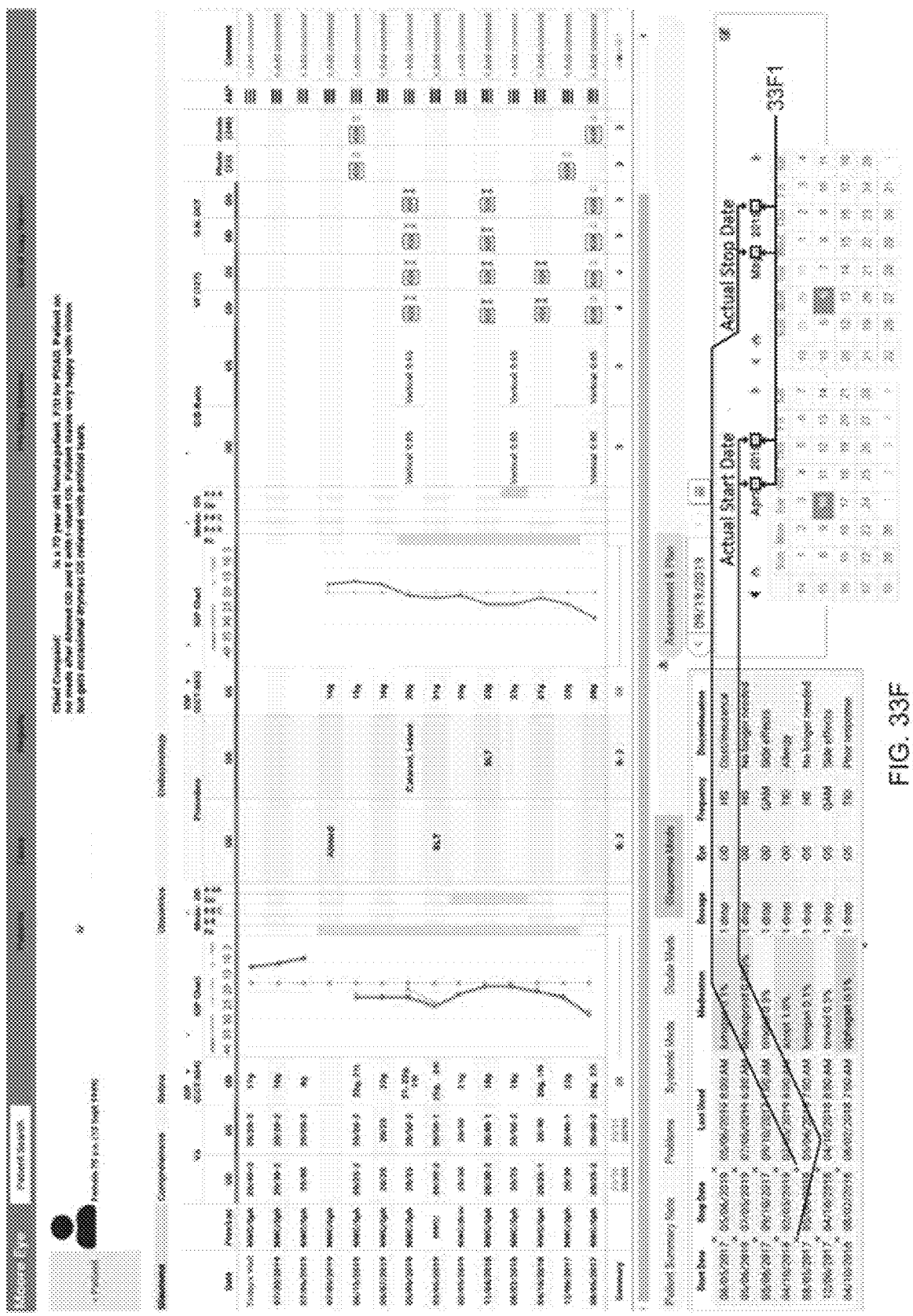
FIG. 33F depicts an embodiment of the Medication Management Chart of FIG. 33D in which the control panel can be used to correct start and stop dates for a medication in accordance with an embodiment of the present principles.

FIG. 33F depicts an embodiment of the Medication Management Chart of FIG. 33D in which the control panel can be used to correct start and stop dates for a medication in accordance with an embodiment of the present principles. In the embodiment of FIG. 33F, a drop down menu 33F1 can be used to enable a user to correct/input a date that a medication has been started or stopped.

Figure 33G:
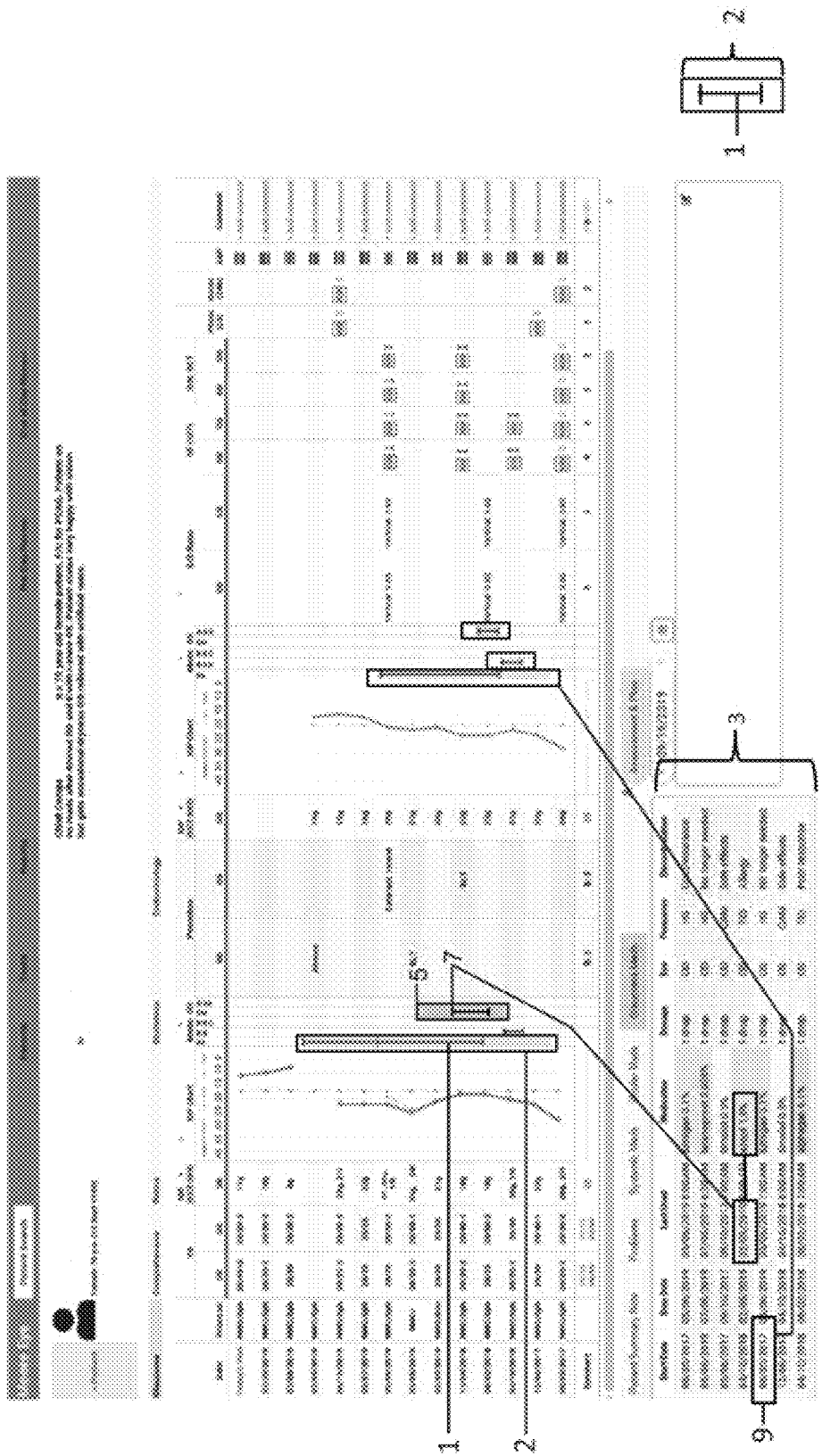
FIG. 33G depicts an embodiment of the Medication Management Chart of FIG. 33D in which both corrected start and stop dates for a medication taken by a patient and incorrect start and stop dates for a medication taken by a patient and listed for example by a $3^{rd}$ party data provider such as an EMR can be displayed simultaneously in accordance with an embodiment of the present principles.

FIG. 33G depicts an embodiment of the Medication Management Chart of FIG. 33D in which both corrected start and stop dates for a medication taken by a patient and incorrect start and stop dates for a medication taken by a patient and listed for example by a 3rd party data provider such as an EMR can be displayed simultaneously in accordance with an embodiment of the present principles. In the embodiment of FIG. 33G, element 1 depicts a line depicting a start and stop date of a medication being taken by a patient as listed in an EMR. In FIG. 33G the line pointed out by element 1 is displayed within a bar pointed out by element 2, which depicts start and stop dates of a medication being taken by a patient as identified by a user. FIG. 33G also depicts an alternative embodiment. That is, FIG. 33G depicts an orange bar depicting a medication being taken by the patient. The orange bar depicts start and stop dates of the medication as listed in an EMR and a black line within the orange bar which depicts start and stop dates of the medication as determined by the user. Importantly and in accordance with the present principles, FIG. 33G depicts that more than one stop and stop date can be depicted for each medication in a Medication Management Chart of the present principles.

Figure 33H:
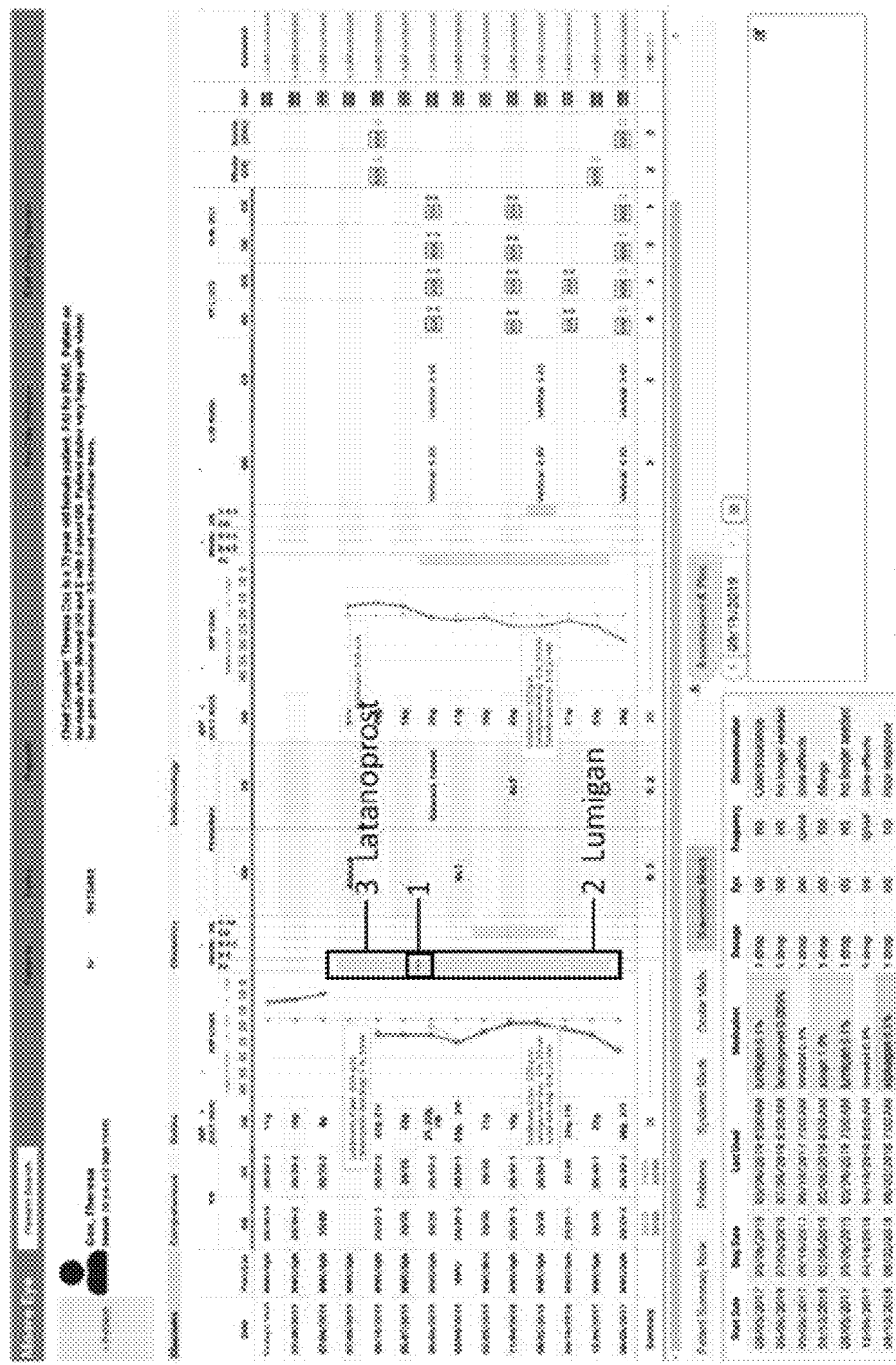
FIG. 33H depicts an embodiment of the Medication Management Chart of FIG. 33D in which a user is alerted that a medication being taken by a patient has changed, even if medications are being listed by class and the new medication is of the same class as the old medication in accordance with an embodiment of the present principles.

FIG. 33H depicts an embodiment of the Medication Management Chart of FIG. 33D in which a user is alerted that a medication being taken by a patient has changed, even if medications are being listed by class and the new medication is of the same class as the old medication in accordance with an embodiment of the present principles. For example, in the embodiment of FIG. 33H, element 1 depicts a horizontal line in the bar of the medication that is being taken by the patient and that is being changed. element 2 of FIG. 33H depicts that before a change the medication being taken by the patient is Lumigan. The line pointed out by element 1 depicts a change in medication and element 3 depicts that the medication being taken after the change is Latanoprost, which is in the same class of medications as Lumigan.

Figure 33I:
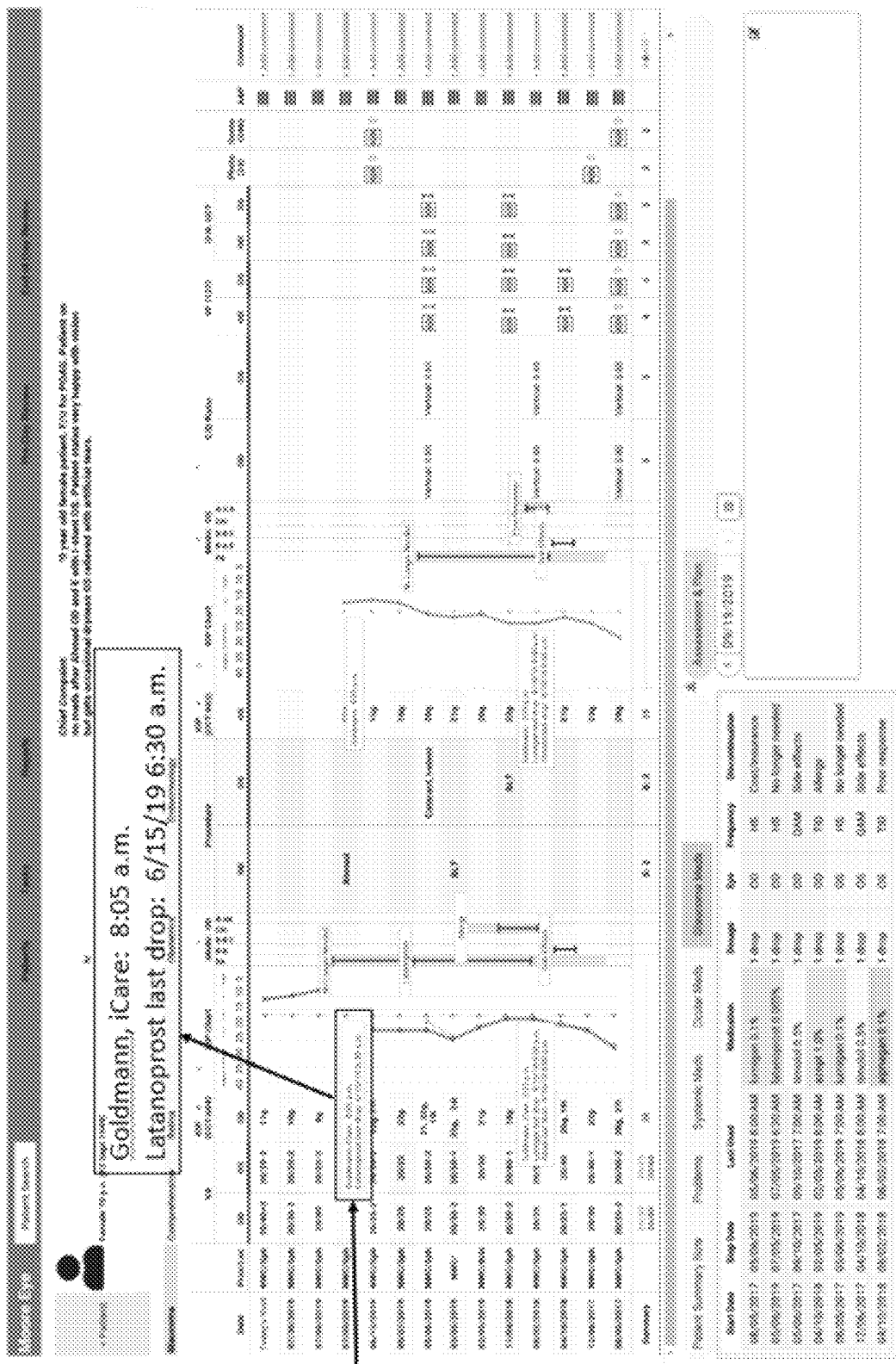
FIG. 33I depicts an embodiment of the Medication Management Chart of FIG. 33H in which a user is able to select a portion of a graph to bring up additional information associated with the graph in accordance with an embodiment of the present principles.

FIG. 33I depicts an embodiment of the Medication Management Chart of FIG. 33H in which a user is able to select a portion of a graph to bring up additional information associated with the graph in accordance with an embodiment of the present principles. For example, in the embodiment of FIG. 33I, when a user hovers a selection tool (e.g., mouse) over a specific date portion of an IOP graph, a window 3311 appears displaying to the user information detailing, for example, when and/or where on that particular day an intraocular pressure was measured. Similarly and as depicted in FIG. 33I, when a user hovers over a specific date portion of a medications graph, the window 3311 appears displaying to the user information detailing, for example, at what time or how long ago the medication was taken by the patient. In some embodiments, a time between the measurement in the office, for instance, a blood pressure or a pressure of the eye, and how long ago the patient actually took the medication can be measured and displayed, since some medications have a short duration of action and such information would be useful to the user.

In another embodiment and as briefly described above, Medication Management in a Data Command Center in accordance with the present principles exists as a series of intelligent horizontal rows within a correlative graph representing individual medications, classes of medications, categories of medications, or logical groupings of medications, differentiating medications by color or combinations of colors, symbols, and/or text, graphing start and stop dates and times or individual doses, correlated to relevant values and relevant events. In accordance with the present principles, graphical differentiation between medications can consist of individual colors for individual medications, combinations of colors for medications including more than one component, or complex graphical representations. In some embodiments, color standards, such as defined by the American Academy of Ophthalmology, can be used for color coding the medications and/or custom colors can be used. For example, in ophthalmology and with respect to eye care, medications have been assigned in the industry to have a certain color on the eye drop bottle or cap. In some embodiments, these colors can be displayed allowing recognition by the user of the class of medication. For instance, yellow is a beta blocker one of which is Timoptic. In accordance with the present principles, medical care providers who have memorized the color caps can instantly recognize, by viewing a medical records dashboard of the present principles, the class of medication without even seeing the name. Alternatively or in addition, in some embodiments of the present principles a user can identify which generic or brand medication the patient is taking by any means including rolling over the graph and seeing the name of the medication pop up.

Figure 34:
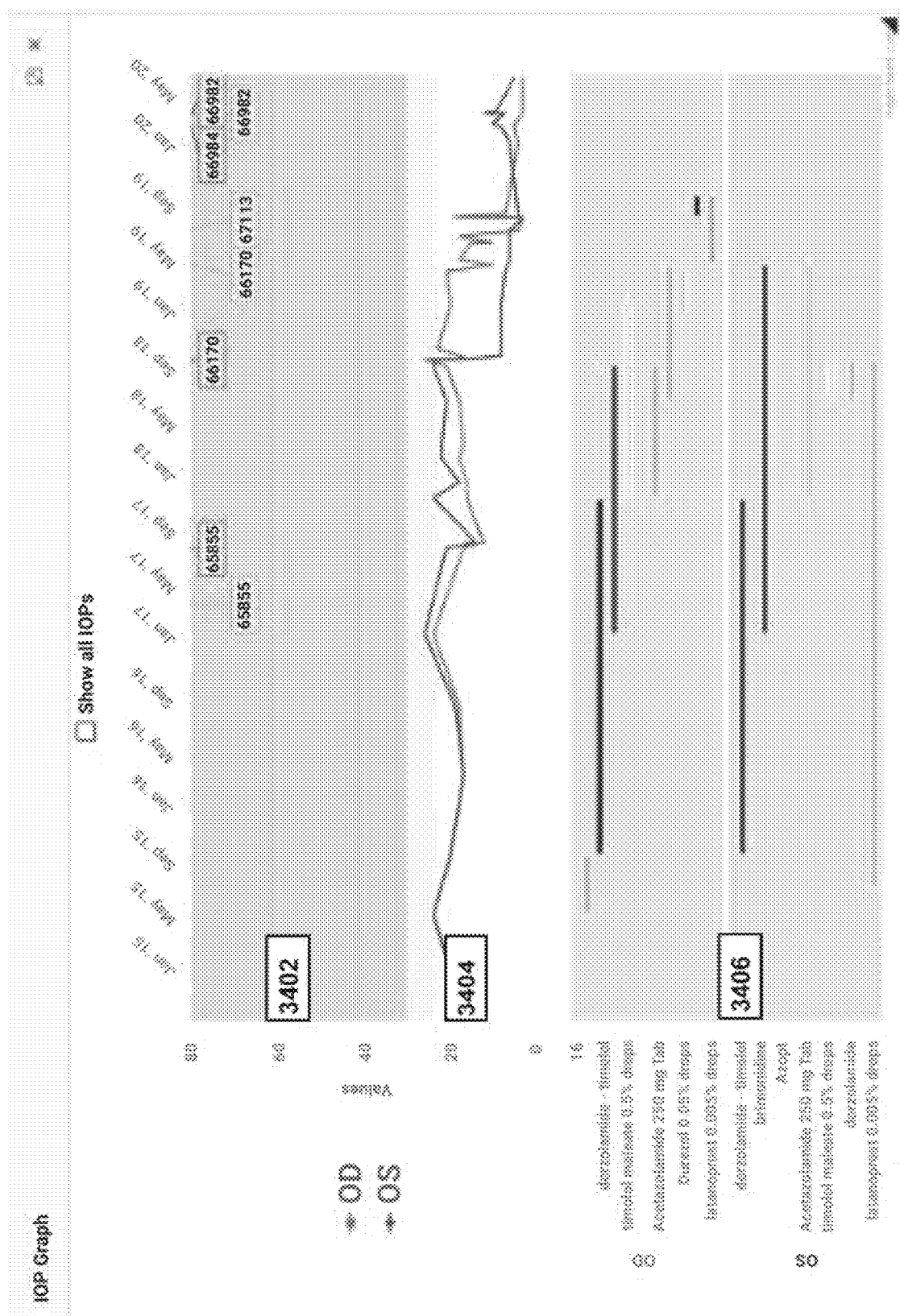
FIG. 34 depicts an illustration of a second embodiment of a Medication Management chart that can be displayed in at least a portion of the medical records dashboard of the present principles in accordance with one embodiment.

FIG. 34 depicts an illustration of a second embodiment of a Medication Management chart that can be displayed in at least a portion of the medical records dashboard of the present principles in accordance with one embodiment. In the embodiment of the present principles depicted in FIG. 34, the medications in the Medication Management chart are color-coded. Illustratively, in the Medication Management chart of FIG. 34, a top section 3402 illustrates dates of relevant events. In some embodiments, such events can include but are not limited to applied medications which can be taken by mouth (orally), given by injection into a vein (intravenously, IV), into a muscle (intramuscularly, IM), into the space around the spinal cord (intrathecally), or beneath the skin (subcutaneously, sc), placed under the tongue (sublingually) or between the gums and cheek (buccally), inserted in the rectum (rectally) or vagina (vaginally), placed in the eye (by the ocular route) or the ear (by the otic route), sprayed into the nose and absorbed through the nasal membranes (nasally), breathed into the lungs, usually through the mouth (by inhalation) or mouth and nose (by nebulization), applied to the skin (cutaneously) for a local (topical) or bodywide (systemic) effect, and/or delivered through the skin by a patch (transdermally) for a systemic effect, surgeries and any other procedures that can affect a patient's well-being.

A second, lower section 3404 of the Medication Management chart of the embodiment of FIG. 34 depicts a line graph correlating the relevant events that can affect a patient's well-being (i.e., the application of medications, surgery, etc.) of the top section 3402 to relevant values of patient well-being data/information (i.e., intraocular pressure) for each of a right eye and a left eye. In the Medication Management chart of FIG. 34, a third, lower section 3406 depicts a horizontal view of medications, which no longer spans a column of appointments, but denotes start/stop dates/times across a linear model. The linear model accounts for dates and key events in the top section of the diagram, such as the application of medications and major surgeries that may also have an effect on the results displayed in the middle section of the diagram. The third lower section 3406 displays an array of medications horizontally in context of the events and factors which can affect results, clearly showing the effect of medications and events on a single, or combination of multiple, tracked values.

Figure 35:
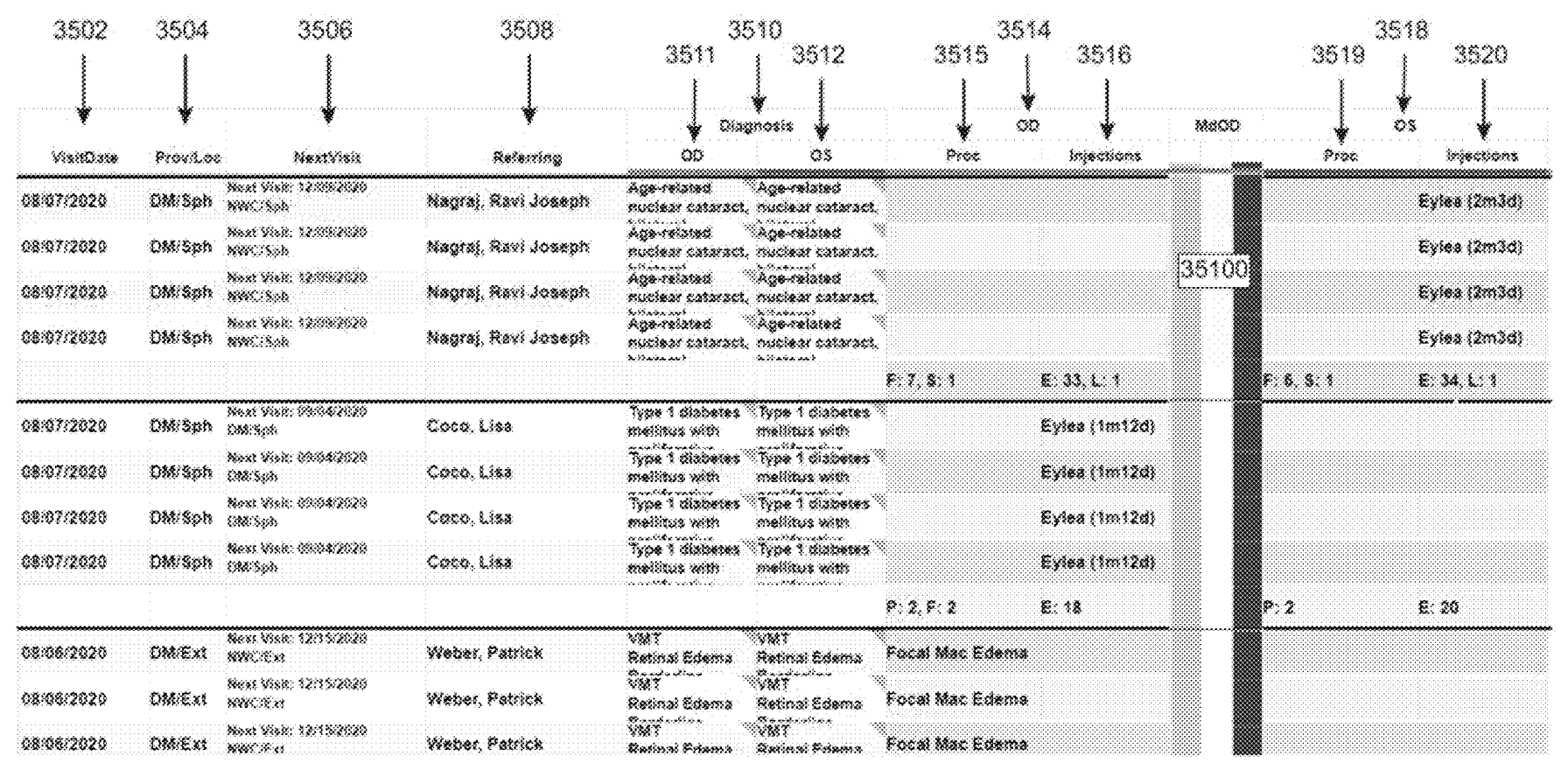

In another embodiment, Medication Management in a Data Command Center in accordance with the present principles exists as a series of intelligent vertical columns representing individual medications, classes of medications, categories of medications, or logical groupings of medications, differentiating medications by color or combinations of colors, symbols, and/or text, graphing start and stop dates and times or individual doses. For example, FIG. 35 depicts a medical records dashboard including a third embodiment of a Medication Management chart in accordance with an embodiment of the present principles. That is, the medical records dashboard of FIG. 35 includes a plurality of rows and columns and a Medication Management chart 35100 in accordance with the present principles. In the embodiment of FIG. 35, the columns of the medical records dashboard include a VisitDate Column 3502 listing the visit date of a patient, a Provider/Location Column 3504, a NextVisit Column 3506 listing a next visit date for the patient, a Referring provider Column 3508 listing the name of, for example, a referring doctor, a Diagnosis Column 3510 including an OD column 3511 and an OS column 3512 including a diagnosis for each of a right and a left eye, a separate OD Column 3514 including a Procedure column 3515 listing procedures performed on a patient's right eye and an Injections column 3516 listing injections performed on the patient's right eye, and a separate OS Column 3518 including a Procedure column 3519 listing procedures performed on a patient's left eye and an Injections column 3520 listing injections performed on the patient's left eye.

In the medical records dashboard of FIG. 35, the Medication Management chart 35100 depicts a representation of color-coded vertical medication columns as described above with respect to the embodiments of FIGS. 30, 32 and 33.

Figure 36:
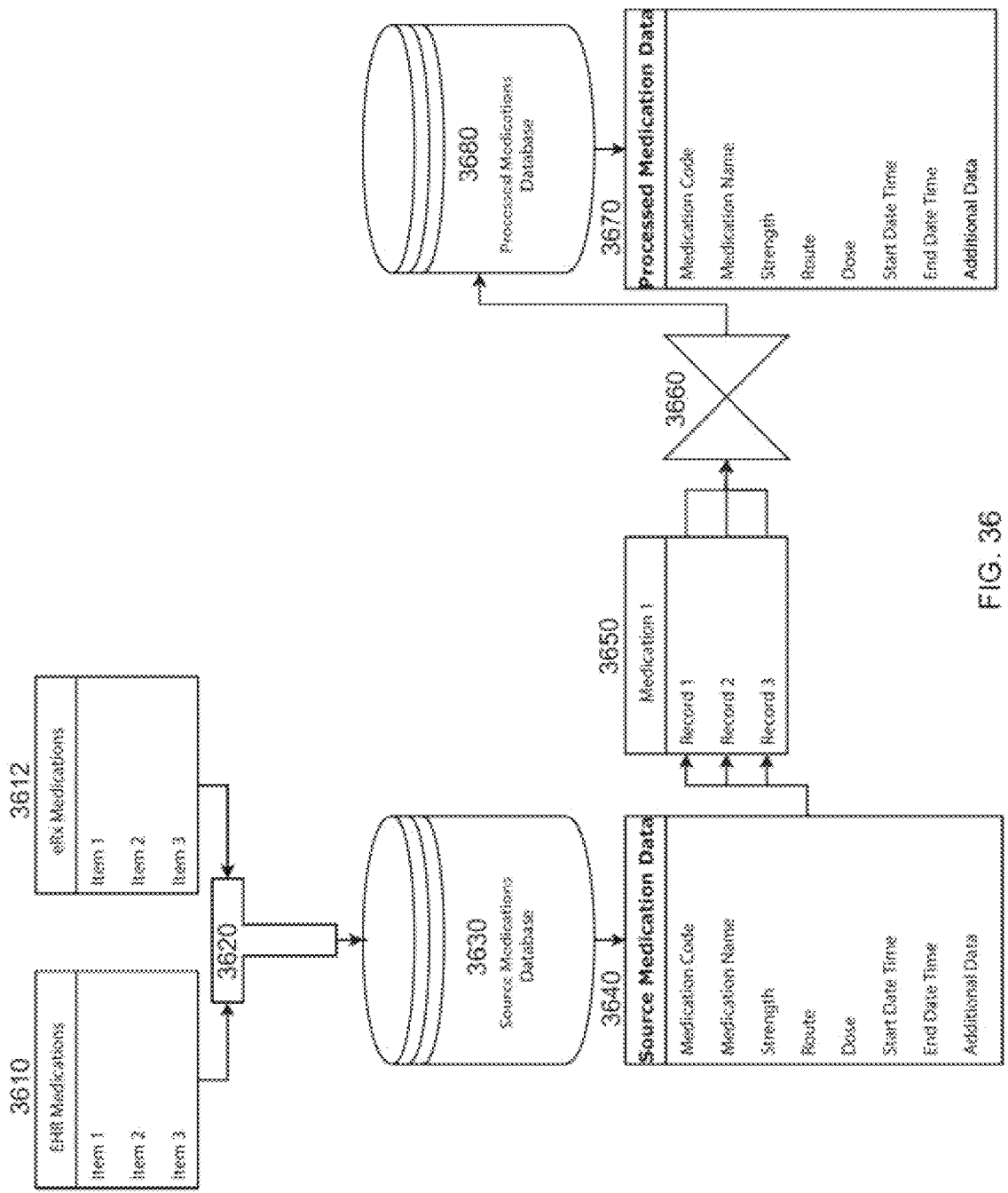
FIG. 36 depicts a high-level workflow diagram of an embodiment of Medication Management in a Data Command Center in accordance with an embodiment of the present principles.

FIG. 36 depicts a high-level workflow diagram of an embodiment of Medication Management in a Data Command Center in accordance with an embodiment of the present principles. In the embodiment of FIG. 36, Medication source data can be stored within an EHR 3610 or eRx platform 3612. In some embodiments, as depicted in FIG. 36, medication data can be imported by an API or other means of digital communication, for example in one embodiment by the integration module 002 of the Data Command center 001 of FIG. 1, and can be compiled into a table 3620 which can be stored in a database 3630. Data from a relevant source stored in the database 3630 can be extracted. Block 3640 depicts an accurate representation of extracted data from the relevant source. The data from the relevant source can then be isolated to at least one specific medication from the source data. Block 3650 of FIG. 36 represents records isolated for a specific medication from the source data. The isolated data can then be processed at 3660 through several intelligent algorithms to surmise a final representation of the view of the specific medication, in some embodiments a longitudinal view. For example, in some embodiments, source data disparities and variance of medication data between sources can be addressed by intelligent algorithms which acquire available data about the medications and data sources and process toward a desired result. Algorithms account for presence if codified data, non-codified data, null values, and other datatypes. Such algorithms can be directed to exporting consistent representations of source data. In some embodiments of the present principles, such algorithms can be applied by the Rules module 004 of the Data Command center 001 of FIG. 1 and can be stored in a means for storage accessible to at least the Rules module 004.

Each medication column or row in a medical records dashboard of the present principles can consist of one or more individual medications as depicted by processed medications data as listed in block 3670, which can be stored in the Processed Medications Database 3680.

In some embodiments, the Display module 006 of the Data Command center 001 of FIG. 1 in accordance with the present principles causes the display of the Medication Management data in a medical records dashboard of the present principles as described above, and specifically in at least one of the vertical, horizontal, and textual embodiments described above and in accordance with individual medications, classes of medications, categories of medications, or logical groupings of medications, differentiating medications by color and/or combinations of colors, symbols, and/or text, graphing start and stop dates and times or individual doses, correlated to relevant values and relevant events as described above.

In some embodiments of at least one of a medical records dashboard and a Medication Management chart in accordance with the present principles, Medication columns and rows can expand, contract, hide, or be display based on a medical care provider's specialty, the identity of a medical care provider and/or a patient, patient conditions, patient procedures, risk factors, diagnostic results, future orders, future appointments, values recorded, values not recorded, calculated values, and absolute values for display, unless otherwise disallowed in accordance with Collapsible Columns and/or Rows that can Collapse and Expand.

In some instances, medication data can be sourced from misleading, unreliable, or inconsistent records reflecting multiple start and stop dates and times for a single medication due to each individual reorder of a medication stopping a prior prescription and starting a new one, or not stopping but adding a new start date and time, and may not reflect actual patient usage of said medication. As such, in some embodiments a Data Command Center via at least of a medical records dashboard and a Medication Management chart in accordance with an embodiment of the present principles enables a user to manually override misleading, unreliable, or inconsistent records to accurately represent medication usage. In such embodiments, each instance of source medication data being altered can be recorded in an audit log to account for data integrity as well as data accuracy. In some embodiments, the source medication data itself is never altered, updated, added, or removed. In some embodiments, updating medication data in any instance of Medication Management in accordance with the present principles reflects in every instance of the Medication Management. For example, editing a stop date and time in a list view of a medical records dashboard can also update the stop date and time in all graphical views. In some embodiments, medication updates can be stored separately from source medication data.

In general, in accordance with the present principles, embodiments of a Data Command Center via at least one of a medical records dashboard and a Medication Management chart of the present principles enable medical care providers to visualize medications, respective start and stop dates, reasons for discontinuation, and enables medical care providers to manage and change a display based on facts able to be confirmed with a patient at a point of care and even with home monitoring devices that can be linked. As described above, in some embodiments each medication can be represented by a bar graph or a linear graph or other visual method or means that in either the vertical direction or in a horizontal direction, a medical care provider can visualize the actual start and stop dates of all relevant medications for their specialty or for that patient all seen simultaneously with any other relevant data that the medications can impact. The medications and any encounters or clinical services or measurements that the patient takes at home or home monitoring devices can all be automatically or manually inputted. The Medication Management chart/Medication Management tool of the present principles can initially be populated by information in the EMR, which may or may not be accurate, or from E-prescribe systems. A medical care provider using, for example a medical records dashboard, can make changes and through a linear bar graph or other means, each column or row can represent a particular medication or class of medication. With all of the patient's medications that are relevant to that medical care provider or the condition being treated, all medications that the patient is taking now or in the past, can be displayed so that medical care providers will know all the medications that the patient has ever taken.

Embodiments of the present principles provide access to whatever information is relevant to the treatment of a patient and is enabled to share this information with all other medical care providers. All medication that can be used to manage a particular condition can all be displayed on a single screen if there is room or collapsed so doctors can visualize other options. In some embodiments, just the columns and/or rows are automatically displayed and other medication alternatives hidden until, through any means, a user accesses hidden patient-related information. In some embodiments, a Data Command Center via, for example at least one of a medical records dashboard and a Medication Management chart of the present principles, can offer clinical decision support in that if there is a set preferred treatment plan or the Data Command Center has programmed proper alternatives that a medical care provider should consider, the medical care provider can start the patient on a particular medication that can be suggested in a blank row or column next to other medications with the name of the suggested medicine.

In some embodiments, each user can move the columns and rows on which the medications are on to a particular section while being able to collapse and expand the entire history of every medication that the patient has taken. Each column or row, depending on whether a horizontal or vertical display is preferable, would be displayed from a start to a stop date and each corresponding date can be listed by office visit of encounter with different medical care providers and or by month, by day, by year, by hour or even minutes especially useful if the patient is hospitalized. In some embodiments of the present principles, a Data Command Center can receive inputs from a user via a user interface on how at least one of a medical records dashboard and a Medication Management chart should be configured to display patient related information from outside sources. For example, in some embodiments patient-related data/information from outside sources can be integrated into the Data Command center 001 via the Integration module 002 of the Data Command center 001 of FIG. 1. Once patient-related data/information is received by the Data Command center 001, the data can be compared to rules to be executed by the Rules module 004, which determine how and if received patient-related data should be displayed. As described above, in some embodiments, at least some of the rules for handling patient-related data/information can be provided to the Rules module 004 of the Data Command center 001 using a user interface. Patient-related data/information can then be caused to be displayed by the Display module 006 on at least the medical records dashboard of the present principles in accordance with the rules of the Rules module 004.

In some embodiments, multiple start and stop dates can exist for a medication based on when a patient admits that they really took the medication. As such, a medication bar graph might appear interrupted because, for example, the same medication might have been taken in 1993 and then re-started again in 2003 or the patient only took the medication for 10 months out of 12 months in a particular year. Such findings can be critical to patient care because if a patient does not take the medication as prescribed it can have an impact on a clinical finding or symptom or disease progression such as high blood pressure. Should a patient have blood pressure measured and suddenly the blood pressure is high, a medical care provider needs to know if it is not that the medication did not work, but perhaps that the patient did not take the medication.

An onset of other medical conditions or interventions such as surgeries or other life events like a death in the family can also be displayed in at least one of a medical records dashboard and a Medication Management chart of the present principles so a medical care provider can determine and take into all the information that can impact the well-being of a patient. As such in some embodiments, a medical records dashboard and a Medication Management chart of the present principles can display clinical findings, measurements, the laboratory findings, and/or whatever the medication impacts a patient's well-being such that a true change in a patient's well-being can be measured accurately and a medical care provider can see visualize the true effects of medications along with other medical services, interventions and life events. By way of example, in the field of ophthalmology there are glaucoma medications, which are pressure medications for the eye. Sometimes just one eye drop will make the pressure go down, sometimes two, three and four different types of drops are needed. Usually medical care providers add a medication if an eye pressure is not controlled to the level desired or if the medical care provider wants to replace one medication with another.

In some embodiments, at least one of a medical records dashboard and a Medication Management chart/tool of the present principles enables a medical care provider to document why a medication was started or stopped or if there has been a reaction to the medication. For instance, if the medication has been stopped because the patient is allergic or cannot afford it, or if it did not work. Such reasons can be input into the medical management tool by selecting the choice by any means such as a drop-down menu or through voice recognition software or any means. The information can then be displayed on a bar or line graph of that particular medication and either be permanently displayed or accessed via an icon or other access point.

In various embodiments of a medical records dashboard having a medication management tool (such as displayed in FIG. 30), in addition to a laboratory or clinical finding, there can be included an option to input information regarding procedures performed on a patient. For example, for a particular patient, a surgical procedure might be the reason there has been a sudden change in the well-being of the patient. For instance, there are some glaucoma pressure surgeries which will reduce the pressure and have the same effect as a medication or a laser surgery that might cause a pressure to be lower. It is important that a medical care provider have the option to view what procedure were performed on a patient to determine if a procedure might also have had an effect on the clinical finding, symptoms or disease progression on which the medication can also have an impact. Perhaps it is not the medication that is working, maybe it is the surgery.

Embodiments of the present principles are fully adjustable for all types of conditions, such as high blood pressure, diabetes, rheumatological diseases, and all types of cancer. All of these conditions have certain laboratories and clinical measurements that are taken either at the patient's home or from a testing center or on each visit with a medical care provider (i.e., doctors often record weight and blood pressure of the patient, etc.). In addition, a medical care provider can be enabled via at least on of a medical records dashboard and a Medication Management chart of the present principles to now E-prescribe or place an order for a new medication or cancel a drug. As such, by ordering a next medication, a medical care provider can instantly visualize what is being ordered as the new order can be displayed as a future medication. In such embodiments, a new column or row can appear with, for instance, a new bar graph because the medical care provider is now ordering a new medication.

A Data Command Center of the present principles enables a medical care provider to determine if incompatible medications or procedures have been ordered and/or scheduled. For example, in some embodiments, upon the visual display of ordered medications and/or procedures in at least one of a medical records dashboard and a Medication Management chart of the present principles, a medical care provider, by looking at the display, can visually determine through his/her experience and training that incompatible medications and/or procedures have been ordered or scheduled. Alternatively or in addition, in some embodiments a Rules module, such as the Rules module 004 of the Data Command center 001 of FIG. 1, can be programmed to recognize incompatible medications and/or procedures. As such, when patient-related data/information containing incompatible medications and/or procedures is received or when incompatible medications or procedures have been ordered or scheduled by, for example, a medical care provider using for example at least one of a medical records dashboard and a Medication Management chart of the present principles, the Rules module 004 can cause an alert to be displayed by, for example, the Display module 006, the alert intended to bring to a user's attention that incompatible medications and/or procedures exist. In some embodiments, if such a condition exists, a pop-up can appear to enable a medical care provider to re-do their order and make sure the order is corrected.

In some embodiments, multiple medication graphs can be shown independently or on for example, at least one of a medical records dashboard and a Medication Management chart of the present principles, such that a user is able to compare different reporting of the same medications. For example, in some instances patient-related data from an EMR can be inaccurate. However, it is advantageous for a medical care provider to know what has been documented, even if inaccurate. Embodiments of a medication management tool of the present principles can display two graphs, a first displaying what is actually documented in the EMR and a second displaying patient-related data that has been corrected by a medical care provider. In such embodiments, a medical care provider is enabled to check patient-related information from an EMR for accuracy.

In the medical field, medical care providers, such as doctors, use drug categories according to the affects they have on the human body. Many types of categories can be classified on the basis of chemical nature of the drug. The term of the drug or medication is used for diagnosing, curing, or treating a disease. Drugs classification can include but are not limited to a Chemical nature of the drug, Symptoms or diseases for which they are used (i.e., antihypertensive drugs), Organ system affected, Generations of drugs, such as antimicrobials or oral hypoglycemic agents, Receptor theory, Duration of action, and method of administration. Embodiments of a medical management tool in accordance with the present principles enable medical care providers to display all of a patient's medications by classification by, in some embodiments, selecting from a menu whatever classification method is most intuitive to the medical care provider as the medical care provider is treating the patient. By way of example, in the case of a subspecialist, like an ophthalmologist, the doctor might just want to know all medications of the eye, so the organ system affected is the eye. For instance, in the eyes category of disease can be glaucoma, which includes pressure control in the eyes. For glaucoma, there is a group of medications that control pressure in the eyes. Currently, there are eight classifications. In addition, there is macular degeneration disease or diabetic macular edema disease and there are classifications for those diseases as well. A medical care provider can decide to display, on a single display, either all of the ocular medications that the patient is taking singly or in categories. Alternatively or in addition, a medical care provider can select to display medication by symptoms of the disease, such as the anti-hypertensive medications.

It can also be helpful to a medical care provider to know if a patient is taking an originally prescribed brand of the medication or if the patient is taking a generic medication. Embodiments of a medication management tool of the present principles provide a means for listing whether a patient is taking an originally prescribed brand of the medication or if the patient is taking a generic brand. A difference between the two brands of medication is that one might cost a significant amount more than the other and some can work a little differently and not be as affective. Medical care providers need to know whether the patient is taking a brand name or a generic. Some insurance companies will only pay for certain brands or generics, and mandate that medication be taken. Some medications will have a copay by the patient and the patient has to pay additional money. It can be critical that medical care providers also note cost to patients and to the insurance companies, so that medical care providers can control health care dollars.

In some embodiments of a Medication Management tool of a Data Command Center of the present principles, the Medication Management tool can make suggestions in regards to using a less expensive generic medication and in some embodiments can compare medication and procedure recommendations made by a user/medical care provider against what a patient's insurance will allow. For example, in some embodiments information regarding generic medications that can be substituted for brand name medications can be stored in a storage means accessible to, for example, the Rules module 004 of the Data Command center 001 of FIG. 1. As such, when a user/medical care provider prescribes a medication using the Medication Management tool and/or a medical records dashboard of the present principles, the Rules module 004, via for example the Display module 006, can cause a display of suggested generic medications, in some embodiments in a pop-up window, that can be prescribed to a patient in place of the brand name medication. Similarly, in some embodiments information regarding what medications and procedures can be authorized by a patient's insurance company can be stored in a storage means accessible by, for example, the Rules module 004 of the Data Command center 001 of FIG. 1. As such, when a user/medical care provider prescribes a medication or schedules a procedure using the Medication Management tool and/or a medical records dashboard of the present principles, the Rules module 004 can compare the information regarding what a patient's insurance company will allow and what medication the user/medical care provider has prescribed or what procedure was scheduled to determine if the patient's insurance company will allow the medication and/or procedure. If the Rules module 004 determines that a prescribed medication and/or scheduled procedure is not allowed by a patient's insurance company, the Rules module 004, via for example the Display module 006, can cause a display of an alert to the user/medical care provider to alert the user/medical care provider that a prescribed medication and/or scheduled procedure is not allowed by the patient's insurance company. In some embodiments, information regarding what medications and procedures can be authorized by a patient's insurance company can be stored in a storage means accessible to the Rules module 004 of the Data Command center 001 of FIG. 1.

Figure 37:
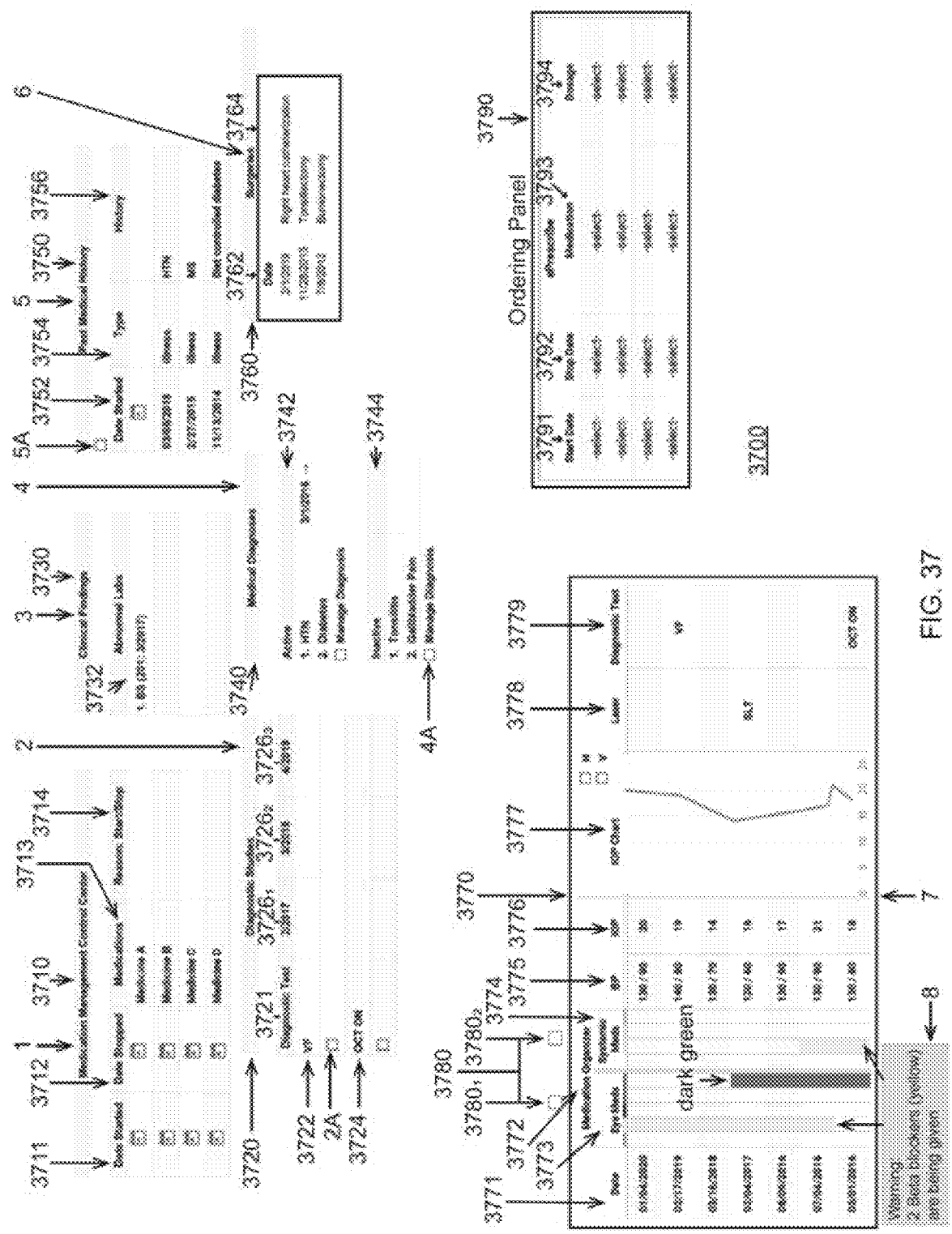
FIG. 37 depicts an exemplary embodiment of a Medications Management chart/tool which does not use rows or columns in accordance with an alternate embodiment of the present principles.

FIG. 37 depicts an exemplary embodiment of a Medications Management chart/tool 3700 which does not use rows or columns in accordance with an alternate embodiment of the present principles. Block 1 of the Medications Management chart/tool 3700 of FIG. 37 depicts a control panel 3710, which can be used to configure the bar graphs of block 7 and 8 described in greater detail below. The control panel 3710 of FIG. 37 illustratively comprises a date started column 3711, a date stopped column 3712, a medications column 3713 illustratively listing medicines A, B C and D, and a start/stop reasons column 3714.

Block 2 of the Medications Management chart/tool 3700 of FIG. 37 depicts a diagnostic studies menu 3720, which can be used to list diagnostic studies performed on a patient. The diagnostic studies menu 3720 of FIG. 37 illustratively comprises a diagnostic test column 3721, including a VF row 3722 and an OCT ON row 3724, and three date columns 3726$_1$, 3726$_2$ and 3726$_3$. In the diagnostic studies menu 3720 of FIG. 37, by hitting 2A, a user can pull up an individual test or get thumbnails of the tests performed on a patient. Block 3 of the Medications Management chart/tool 3700 of FIG. 37 depicts a clinical findings menu 3730, which can be used to list clinical findings on a patient. The clinical findings menu 3730 illustratively comprises an abnormal labs column 3732 for listing abnormal laboratory findings for a patient.

Block 4 of the Medications Management chart/tool 3700 of FIG. 37 depicts a medical diagnosis menu 3740, which can be used to list medical diagnosis made by a user for a patient. As depicted in the embodiment of FIG. 37, the medical diagnosis menu 3740 can be divided into active 3742 and inactive 3744 diseases. In the embodiment of FIG. 37, the various diagnoses or conditions of the patient can be managed on the screen by clicking 4A. Block 5 of the Medications Management chart/tool 3700 of FIG. 37 depicts a past medical history menu 3750, which can be used to list conditions that affect the well-being of a patient. As depicted in the embodiment of FIG. 37, the past medical history menu 3750 illustratively includes a date started column 3752, a type column 3754 and a history column 3756. In the embodiment of the past medical history menu 3750 of FIG. 37, by hitting 5A, a user is able to edit any of the information in the past medical history menu 3750.

Block 6 of the Medications Management chart/tool 3700 of FIG. 37 depicts a surgeries menu 3760, which can be used to list surgeries performed on a patient. As depicted in the embodiment of FIG. 37, the past medical history menu 3750 illustratively includes a date started column 3752, a type column 3754 and a history column 3756.

Block 7 of the Medications Management chart/tool 3700 of FIG. 37 depicts a dashboard 3770. The Dashboard 3770 of the Medications Management chart/tool 3700 of FIG. 37 illustratively comprises a date column 3771, a medication organizer column 3772 including an eye medications column 3773 and a systemic medications column 3774, a blood pressure (BP) column 3775, an intraocular pressure (IOP) column 3776, an IOP chart/graph column 3777, a laser column 3778, and a Diagnostic test column 3779. The Dashboard 3770 of the Medications Management chart/tool 3700 of FIG. 37 illustratively further comprises a respective ordering panel selection block 37801, 37802 for each of the eye medication column 3773 and the systemic medications column 3774. When a user selects either of the ordering panel selection blocks 37801, 37802, an ordering panel 3790 such as an E-prescribed panel is displayed that enables the user to place an order, which can include prescribing a medicine, and comes up in a way that does not block the entire view. The ordering panel 3790 illustratively comprises a start date column 3791, a stop date column 3792, a medication column 3793, and a dosage column 3794.

In the Dashboard 3770 of the Medications Management chart/tool 3700 of FIG. 37, the eye medication column 3773 and the systemic medications column 3774 include bar graph representations of medications associated with the treatment of a patient's eye. Illustratively, in the Medications Management chart/tool 3700 of FIG. 37, a user is being warned in block 8 that two beta blockers, depicted as yellow bars, are being given to the patient. Since there is a relationship between the two, the user needs to know.

Figure 38:
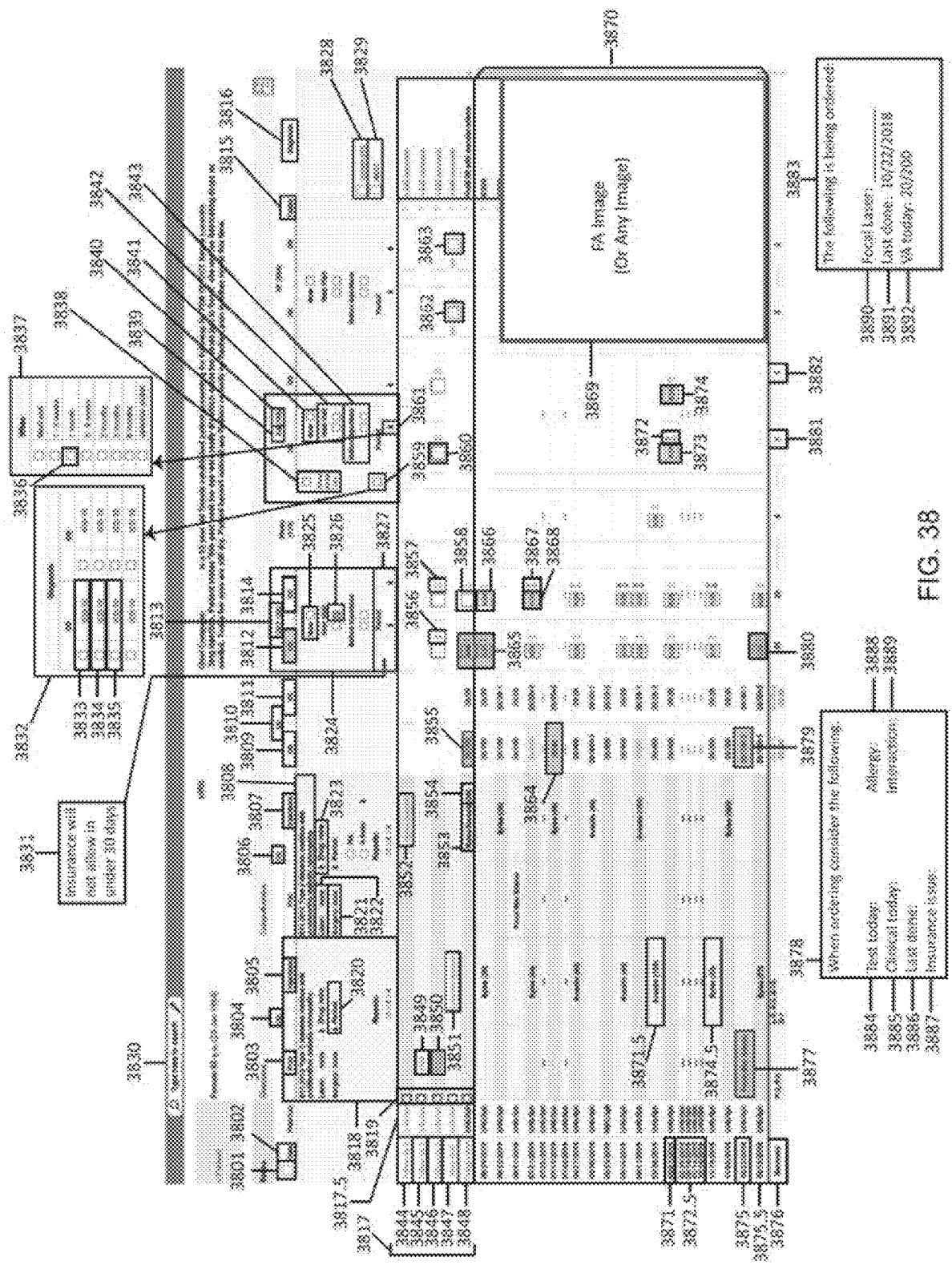
FIG. 38 depicts an embodiment of a medical records dashboard of a Data Command Center in which a user/medical care provider is enabled to place orders in context with other relevant patient data/information.
Figure 38A:
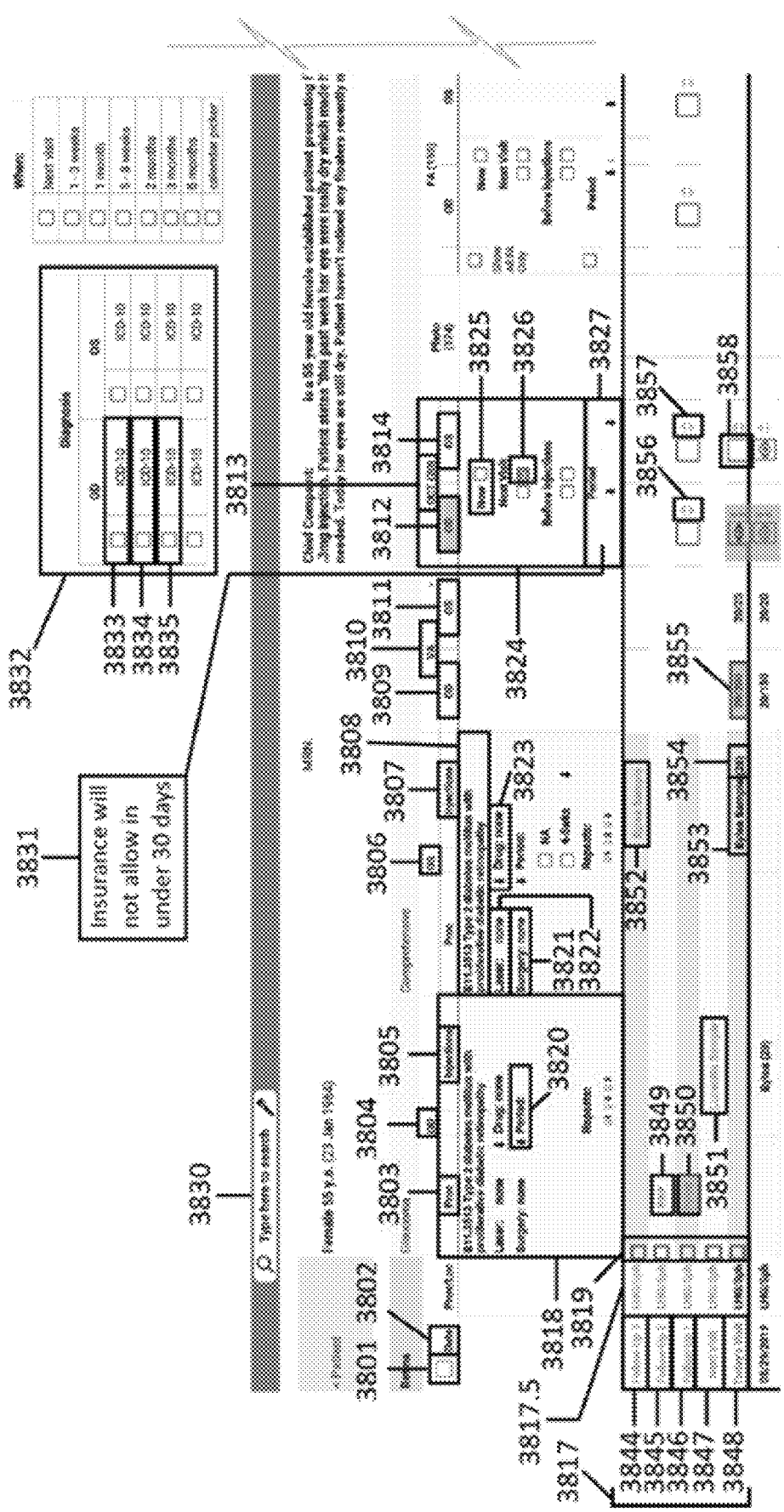
FIG. 38A depicts an embodiment of a medical records dashboard of a Data Command Center in which a user/medical care provider is enabled to place orders in context with other relevant patient data/information.
Figure 38B:
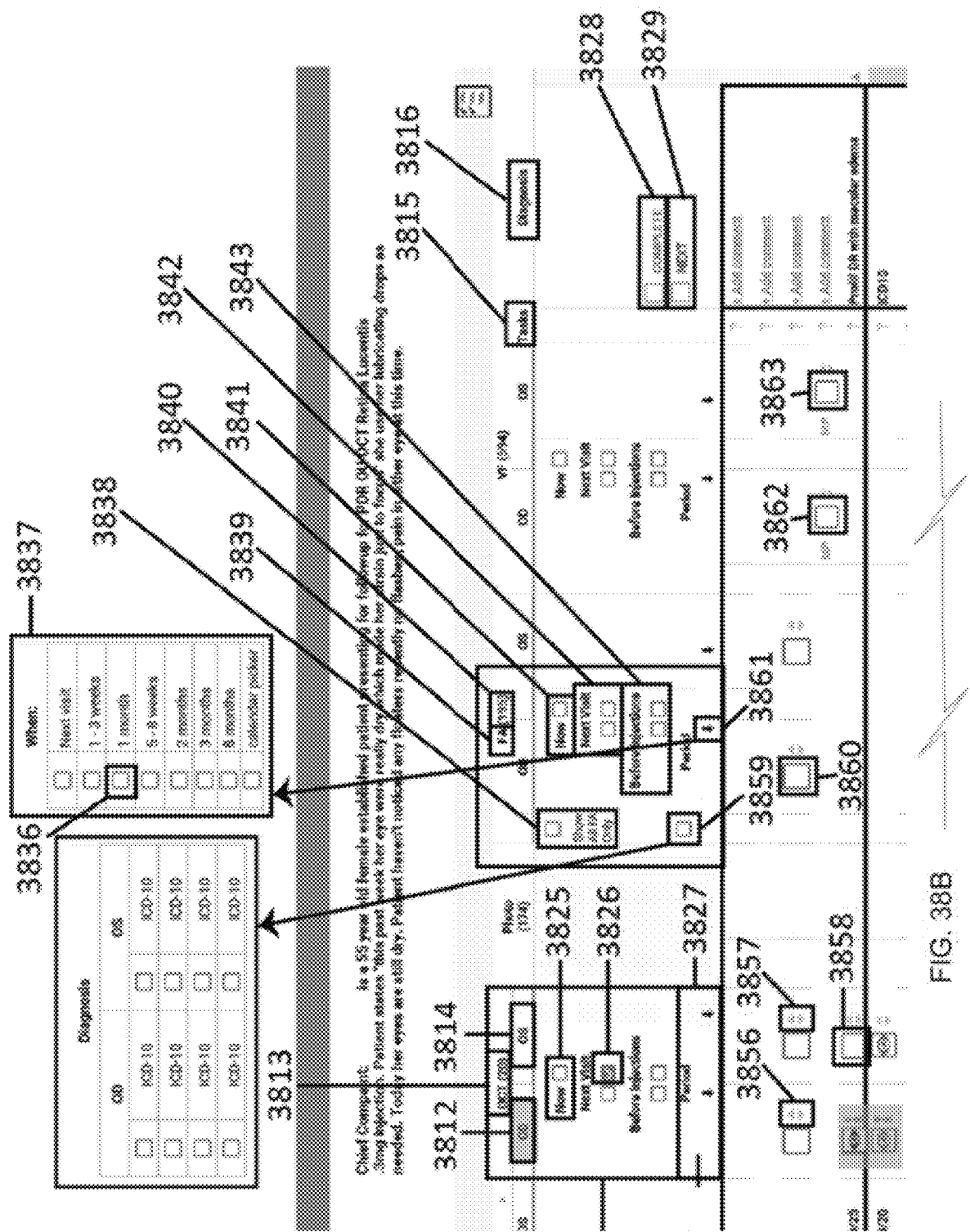
FIG. 38B depicts an embodiment of a medical records dashboard of a Data Command Center in which a user/medical care provider is enabled to place orders in context with other relevant patient data/information.
Figure 38C:
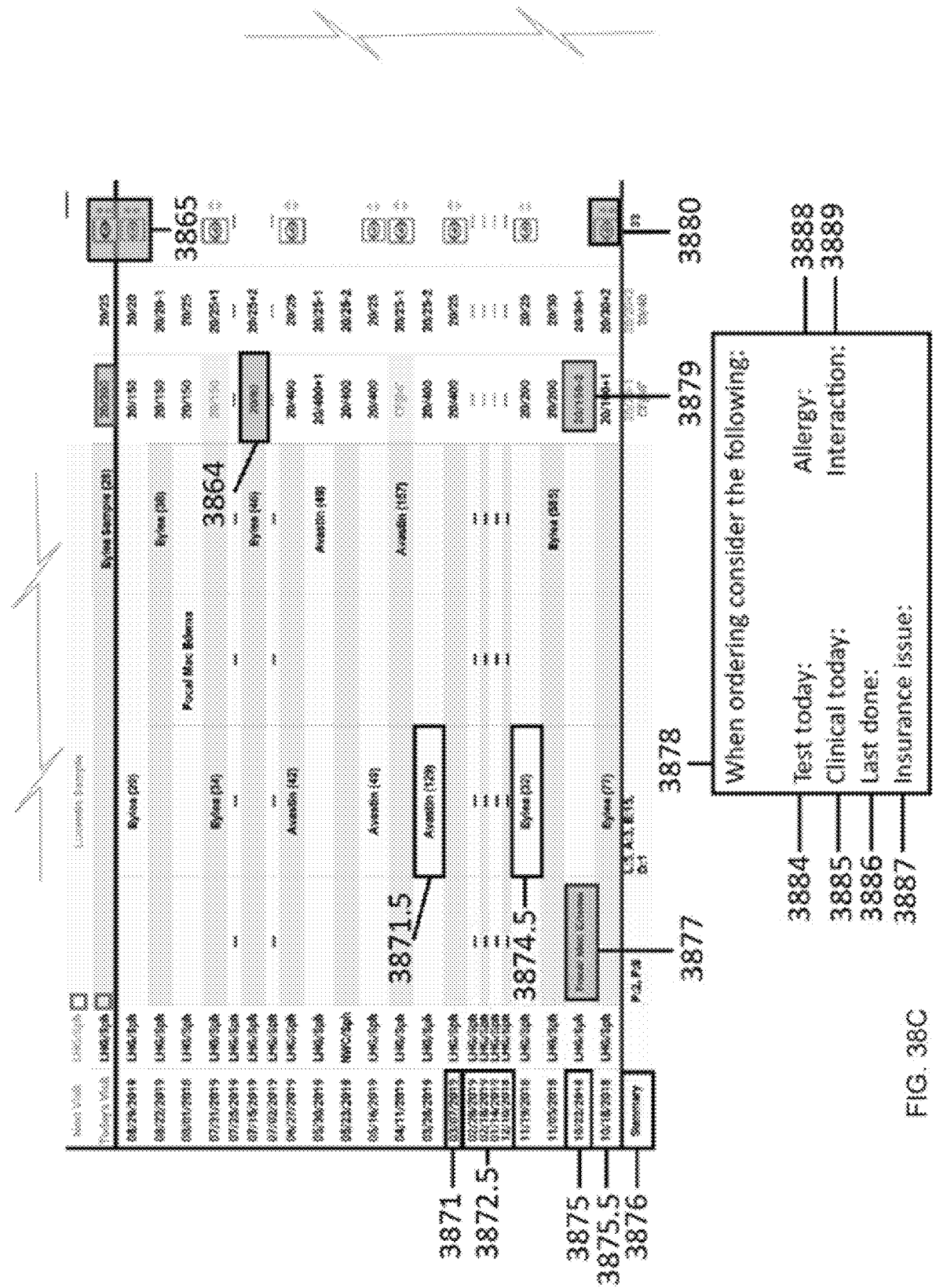
FIG. 38C depicts an embodiment of a medical records dashboard of a Data Command Center in which a user/medical care provider is enabled to place orders in context with other relevant patient data/information.
Figure 38D:
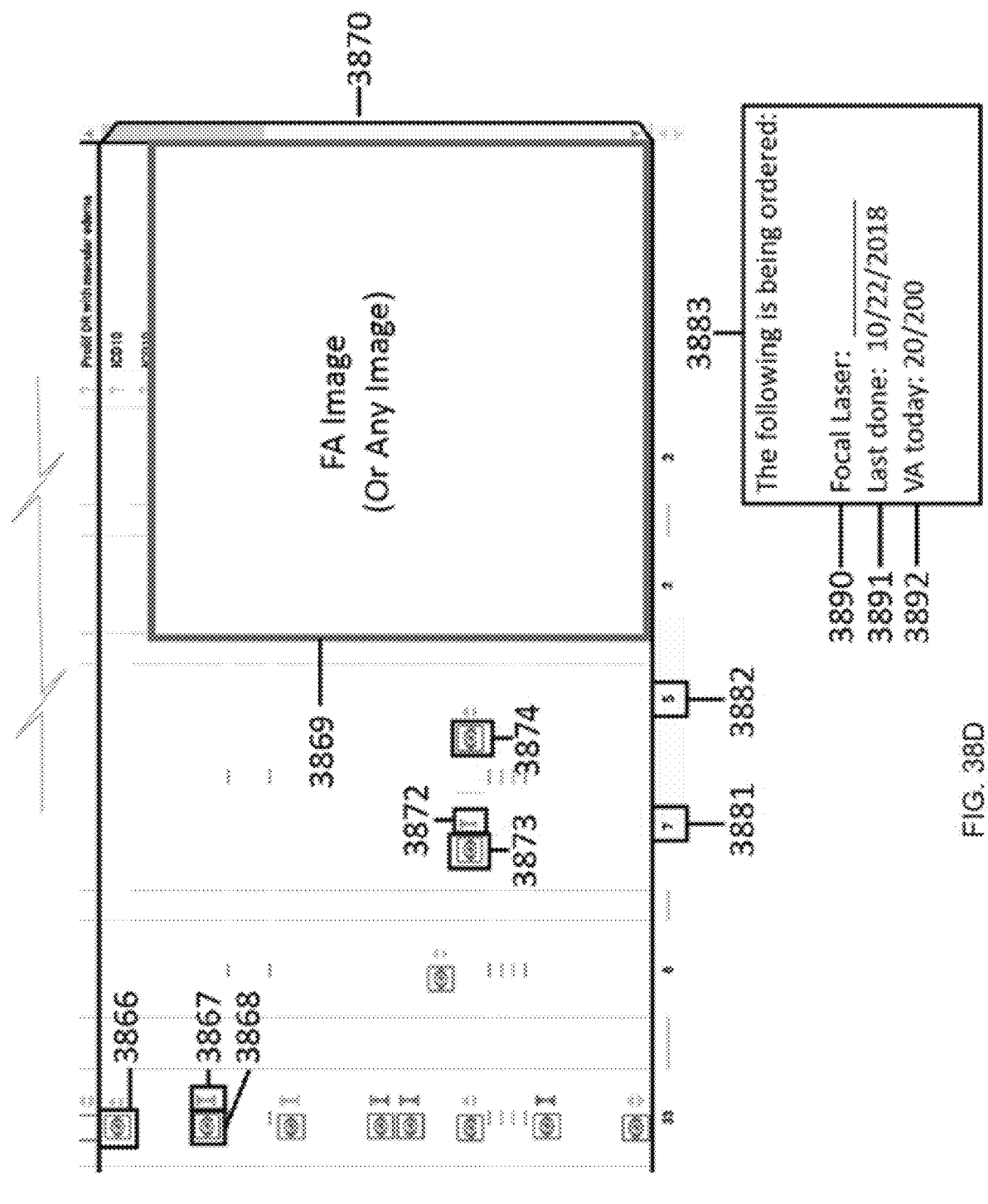
FIG. 38D depicts an embodiment of a medical records dashboard of a Data Command Center in which a user/medical care provider is enabled to place orders in context with other relevant patient data/information.

FIG. 38 depicts an embodiment of a medical records dashboard of a Data Command Center in which a user/medical care provider is enabled to place orders in context with other relevant patient data/information, so as to enable the user/medical care provider to see the future orders in context and confirm that the orders submitted are in fact what the user/medical care provider intends in accordance with the present principles. The details of FIG. 38 are being presented as FIGS. 38A-38D (collectively referred to as FIG. 38 below) to enable more clear visualization of the features of the embodiment of FIG. 38. In some embodiments, a column of the medical records dashboard can be expanded by selecting the column. For example, in FIG. 38, the column 3801 is expanded as depicted by window 3818. In some embodiments, the window 3818 can comprise a pop-up panel for placing orders. In FIG. 38 cells 3804, 3818, and 3839 depict examples of cells displayed in the medical records dashboard that are in the line and above corresponding columns that identify that orders have been made and/or enable the placement of new orders. For example, cell 3804 corresponds to a panel that can be used for placing orders for a right eye (OD) 3803 and is located directly above procedures 3877 performed in the past for the right eye (OD). Another example is the ordering panel 3839 which is above the FA column. Illustratively, in the FA column, a user can identify when the last time something was performed, enabling a user/medical care provider to determine if it is time to order a new procedure. From the medical records dashboard of FIG. 38 it can be determined from 3871 that the last FA 3873 was done (Mar. 7, 2019) and the FA in the header cell 3839 depicts that the last FA, was 195 days ago as depicted in cell 3840. In the embodiment of the medical records dashboard of FIG. 38, a user is enabled place an order while visualizing a particular CPT codes (diagnostic test, procedures, office visit, etc.) ordered in the past and can visualize how often it was performed, when the last time it was performed. In FIG. 38, an illustrated FA 3839, row 3876 reports the total number of times the item to be re-ordered was previously performed. In the example of an FA shown in cell 3881 of FIG. 38, in the right eye (OD) cell 3882 depict that an FA was performed seven times in the past.

As described above, in the embodiment of FIG. 38, expansion of an ordering panel can occur in both in height and in width. In some embodiments, to enable the expansion of an ordering panel, columns that are considered by a user/medical care provider as unnecessary can be collapsed to enable viewing expanded ordering panels in context with information deemed necessary. For example, a clinical measurement, such as vision measurements in columns 3810, 3809, 3811 can be collapsed if a user determines such information is not currently needed, enabling horizontal expansion of ordering panels. In some embodiments, the ordering panels (3839, 3813, 3804) can widen when the user/medical care provider clicks on them to then place an order to enable a user/medical care provider to simultaneously visualize, using a single display, data relevant to the newly placed orders. In accordance with embodiments of the present principles, the display 3830 remains interactive during the display of the ordering panels to enable a user to scroll down to see past FA performed, for example, prior to the Oct. 18, 2018 row 3830 of FIG. 38 depicts a search mechanism enabling the user to type in or ask any questions and whatever rows with the relevant data would be the rows visualized with other rows collapsed or hidden. For instance, cell 3881 depicts that seven FA were done yet only 3871 is displayed in this single view, but all seven dates of service when 3839 were performed, the tool would display those rows for instance clicking on cell 3881, which may be important as a user is ordering a new FA. In this way, as the user orders, for example, an FA, the user is able to visualize what was done in the past.

In the embodiment of FIG. 38, an FA can be ordered by activating ordering panel 3839 to expand the panel. The user could then decide if what the users want displayed in that column, 3839 are just the most recent FAs, in FIG. 38 depicted by cells 3874 and 3873 in row 3871. A user, alternatively, could scroll down and find the other FA's for the earlier dates or by clicking on cells 3881 or 3882. Embodiments of the present principles enable a user to search as depicted in cell 3830 or to scroll to display the seven FA rows. In some embodiments, all of the rows and dates of service can be collapsed to make room to display today's visit in, for example, cell 3848. That is, because an action is being performed by a user, a current row can remain visible. A next visit then can be displayed in a follow up cell 3847 and a future order cell 3846 can become visible, as the user places orders for different future dates of service with row popping-up as user places orders for each future visit. Alternatively, in the embodiment of FIG. 38, a user can prioritize the visualization of rows/cells depicting when FA was performed and collapse other rows/cells by clicking on icon 3852, which enables a collapsing of all rows except the rows when an FA was performed.

In the embodiment of the medical records dashboard of FIG. 38, if a user/medical care provider wants to double check if an order placed is proper and wants to see a related study itself, the user/medical care provider can select cells 3874 and a respective image can be displayed so the ordered study can be interpreted in context of all other information being presented in the medical records dashboard. The user/medical care provider can view directly, an image or even choose multiple icon images of, for example, the FA. The ordering panels that are displayed when selected (i.e., 3801 or 3839) can be customized by specialty, for example in FIG. 38 for a retina specialist. In the embodiment of FIG. 38, a retina specialist can perform injections on a patient, as such in accordance with some embodiments of the present principles, the retina specialist can be presented with an option to perform the FA before an injection, 3843. In such embodiments, the injections are not hidden and can be seen in column 3807. The scheduling for the test (e.g., FA 3839) can then be accomplished by activating cell 3861, at which point an option for selection can be displayed (i.e., 3837) and the user can select form a pull down menu how far in the future (illustratively one month 3836) to order the study.

In some embodiments, a Rules module, such as the Rules module 004 of the Data Command center 001 of the embodiment of FIG. 1, can be configured to determine if a patient's insurance company will disapprove of ordered studies and can further be programmed to determine if a patient has an aversion to an ordered study and can cause a display, for example via the Display module 006, of an alert or information window on the medical records dashboard to inform a user/medical care provider of such instances.

In the embodiment of FIG. 38, cell 3813 can be used to order an OCT test. For example, cell 3814 can be selected by a user to select a left eye then OCT (OS), cell 3826 selects next visit, and cell 3827 can be selected for choosing a time period. In some embodiments, a Rules module, such as the Rules module 004 of the Data Command center 001 of the embodiment of FIG. 1, can have access to a storage means containing rules for scheduling tests (i.e., certain tests have rules for how often the tests can be performed on a patient) and the Rules module 004 be configured to determine if tests/studies have been improperly ordered. In such instances, the Rules module 004 can cause a display, for example via the Display module 006, of an alert or information window on the medical records dashboard to inform a user/medical care provider that perhaps a test/study has been improperly ordered via, for example, a pop-up window 3831.

In the embodiment of FIG. 38, a user/medical care provider is enabled by the medical records dashboard to select a reason for ordering a test or procedure. In the embodiment of FIG. 38, cell 3859 can provide a menu providing options for a user to select for inputting reasons for ordering a test or procedure. In some embodiments, such options provided to a user in cell 3859 can be pre-programmed. Alternatively or in addition, a Rules module, such as the Rules module 004 of the Data Command center 001 of FIG. 1, can be programmed to monitor data/information related to a patient including, but not limited to, previous diagnosis made, previous tests ordered, previous procedures ordered and respective reasons for ordering the tests and procedures, and the Rules module 004 can be configured to learn, for example, through machine learning and/or artificial intelligence means to determine at least a best reason for ordering tests and procedures depending on relevant patient information. In such embodiments, the Rules module 004 can cause the display, for example via the Display module 006, of most logical reasons for ordering a test or procedure in, for example, a drop down menu provided by cell 3859 of the medical records dashboard of FIG. 38. For example, the Rules module 004 can be aware of what CPT codes can be associated with ICDs for a particular patient for which test and/or procedures are being ordered and the most logical diagnostic codes can be presented, for example in cells 3833, 3834, and 3835. In the embodiment of FIG. 38, if a user/medical care provider is unsatisfied with the reasons for ordering provided in, for example, a drop down menu provided by cell 3859, the user/medical care provider can select cell 3832 to see more options or to insert a reason for ordering.

In the embodiment of the medical records dashboard of FIG. 38, a user/medical care provider can select using for example cell 3814, for which eye a test/study/procedure is to be ordered. A diagnosis and information regarding what is ordered is displayed in cells 3848, 3847, 3846, 3845, and 3844 of section 3817 depending on when the order is scheduled. The user can visualize the order, then by any means, confirm it is correct, by selecting cell 3814. The user/medical care provider is able to confirm everything in a row displayed is correct as visualized and confirm the order for that entire future date of service by selecting cell 3819. In the embodiment of FIG. 38, a user can be informed of what is being ordered by displaying in a corresponding row, an empty icon or empty box, for example 3860 of 3846. If the doctor wants to also order an OCT in the right eye, cell 3812 can be selected and the process repeated.

In the embodiment of the medical records dashboard of FIG. 38, cell 3870 shows all past encounters of relevance in which a user can view all of the information by scrolling or viewing on a single display. Cell 3870 keeps track of every encounter and a date and/or time of the encounter, any medical service, ICD 10 with diagnosis or clinical information or procedural information. Cell 3876 includes a summary of how often orders have been placed in any period of time. Row 3848 depicts information regarding "today's visit." Today's visit can be live and in real time in some embodiments. Clinical information, i.e. in this example vision (VA), can be displayed as it is input in corresponding columns 3810, 3809, 3811. Column 3807 depicts what is to be done today and in the embodiment of FIG. 38 depicts an injection with medication 3853, "Eylea sample." Cell 3854 of FIG. 38 depicts that the procedure was to be performed 28 days ago, which, as described above, can be checked by the medical records dashboard for compliance.

In the embodiment of FIG. 38, row 3848 shows under column 3814 an OCT and an empty box 3858. Such configuration can indicate to a user/medical care provider that the ordered procedure/test/study has not yet been performed because in the embodiment of FIG. 38 the order was scheduled in "today's visit," meaning that the user/medical care provider placed the order today. In comparison, cell 3866 is filled in because on the last visit the test had been performed.

In some embodiment of the present principles, an appearance of the cells of the medical records dashboard can be altered to distinguish/highlight the information in the cells. For example, in the embodiment of FIG. 38, cells 3860, 3862, 3863, 3850, 3851, 3849, 3852 are examples of cells containing future orders. In some embodiments, cells can be made lighter or darker to differentiate past versus future actions/orders. In addition and for example, row 3848 of "today's visit" can be made blue. Even further, in some embodiments of the present principles, icons or markers can be included in cells/rows/columns of the medical records dashboard to enable a user to make a determination of the information included in a cell just by looking at the icon/marker. In some embodiments, the icons/markers can also include color to further distinguish between information represented by the icon/marker. For example, icons 3865, 3880 can be shown as colored indicators to indicate a status of the condition of a user's eye described in cell 3867 and 3872.

In the embodiment of the medical records dashboard of FIG. 38, related cells can be highlighted to call a user's attention to relevant patient data when placing an order. For example, cell 3822 enables a user to order a laser. Cell 3850 depicts that a focal laser is to be ordered in the future. In conjunction, cell 3877 can be highlighted to alert the user/medical care provider of the last time a similar focal laser was done. In addition, cell 3879 can be highlighted to alert a user what the vision of the patient was at the time of the last laser performed Oct. 22, 2018. As such, a user/medical care provider can take into account related patient data as they place an order for a focal laser in cell 3803 as displayed in cell 3850 for a follow up row 3846, as scheduled by any means, by way of example, within the pop-up window 3803. By noting a previous condition of the vision of a patient in accordance with the present principles, a user can identify if a patient's condition is getting better, worse or remaining the same. For example, in the embodiment of FIG. 38, icons 3865 and 3897 show red indicators to indicate a worsening of a condition of a patient's eye.

In another example of placing orders, as described above a medical records dashboard of the present principles, via for example a Rules module, can be aware of what the most common ICD10 might be (i.e., via cell 3832) when ordering. Cell 3842 depicts a user selecting a box and an order can be directly linked to the box the user selects, which can be displayed in a pop-up window as depicted in cells 3827, 3861, and 3836. The future encounter can be selected and confirmed in cell 3828 and the next encounter ordered in cell 3829, which in this embodiment means another date of service in the future is to be ordered and displayed, and the process starts again. This functionality enables users/medical care providers to confirm future orders by reviewing available patient related data being simultaneously displayed in the medical records dashboard.

As depicted in the embodiment of FIG. 38, the medical records dashboard can include panel 3878 for assisting a user/medical care provider in placing an order. That is, in some embodiments, when a user/medical care provider is placing an order, panel 3878 can be presented to the user/medical care provider to present to the user/medical care provider a list of things that the user/medical care provider should take into considerations when placing an order. In the embodiment of FIG. 38, the panel 3878 includes considerations such as 3884 a diagnostic test that was done today or on a previous visit, 3885 clinical findings found today, 3886 a last time the same or similar test/study/procedure was done, 3887 insurance issues, 3888 allergy concerns, and 3889 possible interactions with other tests and/or medications. A Rules module, such as the Rules module 004 of the Data Command center 001 of FIG. 1, can be configured to monitor such considerations and alert a user/medical care provider if a problem is determined. Although the panel 3878 of FIG. 38 depicts a specific listing of considerations in panel 3878, in alternate embodiments, the considerations listed in panel 3878 can change dependent upon what is being ordered.

As depicted in the embodiment of FIG. 38, the medical records dashboard can include panel 3883 for assisting a user/medical care provider in placing orders. That is, in some embodiments, when a user/medical care provider is placing an order, panel 3883 can be presented to the user/ medical care provider to present to the user/medical care provider an order summary. In the embodiment of FIG. 38, the panel 3883 includes a listing of 3890 what is being ordered, 3891 a last date the same procedure was performed on the patient, and 3892 any relevant clinical information. Although the panel 3883 of FIG. 38 depicts a specific listing of related order information in panel 3883, in alternate embodiments, the order related information listed in panel 3883 can change dependent upon what is being ordered.

Figure 39:
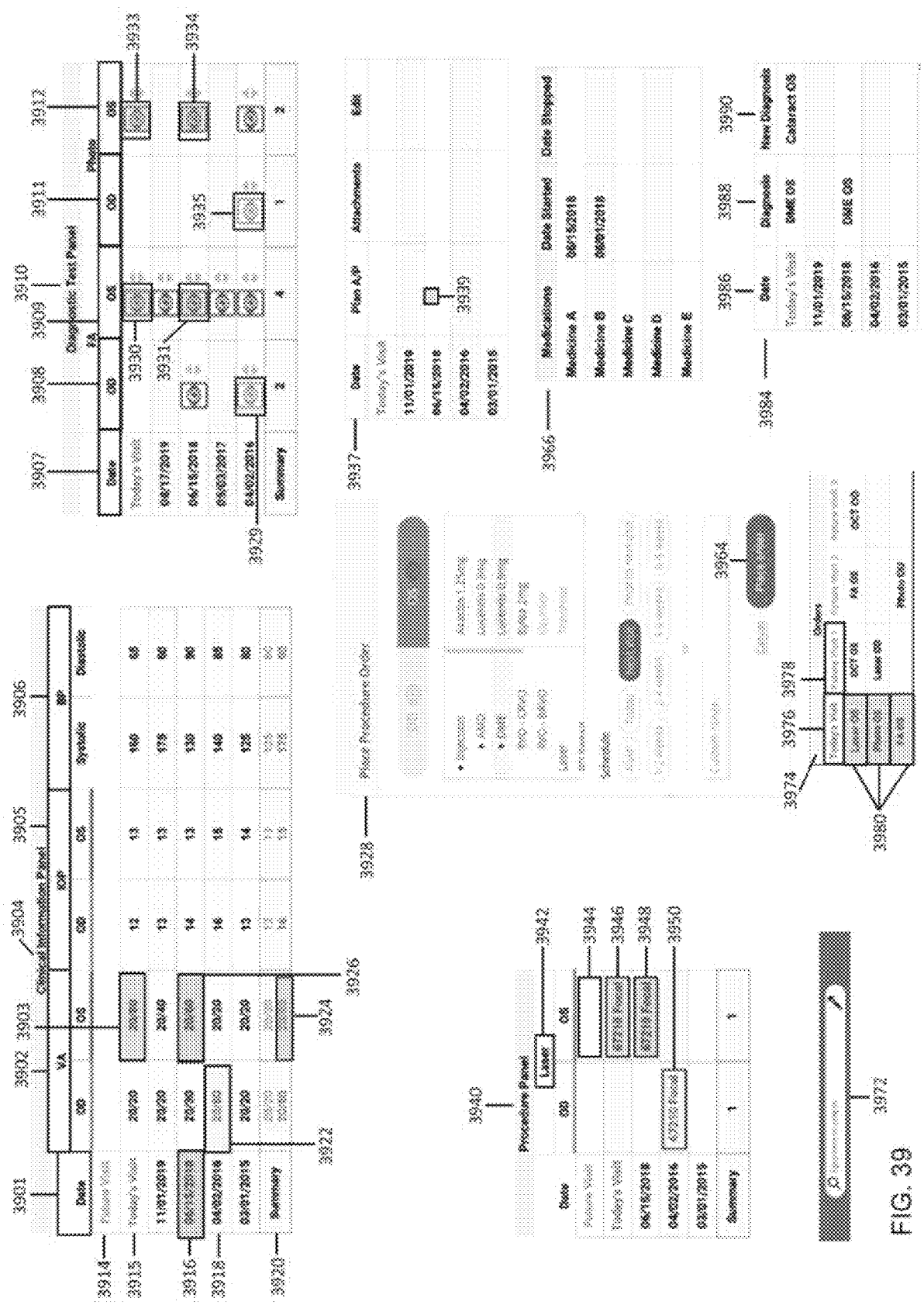
FIG. 39 depicts an embodiment of a medical records dashboard of a Data Command Center in which a user/medical care provider is enabled to place orders in context with other relevant patient data/information, so as to enable the user/medical care provider to see the future orders in context in an embodiment not using rows and columns in accordance with the present principles.

FIG. 39 depicts an embodiment of a medical records dashboard of a Data Command Center in which a user/ medical care provider is enabled to place orders in context with other relevant patient data/information, so as to enable the user/medical care provider to see the future orders in context in an embodiment not using rows and columns in accordance with the present principles. Some doctors or EMR companies may prefer not all relevant data that's related being on one row or column on a screen or dashboard. The invention allows for other options where on a screen there can be multiple areas on that screen that display different data sets that could be grouped into multiple panels, multiple dashboards, or just lists and not in rows and columns. Zooming and scrolling functions are enabled so user can see information that they want to see while always able to see the bird's eye view, so as not to lose overall focus. In FIG. 39, element 3904 depicts a clinical information panel which could also be examination elements for just today or over a period of time. Window/panel 3940 shows procedures, which most commonly are CPT codes, which could be performed in an office setting or operating room and can be individualized and divided in any way the user would best be able to interact with the data. This could include wishes separating right from left, up or down when different parts of the body could be confused. Panel 3910 depicts diagnostic tests of which there can be just one or many which can include any type of medical service most commonly represented by a CPT code including biopsies, chemistries, angiogram's, photographs, x-rays. More than just one panel for diagnostic tests can be on the screen as a user would need for a patient or several patients. Panel 3966 can list all the medicines, including start and stop dates. Another panel could be where a doctor can view a plan and notes can be entered or past plans over time are seen and could, in some embodiments, plans created, edited, and in some embodiments populated elsewhere into the chart.

Unique to this embodiment is the fact that if the user wants any more information, data in the panels can be selected in one embodiment with direct one click access or hovering and pop-up more information, for instance as seen in FIGS. 23 2382 and 2320, for example and displayed with relevant information still on the screen, as seen in FIG. 23. The search the database mechanism number 3972 FIG. 39 can be typed or through voice recognition can search all the data in the tool or EMR or PM system and display only or light up the information in each of the relevant panels that answer the question of the search. If the panels are in date order only the dates of the encounters that are related to the question were displayed in each of the panels 3904, 3940, 3910, 3937, 3966, and 3984. If, for instance, a question is asked, relevant information can be displayed and highlighted for instance if the question is asked 'show me when the last time or all times that a focal laser was done in the right eye' and all relevant information, number 3922 in panel 3904 number 3929, 3935 in panel 3910, number 3950, in panel number 3950 also lights up. All that are highlighted as occurring the last time a laser was performed along with the diagnostic tests and clinical findings on that day. The doctor can also choose to show the immediate previous visit and a visit afterwards to see the effect of the treatments all on one screen.

One embodiment allows actions to be taken, even ordering on this one screen. Panel number 3928 shows an example described elsewhere including in FIG. 38, in this patent how an ordering mechanism while relevant information is in view can be shown. Information as a doctor places an order can be displayed in any of the panels or sections, but shown as an example in how highlighting can work in rows and columns in FIG. 38 number 3850, a focal is ordered for a follow up or future visit 3846 and when the user sees the actual focal appear on the right eye 3850, it is enhanced by some method, then the tool is programmed to know what relevant data should be presented simultaneously, so the doctor can double check their order. Therefore, the relevant numbers 3877, 3855, and 3879 are enhanced. 3877 is the last time that procedure was done. 3877 shows the vision, which is just an example of important information that the doctor should consider when checking and ordering his order. In this case, 3855 is 20/200 vision and to compare it to last vision to see if really worse, 3864 shows a recent good vision of 20/80 reminding doctor it really worsened and 3879 shows what the vision was when the last focal was done. In the case of a retina OCT, measurements are critical in deciding if the retina is getting better, so the entire column of the right eye 3812, which is the eye that is being ordered to be lasered, can be highlighted or just the ones that would be the most relevant, i.e. 3865, 3880 also show red indicators of worsening described in 3872.

In some embodiments is another example of a mechanism for displaying what is ordered. In one embodiment, the tool can take this information and display it on the single screen of the invention and display at least what's being ordered elsewhere on screen displaying relevant information in 3904, 3940, 3910, 3937, 3966, and 3984. In various embodiments, what is being ordered today can be shown under and be specific according to date when being ordered if "now" or "today" would be number 3942 and number 3946, for number 3944 if it's in the future. Number 3948 would show the last time that particular laser was done. It can also, whatever is being ordered, be listed instead of individually on the different sections 3904, 3942, 3910, 3966 be inserted in panel 3974 of today's orders or future scheduling orders of any kind whether it's medications, surgeries, diagnostic test procedures, consultations for other doctors or just follow up visits. All that is being acted upon elsewhere in the EMR, which requires multiple clicks and multiple windows and when ordered is not in context. This tool puts the orders and actions placed elsewhere and shows the user what is being ordered in context displaying relevant information for the doctor to be able to visualize and confirm what is being ordered, even if not ordered on the screen of the tool. One embodiment puts the orders elsewhere on the screen of the invention. Before doctor confirms and actually places the order, they can open this single view, or screen of this embodiment and see, for instance, in number 3974, all in one panel or, for instance, separate panels with highlighted the order number 3946, 3930, and 3933 all that they are ordering and planning in context in comparison to what has happened in the past. Number 3903 shows a clinical finding lighting up that is relevant to the order of a laser today, and if the plan from the last visit is relevant panel 3937, plan icon 3939 also can be highlighted. Unique to the invention, the user can then directly select 3939 and can view that plan or any relevant cell such as 3930 in context, without having to leave the screen. This embodiment also will highlight relevant and important information.

For instance, if the order today is for a focal laser it appears in 3980 or it can appear in 3946, which is today's column for that and the procedure panel 3940 (which can list in columns all procedures that specialist does, but then when laser is ordered by any method, the laser procedure columns come up automatically and focal laser column 3942 can light up, but extremely important also presented would be number 3948 showing the last time that procedure had been done, and today's clinical relevant information number 3903 showing decreased vision 20/80 in this case and the tests that are related lighting up 3930 and 3933 all being shown. But, on 3948, the last time the laser was done Jun. 15, 2018, also perhaps in another color. The clinical information is presented number 3926 showing 20/60 vision and 3931, 3934 can light up so user can realize what had occurred when they last did a focal and user can readily select 3930 and 3931, and the underlying images is displayed for comparison, so user can compare before order is confirmed or treatment performed. All of this information the doctor will quickly be able to understand, but also the embodiment can guide some embodiments since that procedure is being done in the left eye and highlighted can also be the last time that procedure might have been done in the other right eye. Consideration number 3922, 3974, 3901, 3902, 3935 can show the details of when it was done in the right eye even though the order now was been placed in the left eye but the data may well be relevant.

In some embodiments, the Data Command center 001 enables the medical records dashboard to intelligently expand, collapse, display, and/or hide columns, rows and/or any other portion of the medical records dashboard to show precisely what a user wishes to display. For example, in one embodiment, a Flowsheet including patient treatment and health information can be accessed from an EHR system using, in some embodiments, an icon/button, keystroke, or series of keystrokes associated with at least one of the Data Command center 001 and the medical records dashboard. Upon accessing the Flowsheet, a set of Rules and Configurations associated with, for example, the Rules module 004 of the Data Command center 001, can be evaluated to determine which data from the Flowsheet is to be displayed in the medical records dashboard. For example, in some embodiments, the Rules module 004 can include information on what data to display, and in turn what portions of the medical records dashboard to display, based on, including but not limited to, at least one of an identity of a medical care provider, an identity of a patient, a medical care provider's specialty, conditions of a patient, patient procedures, risk factors, diagnostic results, future orders, future appointments, values recorded, values not recorded, calculated values, and absolute values for display.

For example, in some embodiments in accordance with the present principles, Rules and Configurations can be predetermined and stored, for example, in the Rules module 004, for determining which data of a Flowsheet and, as such, which portions of the medical records dashboard to display or hide. Alternatively or in addition, in some embodiments, a user can self-configure the medical records dashboard to display only certain portions or to hide certain data of a Flowsheet and, as such, which portions of the medical records dashboard to display or to hide using, for example, a user interface (not shown) associated with the medical records dashboard. Alternatively or in addition, data of the Flowsheet can contain an indicator (e.g., a flag) that can be identified by, for example, the Rules module 004, for determining when and if a piece of data should be displayed or hidden.

Figure 40A:
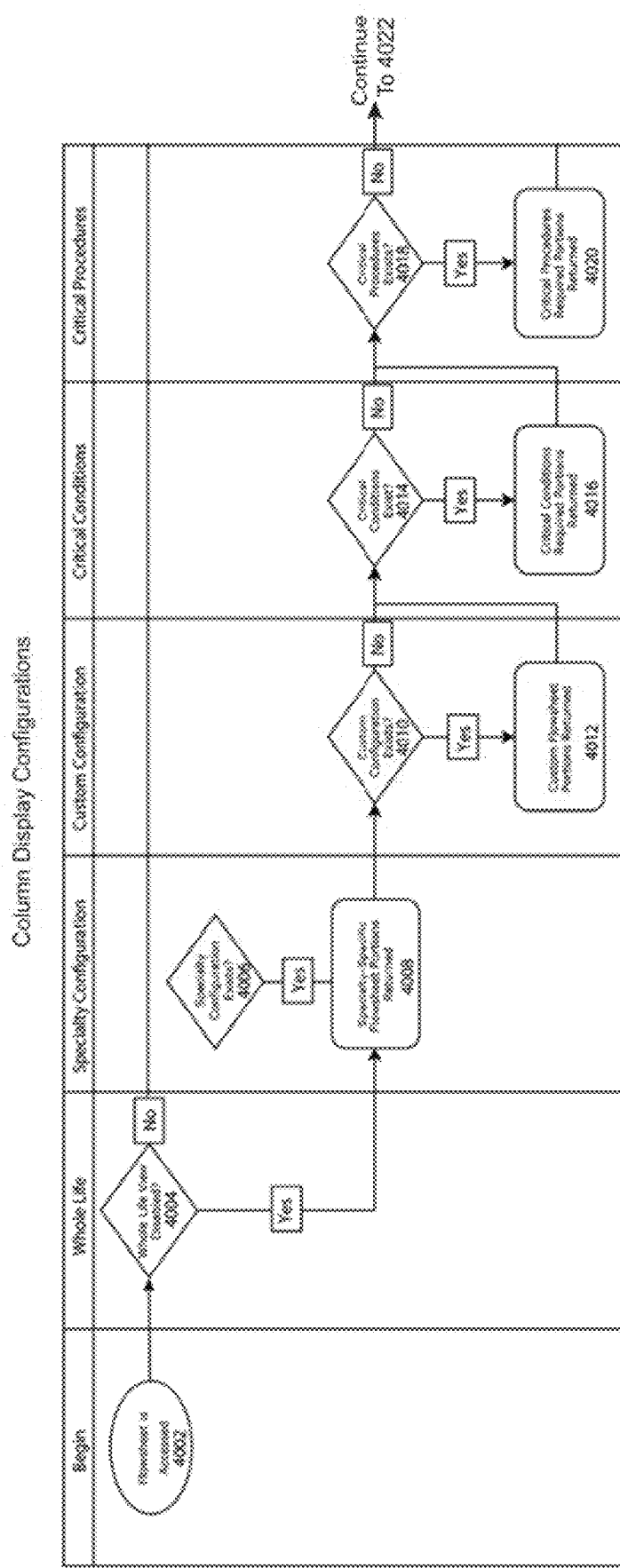
FIG. 40A depicts a workflow diagram of a process for intelligently expanding, collapsing, displaying, and/or hiding columns, rows and/or any other portion of the medical records dashboard in accordance with an embodiment of the present principles.
Figure 40B:
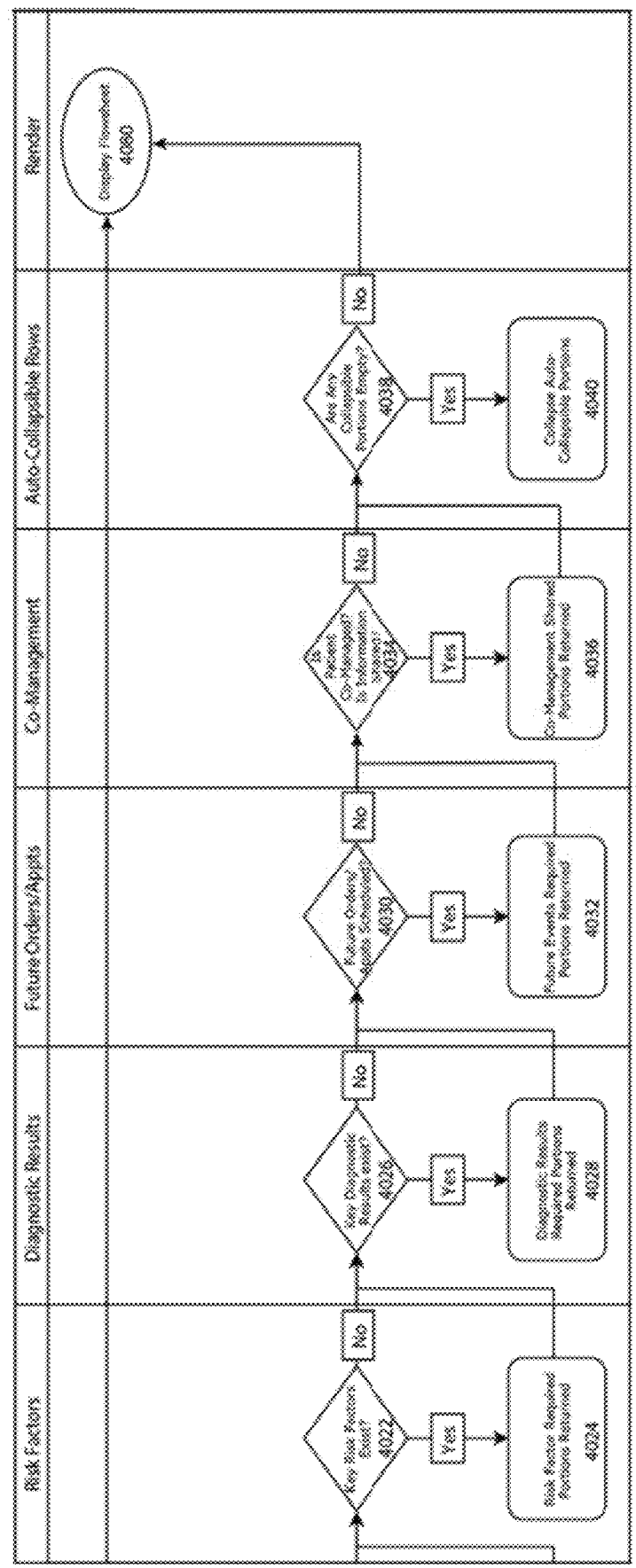
FIG. 40B depicts a workflow diagram of a process for intelligently expanding, collapsing, displaying, and/or hiding columns, rows and/or any other portion of the medical records dashboard in accordance with an embodiment of the present principles.

FIGS. 40A and 40B (referred to collectively herein as FIG. 40) depict a workflow diagram of a process for intelligently expanding, collapsing, displaying, and/or hiding columns, rows and/or any other portion of the medical records dashboard in accordance with an embodiment of the present principles. In the embodiment depicted in FIG. 40 the process begins at 4002 during which a Flowsheet including patient treatment and health information is accessed from, for example, an EHR system. The process illustratively proceeds to 4004. At 4004, it is determined if, what the inventors refer to as a "Whole Life View", is disabled. More specifically, At 4004 it is determined if all the data in the Flowsheet should be displayed in the medical records dashboard. If Whole Life View is disabled, the process proceeds to 4080 during which all of the data from the Flowsheet is displayed in the medical records dashboard. If not, the process illustratively proceeds to 4006.

At 4006, it is determined if at least one Specialty Configuration exists. For example, in some embodiments a Specialty Configuration can include a configuration based on the specialty of a medical care provider. If so, the process proceeds to 4008 during which all Specialty Configurations are identified such that the data from the Flowsheet can be filtered to only display data associated with identified Specialty Configurations. For example, as previously described, in some embodiments information associated with medical care provider specialties and data to be displayed and hidden in the medical records dashboard dependent on the specialties can be predetermined and stored in the Rules module 004. In accordance with the present principles, Specialty Configurations can require certain portions, columns, and/or rows of the medical records dashboard to be displayed or hidden. After the Specialty Configurations are identified and/or if it is determined that a Specialty Configuration does not exist, the process illustratively proceeds to 4010. In accordance with the present principles, data from the Flowsheet to be displayed in or hidden from the medical records dashboard can be filtered using the identified Specialty Configurations.

At 4010, it is determined if at least one Custom Configuration exists. If so, the process proceeds to 4012 during which all Custom Configurations are identified such that the data from the Flowsheet is filtered to only display data or hide data associated with the identified Custom Configurations. For example, in some embodiments custom configurations and data to be displayed in or hidden from the medical records dashboard dependent on the custom configurations can be predetermined and stored in the Rules module 004. Alternatively or in addition, in some embodiments, a user can use a user interface associated with the medical records dashboard to create and/or identify custom configurations. In accordance with the present principles, Custom Configurations can require certain portions, columns, and/or rows of the medical records dashboard to be displayed or hidden. After the Custom Configurations are identified and/or if it is determined that a Custom Configuration does not exist, the process illustratively proceeds to 4014. In accordance with the present principles, data from the Flowsheet to be displayed in or hidden from the medical records dashboard can be filtered using the identified Custom Configurations.

At 4014, it is determined if at least one Critical Condition exists. That is, in some embodiments, critical conditions can be identified that, no matter what rules indicate that certain data should not be displayed or hidden, the identified critical conditions are to be displayed in at least one location of the medical records dashboard 400. In some embodiments, Critical Conditions can be identified and stored in the Rules module 004. Alternatively or in addition, a user can identify Critical Conditions using a user interface associated with the medical records dashboard 400. If it is determined that at least one Critical Condition exists, the process proceeds to 4016 during which the Critical Conditions are identified such that any data from the Flowsheet identified as a Critical Condition can be displayed in at least one portion of the medical records dashboard 400. In accordance with the present principles, Critical Conditions can require certain portions, columns, and/or rows of the medical records dashboard to be displayed or hidden. After the Critical Conditions are identified or if it is determined that a Critical Condition does not exist, the process illustratively proceeds to 4018.

At 4018, it is determined if at least one Critical Procedure exists. That is, in some embodiments, critical procedures can be identified that, no matter what rules indicate that certain data should not be displayed or hidden, data associated with the identified critical procedures are to be displayed in at least one location of the medical records dashboard 400. In some embodiments, Critical Procedures can be identified and stored in the Rules module 004. Alternatively or in addition, a user can identify Critical Procedures using a user interface associated with the medical records dashboard 400. If it is determined that at least one Critical Procedure exists, the process proceeds to 4020 during which data associated the Critical Procedures are identified such that any data from the Flowsheet identified as being associated with a Critical Procedure can be displayed in at least one portion of the medical records dashboard 400. In accordance with the present principles, Critical Procedures can require certain portions, columns, and/or rows of the medical records dashboard to be displayed or hidden. After the Critical Procedures are identified or if it is determined that a Critical Procedure does not exist, the process illustratively proceeds to 4022.

At 4022, it is determined if at least one Risk Factor exists. That is, in some embodiments, Risk Factors can be identified that, no matter what rules indicate that certain data should not be displayed or hidden, the identified Risk Factors are to be displayed in at least one location of the medical records dashboard 400. In accordance with the present principles, Risk Factors can require certain portions, columns, and/or rows of the medical records dashboard to be displayed or hidden. For example, a smoker with high blood pressure, and diabetes having an identified Risk Factor for a heart attack can require a visual field column with an alert to be displayed in at least a portion of the medical records dashboard 400. In some embodiments, Risk Factors can be identified and stored in the Rules module 004. Alternatively or in addition, a user can identify Risk Factors using a user interface associated with the medical records dashboard 400. If it is determined that at least one Risk Factor exists, the process proceeds to 4024 during which the Risk Factors are identified such that any data from the Flowsheet identified as identifying a Risk Factor can be displayed in at least one portion of the medical records dashboard 400. After the Risk Factors are identified or if it is determined that a Risk Factor does not exist, the process illustratively proceeds to 4026.

At 4026, it is determined if at least one Key Diagnostic Result exists. That is, in some embodiments, Diagnostic Results that are considered Key can be identified that, no matter what rules indicate that certain data should not be displayed or should be hidden, data associated with the identified Key Diagnostic Results are to be displayed in at least one location of the medical records dashboard 400. In accordance with the present principles, Key Diagnostic Results can require certain portions, columns, and/or rows of the medical records dashboard to be displayed or hidden. For example, if a lab returns a positive infectious disease test, data associated with that Key Diagnostic Result can be caused to be displayed in at least a portion of the medical records dashboard 400. In some embodiments, Key Diagnostic Results can be identified and stored in the Rules module 004. Alternatively or in addition, a user can identify Key Diagnostic Results using a user interface associated with the medical records dashboard 400. If it is determined that at least one Key Diagnostic Results exists, the process proceeds to 4028 during which the Key Diagnostic Results are identified such that any data from the Flowsheet identified as being associated with a Key Diagnostic Results can be displayed in at least one portion of the medical records dashboard 400. After the Key Diagnostic Results are identified or if it is determined that a Key Diagnostic Results does not exist, the process illustratively proceeds to 4030.

At 4030 of the embodiment of FIG. 40, it is determined if at least one Future Order/Appointment exists. That is, in some embodiments, Future Orders/Appointments can be identified that, no matter what rules indicate that certain data should not be displayed or should be hidden, data associated with the identified Future Order/Appointment are to be displayed in at least one location of the medical records dashboard 400. In accordance with the present principles, Future Orders/Appointments can require certain portions, columns, and/or rows of the medical records dashboard to be displayed or hidden. For example, if an Open-heart surgery is scheduled for the future, it can be desirable for all medical care providers to see the scheduled Open-heart surgery in at least a portion of the medical records dashboard regardless of a medical care provider's specialty. In some embodiments, Future Orders/Appointments can be identified and stored in the Rules module 004. Alternatively or in addition, a user can identify Future Orders/Appointments using a user interface associated with the medical records dashboard 400. If it is determined that at least one Future Order/Appointment exists, the process proceeds to 4032 during which the Future Orders/Appointments are identified such that any data from the Flowsheet identified as being associated with a Future Order/Appointment can be displayed in at least one portion of the medical records dashboard 400. After the Future Orders/Appointments are identified or if it is determined that a Future Order/Appointment does not exist, the process illustratively proceeds to 4034.

At 4034, it is determined if Co-Management of at least one patient is allowed and if patient information sharing is allowed. That is, in some embodiments, Co-Management of patients can require certain portions, columns, and/or rows of the medical records dashboard to be shared or hidden amongst different users/medical care providers. For example, if a medical records dashboard in accordance with the present principles is being used by multiple medical care providers to care for a patient, the patient's primary care physician is able to see lab results from a specialist if the specialist has shared at least the relevant portions of a medical records dashboard. In some embodiments, patient data/information to be shared and, as such, portions of a medical records dashboard to be shared can be identified and stored in the Rules module 004. Alternatively or in addition, a user can identify patient data/information to be shared and, as such, portions of a medical records dashboard to be shared using a user interface associated with the medical records dashboard. If it is determined that Co-Management of at least one patient exists and if patient information sharing is allowed, the process proceeds to 4036 during which the existence of Co-Management of at least one patient and patient information sharing is identified such that any data from the Flowsheet identified as being associated with Co-Management and patient information sharing can be displayed in at least one portion of the medical records dashboard 400. After the Co-Management and patient information sharing is identified or if it is determined that Co-Management and patient information sharing does not exist, the process illustratively proceeds to 4038.

In the embodiment of FIG. 40, at 4038, it is determined if any of the collapsible portions, columns, and/or rows of the medical records dashboard contain no respective values (i.e., are empty). If it is determined that collapsible portions, columns, and/or rows of the medical records dashboard contain no respective values, the process proceeds to 4040 during which the collapsible portions, columns, and/or rows of the medical records dashboard 400 containing no respective values can be collapsed or hidden from display on a least a portion of the medical records dashboard. After all of the display configurations have been determined as described above, at 4080 the data of the Flowsheet to be displayed, as determined by the process of FIG. 40 described above, is displayed in the medical records dashboard 400. The process can then be exited.

In accordance with the present principles and as described above, in some embodiments, rules determine portions, columns, and/or rows of the medical records dashboard to expand or display based on predefined criteria, and also determine portions, columns, and/or rows of the medical records dashboard to collapse or hide based on the predefined criteria, and can also determine portions, columns, and/or rows of the medical records dashboard to flag or highlight based on the predefined criteria. For example, in some embodiments, the entirety of a patient's accessible records can be viewed. In some embodiments, the entirety of a patient's accessible records are evaluated against specialty and user-specific configuration criteria (e.g., Rules), actively collapsing or hiding portions, columns, and/or rows of the medical records dashboard deemed unnecessary for a user or specialty and actively enabling the display of portions, columns, and/or rows of the medical records dashboard deemed relevant to the user or specialty. In some embodiments, an intelligent Rules system actively determines which portions, columns, and/or rows of the medical records dashboard to display based on a user, a user's specialty, a patient, a patient conditions, a patient procedures, risk factors, diagnostic results, future orders, future appointments, values recorded, values not recorded, calculated values, and absolute values for display. In another embodiment, shared portions, columns, and/or rows of the medical records dashboard between medical care providers and facilities can be added or expanded based on preconfigured or point-of-sharing decisions made by the sharing medical care providers.

Although the embodiment of the process for intelligently expanding, collapsing, displaying, and/or hiding columns, rows and/or any other portion of the medical records dashboard of the present principles described with reference to FIG. 40 illustratively comprises specific Rules-based configurations, other embodiments of the process in accordance with the present principles can comprise any combination of some or all of the described Rules-based configurations and can also comprise other Rules-based configurations. Even further, those skilled in the art will appreciate that the order of operations denoted in the process above with reference to FIG. 40 can be non-linear and optimized based on usage and workflow. That is, order, inclusion, and omission can be intelligently determined based on accessibility of data, predefined configurations, real-time user selection, custom configurations, preferred practice patterns, and/or workflow.

In addition, although in the embodiment of the process for intelligently expanding, collapsing, displaying, and/or hiding columns, rows and/or any other portion of the medical records dashboard of the present principles described with reference to FIG. 40 the Rules are described as being stored in the Rules module 004, those skilled in the art will appreciate that rules and configurations of a process of the present principles can be stored in tables, accessed remotely via API or other digital communications technology, or generated on-the-fly as the result of calculations during the operations. Rules and configurations can be stored within the application or reference outside data sources. Rules and configurations can be altered by the user, in some embodiments, by the application, in some embodiments, and/or by outside resources.

In addition, although in the embodiment of the process for intelligently expanding, collapsing, displaying, and/or hiding columns, rows and/or any other portion of the medical records dashboard of the present principles described with reference to FIG. 40 it is described that upon rendering the Flowsheet, data populates within the columns specified, in some embodiments, further rules and configurations can apply post-rendering, based on data returned and/or calculated within columns. In addition, in some embodiments, manual manipulation allows for human interaction with the finally determined dataset. As such, a user can acknowledge and remove portions, columns, and/or rows of the medical records dashboard once they have been rendered. Removal of such portions, columns, and/or rows of the medical records dashboard can be one-time, or permanent unless a subsequent event retriggers the rendering of those portions, columns, and/or rows of the medical records dashboard, and such rendering can be patient-specific, provider-specific, location-specific, or otherwise tied to an event, condition, or trigger.

In one example of the process of the present principles, a dentist can access a Flowsheet for a patient with a rare blood disorder. As a dentist, the returned set of data to be displayed in accordance with a process of the present principles would ordinarily include data germane to dentistry, collapsing or hiding certain portions, columns, and/or rows of the medical records dashboard with no values present and/or deemed unnecessary. The dentist can have also chosen not to view certain portions, columns, and/or rows of the medical records dashboard as a matter of practice. In accordance with embodiments of the present principles, as a patient with a rare blood disorder, additional portions, columns, and/or rows of the medical records dashboard could be added to the display to reflect the patient's condition of the rare blood disorder and such information could be highlighted/flagged to alert a user as to the importance of the information being displayed.

In another example, an ophthalmologist sees a diabetic patient with no diagnostic testing for a chronic illness. As an ophthalmologist, the patient data ordinarily returned for display by a process of the present principles would ordinarily include data germane to ophthalmology, collapsing or hiding certain portions, columns, and/or rows of the medical records dashboard with no values present or data deemed unnecessary for display by the process. In some embodiments, the ophthalmologist can have also chosen not to view certain columns as a matter of practice. As a patient with a lapse in testing and underlying condition requiring testing, portions, columns, and/or rows of the medical records dashboard having no value present which would normally be collapsed/hidden, could now be expanded/displayed, and highlighted or flagged to draw the attention of a user to the lack of testing having been performed on the patient.

In a third example, a primary care physician (PCP) may wish to view an entire patient history. The patient history can consist of patient care provided by the PCP, patient care provided by doctors in the same office as the PCP, and patient care provided by specialists outside the practice that co-manage the patient and have shared data with the PCP. In this arrangement, the entire dataset is provided for viewing on the medical records dashboard for care provided by the PCP and doctors within the same practice, and a shared dataset can be provided for viewing on the medical records dashboard for care provided by the specialists. Columns with no values can be collapsed or hidden if no value exists as described above.

FIG. 41 depicts a flow diagram 4100 of a method for rules-based data display in a data command center comprising a medical records dashboard including one or more windows including information received or derived from at least one patient database, the medical records dashboard comprising a display on a screen, using the one or more windows, of at least one of medical services, clinical data, examination findings, diagnostic tests, and the procedures performed on one or more patients, the one or more windows comprising a plurality of collapsible data entry fields for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, the method beginning at 4102 during which patient data/information from the at least one patient database is received. The method 4100 can proceed to 4104.

At 4104, the received patient information is compared with configuration rules to determine which portions of the received patient data/information are to be displayed and which portions of the received patient data/information is not to be displayed in the medical records dashboard. The method 4100 can proceed to 4106.

At 4106, collapsible data entry fields of the medical records dashboard that are determined to not have any patient data to display are identified as collapsed data entry fields. The method 4100 can proceed to 4108.

At 4108, patient data/information is displayed in the data entry fields of the medical records dashboard in accordance with the configuration rules and data entry fields of the medical records dashboard identified as collapsed data entry fields are collapsed and not displayed. The method 4100 can then be exited.

In some embodiments the collapsible data entry fields identified as collapsed data entry fields comprise at least one of a column and a row of the medical records dashboard.

In some embodiments, the Data Command Center of the present principles, such as the Data Command center 001 of FIG. 1, provides a user(s) with the ability to collate data and visualize the correlation between different, related datapoints, each with their own distinct visualizations (considered by the inventors as a Correlative Line Graph display). Novel to customizable visualizations is to display an array of customized visualizations correlated on a comparative axis or axes. In some embodiments of the preset principles, the customized, correlative display consists of one or more visualizations of patient data and other data related to the Data Command Center data, horizontally, vertically, on a Z axis, or on multiple axes displaying multiple events, results, and/or calculations. In some embodiments, the Customizable, Correlative Line Graph display can be launched from within a medical records dashboard of the present principles using an icon/button, keystroke, or series of keystrokes.

Upon launch, the Customizable, Correlative Line Graph can display as a pop-up window, popover window, pop-out window, or other display format that enables the simultaneous accessibility of the Correlative Line Graph and the medical records dashboard of the present principles. The Graph may overlay or adjoin an underlying medical records dashbaord in opaque or transparent states, be pinned to the medical records dashboard, and/or may hover over or aside the medical records dashboard.

Upon initiating the Customizable, Correlative Graph, a series of actions are performed to determine data and format of data displayed. Preconfigured CCG displays may be stored in tables or generated on-the-fly based on key considerations such as those laid out in Collapsible Columns and Rows, and those laid out in Guiding Actions in a Dashboard.

In one embodiment, relevant data is visualized graphically, as a series of events graphed against a timeline, correlated with a series of results, a series of actions, and a series of contributing factors. Any number of relevant details may be correlated as needed.

Data visualization is achieved with a series of configurations to determine what and how to display. In one embodiment, Source Data consists of a Value, an Inclusion/Exclusion Rule, and a Visual Representation Configuration. The data may consist of one type, a series of data points collected, values captured, validated for inclusion, and visualized across 2 intervals, correlated against a second type, a series of separate data points collected, values captured, validated for inclusion, and visualized across the same 2 intervals, correlated with a third type, a series of data points collected, values captured, validated for inclusion, and visualized across the same 2 intervals.

Rendered Customizable, Correlative Graphs may be interacted with in such ways as to turn on or off represented values in a similar manner to manually expanding/collapsing of columns and rows, i.e. turning on or off subsections of data, individual visualizations categorized by rows or columns, or selecting key elements to only display, selecting key icons within the display, and/or moving elements between positions to achieve a different view.

Those skilled in the art will appreciate additional visualizations may be added, additional flags derived, and a series of rules explained through this patent to manifest in the final rendering. Those skilled in the art will appreciate that the above described algorithm may be non-linear, may be automated in whole or in individual or groups of steps, and algorithms may intelligently update, flag, or otherwise override certain steps of the rendering process. Those skilled in the art will appreciate that single axis representation in the above description does not preclude multi-dimensional representations with multiple parallel representations as well as multiple perpendicular, or otherwise non-parallel representations.

The Customizable, Correlative Graph reaches its logical end at which point all data is rendered, processing of rendered data has occurred, and any/all necessary actions have been taken based on the processed data, including, but not limited to, Flags, Alerts, Clinical Decision Support, and Auto-Tasks. Auto-updates to patient data may initiate refactoring of the Customizable, Correlative Graph.

Figure 42:
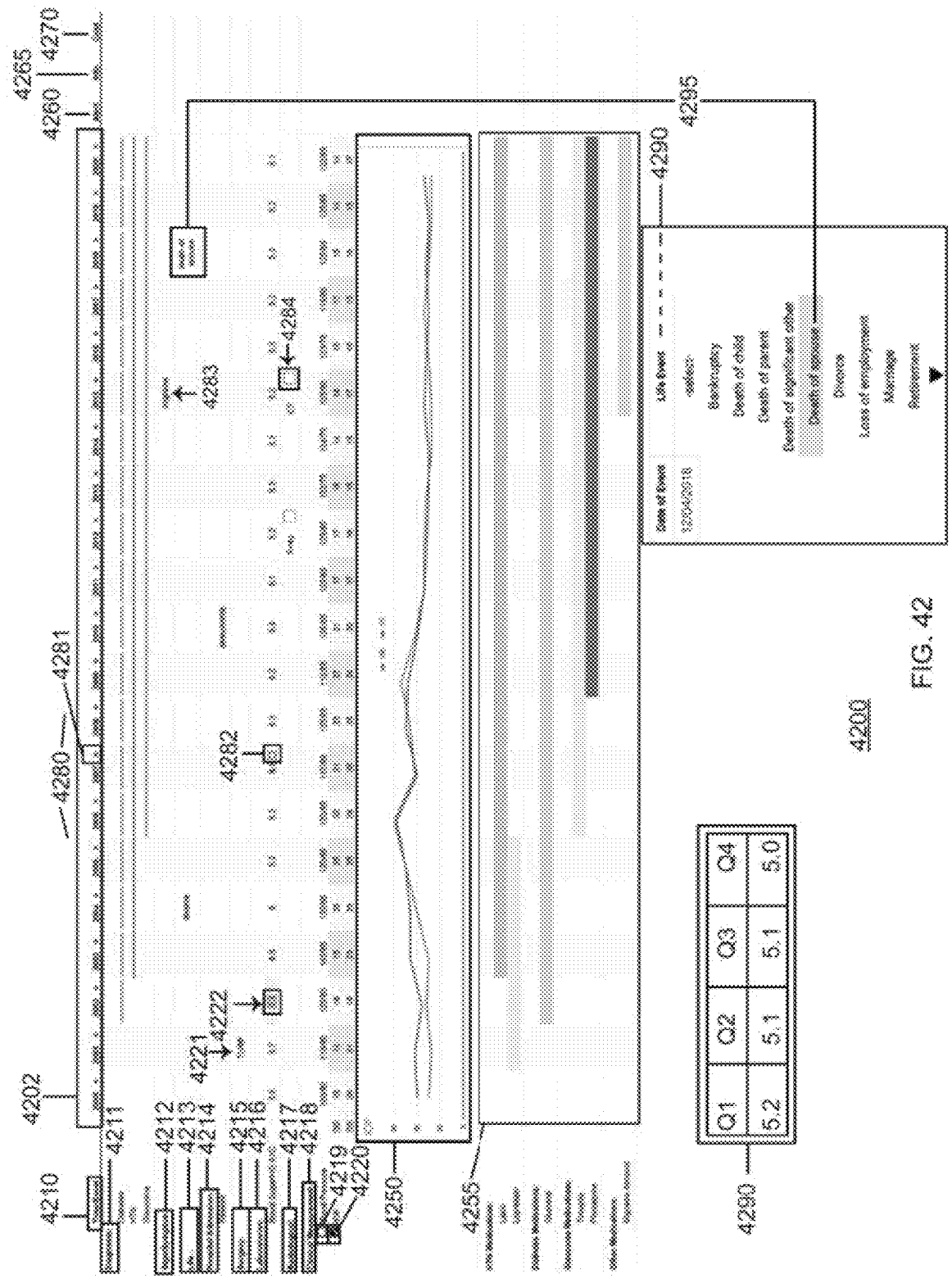
FIG. 42 depicts a graphical view of the entire medical history of a patient as a Whole Life tool in accordance with an embodiment of the present principles.

In some embodiments, the Data Command Center of the present principles, such as the Data Command center 001 of FIG. 1 enables, either as part of a medical records dashboard of the present principles or individually as a Whole Life tool, a user/medical care provider to graphically view, in a single display, a patient's entire medical history. For example, FIG. 42 depicts a graphical view of the entire medical history of a patient as a Whole Life tool in accordance with an embodiment of the present principles. In the embodiment of FIG. 42, the Whole Life tool 4200 illustratively lists dates, in one year incremented columns, across a top row 4202 of the Whole Life tool for a period of 20 years from 2000 through 2020. Although in the embodiment of FIG. 42 the time increments are illustratively one year increments, in other embodiments the time increments can be substantially any time increments chosen by the user/medical care provider.

In the embodiment of FIG. 42, the Whole Life tool 4200 in a first column 4210 lists a series of life events that occurred in a patient's life including diagnosis 4211 given to the patient, signs and symptoms 4212 the patient has had, major life events 4213 of the patient, hospital admissions 4214, surgeries 4215 the patient has had, laboratories 4216 performed on the patient, radiological procedures 4217 performed on the patient, and clinical measurements 4218 made on the patient. The Whole Life tool 4200 of FIG. 42 further illustratively includes an IOP section 4250 graphically displaying the intraocular pressure of a patient's right eye (OD) and the patient's left eye (OS) as a line graph spanning the 20 depicted years of the patient's medical history. In the embodiment of FIG. 42, the line graph of the IOP of a patient's right eye (OD) is color-coded red and the line graph of the IOP of the patient's left eye is color-coded blue for easier distinction. In the embodiment of the Whole Life tool 4200 of FIG. 42, a lower section 4260 graphically displays a medication history for the patient. In FIG. 42, horizontal bar graphs depict a history of the medication taken by and/or prescribed to a patient spanning the 20 depicted years of the patient's medical history. In the embodiment of FIG. 42, the various medication bar graphs can be color-coded to more easily distinguish between medications. In some embodiments, color standards, such as defined by the American Academy of Ophthalmology, can be used for color coding the medications. Alternatively or in addition, in some embodiment custom colors can be used.

In the Whole Life tool 4200 of FIG. 42 any column, 4281, can be selected 4280 and expanded to take up the entire page, or a partial part of the page, or a navigation template 4290 may be used to navigate the timeline by date range or to zoom in on specific results for that time increment 4282. For example, if a user/medical provider selects the year 2007, that particular year can expand so that instead of displaying one full year as depicted in FIG. 42, the Whole Life tool 4200 can display 12 months in the year in one month increments or quarterly or in any other increments, for example, for every medical encounter the patient has had. In some embodiments, a user/medical care provider is enabled to select whether to display all the encounters that the patient has had with any medical care providers or just particular medical care providers. In some embodiments, a zoom view of a particular time span can be displayed on another monitor such that a user/medical care provider is able to view the zoomed time increment simultaneously with the whole life view.

In the embodiment of the Whole Life tool 4200 of FIG. 42, the patient illustratively had three major disease states, diabetes, hypertension, and glaucoma, as listed in the diagnosis row 4211. The Whole Life tool 4200 enables a user/medical care provider to select any of the identified major disease states to find out more detailed data regarding the selected disease state and update start/stop dates or activate/inactive a diagnosis. As depicted in FIG. 42, a user/medical care provider is able to determine when the disease exactly occurred by referring to the Whole Life tool 4200. In the embodiment of FIG. 42, the diabetes occurred in 2002, 2003 was hypertension, and 2006 was glaucoma. These are chronic diseases, and these are the dates of onset. In some embodiments, the Whole Life tool can include a bar graph that can continue along a horizontal date line displaying the time period that the patient had that diagnosis, and if for some reason they no longer had that diagnosis, the bar graph could stop.

The Whole Life tool 4200 of FIG. 42 displays for a user/medical care provider in row 4212 when a patient developed a symptom and identify the symptom 4283. Similarly, the Whole Life tool 4200 of FIG. 42 is able to display for a user/medical care provider in row 4213 when a major life event that can affect the well-being of a patient occurred such as a divorce or the loss of a loved one, etc. As previously described, in row 4214, the Life tool 4200 of FIG. 42 is able to display for a user/medical care provider hospital admissions the patient had over the 20 years spanning the patient's recorded medical history. In the embodiment of FIG. 42, in 2010, the patient was hospitalized for pneumonia. As depicted in row 4215 of the Whole Life tool 4200 of FIG. 42, the patient had a surgery, transurethral resection of the prostate, in 2001. In addition, row 4216 of the Whole Life tool 4200 of FIG. 42 depicts that the patient has had laboratories, illustratively, blood sugars labs were performed, like hemoglobin A1C and update start/stop dates or activate/inactive a diagnosis. It should be noted that in the embodiment of the Whole Life tool 4200 of FIG. 42, a valued displayed in some rows and/or columns can be an average value of a measured parameter for the time increment depicted by the column. That is, in some embodiments each row and/or column can be a smart row or column and if a laboratory was taken four times in a year, the Whole Life tool 4200 can be configured to display an average of all values measured during the time increment. In some embodiments, by selecting a value in a row, patient data/information can be displayed in a window or other display means depicting all of the values measured and/or laboratories for the time increment. Even further, by selecting a particular measured value or laboratory, further detailed information for that particular value or laboratory can be displayed to a user/medical provider. Although the embodiment of FIG. 42 is described as displaying an average value, in some embodiments a high, low or other particular value can be selected by a user to be displayed 4222 represents an alert for an abnormal result.

In row 4217 of the Whole Life tool 4200 of FIG. 42, radiological procedures performed on the patient are displayed. For example, in FIG. 42, a CT scan was performed on the patient in 2015. In accordance with the present principles, by selectin the indicator in row 4217 of the year 2105, the image of the CT scan can be displayed to the user/medical care provider. In row 4217 of the Whole Life tool 4200 of FIG. 42, clinical measurement taken on the patient can be displayed. Such clinical measurement can include blood pressures taken at each doctor's visit. In some embodiments, the results can be displayed as a number. Alternative or in addition, in some embodiments, by selecting an icon associated with the clinical measurements, a graph representing the clinical measurements over time can be displayed. 4219 and 4220 represent radiological procedures and show how they may be toggled between one, many, or all. Images may be directly accessed and viewed within context by selecting them 4284.

In accordance with the present principles, in the Whole Life tool 4200 of FIG. 42, substantially any portion of a time increment or presentation of patient-related data/information can be selected to cause a display of a more detailed view of the selected time period/value.

In the Medications section (4255) of the Whole Life tool 4200 of FIG. 42, start dates and stop dates for each of the medications are displayed and may be interacted with in accordance with Medication Management protocols described herein.

The Whole Life tool 4200 of FIG. 42 illustratively comprises three optional columns; an alert column 4260, an info column 4265 and a cost column 4270. The alert column 4260 can be used to alert a user/medical care provider of an issue that requires further attention. In some embodiment alerts are automatically created by, for example a Rules module (described in greater detail below), and alternatively or in addition, alerts can be input by the user/medical providers with access to the Whole Life tool 4200.

Whole Life view may be interacted with whereby a doctor may choose to update an event, such as a life event (4290) by selecting said event and the event will auto-populate on the whole life view (4295).

The info column 4265 of the Whole Life tool 4200 of FIG. 42 can be used to provide information for a user/medical care provider. For example, in some embodiments, links can be provided to direct a user/medical care provider to sources of additional information, such as PUBMED, if the user/medical care provider is interested in learning about medications. Alternatively or in addition, the info column 4265 can be used by users/medical care providers to provide information to other users/medical care providers.

The cost column 4270 of the Whole Life tool 4200 of FIG. 42 can be used to display to a user/medical care provider information associated with cost in providing medical care a patient. For example, in some embodiments, the cost column 4270 can be used to provide to a user/medical care provider information regarding what a patient's insurance company will authorize. Alternatively or in addition, in some embodiments that cost column 4270 of the Whole Life tool 4200 can display to a user/medical care provider information regarding bills, paid or unpaid, associated with a patient.

In some embodiments, a user/medical care provider can input patient-related data/information into a Whole Life tool of the present principles. Alternatively or in addition, a Rules module can auto-populate patient-related data/information into a Whole Life tool of the present principles. For example, in some embodiments, an integration module of the present principles, such as the integration module 002 of the Data Command Center 001 of FIG. 1, can collect patient data/information from outside sources (e.g., an EMR system). The patient data/information is made accessible, for example via a storage means, to a Rules module of the present principles, such as the Rules module 004 of the Data Command Center of FIG. 1. In addition to having access to the data/information collected by the Integration module

002, the Rules module 004 can have access to all information input by a user/medical care provider via, for example, a medical records dashboard or any other user interface. Alternatively or in addition, in some embodiments, the Rules module 004 is configured to further have access to patient related information and general medical knowledge including but not limited to medical information regarding health conditions and treatments, symptoms and side effects, procedures, images and diagnosis, and other related medical information. As such, in some embodiments, the Rules module 004 can auto-populate at least portions of a Whole Life tool of the present principles. The Rules module 004 can then, via for example a Display module, such as the Display module 006 of the Data Command center 001 of FIG. 1, can cause the display of any portion or zoomed-in portion of a Whole Life tool of the present principles.

In some embodiments, the Data Command Center of the present principles, such as the Data Command center 001 of FIG. 1, can provide, either via a medical records dashboard of the present principles or individually, a Medical Guidance tool to assist users/medical care providers to plan and schedule health services for patients. In some embodiments, the medical guidance tool of the present principles enables a scheduling of patients with automated methodology by, for example, prioritizing the risks of symptoms and diseases, and associating these with past procedures, diagnostic tests and other critical items that need to be evaluated. With such methodology, a medical guidance tool of the present principles guides users/medical care providers in determining, which patients needs the timeliest interventions, appointments and follow up. In some embodiment, the medical guidance tool is configured to examine patient records and information to determine if medications ordered, procedures ordered, follow up visits ordered and if a plan of treatment determined for the patient by a user/medical care provider are accurate or contain any errors.

Alternatively or in addition, in some embodiments a medical guidance tool of the present principles can determine if a patient has missed an appointment and, in response, can alert a user/medical care provider to the fact that a patient has missed an appointment and/or can schedule a task for a user to at least contact the patient to schedule another appointment. In some embodiments, in addition to determining that the patient has missed an appointment, a medical guidance tool of the present principles can determine a level of risk presented to the patient's health by that patient missing the appointment. As such, patient's whose health is at a high risk by missing the appointment can be identified and contacted in an urgent manner to reschedule the missed appointment. In addition, the number of missed appointments can be tracked, whether the patient cancels or the practice cancels, and a pattern identified for the user/medical care provider.

In some embodiments of a medical guidance tool of the present principles, tasks can be generated for different users (e.g., doctors, staff, schedulers, etc) and such tasks can be presented to different users depending on a determined level of risk or urgency to a patient. For example, doctors typically do no schedule follow up appointments for patients. Such task is usually performed by a scheduler. As such, typically scheduling tasks generated by a medical guidance tool of the present principles are generally directed to an identified scheduler. In some embodiments however, if a patient misses an appointment and the a medical guidance tool of the present principles determines that missing the appointment presents an elevated risk to a patient's health, the medical guidance tool of the present principles can generate a rescheduling task that is now directed to the doctor. Alternatively or in addition, the medical guidance tool of the present principles can generate an alert to be present to a user/medical care provider that the missed appointment presents an elevated risk to the health of the patient.

For example, in a scheduling embodiment, an integration module of the present principles, such as the integration module 002 of the Data Command Center 001 of FIG. 1, can collect patient data/information from outside sources (e.g., an EMR system). The patient data/information is made accessible, for example via a storage means, to a Rules module of the present principles, such as the Rules module 004 of the Data Command Center of FIG. 1. In addition to having access to the data/information collected by the Integration module 002, the Rules module 004 has access to all information input by a user/medical care provider via, for example, a medical records dashboard, such as the medical records dashboard 400. In some embodiments, the Rules module 004 is configured to further have access to patient related information and general medical knowledge including but not limited to medical information regarding health conditions and treatments, symptoms and side effects, procedures, images and diagnosis, and other related medical information. As such, in some embodiments, the Rules module 004 can monitor patient data/information and can be configured to monitor patient scheduling. As such, when a Rules module 004 determines that a patient has missed a scheduled appointment, by for example determining if a user/medical care provider has interacted with the patient that day or not by determining if any information has been entered into a medical records dashboard or other user system for that patient that day, a Rules module 004 can determine if a patient has missed a scheduled appointment. If the Rules module 004 determines that a patient has missed a scheduled appointment, the Rules module 004, via for example a Display module of the present principles, such as the Display module 006 of the Data Command center 001 of FIG. 1, can cause a display of an alert, to call to the attention of a user/medical care provider that the patient has missed a scheduled appointment. Alternatively or in addition, the Rules module 004 can cause the scheduling of a task to be presented to a user/medical care provider such that a new appointment can be scheduled for the patient.

In some embodiments, having information regarding at least patient medical conditions, general and specific treatments and procedures, patient scheduling and other patient-related data/information, the Rules module 004 is able to determine if missing the scheduled appointment place the patient's health at an elevated risk. If so, the Rules module 004 can cause, for example via the Display module 006, a display of an alert, to call to the attention of a user/medical care provider that the patient's missed appointment results in an elevated risk to the patient's health. As described above, the determination of the elevated risk can cause the alert to be directed to a higher-level user such as a doctor instead of an administrator. In some embodiments of the present principles, the display of the alert itself can change and can be caused to be presented in a different color than usual or with other visual attributes, such as blinking or appear large on a display.

In some embodiments, a Medical Guidance tool of the present principles can assist in the scheduling of an appointment for a patient. For example, in an embodiment in which a scheduler is inputting patient data/information into an electronic system/spreadsheet/form, the Rules module 004 of the present principles can be configured to monitor such input patient data/information. Using the monitored input data/information and medical information known to the Rules module 004, the Rules module 004 can cause a display of a suggested appointment date to a user. For example, if a patient is known to have had a procedure performed and such procedure has a post-operative appointment typically scheduled for 30 days, the Rules module 004 can cause a display of a suggestion to a user that an appointment be scheduled for 30 days after the procedure was performed. In some embodiments, for suggesting an appointment, the Rules module 004 can further consider parameters such as time since a last procedure, symptoms since the last procedure, the doctor that performed the last procedure, medical history of the patient, the patient's disease state, and the like. In some embodiments, for new patients, the Rules module 004 can even take into account, who is referring the patient. If a patient referral comes from a doctor in a subspecialty that clearly would know what is an emergency, like another eye doctor, the Rules module 004 might suggest that an early appointment date must be made. In some embodiments, the Rules module 004 can create tasks for a user to make appointments on a suggested date or alternatively or in addition can schedule appointments without the need for a user intervention.

In some embodiments of the present principles, a Medical Guidance tool can assist in scheduling a patient to see a different doctor than the patient came to see. By way of example, in ophthalmology there may be in one office a general ophthalmologist, an optometrist, a retina surgeon and a glaucoma surgeon. A patient with diabetes and glaucoma may need to see the retina surgeon four times a year and the glaucoma surgeon three times a year. A scheduler for the practice or even the patient themselves can get confused as to which doctor to see. For instance, if the glaucoma doctor sees the patient and does not schedule the patient to return to the retina doctor, who handles another type of disease, not infrequently, patients can be totally lost and the wrong provider is assigned to give care. While one provider may be taking care of one disease state, (i.e. glaucoma), the other states (i.e., diabetic eye disease or macular degeneration), can be inadvertently neglected. The same can be true in a multispecialty practice of internists, cardiologists and pulmonologists. For example, an internist can have a good working relationship with the patient and sees the patient on a regular basis, however, the internist may not realize that the patient did not keep or ever get scheduled for an appointment with a cardiologist.

In some embodiments in accordance with the present principles, the Rules module 004, having knowledge of a patient's entire medical history, conditions, current procedures and treatments and having general knowledge of medicine and specifically the relationship between treatments and procedures of internists and cardiologists, can cause a display, for example via the display module 006, of at least one of an alert, suggestion and/or a task that causes the patient to be scheduled for an appointment with a cardiologist. A Medical Guidance tool of the present principles is able to determine when a patient is supposed to return for an appointment, what the high-risk scenarios exist, whether there was a procedure performed on a patient that requires a follow up with a particular doctor, whether a follow up appointment is kept by the patient, and is able to suggest or remind a user/medical care provider that they should consider sending a patient to another doctor. In some embodiments, not only are there indicators and alerts sent to the doctor who sees the patient, but indicator and alerts can be sent to an original doctor whose appointment has been missed, to a practice manager, or to anyone else in the practice to be able to determine whether a particular patient should be seeing a particular doctor or if the patient has been lost in the shuffle of so many visits. Such mistakes can happen in health systems and hospitals in which a patient who is not knowledgeable about medicine makes the assumption that each doctor talks to one another and shares records and therefore the patient assumes that if one doctor does not suggest that the patient sees another doctor, that the original doctor will be taking care of everything and the patient does not need follow-up care from a different doctor.

In some embodiments, a Medical Guidance tool of the present principles can monitor patient-related information intended to be reviewed by at least one user/medical care provider to determine if that information has been reviewed by the at least one user. For example, in some embodiments, the Medical Guidance tool, for example via the Rules module 004 can identify if results from tests ordered or notes from other medical care providers or any other "attachments" sent to for example a medical records dashboard, have been reviewed by all intended users/medical care providers for which they were intended. If the patient-related data/information intended for review by users/medical care providers has not been reviewed, the Medical Guidance tool can cause a display of an alert to the users/medical care providers that have not reviewed the patient-related data/information and for which the patient-related data/information was intended. Alternatively or in addition, the Medical Guidance tool can create a task for at least one of users/medical care providers for which the patient-related data/information was intended and whom have not reviewed the patient-related data.

For example, in a multispecialty practice, if the pathology results of a biopsy of a skin lesion was received and a family doctor sees the results, but the dermatologist who ordered the biopsy does not see the results, an alert can be sent out to either one or both of the doctors or alternatively or in addition, a task can be created for one or both of the doctors to view the results of the biopsy.

In some embodiments, a Medical Guidance tool of the present principles enables the pre-analysis of current and future patent visits. Such functionality enables users/medical are providers to prepare for patient visits and review scheduling of patients and test/procedures to determine if any errors exist. A user/medical care provider can review tests/procedures scheduled for a patient, when the patient last had similar tests, what patient's disease states are, what the likelihood is that the patient might need additional tests or another type of procedure, and even whether or not something might have been scheduled in error because information from the previous visit doesn't match up. For example, if a patient treatment plan indicates that an injection is to be done in the left eye but the schedule says injection in the right eye, the Medical Guidance tool via, for example, the Rules module 004, can discover the discrepancy and cause an alert to be displayed to a user/medical care provider to warn of the discrepancy.

In some embodiments, a Medical Guidance tool of the present principles enables the post-analysis of patent visits. Such functionality enables users/medical care providers to pull up patient data/information related to visits of any past patients seen in any office or a particular patient seen with certain disease states or procedures or diagnostic tests and see what was done on any given time period or visit. Such functionality can be especially useful if a user/medical care provider references, for example, a medical records dashboard on the same day of a visit or shortly thereafter when the memory of patients are fresh in their memory. During such review, a user/medical care provider can review to determine if their examinations were filled out correctly and that any diagnostic and/or procedural matters were performed and performed correctly and determine if any tests or orders were missed.

Figure 43:
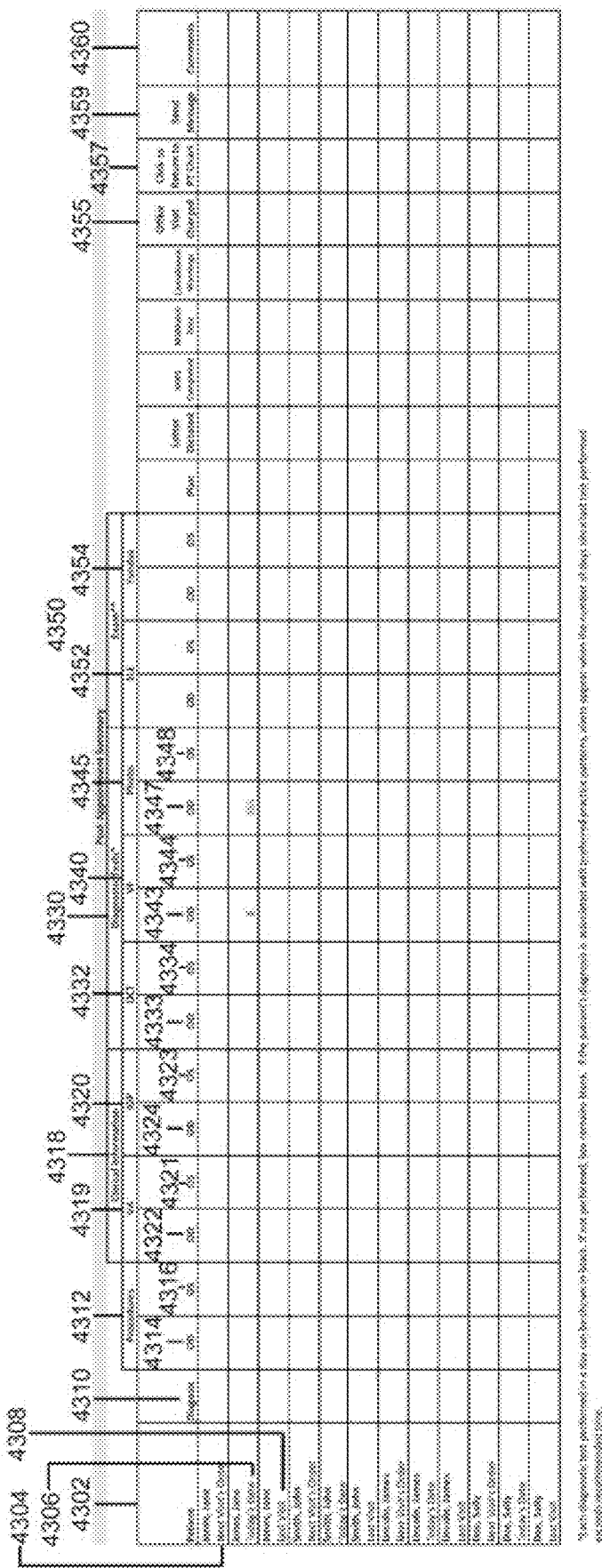
FIG. 43 depicts a post appointment summary chart of a Medical Guidance tool in accordance with an embodiment of the present principles.

FIG. 43 depicts a post appointment summary chart 4300 of a Medical Guidance tool in accordance with an embodiment of the present principles. The post appointment summary chart 4300 illustratively includes a first column 4302 listing a next visit's order row 4304, a today's date visit row 4306, and a last visit's row 4308. The post appointment summary chart 4300 has a plurality of other columns including a diagnosis column 4310, a Procedures column 4312 including a right eye column 4314 and a left eye column 4316, a Clinical information column 4318, including a VA column 4319 and an IOP column 4320, each having respective right eye columns 4322, 4324, and respective left eye columns 4321, 4323, and a Diagnosis Tests column 4330, including an OCT column 4332, a VF column 4340 and a Photo column 4345, each including respective right eye columns 4333, 4343, 4347, and respective left eye columns 4334, 4344, 4348.

The appointment summary chart 4300 of FIG. 43 further illustratively includes an Exam column 4350 including an SLE column 4352 and a Fundus column 4354, an Office Visit charged column 4355, a Click to return to PT chart column 4357, a Send message column 4359, and a Comments column 4360. Although in the embodiment of FIG. 43 the appointment summary chart 4300 illustratively includes specific columns and rows for providing the illustrated patient related data/information, in some other embodiments different patent related data/information can comprise the appointment summary chart 4300. In addition, although in the embodiment of FIG. 43 the appointment summary chart 4300 illustratively comprises a post appointment summary chart of the present principles, the appointment summary chart 4300 can comprise a pre appointment summary chart in accordance with the present principles. In some embodiments, at least some of the rows and columns of the appointment summary chart 4300 can be auto-populated.

In some embodiments, a Medical Guidance tool of the present principles enables users/medical care providers to create a preferred practice method. For example, in some embodiments, a Rules module 004 is programmed with a preferred practice method of a user/medical care provider. The Rules module 004 can then provide services, such as assisting in the creation of appointments and determining if patients kept their scheduled appointments in accordance with the preferred practice method of the user/medical care provider.

In some embodiments, a Medical Guidance tool of the present principles enables a tracking of payments in accordance with the present principles. Current EMR systems require user driven reports to be run manually to identify items that have not been paid or are rejected by insurance carriers. Most insurance companies send payment for hundreds of separate patient claims on the same electronic check that is then posted automatically to many different patient accounts without inspection or review by a billing or staff member. This electronic process was developed to reduce workloads on staff who before were required to read the explanation of benefits and apply the payment manually to each individual claim item in the billing system, which allowed for greater oversight of incorrect payments and rejections.

In some embodiments of a Medical Guidance tool of the present principles, a Rules module, such as the Rules module 004 of the Data Command center 001 of FIG. 1, can be configured to monitor individual CPT codes in, for example in some embodiments, a medical records dashboard of the present principles, to identify when bills are not completely paid or are rejected. In some embodiments, if it is determined that a bill is not completely paid or rejected, the Rules module 004 can cause, for example via the Display module 006, a display of an alert to alert a user/medical care provider that a bill was not completely paid. Alternatively or in addition, a task can be created for a user/medical care provider to correct the unpaid bill. In such embodiments, the Rules module 004 can have access to such information as specific insurance payors information, patients with high deductible plans, amount of billing, and the like. All pertinent data can be analyzed by, for example, the Rules module 004 and an indicator or a task can be created to alert the appropriate staff members and physicians enabling the users to make corrections rapidly. In some embodiments, based on user preferences, fully automated queries can generate indicators that can be viewed live while a patient is being treated.

In some embodiments of the present principles, a Medical Guidance tool of the present principles provides an electronic patient interface. For example, when a patient calls for an appointment or to ask questions or emails to schedule an appointment or ask questions, a user interface enables a patient to ask and answer questions, enter information, refill medications and the like. The reality is doctors often do not have the time to communicate with each and every single patient. In some embodiments, a Rules module of the present principles, such as the Rules module 004 of the Data Command center 001 of FIG. 1, having knowledge of all patient related data/information is also provided access to all information provided by a patient via the caller or email user interface. The Rules module 004 can evaluate every patient query in light of the information available to the Rules module 004. In some embodiments, the Rules module 004 determines if the patient is a current patient and if so, if the patient h had procedures or a risky diagnosis so that the Rules module 004 can present to a user/medical care provider a most complete picture of a patient as possible including which patients might be more problematic and urgent based on patient's symptoms, diagnosis, past procedures and other patient history In some embodiments the Rules module 004 can generate an alert directed to a user/medical care provider, the alert including the details of the patient developed by the Rules module 004. Alternatively or in addition, the Rules module 004 can create a task for a user/medical care provider, the task including the details of the patient developed by the Rules module 004. If the alert/task is not responded to within a certain amount of time by the user/medical care provider, the Rules module 004 can generate another alert and/or task directed to another user/medical care provider to attempt to elicit a response for the patient.

In some embodiments, a method for rules-based data display in a data command center including a medical records dashboard including one or more windows including information received or derived from at least one patient database, the medical records dashboard comprising a display on a screen, using the one or more windows, of at least one of medical services, clinical data, examination findings, diagnostic tests, and the procedures performed on one or more patients, the one or more windows comprising a plurality of data entry fields, including at least one collapsible data entry field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, the method includes receiving patient-related data from the at least one patient database, comparing the received patient-related data with configuration rules to determine which portions of the received patient-related data are to be displayed in data entry fields of the medical records dashboard, identifying collapsible data entry fields of the at least one collapsible data entry field of the medical records dashboard that are determined to not have any patient-related data to display as collapsed data entry fields, displaying patient-related data in the data entry fields of the medical records dashboard in accordance with the configuration rules and collapsing data entry fields of the medical records dashboard identified as collapsed data entry fields.

In some embodiments, a data command center visual display system that displays data on a display screen includes a computing device comprising at least one processor, a non-transitory computer-readable medium, having stored thereon, software instructions that when executed by the at least one processor of the computing device, cause the computing device to perform operations comprising at least, linking to and receiving patient related medical records including patient data from at least one patient data source, and displaying a medical records dashboard including one or more windows, the medical record dashboard capable of displaying, using the one or more windows, patient data from at least one patient data source including at least one of medical services, clinical data, examination findings, diagnostic tests, and the procedures performed on one or more patients, the one or more windows comprising a plurality of data entry fields, including at least one collapsible data entry field, for displaying the information received or derived from the at least one patient database, wherein the at least one of the medical services, the clinical data, the examination findings, the diagnostic tests, and the procedures are arranged in rows or columns on the screen according to at least one of a time and a date that the medical services, the clinical data, the examination findings, the diagnostic tests and the procedures were performed on the one or more patients, wherein a display of patient data in the medical records dashboard is determined by: comparing the patient data with configuration rules to determine which portions of the patient data are to be displayed in the data entry fields of the medical records dashboard, identifying collapsible data entry fields of the at least one collapsible data entry field of the medical records dashboard that are determined to not have patient data to display as collapsed data entry fields, and displaying patient data in the data entry fields of the medical records dashboard in accordance with the configuration rules and collapsing data entry fields of the medical records dashboard identified as collapsed data entry fields.

In some embodiments, a method for unique patient identification of a subject patient in a data command center including patient-related data received or derived from at least one patient database includes collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning phase.

In some embodiments, a data command center visual display system for determining a unique patient identification includes a computing device comprising at least one processor, a non-transitory computer-readable medium, having stored thereon, software instructions that when executed by the at least one processor of the computing device, cause the computing device to perform operations comprising at least: linking to and receiving patient related medical records including patient data from at least one patient data source, collecting patient-related data having different data classifications from the at least one patient database, assigning a level of accuracy score for each of the patient-related data of the different classifications, adding, the level of accuracy scores for each of the patient-related data of the different classifications, comparing a total of the added level of accuracy scores to a previously determined matching threshold, if the total of the added level of accuracy scores exceeds the matching threshold, establishing an identification of the subject patient, and if the total of the added level of accuracy scores does not exceed the matching threshold, collecting additional patient-related data and returning to the assigning.

In some embodiments, a method for medication management and display in a data command center comprising one or more windows for display and including information received or derived from at least one patient database, the data command center displaying on a screen, using the one or more windows, at least one of medical services, clinical data, examination findings, diagnostic tests, and procedures performed on one or more patients, the one or more windows comprising a plurality of data entry fields for displaying the information received or derived from the at least one patient database, wherein the at least one of the medical services, the clinical data, the examination findings, the diagnostic tests, and the procedures are arranged in on the screen according to at least one of a time and a date that the medical services, the clinical data, the examination findings, the diagnostic tests and the procedures were performed on the one or more patients, includes determining, from at least one of the information received or derived from the at least one patient database and the at least one of the medical services, the clinical data, the examination findings, the diagnostic tests, and the procedures, medications administered to the one or more patients, generating a respective graphical representation for each of the determined medications administered to the one or more patients, and displaying at least one generated, respective graphical representation of at least one medication administered to a patient in the at least one or more windows in context with at least one of the information received or derived from the at least one patient database and the at least one of the medical services, the clinical data, the examination findings, the diagnostic tests, and the procedures, wherein the at least one generated, respective graphical representation of the at least one medication administered to the patient is arranged in on the screen according to at least one of the times and the dates that the at least one medication was being administered to the patient.

In some embodiments, a data command center visual display system that displays data on a display screen includes a computing device comprising at least one processor, a non-transitory computer-readable medium, having stored thereon, software instructions that when executed by the at least one processor of the computing device, cause the computing device to perform operations including at least, linking to and receiving patient related medical records including patient data from at least one patient data source, wherein the patient data includes at least one of medical services, clinical data, examination findings, diagnostic tests, and procedures performed on one or more patients, determining, from at least one of the patient data and the at least one of the medical services, the clinical data, the examination findings, the diagnostic tests, and the procedures, medications administered to the one or more patients, generating a respective graphical representation for each of the determined medications administered to the one or more patients, and displaying using the one or more windows, at least one of medical services, clinical data, examination findings, diagnostic tests, and procedures performed on one or more patients and at least one generated, respective graphical representation of at least one medication administered to a patient in context with at least one of the patient data and the at least one of the medical services, the clinical data, the examination findings, the diagnostic tests, and the procedures, wherein the at least one of the medical services, the clinical data, the examination findings, the diagnostic tests, and the procedures are arranged on the screen according to at least one of a time and a date that the medical services, the clinical data, the examination findings, the diagnostic tests and the procedures were performed on the one or more patients, and wherein the at least one generated, respective graphical representation of the at least one medication administered to the patient is arranged on the screen according to at least one of the times and the dates that the at least one medication was being administered to the patient.

In some embodiments, a method for a display of a graphical representation of complete medical history of a patient in a data command center comprising one or more windows for display and including patient-related data received or derived from at least one patient database, the method includes determining, from the patient-related data, a complete medical history of at least one patient including at least one of medical services, clinical data, examination findings, diagnostic tests, medications administered to and procedures performed on a patient, generating a graphical representation of the determined complete medical history of the patient including the at least one of medical services, clinical data, examination findings, diagnostic tests, medications administered to and procedures performed on the patient, and displaying the generated graphical representation in the at least one or more windows according to at least one of a time and a date that the at least one of the medical services, the clinical data, the examination findings, the diagnostic tests, and the procedures the medical services, the clinical data, the examination findings, the diagnostic tests and the procedures were performed on the one or more patients and at least one of the times and the dates that the medications were being administered to the patient, wherein a user is enabled to select a location in the displayed graphical representation and details regarding the at least one of medical services, clinical data, examination findings, diagnostic tests, medications administered to and procedures performed on the patient related to that selected location are presented to the user.

The methods and processes described herein may be implemented in software, hardware, or a combination thereof, in different embodiments. In addition, the order of methods can be changed, and various elements can be added, reordered, combined, omitted or otherwise modified. All examples described herein are presented in a non-limiting manner. Various modifications and changes can be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances can be provided for components described herein as a single instance. Boundaries between various components, operations and data stores are somewhat arbitrary, and particular operations are illustrated in the context of specific illustrative configurations. Other allocations of functionality are envisioned and can fall within the scope of claims that follow. Structures and functionality presented as discrete components in the example configurations can be implemented as a combined structure or component. These and other variations, modifications, additions, and improvements can fall within the scope of embodiments as defined in the claims that follow.

In the foregoing description, numerous specific details, examples, and scenarios are set forth in order to provide a more thorough understanding of the present disclosure. It will be appreciated, however, that embodiments of the disclosure can be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described can include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Embodiments in accordance with the disclosure can be implemented in hardware, firmware, software, or any combination thereof. Embodiments can also be implemented as instructions stored using one or more machine-readable media, which may be read and executed by one or more processors. A machine-readable medium can include any mechanism for storing or transmitting information in a form readable by a machine (e.g., a computing device or a "virtual machine" running on one or more computing devices). For example, a machine-readable medium can include any suitable form of volatile or non-volatile memory.

Modules, data structures, and the like defined herein are defined as such for ease of discussion and are not intended to imply that any specific implementation details are required. For example, any of the described modules and/or data structures can be combined or divided into sub-modules, sub-processes or other units of computer code or data as can be required by a particular design or implementation.

In the drawings, specific arrangements or orderings of schematic elements can be shown for ease of description. However, the specific ordering or arrangement of such elements is not meant to imply that a particular order or sequence of processing, or separation of processes, is required in all embodiments. In general, schematic elements used to represent instruction blocks or modules can be implemented using any suitable form of machine-readable instruction, and each such instruction can be implemented using any suitable programming language, library, application-programming interface (API), and/or other software development tools or frameworks. Similarly, schematic elements used to represent data or information can be implemented using any suitable electronic arrangement or data structure. Further, some connections, relationships or associations between elements can be simplified or not shown in the drawings so as not to obscure the disclosure.

This disclosure is to be considered as exemplary and not restrictive in character, and all changes and modifications that come within the guidelines of the disclosure are desired to be protected.

The invention claimed is:

1. A data visual display system that displays data on a display, comprising:
   a computing device comprising at least one processor;
   a non-transitory computer-readable medium, having stored thereon, software instructions that when executed by the at least one processor of the computing device, cause the computing device to perform operations comprising at least:
   linking to and receiving patient data from at least one patient data source; and
   displaying a medical records dashboard including one or more windows, the medical record dashboard capable of displaying, using the one or more windows, patient data selected from the group consisting of medical services, clinical data, examination findings, diagnostic tests, images, medications, medical records, medical documents, plans, life events, office visits, claim information, and procedures performed on one or more patients, the one or more windows comprising a plurality of data fields, each data field corresponding to one type of information from the patient data from the group and for displaying the one type of information received or derived from the at least one patient data source, wherein at least one of the medical services, the clinical data, the examination findings, the diagnostic tests, images, medications, medical records, medical documents, plans, life events, office visits, claim information, and the procedures are arranged on the display according to a time that the medical services, the clinical data, the examination findings, the diagnostic tests, images, medications, medical records, medical documents, plans, life events, office visits, claim information, and the procedures were performed on the one or more patients;
   wherein a display of patient data in the medical records dashboard is determined by:
   comparing the patient data with configuration rules to determine which portions of the patient data are to be displayed in the data fields of the medical records dashboard;
   identifying at least one data field to collapse, display, or expand based on the configuration rules to generate a new dashboard configuration; and
   displaying patient data in the data fields of the medical records dashboard in accordance with the configuration rules such that at least one data field is collapsed and not displayed, or a hidden data field is expanded, or a data field not previously present is displayed using the new dashboard configuration.

2. The data visual display system of claim 1, wherein the information to be displayed is filtered by a combination of a professional specialty of a user of the visual display system and at least one medical condition of a respective one of the one or more patients.

3. The system of claim 1 wherein the new dashboard configuration includes multiple collapsed, hidden, removed, expanded, truncated, or newly displayed data fields.

4. The system of claim 1, wherein information received from or derived from the at least one data source includes information corresponding to more than one provider sharing care of the one or more patients, and where detecting a change of patient related data comprises detecting a change in patient related data corresponding to a different provider than a provider for which the data display was generated.

5. The system of claim 1, wherein information received from or derived from the at least one data source includes information corresponding to more than one provider sharing care of the one or more patients, and wherein modifying the new dashboard configuration comprises adding one or more data fields from another provider that shares the care of the patient.

6. The system of claim 1, wherein the data visual display system is configured to link to at least one electronic health records system, a health information exchange, an image management system, healthcare information technology system, picture archiving and communication system, claims-based system, insurance companies billing system, or practice management system.

7. The system of claim 1 wherein the configuration rules are user configurable.

8. The system of claim 1 wherein the patient data in at least one data field not previously present or present is displayed is highlighted.

9. The system of claim 1 wherein the configuration rules are identified based on a changed parameter value or medical treatment guidelines, clinical decision support, national coverage determination, local coverage determination or preferred practice patterns.

10. The system of claim 1 wherein the medical records dashboard includes rows and columns of data fields and the new dashboard configuration identifies rows or columns of data fields such that rows or columns are collapsed, hidden, expanded, or displayed.

11. The system of claim 1, wherein the at least one of medical services, medications, clinical data, examination findings, diagnostic tests, images, medications, medical documents, plans, life events, claims, and procedures are represented in at least one of the at least one data field using respective icons, indicators, graphical markers, or displayed visual representation, identifying the existence of underlying patient data corresponding to the medical services, clinical data, examination findings, diagnostic tests, images, medications, medical documents, plans, life events, claims, and procedures.

12. The system of claim 11 and further comprising enabling a user to access underlying information of at least one of medical services, clinical data, examination findings, diagnostic tests, images, medications, medical documents, plans, life events, claims, and procedures by providing a selectable icon, indicator, graphical marker or displayed visual representation in one of the data fields to access linked underlying patient information.

13. The system of claim 11 wherein the underlying patient information is displayed in a new window of the display.

14. The system of claim 1, wherein the configuration rules identify information considered critical such that critical information is always displayed.

15. The system of claim 1 wherein a data field not previously present is expanded in comparison to other data fields or any other previously displayed data field is made smaller or larger or enhanced.

16. The system of claim 1 wherein selected displayed information is emphasized in accordance with execution of the rules.

17. The system of claim 1 wherein at least two of the medical services, medications, the clinical data, the examination findings, the diagnostic tests, images, medical documents, plans, life events, office visits, claim information, and the procedures are arranged on the display according to a time that the medical services, the clinical data, the examination findings, the diagnostic tests, images, medications, medical documents, plans, life events, office visits, claim information, and the procedures were performed on the one or more patients.

18. A method for medication information display in one or more windows of a display and including other information from at least one data source, the other information including information selected from the group consisting of at least one of medical services, clinical data, examination findings, life events, diagnostic tests, images, plans, medical documents, medical diagnoses, claim information, and procedures associated with one or more patients, the one or more windows comprising a plurality of data fields, each data field corresponding to one type of the other information from the group, for displaying the other information, wherein the at least one of the other information are arranged in on the display according to a time that the medications were taken, ordered, prescribed, or administered by or for the patient or patients for comparison to the other information, the method comprising:

determining, from the at least one data source, medications taken, administered, ordered, or prescribed to the one or more patients;

generating a respective graphical representation for each of the determined medications, taken, administered, ordered, or prescribed to each of the one or more patients; and displaying at least one generated, respective graphical representation of at least one medication taken, administered, ordered, or prescribed to a patient in the at least one or more windows in context with at least the other information, wherein the at least one generated, respective graphical representation of the at least one medication taken, administered, ordered, or prescribed to the patient is arranged on the display according to a time that the at least one medication was being taken, administered, ordered, or prescribed to the patient; and wherein the at least one or more data fields displaying the graphical representations are dynamically collapsible, displayable, and expandable in accordance with configuration rules to generate a new configuration of graphical representations in the data fields in windows such that at least one of the data fields is collapsed and not displayed, or a hidden or expanded data field not previously present is displayed using the new configuration.

19. The method of claim 18, wherein the at least one generated, respective graphical representation enables a user to immediately identify on sight a respective medication without having to read a name of the medication.

20. The method of claim 18, wherein the generated, respective graphical representations includes information corresponding to at least one of claims data, cost and charges for the one or more of the respective graphical representations of the medications.

21. The method of claim 18, wherein the generated, respective graphical representations differentiate medications by at least one of color, combinations of colors, or visual representation.

22. The method of claim 21, wherein the colors are colors standardized by the American Academy of Ophthalmology.

23. The method of claim 18, wherein respective graphical representations are generated for and separately listed by each condition of a patient for which medications are being administered.

24. The method of claim 18, further comprising:
generating and displaying an alert if a medication associated with a respective one of the one or more patients has changed since a last visit, or a potential interaction between medications is detected, or the patient has a clinical finding that suggests an adverse reaction to a medication.

25. The method of claim 18, and further comprising linking to at least one electronic health records system, a health information exchange, an image management system, healthcare information technology system, picture archiving and communication system, claims-based system, insurance companies billing system, or practice management system.

26. The method of claim 18 wherein the information selected from the group includes at least two of medical services, clinical data, examination findings, life events, diagnostic tests, images, plans, medical documents, medical diagnoses, claim information, and procedures associated with one or more patients.

27. The method of claim 18, wherein the graphical representation of a medication is manually adjustable to show when the medication was taken, ordered, administered, or prescribed.

28. The method of claim 18 wherein the display includes rows and columns of other information.

29. The method of claim 18 and further comprising displaying a means for placing an order, administering or prescribing a medication, a procedure, diagnostic test, image, medical service.

30. The method of claim 18 wherein the information in at least one data field not previously present or present is displayed is highlighted.

31. The method of claim 18, wherein the at least one of medical services, medications, clinical data, examination findings, diagnostic tests, images, medical documents, plans, life events, claims, and procedures are represented in at least one of the at least one data field using respective icons, indicators, graphical markers, or displayed visual representation, identifying the existence of underlying patient data corresponding to the medical services, clinical data, examination findings, diagnostic tests, images, medications, medical documents, plans, life events, claims, and procedures.

32. The method of claim 31 and further comprising enabling a user to access underlying information of at least one of medical services, clinical data, examination findings, diagnostic tests, images, medical documents, plans, life events, claims, and procedures by providing a selectable icon, indicator, graphical marker or displayed visual representation in one of the data fields to access linked underlying information.

33. The method of claim 32, wherein the selection of an icon, indicator, graphical marker or displayed visual representation comprises clicking or hovering over the icon, indicator, graphical marker or displayed visual representation using a pointing device.

34. The method of claim 33 wherein the modified dashboard configuration includes a new window displaying additional underlying information.

35. The method of claim 18, wherein information received from or derived from the at least one data source includes information corresponding to more than one provider sharing care of the one or more patients, and where configuration rules wherein the at least one or more data fields displaying the graphical representations are dynamically collapsible, removable, displayable, and expandable in accordance with configuration rules to generate a new configuration of graphical representations in the data fields in windows such that at least one of the data fields is collapsed or removed and not displayed, or a hidden or expanded data field not previously present is displayed using the new configuration.

36. The method of claim 18, wherein information received from or derived from the at least one data source includes information corresponding to more than one provider sharing care of the one or more patients, and wherein displaying comprises adding one or more data fields from another provider that shares the care of the patient.

37. A data visual display system that displays data on a display, comprising:
a computing device comprising at least one processor;
a non-transitory computer-readable medium, having stored thereon, software instructions that when executed by the at least one processor of the computing device, cause the computing device to perform operations comprising at least:
linking to and receiving patient related medical records including patient data from at least one data source, wherein the patient data includes at least one type of information corresponding to medical services, clinical data, examination findings, diagnostic tests, images, plans, medical documents, medical diagnosis, claim information, life events, and procedures associated with one or more patients;
determining, from at least one of the patient data and the at least one of the medical services, the clinical data, the examination findings, the diagnostic tests, images, plans, medical documents, medical diagnosis, claim information, life events, and the procedures, as well as medications taken, ordered, administered, or prescribed to each of the one or more patients;
generating a respective graphical representation for each of the determined medications taken, ordered, administered, or prescribed to each of the one or more patients; and
displaying at least one of medical services, clinical data, examination findings, diagnostic tests, images, plans, medical documents, medical diagnosis, claim information, life events, and procedures associated with one or more patients and at least one generated, respective graphical representation of at least one medication taken, ordered, administered, or prescribed to a patient in context with at least one of the patient data and the at least one of the medical services, the clinical data, the examination findings, the diagnostic tests, images, plans, medical documents, medical diagnosis, claim information, life events, and the procedures;
wherein the at least one of the medical services, the clinical data, the examination findings, the diagnostic tests, images, plans, medical documents, medical diagnosis, claim information, life events, and the procedures are arranged in at least one data field, each data field corresponding to one type of information from the patient data, on the display according to a time that the medical services, the clinical data, the examination findings, the diagnostic tests, life events, and the procedures were performed on the one or more patients;

wherein the at least one generated, respective graphical representation of the at least one medication taken, ordered, administered, or prescribed to the patient is arranged on the display according to at least one of the times that the at least one medication was being taken, ordered, administered, or prescribed to the patient; and wherein the at least one or more data fields and graphical representations are dynamically collapsible, displayable, and expandable in accordance with configuration rules to generate a new configuration of data fields and graphical representations of medications such that at least one of the data fields or graphical representations is collapsed and is not displayed, or a hidden or expanded data field or graphical representation not previously present is displayed using the new configuration.

38. The data visual display system of claim 37, wherein the at least one generated, respective graphical representation enables a user to immediately identify on sight a respective medication without having to read a name of the medication.

39. The data visual display system of claim 37, wherein the generated, respective graphical representations represent at least one of individual medications, classes of medications, combinations of medications, or logical groupings of medications.

40. The data visual display system of claim 37, wherein the generated respective graphical representations of the medications are on a same axis as at least one of information corresponding to a medical service, the clinical data, the examination findings, life events, the diagnostic tests, images, plans, medical documents, claim information and the procedures that impact the taking, ordering, administration or prescribing of the medication and wherein the generated, respective graphical representations differentiate medications by at least one of color, combinations of colors, visual representation or symbols.

41. The data visual display system of claim 40, wherein the colors are colors standardized by the American Academy of Ophthalmology.

42. The data visual display system of claim 37, wherein respective graphical representations are generated for and separately listed by each condition of a patient for which medications are being taken, ordered, prescribed, or administered.

43. The data visual display system of claim 37, wherein the graphical representation of a medication can manually be adjusted as to when the medication was taken, ordered, administered, or prescribed.

44. The data visual display system of claim 37, wherein the data visual display system is configured to link to at least one electronic health records system, a health information exchange, an image management system, healthcare information technology system, picture archiving and communication system, claims-based system, insurance companies billing system, or practice management system.

45. The system of claim 37, wherein the at least one of medical services, clinical data, examination findings, diagnostic tests, images, medical documents, plans, life events, claims, and procedures are represented in at least one of the at least one data field using respective icons, indicators, graphical markers, or displayed visual representation, identifying the existence of underlying patient data corresponding to the medical services, clinical data, examination findings, diagnostic tests, images, medical documents, plans, life events, claims, and procedures.

46. The system of claim 45 and further comprising enabling a user to access underlying information of at least one of medical services, clinical data, examination findings, diagnostic tests, images, medical documents, plans, life events, claims, and procedures by providing a selectable icon, indicator, graphical marker or displayed visual representation in one of the data fields to access linked underlying patient related information.

47. The visual display system of claim 37 wherein the patient data includes at least two types of information corresponding to medical services, clinical data, examination findings, diagnostic tests, images, plans, medical documents, medical diagnosis, claim information, life events, and procedures associated with one or more patients.

48. The visual display system of claim 37 wherein the patient data in at least one data field not previously present or present is displayed is highlighted.

49. A computer implemented method for displaying data on a display, the method comprising:
  linking to and receiving patient data from at least one patient data source; and
  displaying a medical records dashboard including one or more windows, the medical record dashboard capable of displaying, using the one or more windows, patient data selected from the group consisting of medical services, clinical data, examination findings, diagnostic tests, images, medications, medical records, medical documents, plans, life events, office visits, claim information, and procedures performed on one or more patients, the one or more windows comprising a plurality of data fields, each data field corresponding to one type of information from the patient data from the group and for displaying the one type of information received or derived from the at least one patient data source, wherein at least one of the medical services, the clinical data, the examination findings, the diagnostic tests, images, medications, medical records, medical documents, plans, life events, office visits, claim information, and the procedures are arranged on the display according to a time that the medical services, the clinical data, the examination findings, the diagnostic tests, images, medications, medical records, medical documents, plans, life events, office visits, claim information, and the procedures were performed on the one or more patients;
  wherein a display of patient data in the medical records dashboard is determined by:
  comparing the patient data with configuration rules to determine which portions of the patient data are to be displayed in the data fields of the medical records dashboard;
  identifying at least one data field to collapse, display, or expand based on the configuration rules to generate a new dashboard configuration; and
  displaying patient data in the data fields of the medical records dashboard in accordance with the configuration rules such that at least one data field is collapsed and not displayed, or a hidden data field is expanded, or a data field not previously present is displayed using the new dashboard configuration.

50. The data visual display system of claim 49, wherein the information to be displayed is filtered by a combination of a professional specialty of a user of the visual display system and at least one medical condition of a respective one of the one or more patients.

51. The method of claim 49, wherein the new dashboard configuration includes multiple collapsed, hidden, removed, expanded, truncated, or newly displayed data fields.

52. The method of claim 49, wherein information received from or derived from the at least one data source includes information corresponding to more than one provider sharing care of the one or more patients, and where detecting a change of patient related data comprises detecting a change in patient related data corresponding to a different provider than a provider for which the data display was generated.

53. The method of claim 49, wherein information received from or derived from the at least one data source includes information corresponding to more than one provider sharing care of the one or more patients, and wherein modifying the new dashboard configuration comprises adding one or more data fields from another provider that shares the care of the patient.

54. The method of claim 49, wherein the display is configured to link to at least one electronic health records system, a health information exchange, an image management system, healthcare information technology system, picture archiving and communication system, claims-based system, insurance companies billing system, or practice management system.

55. The method of claim 49 wherein the configuration rules are user configurable.

56. The method of claim 49 wherein the patient data in at least one data field not previously present or present is displayed is highlighted.

57. The method of claim 49 wherein the configuration rules are identified based on a changed parameter value or ICD 10, a CPT code or medical treatment guidelines, clinical decision support, national coverage determination, local coverage determination or preferred practice patterns.

58. The method of claim 49 wherein the medical records dashboard includes rows and columns of data fields and the new dashboard configuration identifies rows or columns of data fields such that rows or columns are collapsed, hidden, expanded, or displayed.

59. The method of claim 49, wherein the at least one of medical services, medications, clinical data, examination findings, diagnostic tests, images, medications, medical documents, plans, life events, claims, and procedures are represented in at least one of the at least one data field using respective icons, indicators, graphical markers, or displayed visual representation, identifying the existence of underlying patient data corresponding to the medical services, clinical data, examination findings, diagnostic tests, images, medications, medical documents, plans, life events, claims, and procedures.

60. The method of claim 59, and further comprising enabling a user to access underlying information of at least one of medical services, clinical data, examination findings, diagnostic tests, images, medications, medical documents, plans, life events, claims, and procedures by providing a selectable icon, indicator, graphical marker or displayed visual representation in one of the data fields to access linked underlying patient information.

61. The method of claim 60, wherein the selection of an icon, indicator, graphical marker or displayed visual representation comprises clicking or hovering over the icon, indicator, graphical marker or displayed visual representation using a pointing device.

62. The method of claim 59, wherein the underlying patient information is displayed in a new window of the display.

63. The method of claim 49, wherein the configuration rules identify information considered critical such that critical information is always displayed.

64. The method of claim 49, wherein a data field not previously present is expanded in comparison to other data fields or any other previously displayed data field is made smaller or larger or enhanced.

65. The method of claim 49, wherein selected displayed information is emphasized in accordance with execution of the rules.

66. The method of claim 49, wherein at least two of the medical services, medications, the clinical data, the examination findings, the diagnostic tests, images, medical documents, plans, life events, office visits, claim information, and the procedures are arranged on the display according to a time that the medical services, the clinical data, the examination findings, the diagnostic tests, images, medications, medical documents, plans, life events, office visits, claim information, and the procedures were performed on the one or more patients.

67. The visual display system of claim 49, and further comprising:
receiving an edit to information provided in at least one of the respective data fields or windows of the data visual display system; and
auto-populating the in the at least one of the respective data fields or windows on the data visual display system to the at least one data source.

68. The visual display system of claim 49, wherein at least one data field comprises at least one of a visual cue, icon, indicator and graphical marker able to change in appearance based on a status of underlying information of at least one of medical services, clinical data, medications examination findings, diagnostic tests, images, medical documents, plans, life events, claims, and procedures.

69. The visual display system of claim 49, wherein the received information comprises order information or information received from the data source.

70. The visual display system of claim 49, wherein the clinical data patient-related information comprises multiple types of information corresponding to different patient measurements taken in a clinical setting.

\* \* \* \* \*

UNITED STATES PATENT AND TRADEMARK OFFICE
CERTIFICATE OF CORRECTION

Page 1 of 3

PATENT NO. : 11,837,334 B2
APPLICATION NO. : 17/008586
DATED : December 5, 2023
INVENTOR(S) : Ginsburg et al.

It is certified that error appears in the above-identified patent and that said Letters Patent is hereby corrected as shown below:

In the Claims

In Column 105, Line 8, in Claim 3, after "The", insert --data visual display--

In Column 105, Line 11, in Claim 4, after "The", insert --data visual display--

In Column 105, Line 18, in Claim 5, after "The", insert --data visual display--

In Column 105, Line 21, in Claim 5, after "wherein", delete "modifying"

In Column 105, Line 22, in Claim 5, delete "comprises adding" and insert --adds-- therefor In Column 105, Line 25, in Claim 6, after "The", insert --data visual display--

In Column 105, Line 32, in Claim 7, after "The", insert --data visual display--

In Column 105, Line 34, in Claim 8, after "The", insert --data visual display--

In Column 105, Line 37, in Claim 9, after "The", insert --data visual display--

In Column 105, Line 42, in Claim 10, after "The", insert --data visual display--

In Column 105, Line 47, in Claim 11, after "The", insert --data visual display--

In Column 105, Line 58, in Claim 12, after "The", insert --data visual display--

In Column 105, Line 66, in Claim 13, after "The", insert --data visual display--

In Column 105, Line 67, in Claim 13, delete "information" and insert --data-- therefor Signed and Sealed this
Nineteenth Day of August, 2025

Coke Morgan Stewart
*Acting Director of the United States Patent and Trademark Office*

CERTIFICATE OF CORRECTION (continued)
U.S. Pat. No. 11,837,334 B2

In Column 106, Line 1, in Claim 14, after "The", insert --data visual display--

In Column 106, Line 4, in Claim 15, after "The", insert --data visual display--

In Column 106, Line 8, in Claim 16, after "The", insert --data visual display--

In Column 106, Line 11, in Claim 17, after "The", insert --data visual display--

In Column 108, Lines 4-5, in Claim 34, delete "modified dashboard" and insert --new-- therefor In Column 109, Line 64, in Claim 45, after "The", insert --data visual display--

In Column 110, Line 7, in Claim 46, after "The", insert --data visual display--

In Column 110, Line 16, in Claim 47, after "The", insert --data--

In Column 110, Line 22, in Claim 48, after "The", insert --data--

In Column 111, Line 1, in Claim 50, delete "data visual display system" and insert --computer implemented method-- therefor In Column 111, Line 6, in Claim 51, after "The", insert --computer implemented--

In Column 111, Line 9, in Claim 52, after "The", insert --computer implemented--

In Column 111, Line 17, in Claim 53, after "The", insert --computer implemented--

In Column 111, Line 21, in Claim 53, before "the", delete "modifying"

In Column 111, Lines 21-22, in Claim 53, delete "comprises adding" and insert --includes-- therefor In Column 111, Line 24, in Claim 54, after "The", insert --computer implemented--

In Column 111, Line 31, in Claim 55, after "The", insert --computer implemented--

In Column 111, Line 33, in Claim 56, after "The", insert --computer implemented--

In Column 111, Line 36, in Claim 57, after "The", insert --computer implemented--

In Column 111, Line 41, in Claim 58, after "The", insert --computer implemented--

In Column 111, Line 46, in Claim 59, after "The", insert --computer implemented--

In Column 111, Line 57, in Claim 60, after "The", insert --computer implemented--

CERTIFICATE OF CORRECTION (continued)
U.S. Pat. No. 11,837,334 B2

In Column 112, Line 6, in Claim 61, after "The", insert --computer implemented--

In Column 112, Line 11, in Claim 62, after "The", insert --computer implemented--

In Column 112, Line 12, in Claim 62, delete "information" and insert --data-- therefor In Column 112, Line 14, in Claim 63, after "The", insert --computer implemented--

In Column 112, Line 17, in Claim 64, after "The", insert --computer implemented--

In Column 112, Line 22, in Claim 65, after "The", insert --computer implemented--

In Column 112, Line 25, in Claim 66, after "The", insert --computer implemented--

In Column 112, Line 35, in Claim 67, delete "visual display system" and insert --computer implemented method-- therefor In Column 112, Line 41, in Claim 67, before "in", delete "the"

In Column 112, Line 44, in Claim 68, delete "visual display system" and insert --computer implemented method-- therefor In Column 112, Line 51, in Claim 69, delete "visual display system" and insert --computer implemented method-- therefor In Column 112, Line 54, in Claim 70, delete "visual display system" and insert --computer implemented method-- therefor In Column 112, Line 55, in Claim 70, delete "patient-related information" and insert --patient data-- therefor